United States Patent
Siegwart et al.

(10) Patent No.: US 10,562,849 B2
(45) Date of Patent: *Feb. 18, 2020

(54) CATIONIC SULFONAMIDE AMINO LIPIDS AND AMPHIPHILIC ZWITTERIONIC AMINO LIPIDS

(71) Applicant: The Board of Regents of the University of Texas System, Austin, TX (US)

(72) Inventors: Daniel J. Siegwart, Dallas, TX (US); Jason B. Miller, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/597,049

(22) Filed: May 16, 2017

(65) Prior Publication Data
US 2017/0349543 A1 Dec. 7, 2017

Related U.S. Application Data

(60) Provisional application No. 62/337,196, filed on May 16, 2016.

(51) Int. Cl.
| | | |
|---|---|---|
| C07C 311/32 | (2006.01) | |
| A61K 48/00 | (2006.01) | |
| C07C 309/14 | (2006.01) | |
| C12N 15/11 | (2006.01) | |
| C12N 15/113 | (2010.01) | |

(52) U.S. Cl.
CPC ........ *C07C 311/32* (2013.01); *A61K 48/0033* (2013.01); *C07C 309/14* (2013.01); *C12N 15/11* (2013.01); *C12N 15/113* (2013.01); *C12N 2310/14* (2013.01); *C12N 2310/20* (2017.05); *C12N 2320/32* (2013.01)

(58) Field of Classification Search
CPC .... C07C 311/32; C07C 229/06; C07C 309/14
See application file for complete search history.

(56) References Cited

U.S. PATENT DOCUMENTS 6,656,498 B1 * 12/2003 Gao ............... A61K 9/1272
424/450
2014/0315797 A1  10/2014 Madsen et al.

FOREIGN PATENT DOCUMENTS

| WO | WO 2001/006011 | 1/2001 | |
|---|---|---|---|
| WO | WO 2004/044137 | 5/2004 | |
| WO | WO 2007/071658 | 6/2007 | |
| WO | WO 2009/126933 | 10/2009 | |
| WO | WO 2010/054266 | 5/2010 | |
| WO | WO 2011/056682 | 5/2011 | |
| WO | WO 2011/077405 | 6/2011 | |
| WO | WO 2012/170957 | 12/2012 | |
| WO | WO 2014/195872 | 12/2014 | |
| WO | WO 2015/082656 | 6/2015 | |
| WO | WO 2015/082656 A1 * | 6/2015 | ............. C09K 11/02 |
| WO | WO 2015/110262 | 7/2015 | |

OTHER PUBLICATIONS

PCT International Search Report and Written Opinion issued in International Application No. PCT/US2017/032950, dated Sep. 25, 2017.
Extended European Search Report issued in European Application No. 17800030.3, dated Nov. 25, 2019.
Miller et al., "The systematic design and biophysical evaluation of cationic sulfonamide aminolipids for siRNA delivery," *Front. Bioeng. Biotechnol. Conference Abstract:* 10th *World Biomaterials Congress*, 2016.

* cited by examiner

*Primary Examiner* — Pancham Bakshi
(74) *Attorney, Agent, or Firm* — Parker Highlander PLLC

(57) ABSTRACT

The present disclosure provides one or more amino lipids such as an amino lipids containing a sulfonic acid or sulfonic acid derivative of the formulas:

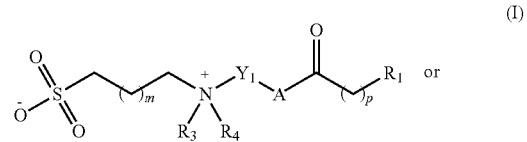

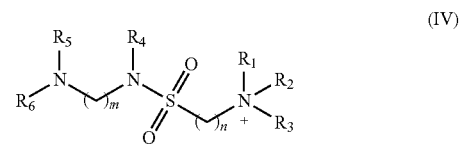

wherein the variables are as defined herein. These amino lipids may be used in compositions with one or more helper lipids and a nucleic acid therapeutic agent. These compositions may be used to treat a disease or disorder such as cancer, cystic fibrosis, or other genetic diseases.

18 Claims, 86 Drawing Sheets
(4 of 86 Drawing Sheet(s) Filed in Color)
Specification includes a Sequence Listing.

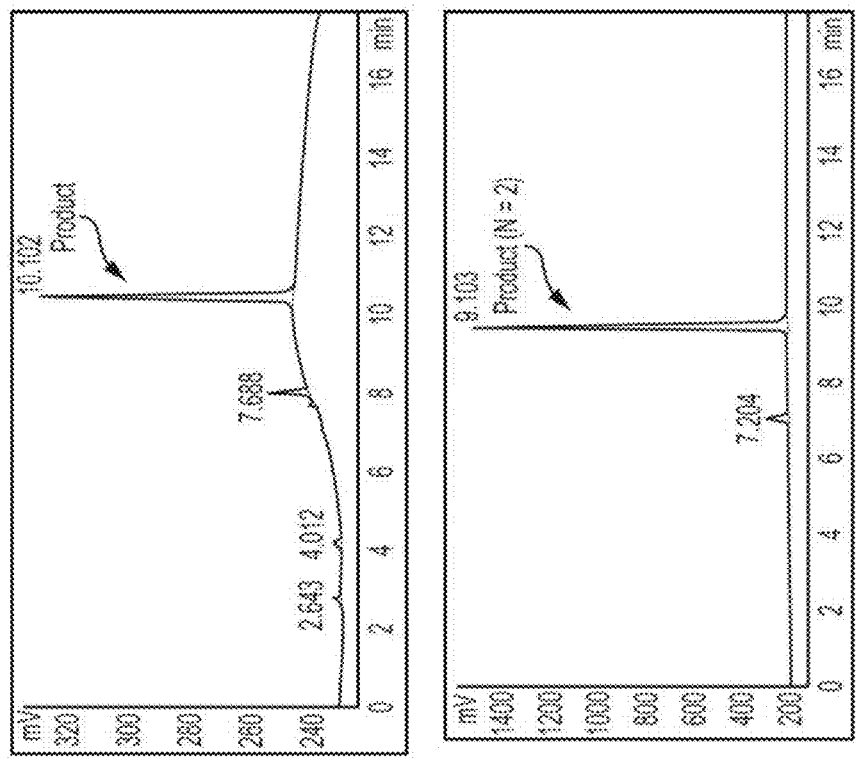
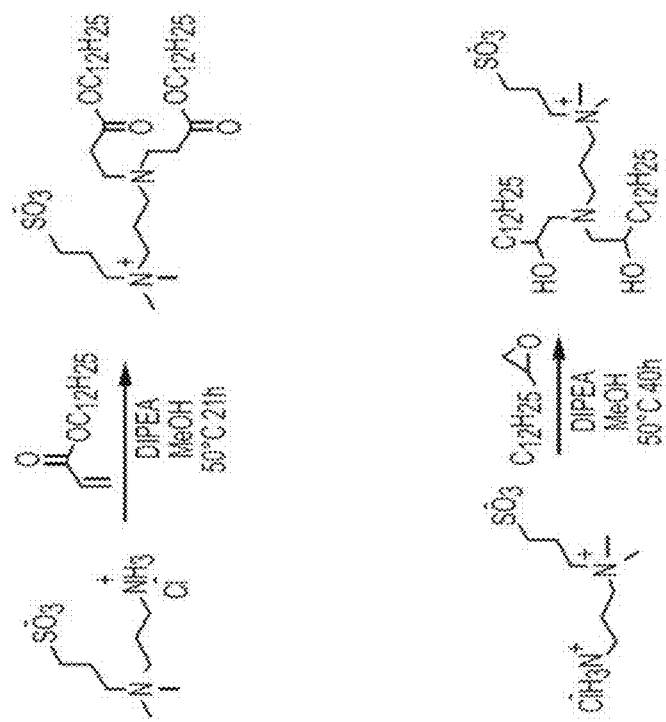
FIG. 39
CONTINUED

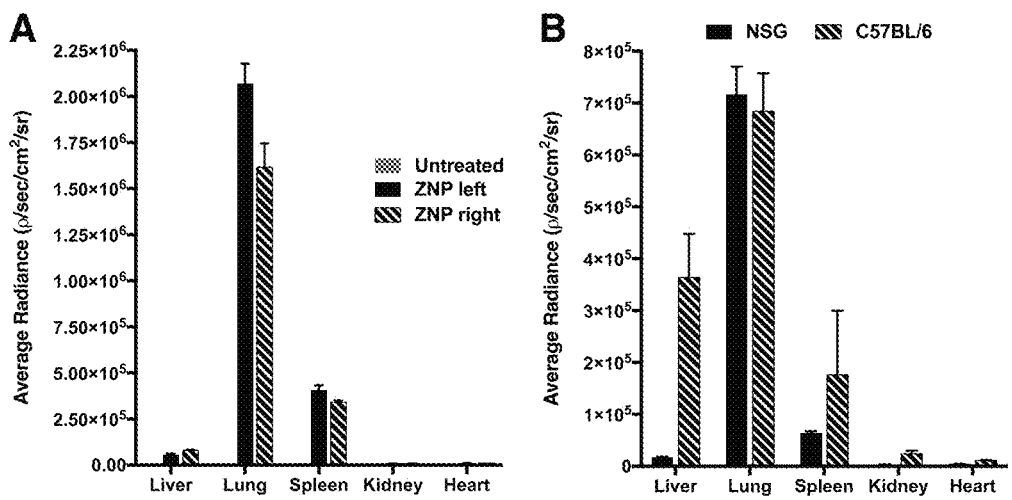
FIGS. 53A & 53B
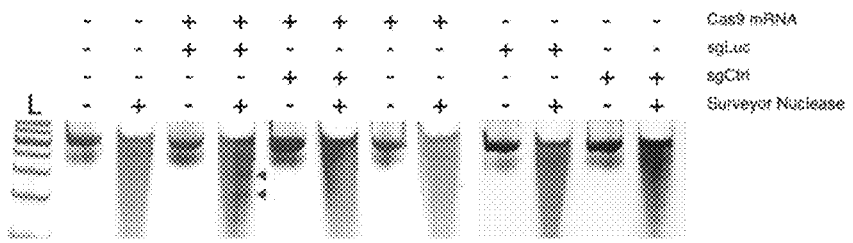
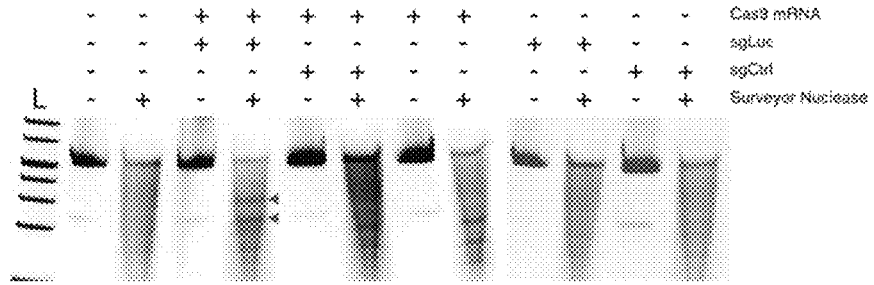
FIG. 54

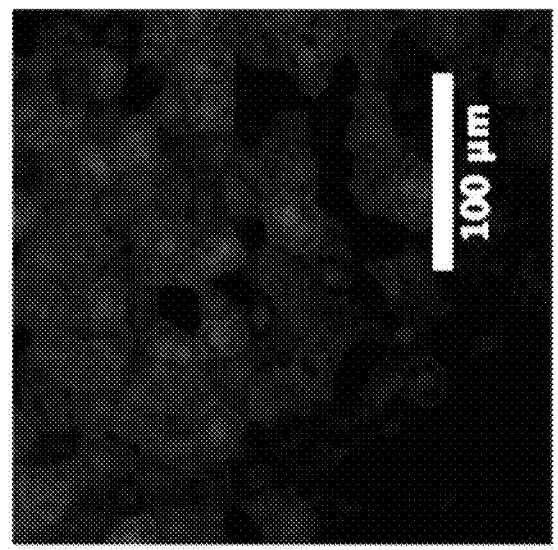
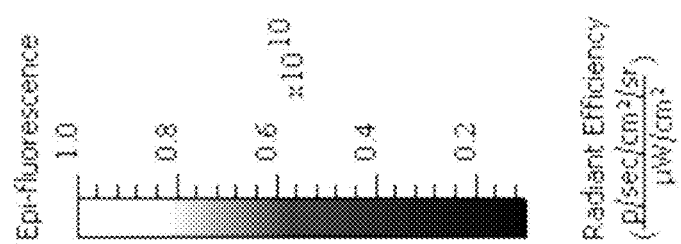
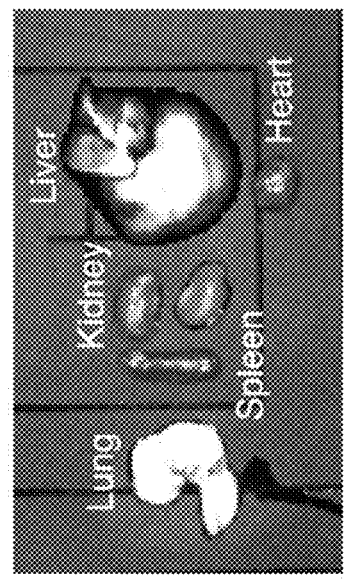
FIG. 58

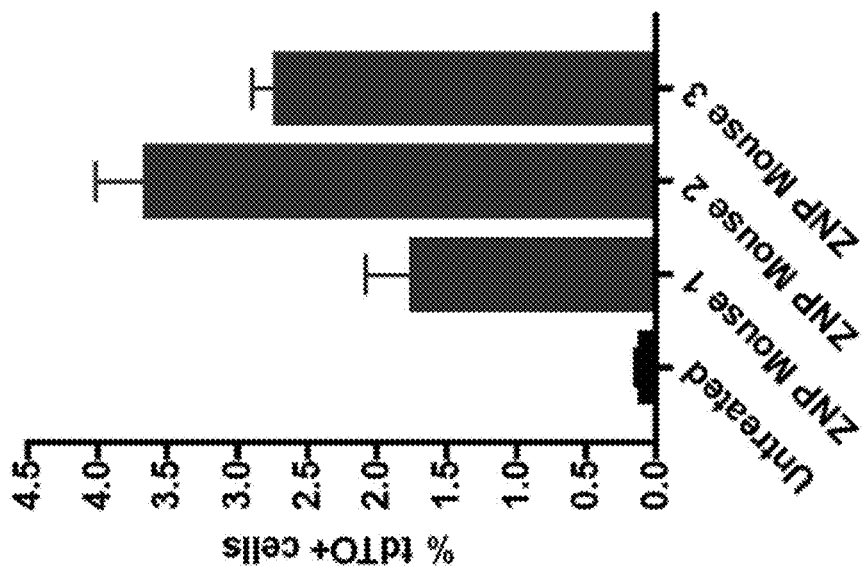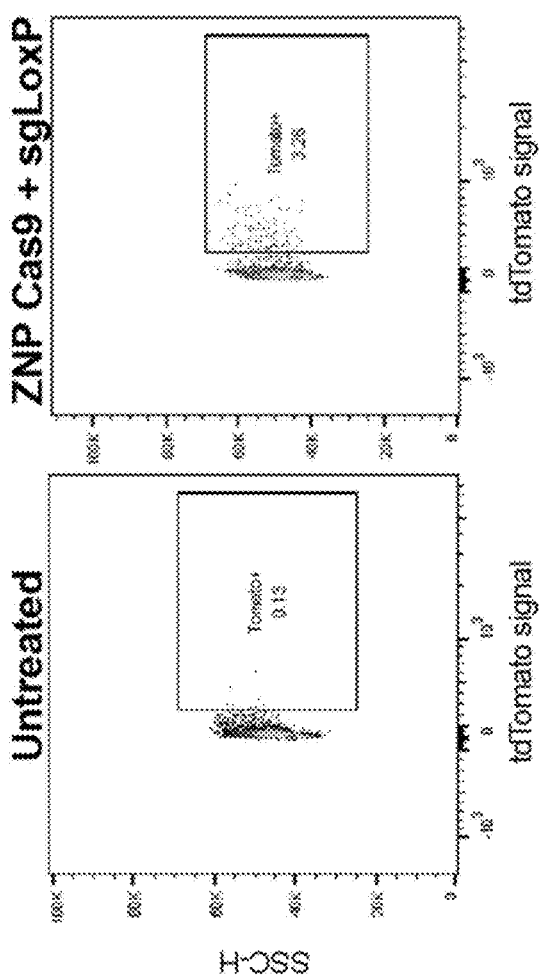
FIG. 61

SEQUENCE LISTING

<160> NUMBER OF SEQ ID NOS: 37

<210> SEQ ID NO 1
<211> LENGTH: 21
<212> TYPE: DNA
<213> ORGANISM: Artificial sequence
<220> FEATURE:
<223> OTHER INFORMATION: Synthetice oligo

<400> SEQUENCE: 1
gauuaugucc gguuauguat t                                             21

<210> SEQ ID NO 2
<211> LENGTH: 21
<212> TYPE: DNA
<213> ORGANISM: Artificial sequence
<220> FEATURE:
<223> OTHER INFORMATION: Synthetice oligo

<400> SEQUENCE: 2
uacauaaccg gacauaauct t                                             21

<210> SEQ ID NO 3
<211> LENGTH: 21
<212> TYPE: DNA
<213> ORGANISM: Artificial sequence
<220> FEATURE:
<223> OTHER INFORMATION: Synthetice oligo

<400> SEQUENCE: 3
gcgcgauagc gcgaauauat t                                             21

<210> SEQ ID NO 4
<211> LENGTH: 21
<212> TYPE: DNA
<213> ORGANISM: Artificial sequence
<220> FEATURE:
<223> OTHER INFORMATION: Synthetice oligo

<400> SEQUENCE: 4
uauauucgcg cuaucgcgct t                                             21

<210> SEQ ID NO 5

```
<211> LENGTH: 20
<212> TYPE: DNA
<213> ORGANISM: Artificial sequence
<220> FEATURE:
<223> OTHER INFORMATION: Synthetice oligo

<400> SEQUENCE: 5
cttcgaaatg tccgttcggt                                              20

<210> SEQ ID NO 6
<211> LENGTH: 20
<212> TYPE: DNA
<213> ORGANISM: Artificial sequence
<220> FEATURE:
<223> OTHER INFORMATION: Synthetice oligo

<400> SEQUENCE: 6
cccggcgcca ttctatccgc                                              20

<210> SEQ ID NO 7
<211> LENGTH: 20
<212> TYPE: DNA
<213> ORGANISM: Artificial sequence
<220> FEATURE:
<223> OTHER INFORMATION: Synthetice oligo

<400> SEQUENCE: 7
tccagcggat agaatggcgc                                              20

<210> SEQ ID NO 8
<211> LENGTH: 20
<212> TYPE: DNA
<213> ORGANISM: Artificial sequence
<220> FEATURE:
<223> OTHER INFORMATION: Synthetice oligo

<400> SEQUENCE: 8
ggattctaaa acggattacc                                              20

<210> SEQ ID NO 9
<211> LENGTH: 20
<212> TYPE: DNA
<213> ORGANISM: Artificial sequence
<220> FEATURE:
<223> OTHER INFORMATION: Synthetice oligo

<400> SEQUENCE: 9
ataaataacg cgcccaacac                                              20

<210> SEQ ID NO 10
<211> LENGTH: 20
<212> TYPE: DNA
<213> ORGANISM: Artificial sequence
<220> FEATURE:
<223> OTHER INFORMATION: Synthetice oligo

<400> SEQUENCE: 10
cgtatagcat acattatacg                                              20

<210> SEQ ID NO 11
<211> LENGTH: 20
<212> TYPE: DNA
<213> ORGANISM: Artificial sequence
<220> FEATURE:
<223> OTHER INFORMATION: Synthetice oligo

<400> SEQUENCE: 11
```

```
gcttcgataa tatccgctac                                              20

<210> SEQ ID NO 12
<211> LENGTH: 25
<212> TYPE: DNA
<213> ORGANISM: Artificial sequence
<220> FEATURE:
<223> OTHER INFORMATION: Synthetice oligo

<400> SEQUENCE: 12
caccgcttcg aaatgtccgt tcggt                                        25

<210> SEQ ID NO 13
<211> LENGTH: 25
<212> TYPE: DNA
<213> ORGANISM: Artificial sequence
<220> FEATURE:
<223> OTHER INFORMATION: Synthetice oligo

<400> SEQUENCE: 13
aaacaccgaa cggacatttc gaagc                                        25

<210> SEQ ID NO 14
<211> LENGTH: 25
<212> TYPE: DNA
<213> ORGANISM: Artificial sequence
<220> FEATURE:
<223> OTHER INFORMATION: Synthetice oligo

<400> SEQUENCE: 14
caccgcccgg cgccattcta tccgc                                        25

<210> SEQ ID NO 15
<211> LENGTH: 25
<212> TYPE: DNA
<213> ORGANISM: Artificial sequence
<220> FEATURE:
<223> OTHER INFORMATION: Synthetice oligo

<400> SEQUENCE: 15
aaacgcggat agaatggcgc cgggc                                        25

<210> SEQ ID NO 16
<211> LENGTH: 25
<212> TYPE: DNA
<213> ORGANISM: Artificial sequence
<220> FEATURE:
<223> OTHER INFORMATION: Synthetice oligo

<400> SEQUENCE: 16
caccgtccag cggatagaat ggcgc                                        25

<210> SEQ ID NO 17
<211> LENGTH: 25
<212> TYPE: DNA
<213> ORGANISM: Artificial sequence
<220> FEATURE:
<223> OTHER INFORMATION: Synthetice oligo

<400> SEQUENCE: 17
aaacgcgcca ttctatccgc tggac                                        25

<210> SEQ ID NO 18
<211> LENGTH: 25
<212> TYPE: DNA
```

<210> SEQ ID NO 18 (implied continuation)
<213> ORGANISM: Artificial sequence
<220> FEATURE:
<223> OTHER INFORMATION: Synthetice oligo

<400> SEQUENCE: 18
caccgggatt ctaaaacgga ttacc                                              25

<210> SEQ ID NO 19
<211> LENGTH: 25
<212> TYPE: DNA
<213> ORGANISM: Artificial sequence
<220> FEATURE:
<223> OTHER INFORMATION: Synthetice oligo

<400> SEQUENCE: 19
aaacggtaat ccgttttaga atccc                                              25

<210> SEQ ID NO 20
<211> LENGTH: 25
<212> TYPE: DNA
<213> ORGANISM: Artificial sequence
<220> FEATURE:
<223> OTHER INFORMATION: Synthetice oligo

<400> SEQUENCE: 20
caccgataaa taacgcgccc aacac                                              25

<210> SEQ ID NO 21
<211> LENGTH: 25
<212> TYPE: DNA
<213> ORGANISM: Artificial sequence
<220> FEATURE:
<223> OTHER INFORMATION: Synthetice oligo

<400> SEQUENCE: 21
aaacgtgttg ggcgcgttat ttatc                                              25

<210> SEQ ID NO 22
<211> LENGTH: 25
<212> TYPE: DNA
<213> ORGANISM: Artificial sequence
<220> FEATURE:
<223> OTHER INFORMATION: Synthetice oligo

<400> SEQUENCE: 22
caccgcgtat agcatacatt atacg                                              25

<210> SEQ ID NO 23
<211> LENGTH: 25
<212> TYPE: DNA
<213> ORGANISM: Artificial sequence
<220> FEATURE:
<223> OTHER INFORMATION: Synthetice oligo

<400> SEQUENCE: 23
aaaccgtata atgtatgcta tacgc                                              25

<210> SEQ ID NO 24
<211> LENGTH: 25
<212> TYPE: DNA
<213> ORGANISM: Artificial sequence
<220> FEATURE:
<223> OTHER INFORMATION: Synthetice oligo

<400> SEQUENCE: 24
caccggcttc gataatatcc gctac                                              25

<210> SEQ ID NO 25
<211> LENGTH: 25
<212> TYPE: DNA
<213> ORGANISM: Artificial sequence
<220> FEATURE:
<223> OTHER INFORMATION: Synthetice oligo

<400> SEQUENCE: 25
aaacgtagcg gatattatcg aagcc                                         25

<210> SEQ ID NO 26
<211> LENGTH: 40
<212> TYPE: DNA
<213> ORGANISM: Artificial sequence
<220> FEATURE:
<223> OTHER INFORMATION: Synthetic primer

<400> SEQUENCE: 26
taatacgact cactataggg ataaataacg cgcccaacac                          40

<210> SEQ ID NO 27
<211> LENGTH: 40
<212> TYPE: DNA
<213> ORGANISM: Artificial sequence
<220> FEATURE:
<223> OTHER INFORMATION: Synthetic primer

<400> SEQUENCE: 27
taatacgact cactataggg cgtatagcat acattatacg                          40

<210> SEQ ID NO 28
<211> LENGTH: 40
<212> TYPE: DNA
<213> ORGANISM: Artificial sequence
<220> FEATURE:
<223> OTHER INFORMATION: Synthetic primer

<400> SEQUENCE: 28
taatacgact cactataggg gcttcgataa tatccgctac                          40

<210> SEQ ID NO 29
<211> LENGTH: 20
<212> TYPE: DNA
<213> ORGANISM: Artificial sequence
<220> FEATURE:
<223> OTHER INFORMATION: Synthetic primer

<400> SEQUENCE: 29
aaaagcaccg actcggtgcc                                               20

<210> SEQ ID NO 30
<211> LENGTH: 20
<212> TYPE: DNA
<213> ORGANISM: Artificial sequence
<220> FEATURE:
<223> OTHER INFORMATION: Synthetic primer

<400> SEQUENCE: 30
ggaaccgctg gagagcaact                                               20

<210> SEQ ID NO 31
<211> LENGTH: 23
<212> TYPE: DNA
<213> ORGANISM: Artificial sequence
<220> FEATURE:

<223> OTHER INFORMATION: Synthetic primer

<400> SEQUENCE: 31
gtccctatcg aaggactctg gca                                         23

<210> SEQ ID NO 32
<211> LENGTH: 20
<212> TYPE: DNA
<213> ORGANISM: Artificial sequence
<220> FEATURE:
<223> OTHER INFORMATION: Synthetic primer

<400> SEQUENCE: 32
gctggagagc aactgcataa                                             20

<210> SEQ ID NO 33
<211> LENGTH: 24
<212> TYPE: DNA
<213> ORGANISM: Artificial sequence
<220> FEATURE:
<223> OTHER INFORMATION: Synthetic primer

<400> SEQUENCE: 33
catcgactga aatccctggt aatc                                        24

<210> SEQ ID NO 34
<211> LENGTH: 20
<212> TYPE: DNA
<213> ORGANISM: Artificial sequence
<220> FEATURE:
<223> OTHER INFORMATION: Synthetic primer

<400> SEQUENCE: 34
ggaaccgctg gagagcaact                                             20

<210> SEQ ID NO 35
<211> LENGTH: 23
<212> TYPE: DNA
<213> ORGANISM: Artificial sequence
<220> FEATURE:
<223> OTHER INFORMATION: Synthetic primer

<400> SEQUENCE: 35
gtccctatcg aaggactctg gca                                         23

<210> SEQ ID NO 36
<211> LENGTH: 21
<212> TYPE: DNA
<213> ORGANISM: Artificial sequence
<220> FEATURE:
<223> OTHER INFORMATION: Synthetic primer

<400> SEQUENCE: 36
agaaggattc ctatgtgggc g                                           21

<210> SEQ ID NO 37
<211> LENGTH: 21
<212> TYPE: DNA
<213> ORGANISM: Artificial sequence
<220> FEATURE:
<223> OTHER INFORMATION: Synthetic primer

<400> SEQUENCE: 37
catgtcgtcc cagttggtga c                                           21

CATIONIC SULFONAMIDE AMINO LIPIDS AND AMPHIPHILIC ZWITTERIONIC AMINO LIPIDS

This application claims the benefit of priority to U.S. Provisional Application No. 62/337,196, filed on May 16, 2016, the entirety of which is incorporated herein by reference.

BACKGROUND

1. Field

The present disclosure relates generally to the fields of lipids and nanoparticles. In particular, it relates to compositions which comprises a nucleic acid. More particularly, it relates to lipid compositions for the delivery of the nucleic acid.

2. Description of Related Art

Numerous genetic diseases can be corrected by nucleic acid therapeutics. However, these therapies require delivery systems to transport nucleic acid drugs into cells. There has been a continuous search for optimal delivery carriers. Formulated lipid nanoparticles (LNPs) containing a cationic/ionizable lipid, cholesterol, lipid PEG, and structural lipids such as DSPC are currently the most effective siRNA delivery system and are used in Phase 2 and 3 clinical trials. Yet, new lipids, dendrimers, and lipid-like materials are needed to address future therapeutic targets and overcome current limits with existing materials.

Materials that can deliver nucleic acids (siRNA, miRNA, mRNA, CRISPR, tRNA, sgRNA, tracRNA, etc.) are of therapeutic importance. Given the numerous barriers to successful delivery, there remains a great therapeutic need for new materials which can delivery nucleic acid therapeutics.

SUMMARY

In some aspects, the present disclosure provides a compound of the formula:

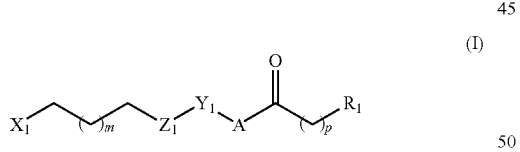

(I)

wherein:
$X_1$ is —S(O)$_2$O$^-$, —OP(O)OR$_e$O$^-$, —(CHR$_f$)$_z$C(O)O$^-$, or —NR$_g$R$_h$R$_i^+$, wherein:
  $R_e$, $R_g$, $R_h$, and $R_i$ are each independently hydrogen, alkyl$_{(C\le6)}$, or substituted alkyl$_{(C\le6)}$;
  $R_f$ is hydrogen, amino, hydroxy, or alkyl$_{(C\le12)}$, aryl$_{(C\le12)}$, aralkyl$_{(C\le12)}$, heteroaryl$_{(C\le12)}$, acyl$_{(C\le12)}$, alkoxy$_{(C\le12)}$, acyloxy$_{(C\le12)}$, amido$_{(C\le12)}$, alkoxy$_{(C\le12)}$, alkoxy$_{(C\le12)}$, or a substituted version of any of the last ten groups; and
  z is 1, 2, 3, or 4;
$Y_1$ is alkanediyl$_{(C\le12)}$, alkenediyl$_{(C\le12)}$, arenediyl$_{(C\le12)}$, heteroarenediyl$_{(C\le12)}$, heterocycloalkanediyl$_{(C\le12)}$, -alkanediyl$_{(C\le8)}$-heterocycloalkanediyl$_{(C\le12)}$, -alkanediyl$_{(C\le8)}$-heterocycloalkanediyl$_{(C\le12)}$-alkanediyl$_{(C\le8)}$, -alkane-diyl$_{(C\le8)}$-heteroarenediyl$_{(C\le12)}$, -alkanediyl$_{(C\le8)}$-heteroarenediyl$_{(C\le12)}$-alkanediyl$_{(C\le8)}$, or a substituted version of any of these groups;
$Z_1$ is —N$^+$R$_3$R$_4$— or —OP(O)O$^-$O$^-$
A is —NR$_a$—, —S—, or —O—; wherein:
  $R_a$ is hydrogen, alkyl$_{(C\le6)}$, or substituted alkyl$_{(C\le6)}$, or $R_a$ is taken together with either $R_3$ or $R_4$ and is alkanediyl$_{(C\le8)}$, alkenediyl$_{(C\le8)}$, alkoxydiyl$_{(C\le8)}$, alkylaminodiyl$_{(C\le8)}$, or a substituted version of any of these groups;
$R_1$ is a group of the formula:

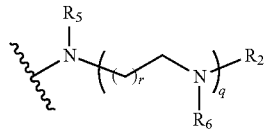

wherein:
$R_5$, $R_6$, and $R_2$ are each independently hydrogen or alkyl$_{(C\le8)}$, -alkanediyl$_{(C\le6)}$-NH$_2$, -alkanediyl$_{(C\le6)}$-alkylamino$_{(C\le8)}$, -alkanediyl$_{(C\le6)}$-dialkyl-amino$_{(C\le12)}$, -alkanediyl$_{(C\le6)}$NR'R", or a substituted version of any of these groups wherein:
  R' and R" are each independently hydrogen, alkyl$_{(C\le8)}$, substituted alkyl$_{(C\le8)}$, or —Z$_2$A'R$_7$; wherein:
    $Z_2$ is alkanediyl$_{(C\le6)}$, substituted alkanediyl$_{(C\le6)}$, or a group of the formula:

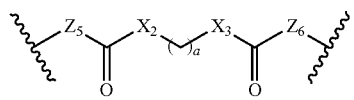

wherein:
  $Z_5$ and $Z_6$ are each independently alkanediyl$_{(C\le6)}$ or substituted alkanediyl$_{(C\le6)}$;
  $X_2$ and $X_3$ are each independently —O—, —S—, or —NR$_m$—; wherein: $R_m$ is hydrogen, alkyl$_{(C\le6)}$, or substituted alkyl$_{(C\le6)}$; and
  a is 0, 1, 2, 3, 4, 5, or 6;
  A' is —CHR$_j$—, —C(O)O—, or —C(O)NR$_b$—;
    $R_b$ is hydrogen, alkyl$_{(C\le6)}$, or substituted alkyl$_{(C\le6)}$; and
    $R_j$ is hydrogen, halo, hydroxy, acyloxy$_{(C\le24)}$, or substituted acyloxy$_{(C\le24)}$;
  $R_7$ is alkyl$_{(C6-24)}$, substituted alkyl$_{(C6-24)}$, alkenyl$_{(C6-24)}$, substituted alkenyl$_{(C6-24)}$; or
$R_5$, $R_6$, and $R_2$ are each independently —Z$_3$A"R$_8$; wherein:
  $Z_3$ is alkanediyl$_{(C\le6)}$, substituted alkanediyl$_{(C\le6)}$, or a group of the formula:

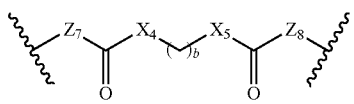

wherein:
  $Z_7$ and $Z_8$ are each independently alkanediyl$_{(C\le6)}$ or substituted alkanediyl$_{(C\le6)}$;
  $X_4$ and $X_5$ are each independently —O—, —S—, or —NR$_n$—; wherein:

$R_n$ is hydrogen, alkyl$_{(C \leq 6)}$, or substituted alkyl$_{(C \leq 6)}$; and b is 0, 1, 2, 3, 4, 5, or 6;

A" is —CHR$_k$—, —S—, —C(O)O—, or —C(O)NR$_l$—;

$R_l$ is hydrogen, alkyl$_{(C \leq 6)}$, or substituted alkyl$_{(C \leq 6)}$; and $R_k$ is hydrogen, halo, hydroxy, acyloxy$_{(C \leq 24)}$, or substituted acyloxy$_{(C \leq 24)}$; and $R_8$ is alkyl$_{(C6-24)}$, substituted alkyl$_{(C6-24)}$, alkenyl$_{(C6-24)}$, substituted alkenyl$_{(C6-24)}$;

q is 1, 2, or 3; and r is 1, 2, 3, or 4;

$R_1$ is a group of the formula:

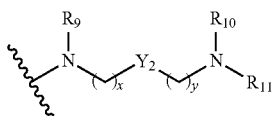

wherein:

$Y_2$ is arenediyl$_{(C \leq 12)}$, heterocycloalkanediyl$_{(C \leq 12)}$, heteroarenediyl$_{(C \leq 12)}$, alkoxydiyl$_{(C \leq 12)}$, or a substituted version of any of these groups;

$R_9$, $R_{10}$, and $R_{11}$ are each independently hydrogen, alkyl$_{(C \leq 8)}$, substituted alkyl$_{(C \leq 8)}$, or —Z$_4$A'''R$_{12}$; wherein:

$Z_4$ is alkanediyl$_{(C \leq 6)}$, substituted alkanediyl$_{(C \leq 6)}$, or a group of the formula:

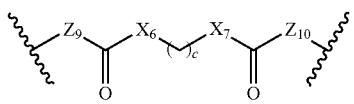

wherein:

$Z_9$ and $Z_{10}$ are each independently alkanediyl$_{(C \leq 6)}$ or substituted alkanediyl$_{(C \leq 6)}$;

$X_6$ and $X_7$ are each independently —O—, —S—, or —NR$_0$—; wherein:

$R_0$ is hydrogen, alkyl$_{(C \leq 6)}$, or substituted alkyl$_{(C \leq 6)}$; and c is 0, 1, 2, 3, 4, 5, or 6;

A''' is —CHR$_k$—, —S—, —C(O)O—, or —C(O)NR$_l$—;

$R_l$ is hydrogen, alkyl$_{(C \leq 6)}$, or substituted alkyl$_{(C \leq 6)}$; and $R_k$ is hydrogen, halo, hydroxy, acyloxy$_{(C \leq 24)}$, or substituted acyloxy$_{(C \leq 24)}$; and $R_{12}$ is alkyl$_{(C6-24)}$, substituted alkyl$_{(C6-24)}$, alkenyl$_{(C6-24)}$, substituted alkenyl$_{(C6-24)}$; and x and y are 0, 1, 2, 3, or 4;

$R_3$ and $R_4$ are each independently hydrogen, alkyl$_{(C \leq 6)}$, or substituted alkyl$_{(C \leq 6)}$, or $R_3$ or $R_4$ are taken together with $R_a$ and is alkanediyl$_{(C \leq 8)}$, alkenediyl$_{(C \leq 8)}$, alkoxydiyl$_{(C \leq 8)}$, alkylaminodiyl$_{(C \leq 8)}$, or a substituted version of any of these groups; and m, n, and p are each independently an integer selected from 0, 1, 2, 3, 4, 5, or 6;

provided that if $X_1$ is positively charged then $Z_1$ is negatively charged, and if $X_1$ is negatively charged, then $Z_1$ is positively charged;

or a pharmaceutically acceptable salt thereof.

In some embodiments, the compound is further defined as:

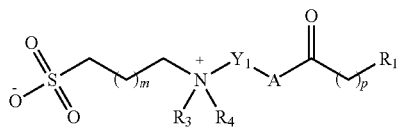

(I)

wherein:

$Y_1$ is alkanediyl$_{(C \leq 12)}$, alkenediyl$_{(C \leq 12)}$, arenediyl$_{(C \leq 12)}$, heteroarenediyl$_{(C \leq 12)}$, heterocycloalkanediyl$_{(C \leq 12)}$, -alkanediyl$_{(C \leq 8)}$heterocycloalkanediyl$_{(C \leq 12)}$, -alkanediyl$_{(C \leq 8)}$heterocycloalkanediyl$_{(C \leq 12)}$-alkanediyl$_{(C \leq 8)}$, -alkane-diyl$_{(C \leq 8)}$-heteroarenediyl$_{(C \leq 12)}$, -alkanediyl$_{(C \leq 8)}$-heteroarenediyl$_{(C \leq 12)}$-alkanediyl$_{(C \leq 8)}$, or a substituted version of any of these groups;

A is —NR$_a$—, —S—, or —O—; wherein:

$R_a$ is hydrogen, alkyl$_{(C \leq 6)}$, or substituted alkyl$_{(C \leq 6)}$, or $R_a$ is taken together with either $R_3$ or $R_4$ and is alkanediyl$_{(C \leq 8)}$, alkenediyl$_{(C \leq 8)}$, alkoxydiyl$_{(C \leq 8)}$, alkylaminodiyl$_{(C \leq 8)}$, or a substituted version of any of these groups;

$R_1$ is a group of the formula:

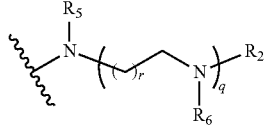

wherein:

$R_5$, $R_6$, and $R_2$ are each independently hydrogen or alkyl$_{(C \leq 8)}$, -alkanediyl$_{(C \leq 6)}$-NH$_2$, -alkanediyl$_{(C \leq 6)}$-alkylamino$_{(C \leq 8)}$, -alkanediyl$_{(C \leq 6)}$-dialkylamino$_{(C \leq 12)}$, -alkanediyl$_{(C \leq 6)}$NR'R", or a substituted version of any of these groups wherein:

R' and R" are each independently hydrogen, alkyl$_{(C \leq 8)}$, substituted alkyl$_{(C \leq 8)}$, —(CH$_2$)$_s$CH(OH)R$_7$, —(CH$_2$)$_s$C(O)OR$_7$, or —(CH$_2$)$_s$C(O)(NR$_b$)R$_7$; wherein:

s is 1, 2, 3, or 4;

$R_b$ is hydrogen, alkyl$_{(C \leq 6)}$, or substituted alkyl$_{(C \leq 6)}$; and $R_7$ is alkyl$_{(C6-24)}$, substituted alkyl$_{(C6-24)}$, alkenyl$_{(C6-24)}$, substituted alkenyl$_{(C6-24)}$; or $R_5$, $R_6$, and $R_2$ are each independently —(CH$_2$)$_t$CH(OH)R$_8$, —(CH$_2$)$_t$C(O)OR$_8$, —(CH$_2$)$_t$C(O)(NR$_c$)R$_8$; wherein:

t is 1, 2, 3, or 4;

$R_c$ is hydrogen, alkyl$_{(C \leq 6)}$, or substituted alkyl$_{(C \leq 6)}$; and $R_8$ is alkyl$_{(C6-24)}$, substituted alkyl$_{(C6-24)}$, alkenyl$_{(C6-24)}$, substituted alkenyl$_{(C6-24)}$; or q is 1, 2, or 3; and r is 1, 2, 3, or 4;

$R_1$ is a group of the formula:

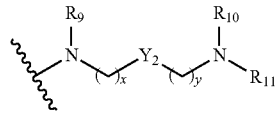

wherein:
- $Y_2$ is arenediyl$_{(C\leq12)}$, heterocycloalkanediyl$_{(C\leq12)}$, heteroarenediyl$_{(C\leq12)}$, or a substituted version of any of these groups;
- $R_9$, $R_{10}$, and $R_{11}$ are each independently selected from hydrogen, alkyl$_{(C\leq8)}$, substituted alkyl$_{(C\leq8)}$, —(CH$_2$)$_u$CH(OH)R$_{12}$, —(CH$_2$)$_u$C(O)OR$_{12}$, —(CH$_2$)$_u$C(O)(NR$_d$)R$_{12}$; wherein:
  - u is 1, 2, 3, or 4;
  - $R_d$ is hydrogen, alkyl$_{(C\leq6)}$, or substituted alkyl$_{(C\leq6)}$; and
  - $R_{12}$ is alkyl$_{(C6-24)}$, substituted alkyl$_{(C6-24)}$, alkenyl$_{(C6-24)}$, substituted alkenyl$_{(C6-24)}$; and
- x and y are 1, 2, 3, or 4;
- $R_3$ and $R_4$ are each independently hydrogen, alkyl$_{(C\leq6)}$, or substituted alkyl$_{(C\leq6)}$, or $R_3$ or $R_4$ are taken together with $R_a$ and is alkanediyl$_{(C\leq8)}$, alkenediyl$_{(C\leq8)}$, alkoxydiyl$_{(C\leq8)}$, alkylaminodiyl$_{(C\leq8)}$, or a substituted version of any of these groups; and
- m, n, and p are each independently an integer selected from 0, 1, 2, 3, 4, 5, or 6;

or a pharmaceutically acceptable salt thereof. In some embodiments the compounds are further defined as:

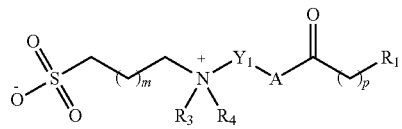

(I)

wherein:
- $Y_1$ is alkanediyl$_{(C\leq12)}$, heterocycloalkanediyl$_{(C\leq12)}$, -alkanediyl$_{(C\leq8)}$heterocycloalkanediyl$_{(C\leq12)}$, -alkanediyl$_{(C\leq8)}$-heterocycloalkanediyl$_{(C\leq12)}$-alkanediyl$_{(C\leq8)}$, or a substituted version of any of these groups;
- A is —NR$_a$— or —O—; wherein:
- $R_a$ is hydrogen, alkyl$_{(C\leq6)}$, or substituted alkyl$_{(C\leq6)}$, or $R_a$ is taken together with either $R_3$ or $R_4$ and is alkanediyl$_{(C\leq8)}$, alkenediyl$_{(C\leq8)}$, alkoxydiyl$_{(C\leq8)}$, alkylaminodiyl$_{(C\leq8)}$, or a substituted version of any of these groups;
- $R_1$ is a group of the formula:

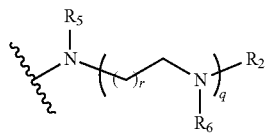

wherein:
- $R_5$, $R_6$, and $R_2$ are each independently hydrogen or alkyl$_{(C\leq8)}$, -alkanediyl$_{(C\leq6)}$-NH$_2$, -alkanediyl$_{(C\leq6)}$alkylamino$_{(C\leq8)}$, -alkanediyl$_{(C\leq6)}$-dialkylamino$_{(C\leq12)}$, -alkanediyl$_{(C\leq6)}$-NR'R", or a substituted version of any of these groups wherein:
- R' and R" are each independently hydrogen, alkyl$_{(C\leq8)}$, substituted alkyl$_{(C\leq8)}$, or —Z$_2$A'R$_7$; wherein:
  - $Z_2$ is alkanediyl$_{(C\leq4)}$ or substituted alkanediyl$_{(C\leq4)}$;
  - A' is —CHR$_j$—, —C(O)O—, or —C(O)NR$_b$—;
    - $R_b$ is hydrogen, alkyl$_{(C\leq6)}$, or substituted alkyl$_{(C\leq6)}$; and
    - $R_j$ is hydrogen, halo, hydroxy, acyloxy$_{(C\leq24)}$, or substituted acyloxy$_{(C\leq24)}$;
  - $R_7$ is alkyl$_{(C6-24)}$, substituted alkyl$_{(C6-24)}$, alkenyl$_{(C6-24)}$, substituted alkenyl$_{(C6-24)}$; or
- $R_5$, $R_6$, and $R_2$ are each independently —Z$_3$A"R$_8$; wherein:
  - $Z_3$ is alkanediyl$_{(C\leq4)}$ or substituted alkanediyl$_{(C\leq4)}$;
  - A" is —CHR$_k$—, —C(O)O—, or —C(O)NR$_l$—;
    - $R_l$ is hydrogen, alkyl$_{(C\leq6)}$, or substituted alkyl$_{(C\leq6)}$; and
    - $R_k$ is hydrogen, halo, hydroxy, acyloxy$_{(C\leq24)}$, or substituted acyloxy$_{(C\leq24)}$; and
  - $R_8$ is alkyl$_{(C6-24)}$, substituted alkyl$_{(C6-24)}$, alkenyl$_{(C6-24)}$, substituted alkenyl$_{(C6-24)}$;
- q is 1, 2, or 3; and
- r is 1, 2, 3, or 4;
- $R_1$ is a group of the formula:

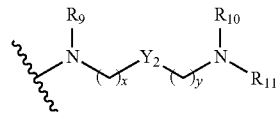

wherein:
- $Y_2$ is arenediyl$_{(C\leq12)}$, heterocycloalkanediyl$_{(C\leq12)}$, heteroarenediyl$_{(C\leq12)}$, alkoxydiyl$_{(C\leq12)}$, or a substituted version of any of these groups;
- $R_9$, $R_{10}$, and $R_{11}$ are each independently selected from hydrogen, alkyl$_{(C\leq8)}$, substituted alkyl$_{(C\leq8)}$, or —Z$_4$A'''R$_{12}$; wherein:
  - $Z_4$ is alkanediyl$_{(C\leq4)}$ or substituted alkanediyl$_{(C\leq4)}$;
  - A''' is —CHR$_k$—, —C(O)O—, or —C(O)NR$_l$—;
    - $R_l$ is hydrogen, alkyl$_{(C\leq6)}$, or substituted alkyl$_{(C\leq6)}$; and
    - $R_k$ is hydrogen, halo, hydroxy, acyloxy$_{(C\leq24)}$, or substituted acyloxy$_{(C\leq24)}$; and
  - $R_{12}$ is alkyl$_{(C6-24)}$, substituted alkyl$_{(C6-24)}$, alkenyl$_{(C6-24)}$, substituted alkenyl$_{(C6-24)}$; and
- x and y are 1, 2, 3, or 4;
- $R_3$ and $R_4$ are each independently hydrogen, alkyl$_{(C\leq6)}$, or substituted alkyl$_{(C\leq6)}$, or $R_3$ or $R_4$ are taken together with $R_a$ and is alkanediyl$_{(C\leq8)}$, alkenediyl$_{(C\leq8)}$, alkoxydiyl$_{(C\leq8)}$, alkylaminodiyl$_{(C\leq8)}$, or a substituted version of any of these groups; and
- m, n, and p are each independently an integer selected from 0, 1, 2, 3, 4, 5, or 6;

or a pharmaceutically acceptable salt thereof. In some embodiments, the compounds are further defined as:

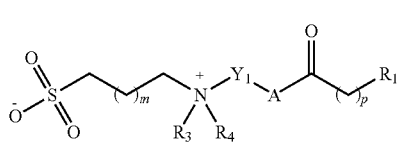

(I)

wherein:
- $Y_1$ is alkanediyl$_{(C\leq12)}$, heterocycloalkanediyl$_{(C\leq12)}$, -alkanediyl$_{(C\leq8)}$-heterocycloalkanediyl$_{(C\leq12)}$, -alkanediyl$_{(C\leq8)}$-heterocycloalkanediyl$_{(C\leq12)}$-alkanediyl$_{(C\leq8)}$, or a substituted version of any of these groups;
- A is —NR$_a$— or —O—; wherein:
- $R_a$ is hydrogen, alkyl$_{(C\leq6)}$, or substituted alkyl$_{(C\leq6)}$, or $R_a$ is taken together with either $R_3$ or $R_4$ and is alkanediyl$_{(C≤8)}$, alkenediyl$_{(C≤8)}$, alkoxydiyl$_{(C≤8)}$, alkylaminodiyl$_{(C≤8)}$, or a substituted version of any of these groups;

$R_1$ is a group of the formula:

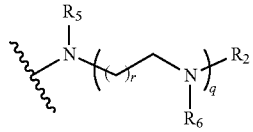

wherein:
  $R_5$, $R_6$, and $R_2$ are each independently hydrogen or alkyl$_{(C≤8)}$, -alkanediyl$_{(C≤6)}$-NH$_2$, -alkanediyl$_{(C≤6)}$-alkylamino$_{(C≤8)}$, -alkanediyl$_{(C≤6)}$-dialkylamino$_{(C≤12)}$, -alkanediyl$_{(C≤6)}$-NR'R'', or a substituted version of any of these groups wherein:
    R' and R'' are each independently hydrogen, alkyl$_{(C≤8)}$, substituted alkyl$_{(C≤8)}$, —(CH$_2$)$_s$CH(OH)R$_7$, —(CH$_2$)$_s$C(O)OR$_7$, or —(CH$_2$)$_s$C(O)(NR$_b$)R$_7$; wherein:
      s is 1, 2, 3, or 4;
      $R_b$ is hydrogen, alkyl$_{(C≤6)}$, or substituted alkyl$_{(C≤6)}$; and
      $R_7$ is alkyl$_{(C6-24)}$, substituted alkyl$_{(C6-24)}$, alkenyl$_{(C6-24)}$, substituted alkenyl$_{(C6-24)}$, or
  $R_5$, $R_6$, and $R_2$ are each independently —(CH$_2$)$_t$CH(OH)R$_8$, —(CH$_2$)$_t$C(O)OR$_8$, —(CH$_2$)$_t$C(O)(NR$_c$)R$_8$; wherein:
    t is 1, 2, 3, or 4;
    $R_c$ is hydrogen, alkyl$_{(C≤6)}$, or substituted alkyl$_{(C≤6)}$; and
    $R_8$ is alkyl$_{(C6-24)}$, substituted alkyl$_{(6-24)}$, alkenyl$_{(C6-24)}$, substituted alkenyl$_{(C6-24)}$; or
  q is 1, 2, or 3; and
  r is 1, 2, 3, or 4;

$R_1$ is a group of the formula:

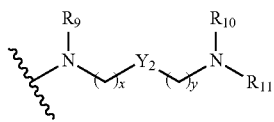

wherein:
  $Y_2$ is arenediyl$_{(C≤12)}$, heterocycloalkanediyl$_{(C≤12)}$, heteroarenediyl$_{(C≤12)}$, or a substituted version of any of these groups;
  $R_9$, $R_{10}$, and $R_{11}$ are each independently selected from hydrogen, alkyl$_{(C≤8)}$, substituted alkyl$_{(C≤8)}$, —(CH$_2$)$_u$CH(OH)R$_{12}$, —(CH$_2$)$_u$C(O)OR$_{12}$, —(CH$_2$)$_u$C(O)(NR$_d$)R$_{12}$; wherein:
    u is 1, 2, 3, or 4;
    $R_d$ is hydrogen, alkyl$_{(C≤6)}$, or substituted alkyl$_{(C≤6)}$; and
    $R_{12}$ is alkyl$_{(C6-24)}$, substituted alkyl$_{(C6-24)}$, alkenyl$_{(C6-24)}$, substituted alkenyl$_{(C6-24)}$; and
  x and y are 1, 2, 3, or 4;
$R_3$ and $R_4$ are each independently hydrogen, alkyl$_{(C≤6)}$, or substituted alkyl$_{(C≤6)}$, or $R_3$ or $R_4$ are taken together with $R_a$ and is alkanediyl$_{(C≤8)}$, alkenediyl$_{(C≤8)}$, alkoxydiyl$_{(C≤8)}$, alkylaminodiyl$_{(C≤8)}$, or a substituted version of any of these groups; and
m, n, and p are each independently an integer selected from 0, 1, 2, 3, 4, 5, or 6;

or a pharmaceutically acceptable salt thereof. In some embodiments the compounds are further defined as:

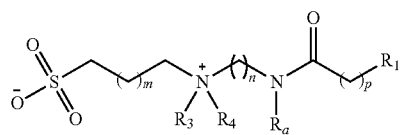

(IIa)

wherein:
  $R_1$ is a group of the formula:

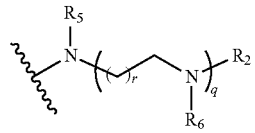

wherein:
  $R_5$, $R_6$, and $R_2$ are each independently hydrogen or alkyl$_{(C≤8)}$, -alkanediyl$_{(C≤6)}$-NH$_2$, -alkanediyl$_{(C≤6)}$-alkylamino$_{(C≤8)}$, -alkanediyl$_{(C≤6)}$-dialkylamino$_{(C≤12)}$, -alkanediyl$_{(C≤6)}$-NR'R'', or a substituted version of any of these groups wherein:
    R' and R'' are each independently hydrogen, alkyl$_{(C≤8)}$, substituted alkyl$_{(C≤8)}$, or —Z$_2$A'R$_7$; wherein:
      $Z_2$ is alkanediyl$_{(C≤4)}$ or substituted alkanediyl$_{(C≤4)}$;
      A' is —CHR$_j$—, —C(O)O—, or —C(O)NR$_b$—;
      $R_b$ is hydrogen, alkyl$_{(C≤6)}$, or substituted alkyl$_{(C≤6)}$; and
      $R_j$ is hydrogen, halo, hydroxy, acyloxy$_{(C≤24)}$, or substituted acyloxy$_{(C≤24)}$;
      $R_7$ is alkyl$_{(C6-24)}$, substituted alkyl$_{(C6-24)}$, alkenyl$_{(C6-24)}$, substituted alkenyl$_{(C6-24)}$; or
  $R_5$, $R_6$, and $R_2$ are each independently —Z$_3$A''R$_8$; wherein:
    $Z_3$ is alkanediyl$_{(C≤4)}$ or substituted alkanediyl$_{(C≤4)}$;
    A'' is —CHR$_k$—, —C(O)O—, or —C(O)NR$_l$—;
    $R_l$ is hydrogen, alkyl$_{(C≤6)}$, or substituted alkyl$_{(C≤6)}$; and
    $R_k$ is hydrogen, halo, hydroxy, acyloxy$_{(C≤24)}$, or substituted acyloxy$_{(C≤24)}$; and
    $R_8$ is alkyl$_{(C6-24)}$, substituted alkyl$_{(C6-24)}$, alkenyl$_{(C6-24)}$, substituted alkenyl$_{(C6-24)}$;
  q is 1, 2, or 3; and
  r is 1, 2, 3, or 4;
$R_a$, $R_3$, and $R_4$ are each independently hydrogen, alkyl$_{(C≤6)}$, or substituted alkyl$_{(C≤6)}$; and
m, n, and p are each independently an integer selected from 0, 1, 2, 3, 4, 5, or 6;

or a pharmaceutically acceptable salt thereof. In some embodiments, the compounds are further defined as:

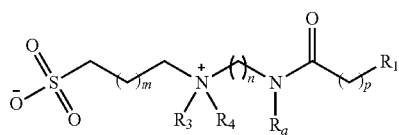

(II)

wherein:

$R_1$ is a group of the formula:

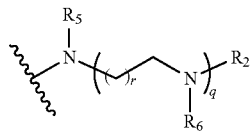

wherein:
$R_5$, $R_6$, and $R_2$ are each independently hydrogen or alkyl$_{(C \leq 8)}$, -alkanediyl$_{(C \leq 6)}$-NH$_2$, -alkanediyl$_{(C \leq 6)}$-alkylamino$_{(C \leq 8)}$, -alkanediyl$_{(C \leq 6)}$-dialkylamino$_{(C \leq 12)}$, -alkanediyl$_{(C \leq 6)}$-NR'R", or a substituted version of any of these groups wherein:
R' and R" are each independently hydrogen, alkyl$_{(C \leq 8)}$, substituted alkyl$_{(C \leq 8)}$, —(CH$_2$)$_s$CH(OH)R$_7$, —(CH$_2$)$_s$C(O)OR$_7$, or —(CH$_2$)$_s$C(O)(NR$_b$)R$_7$; wherein:
s is 1, 2, 3, or 4;
$R_b$ is hydrogen, alkyl$_{(C \leq 6)}$, or substituted alkyl$_{(C \leq 6)}$; and
$R_7$ is alkyl$_{(C6-24)}$, substituted alkyl$_{(C6-24)}$, alkenyl$_{(C6-24)}$, substituted alkenyl$_{(C6-24)}$, or
$R_5$, $R_6$, and $R_2$ are each independently —(CH$_2$)$_t$CH(OH)R$_8$, —(CH$_2$)$_t$C(O)OR$_8$, —(CH$_2$)$_t$C(O)(NR$_c$)R$_8$; wherein:
t is 1, 2, 3, or 4;
$R_c$ is hydrogen, alkyl$_{(C \leq 6)}$, or substituted alkyl$_{(C \leq 6)}$; and
$R_8$ is alkyl$_{(C6-24)}$, substituted alkyl$_{(C6-24)}$, alkenyl$_{(C6-24)}$, substituted alkenyl$_{(C6-24)}$; or
q is 1, 2, or 3; and
r is 1, 2, 3, or 4;
$R_a$, $R_3$, and $R_4$ are each independently hydrogen, alkyl$_{(C \leq 6)}$, or substituted alkyl$_{(C \leq 6)}$; and
m, n, and p are each independently an integer selected from 0, 1, 2, 3, 4, 5, or 6;

or a pharmaceutically acceptable salt thereof. In other embodiments, the compounds are further defined as:

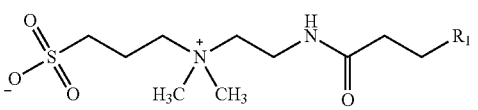

(III)

wherein:
$R_1$ is a group of the formula:

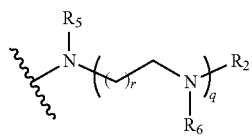

wherein:
$R_5$, $R_6$, and $R_2$ are each independently hydrogen or alkyl$_{(C \leq 8)}$, -alkanediyl$_{(C \leq 6)}$-NH$_2$, -alkanediyl$_{(C \leq 6)}$-alkylamino$_{(C \leq 8)}$, -alkanediyl$_{(C \leq 6)}$-dialkylamino$_{(C \leq 12)}$, -alkanediyl$_{(C \leq 6)}$-NR'R", or a substituted version of any of these groups wherein:
R' and R" are each independently hydrogen, alkyl$_{(C \leq 8)}$, substituted alkyl$_{(C \leq 8)}$, —(CH$_2$)$_s$CH(OH)R$_7$, —(CH$_2$)$_s$C(O)OR$_7$, or —(CH$_2$)$_s$C(O)(NR$_b$)R$_7$; wherein:
s is 1, 2, 3, or 4;
$R_b$ is hydrogen, alkyl$_{(C \leq 6)}$, or substituted alkyl$_{(C \leq 6)}$; and
$R_7$ is alkyl$_{(C6-24)}$, substituted alkyl$_{(C6-24)}$, alkenyl$_{(C6-24)}$, substituted alkenyl$_{(C6-24)}$, or
$R_5$, $R_6$, and $R_2$ are each independently —(CH$_2$)$_t$CH(OH)R$_8$, —(CH$_2$)$_t$C(O)OR$_8$, —(CH$_2$)$_t$C(O)(NR$_c$)R$_8$; wherein:
t is 1, 2, 3, or 4;
$R_c$ is hydrogen, alkyl$_{(C \leq 6)}$, or substituted alkyl$_{(C \leq 6)}$; and
$R_8$ is alkyl$_{(C6-24)}$, substituted alkyl$_{(C6-24)}$, alkenyl$_{(C6-24)}$, substituted alkenyl$_{(C6-24)}$; or
q is 1, 2, or 3; and
r is 1, 2, 3, or 4; and
m, n, and p are each independently an integer selected from 0, 1, 2, 3, 4, 5, or 6;

or a pharmaceutically acceptable salt thereof. In some embodiments, the compounds are further defined as:

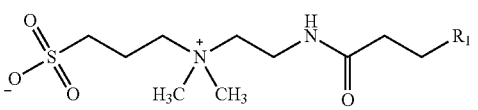

(IV)

wherein:
$R_1$ is a group of the formula:

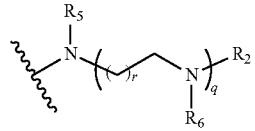

wherein:
$R_5$, $R_6$, and $R_2$ are each independently hydrogen or alkyl$_{(C \leq 8)}$, -alkanediyl$_{(C \leq 6)}$-NH$_2$, -alkanediyl$_{(C \leq 6)}$-alkylamino$_{(C \leq 8)}$, -alkanediyl$_{(C \leq 6)}$-dialkylamino$_{(C \leq 12)}$, -alkanediyl$_{(C \leq 6)}$-NR'R", or a substituted version of any of these groups wherein:
R' and R" are each independently are each independently hydrogen, alkyl$_{(C \leq 8)}$, substituted alkyl$_{(C \leq 8)}$, —(CH$_2$)$_s$CH(OH)R$_7$, —(CH$_2$)$_s$C(O)OR$_7$, or —(CH$_2$)$_s$C(O)(NR$_b$)R$_7$; wherein:
s is 1, 2, 3, or 4;
$R_b$ is hydrogen, alkyl$_{(C \leq 6)}$, or substituted alkyl$_{(C \leq 6)}$; and
$R_7$ is alkyl$_{(C6-24)}$, substituted alkyl$_{(C6-24)}$, alkenyl$_{(C6-24)}$, substituted alkenyl$_{(C6-24)}$; or
$R_5$, $R_6$, and $R_2$ are each independently —(CH$_2$)$_t$CH(OH)R$_8$, —(CH$_2$)$_t$C(O)OR$_8$, —(CH$_2$)$_t$C(O)(NR$_c$)R$_8$; wherein:
t is 1, 2, 3, or 4;
$R_c$ is hydrogen, alkyl$_{(C \leq 6)}$, or substituted alkyl$_{(C \leq 6)}$; and
$R_8$ is alkyl$_{(C6-24)}$, substituted alkyl$_{(C6-24)}$, alkenyl$_{(C6-24)}$, substituted alkenyl$_{(C6-24)}$; or
q is 1, 2, or 3; and
r is 1, 2, 3, or 4;

or a pharmaceutically acceptable salt thereof. In some embodiments, the compounds are further defined as:

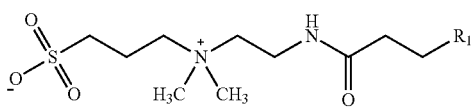

wherein:
R₁ is a group of the formula:

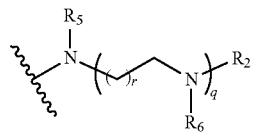

wherein:
R₅ is —(CH₂)ₜCH(OH)R₈, —(CH₂)ₜC(O)OR₈, —(CH₂)ₜC(O)(NH)R₈; wherein:
t is 1 or 2; and
R₈ is alkyl$_{(C6-24)}$, substituted alkyl$_{(C6-24)}$, alkenyl$_{(C6-24)}$, substituted alkenyl$_{(C6-24)}$;
R₆ is alkyl$_{(C≤8)}$ or substituted alkyl$_{(C≤8)}$; and
R₂ is -alkanediyl$_{(C≤6)}$-NR'R" or a substituted version of this group wherein:
R' and R" are each independently —(CH₂)ₛCH(OH)R₇, —(CH₂)ₛC(O)OR₇, or —(CH₂)ₛC(O)(NH)R₇; wherein:
s is 1 or 2; and
R₇ is alkyl$_{(C6-24)}$, substituted alkyl$_{(C6-24)}$, alkenyl$_{(C6-24)}$, substituted alkenyl$_{(C6-24)}$; or
q is 1 or 2; and
r is 1 or 2;
or a pharmaceutically acceptable salt thereof. In some embodiments, the compounds are further defined as:

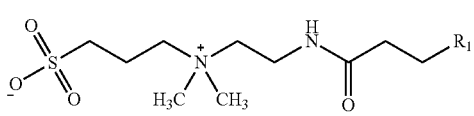

wherein:
R₁ is a group of the formula:

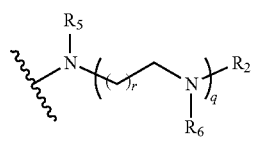

wherein:
R₅ is alkyl$_{(C≤8)}$ or substituted alkyl$_{(C≤8)}$;
R₆ is -alkanediyl$_{(C≤6)}$-NR'R" or a substituted version of this group wherein:
R' and R" are each independently alkyl$_{(C≤8)}$, substituted alkyl$_{(C≤8)}$, —(CH₂)ₛCH(OH)R₇, —(CH₂)ₛC(O)OR₇, or —(CH₂)ₛC(O)(NH)R₇; wherein:
s is 1 or 2; and
R₇ is alkyl$_{(C6-24)}$, substituted alkyl$_{(C6-24)}$, alkenyl$_{(C6-24)}$, substituted alkenyl$_{(C6-24)}$; and
R₂ is -alkanediyl$_{(C≤6)}$-NR'R" or a substituted version of this group wherein:
R' and R" are each independently alkyl$_{(C≤8)}$, substituted alkyl$_{(C≤8)}$, —(CH₂)ₛCH(OH)R₇, —(CH₂)ₛC(O)OR₇, or —(CH₂)ₛC(O)(NH)R₇; wherein:
s is 1 or 2; and
R₇ is alkyl$_{(C6-24)}$, substituted alkyl$_{(C6-24)}$, alkenyl$_{(C6-24)}$, substituted alkenyl$_{(C6-24)}$;
q is 1 or 2; and
r is 1 or 2;
or a pharmaceutically acceptable salt thereof. In some embodiments, the compounds are further defined as:

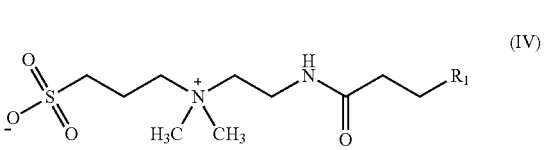

wherein:
R₁ is a group of the formula:

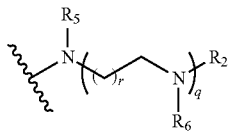

wherein:
R₅ is —(CH₂)ₜCH(OH)R₈, —(CH₂)ₜC(O)OR₈, —(CH₂)ₜC(O)(NH)R₈; wherein:
t is 1 or 2; and
R₈ is alkyl$_{(C6-24)}$, substituted alkyl$_{(C6-24)}$, -alkenyl$_{(C6-24)}$, substituted alkenyl$_{(C6-24)}$;
R₆ is -alkanediyl$_{(C≤6)}$-NR'R" or a substituted version of this group; wherein:
R' and R" are each independently —(CH₂)ₛCH(OH)R₇, —(CH₂)ₛC(O)OR₇, or —(CH₂)ₛC(O)(NH)R₇; wherein:
s is 1 or 2; and
R₇ is alkyl$_{(C6-24)}$, substituted alkyl$_{(C6-24)}$, alkenyl$_{(C6-24)}$, substituted alkenyl$_{(C6-24)}$; and
R₂ is -alkanediyl$_{(C≤6)}$-NR'R" or a substituted version of this group; wherein:
R' and R" are each independently —(CH₂)ₛCH(OH)R₇, —(CH₂)ₛC(O)OR₇, or —(CH₂)ₛC(O)(NH)R₇; wherein:
s is 1 or 2; and
R₇ is alkyl$_{(C6-24)}$, substituted alkyl$_{(C6-24)}$, alkenyl$_{(C6-24)}$, substituted alkenyl$_{(C6-24)}$;
q is 1 or 2; and
r is 1 or 2;
or a pharmaceutically acceptable salt thereof. In some embodiments the compounds are further defined as:

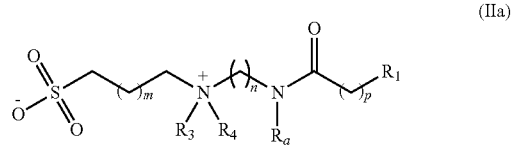

wherein:
R$_1$ is a group of the formula:

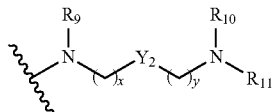

wherein:
- Y$_2$ is arenediyl$_{(C≤12)}$, heterocycloalkanediyl$_{(C≤12)}$, heteroarenediyl$_{(C≤12)}$, alkoxydiyl$_{(C≤12)}$, or a substituted version of any of these groups;
- R$_9$, R$_{10}$, and R$_{11}$ are each independently selected from hydrogen, alkyl$_{(C≤8)}$, substituted alkyl$_{(C≤8)}$, or —Z$_4$A'''R$_{12}$; wherein:
  - Z$_4$ is alkanediyl$_{(C≤4)}$ or substituted alkanediyl$_{(C≤4)}$;
  - A''' is —CHR$_k$—, —C(O)O—, or —C(O)NR$_j$—;
    - R$_j$ is hydrogen, alkyl$_{(C≤6)}$, or substituted alkyl$_{(C≤6)}$; and
    - R$_k$ is hydrogen, halo, hydroxy, acyloxy$_{(C≤24)}$, or substituted acyloxy$_{(C≤24)}$; and
  - R$_{12}$ is alkyl$_{(C6-24)}$, substituted alkyl$_{(C6-24)}$, alkenyl$_{(C6-24)}$, substituted alkenyl$_{(C≤24)}$; and
- x and y are 1, 2, 3, or 4;
- R$_a$, R$_3$, and R$_4$ are each independently hydrogen, alkyl$_{(C≤6)}$, or substituted alkyl$_{(C≤6)}$; and
- m, n, and p are each independently an integer selected from 0, 1, 2, 3, 4, 5, or 6;

or a pharmaceutically acceptable salt thereof.
In other embodiments, the compounds are further defined as:

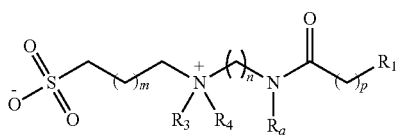

(II)

wherein:
R$_1$ is a group of the formula:

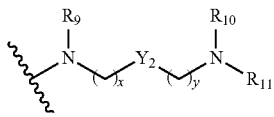

wherein:
- Y$_2$ is arenediyl$_{(C≤12)}$, heterocycloalkanediyl$_{(C≤12)}$, heteroarenediyl$_{(C≤12)}$, or a substituted version of any of these groups;
- R$_9$, R$_{10}$, and R$_{11}$ are each independently selected from hydrogen, alkyl$_{(C≤8)}$, substituted alkyl$_{(C≤8)}$, —(CH$_2$)$_u$CH(OH)R$_{12}$, —(CH$_2$)$_u$C(O)OR$_{12}$, —(CH$_2$)$_u$C(O)(NR$_d$)R$_{12}$; wherein:
  - u is 1, 2, 3, or 4;
  - R$_d$ is hydrogen, alkyl$_{(C≤6)}$, or substituted alkyl$_{(C≤6)}$; and
  - R$_{12}$ is alkyl$_{(C6-24)}$, substituted alkyl$_{(C6-24)}$, alkenyl$_{(C6-24)}$, substituted alkenyl$_{(C6-24)}$; and
- x and y are 1, 2, 3, or 4;
- R$_a$, R$_3$, and R$_4$ are each independently hydrogen, alkyl$_{(C≤6)}$, or substituted alkyl$_{(C≤6)}$; and
- m, n, and p are each independently an integer selected from 0, 1, 2, 3, 4, 5, or 6;

or a pharmaceutically acceptable salt thereof. In some embodiments, the compounds are further defined as:

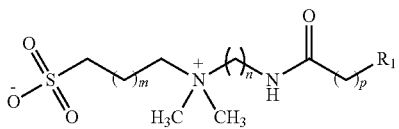

(III)

wherein:
R$_1$ is a group of the formula:

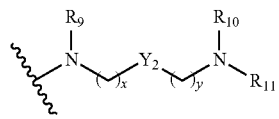

wherein:
- Y$_2$ is arenediyl$_{(C≤12)}$, heterocycloalkanediyl$_{(C≤12)}$, heteroarenediyl$_{(C≤12)}$, or a substituted version of any of these groups;
- R$_9$, R$_{10}$, and R$_{11}$ are each independently selected from hydrogen, alkyl$_{(C≤8)}$, substituted alkyl$_{(C≤8)}$, —(CH$_2$)$_u$CH(OH)R$_{12}$, —(CH$_2$)$_u$C(O)OR$_{12}$, —(CH$_2$)$_u$C(O)(NR$_d$)R$_{12}$; wherein:
  - u is 1, 2, 3, or 4;
  - R$_d$ is hydrogen, alkyl$_{(C≤6)}$, or substituted alkyl$_{(C≤6)}$; and
  - R$_{12}$ is alkyl$_{(C6-24)}$, substituted alkyl$_{(C6-24)}$, alkenyl$_{(C6-24)}$, substituted alkenyl$_{(C6-24)}$; and
- x and y are 1, 2, 3, or 4; and
- m, n, and p are each independently an integer selected from 0, 1, 2, 3, 4, 5, or 6;

or a pharmaceutically acceptable salt thereof. In some embodiments, the compounds are further defined as:

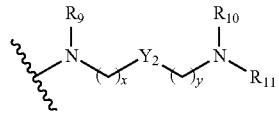

(IV)

wherein:
R$_1$ is a group of the formula:

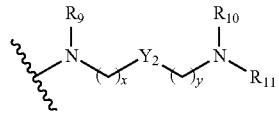

wherein:
- Y$_2$ is arenediyl$_{(C≤12)}$, heterocycloalkanediyl$_{(C≤12)}$, heteroarenediyl$_{(C≤12)}$, or a substituted version of any of these groups;
- R$_9$, R$_{10}$, and R$_{11}$ are each independently selected from hydrogen, alkyl$_{(C≤8)}$, substituted alkyl$_{(C≤8)}$, —(CH$_2$)$_u$CH(OH)R$_{12}$, —(CH$_2$)$_u$C(O)OR$_{12}$, —(CH$_2$)$_u$C(O)(NR$_d$)R$_{12}$; wherein:

u is 1, 2, 3, or 4;

$R_d$ is hydrogen, alkyl$_{(C \leq 6)}$, or substituted alkyl$_{(C \leq 6)}$; and $R_{12}$ is alkyl$_{(C6\text{-}24)}$, substituted alkyl$_{(C6\text{-}24)}$, alkenyl$_{(C6\text{-}24)}$, substituted alkenyl$_{(C6\text{-}24)}$; and x and y are 1, 2, 3, or 4;

or a pharmaceutically acceptable salt thereof. In some embodiments, the compounds are further defined as:

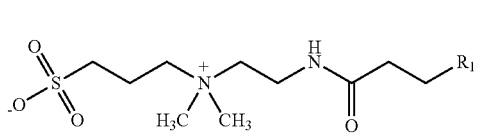
(IV)

wherein:

$R_1$ is a group of the formula:

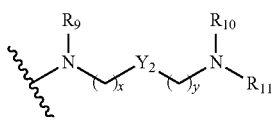

wherein:

$Y_2$ is heterocycloalkanediyl$_{(C \leq 12)}$ or substituted heterocycloalkanediyl$_{(C \leq 12)}$;

$R_9$, $R_{10}$, and $R_{11}$ are each independently selected from hydrogen, alkyl$_{(C \leq 8)}$, substituted alkyl$_{(C \leq 8)}$, —(CH$_2$)$_u$CH(OH)R$_{12}$, —(CH$_2$)$_u$C(O)OR$_{12}$, —(CH$_2$)$_u$C(O)(NR$_d$)R$_{12}$; wherein:

u is 1, 2, 3, or 4;

$R_d$ is hydrogen, alkyl$_{(C \leq 6)}$, or substituted alkyl$_{(C \leq 6)}$; and $R_{12}$ is alkyl$_{(C6\text{-}24)}$, substituted alkyl$_{(C6\text{-}24)}$, alkenyl$_{(C6\text{-}24)}$, substituted alkenyl$_{(C6\text{-}24)}$; and x and y are 1, 2, 3, or 4;

or a pharmaceutically acceptable salt thereof. In some embodiments, the compounds are further defined as:

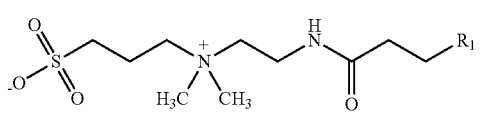
(IV)

wherein:

$R_1$ is a group of the formula:

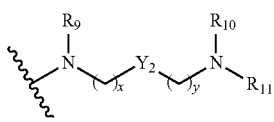

wherein:

$Y_2$ is heterocycloalkanediyl$_{(C \leq 12)}$ or substituted heterocycloalkanediyl$_{(C \leq 12)}$;

$R_9$, $R_{10}$, and $R_{11}$ are each independently selected from hydrogen, —(CH$_2$)$_u$CH(OH)R$_{12}$, —(CH$_2$)$_u$C(O)OR$_{12}$, —(CH$_2$)$_u$C(O)(NH)R$_{12}$; wherein:

u is 1 or 2; and $R_{12}$ is alkyl$_{(C6\text{-}24)}$, substituted alkyl$_{(C6\text{-}24)}$, alkenyl$_{(C6\text{-}24)}$, substituted alkenyl$_{(C6\text{-}24)}$; and x and y are 1, 2, 3, or 4;

or a pharmaceutically acceptable salt thereof. In some embodiments the compounds are further defined as:

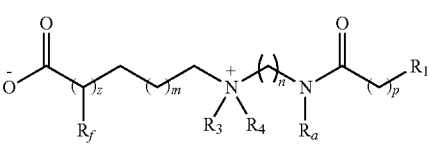
(IIb)

wherein:

$R_f$ is hydrogen, amino, hydroxy, or alkyl$_{(C \leq 12)}$, aryl$_{(C \leq 12)}$, aralkyl$_{(C \leq 12)}$, heteroaryl$_{(C \leq 12)}$, acyl$_{(C \leq 12)}$, alkoxy$_{(C \leq 12)}$, acyloxy$_{(C \leq 12)}$, amido$_{(C \leq 12)}$, alkoxy$_{(C \leq 12)}$, alkoxy$_{(C \leq 12)}$, or a substituted version of any of the last ten groups;

z is 1, 2, 3, or 4;

$R_1$ is a group of the formula:

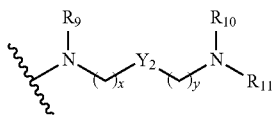

wherein:

$Y_2$ is arenediyl$_{(C \leq 12)}$, heterocycloalkanediyl$_{(C \leq 12)}$, heteroarenediyl$_{(C \leq 12)}$, alkoxydiyl$_{(C \leq 12)}$, or a substituted version of any of these groups;

$R_9$, $R_{10}$, and $R_{11}$ are each independently selected from hydrogen, alkyl$_{(C \leq 8)}$, substituted alkyl$_{(C \leq 8)}$, or —Z$_4$A'|R$_{12}$; wherein:

$Z_4$ is alkanediyl$_{(C \leq 4)}$ or substituted alkanediyl$_{(C \leq 4)}$;

A''' is —CHR$_k$—, —C(O)O—, or —C(O)NR$_l$—;

$R_l$ is hydrogen, alkyl$_{(C \leq 6)}$, or substituted alkyl$_{(C \leq 6)}$; and $R_k$ is hydrogen, halo, hydroxy, acyloxy$_{(C \leq 24)}$, or substituted acyloxy$_{(C \leq 24)}$; and $R_{12}$ is alkyl$_{(C6\text{-}24)}$, substituted alkyl$_{(C6\text{-}24)}$, alkenyl$_{(C6\text{-}24)}$, substituted alkenyl$_{(C6\text{-}24)}$; and x and y are 1, 2, 3, or 4;

$R_a$, $R_3$, and $R_4$ are each independently hydrogen, alkyl$_{(C \leq 6)}$, or substituted alkyl$_{(C \leq 6)}$; and m, n, and p are each independently an integer selected from 0, 1, 2, 3, 4, 5, or 6;

or a pharmaceutically acceptable salt thereof. In some embodiments the compounds are further defined as:

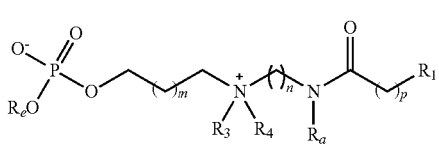
(IIc)

wherein:
$R_e$ is hydrogen, alkyl$_{(C \leq 6)}$, or substituted alkyl$_{(C \leq 6)}$;
$R_1$ is a group of the formula:

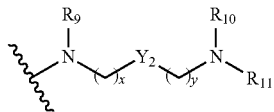

wherein:
$Y_2$ is arenediyl$_{(C \leq 12)}$, heterocycloalkanediyl$_{(C \leq 12)}$, heteroarenediyl$_{(C \leq 12)}$, alkoxydiyl$_{(C \leq 12)}$, or a substituted version of any of these groups;
$R_9$, $R_{10}$, and $R_{11}$ are each independently selected from hydrogen, alkyl$_{(C \leq 8)}$, substituted alkyl$_{(C \leq 8)}$, or —$Z_4A'''R_{12}$; wherein:
$Z_4$ is alkanediyl$_{(C \leq 4)}$ or substituted alkanediyl$_{(C \leq 4)}$;
$A'''$ is —CHR$_k$—, —C(O)O—, or —C(O)NR$_l$—;
$R_l$ is hydrogen, alkyl$_{(C \leq 6)}$, or substituted alkyl$_{(C \leq 6)}$; and
$R_k$ is hydrogen, halo, hydroxy, acyloxy$_{(C \leq 24)}$, or substituted acyloxy$_{(C \leq 24)}$; and
$R_{12}$ is alkyl$_{(C6-24)}$, substituted alkyl$_{(C6-24)}$, alkenyl$_{(C6-24)}$, substituted alkenyl$_{(C6-24)}$; and
x and y are 1, 2, 3, or 4;
$R_a$, $R_3$, and $R_4$ are each independently hydrogen, alkyl$_{(C \leq 6)}$, or substituted alkyl$_{(C \leq 6)}$; and
m, n, and p are each independently an integer selected from 0, 1, 2, 3, 4, 5, or 6;
or a pharmaceutically acceptable salt thereof.
In some embodiments, $R_a$ is hydrogen. In other embodiments, $R_a$ is alkyl$_{(C \leq 8)}$ or substituted alkyl$_{(C \leq 8)}$. In some embodiments, $R_3$ is hydrogen. In other embodiments, $R_3$ is alkyl$_{(C \leq 8)}$ or substituted alkyl$_{(C \leq 8)}$. $R_3$ may be alkyl$_{(C \leq 8)}$ such as methyl. In some embodiments, $R_4$ is hydrogen. In other embodiments, $R_4$ is alkyl$_{(C \leq 8)}$ or substituted alkyl$_{(C \leq 8)}$. $R_4$ may be alkyl$_{(C \leq 8)}$ such as methyl.
In some embodiments, m is 1 or 2. In one instance, m is 1. In another instance, m is 2. In some embodiments, n is 2 or 3. In one instance, n is 2. In another instance, n is 3. In some embodiments, p is 1, 2, or 3. In one instance, p is 1. In another instance, p is 2. In yet another instance, p is 3.
In some embodiments, $R_1$ is a group of the formula:

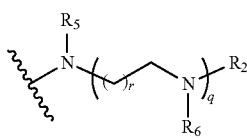

wherein:
$R_5$, $R_6$, and $R_2$ are each independently hydrogen or alkyl$_{(C \leq 8)}$, -alkanediyl$_{(C \leq 6)}$-NH$_2$, -alkanediyl$_{(C \leq 6)}$alkylamino$_{(C \leq 8)}$, -alkanediyl$_{(C \leq 6)}$-dialkylamino$_{(C \leq 12)}$, -alkanediyl$_{(C \leq 6)}$-NR'R", or a substituted version of any of these groups wherein:
R' and R" are each independently hydrogen, alkyl$_{(C \leq 8)}$, substituted alkyl$_{(C \leq 8)}$, —$Z_2A'R_7$;
wherein:
$Z_2$ is alkanediyl$_{(C \leq 4)}$ or substituted alkanediyl$_{(C \leq 4)}$;
$A'$ is —CHR$_j$—, —C(O)O—, or —C(O)NR$_b$—;
$R_b$ is hydrogen, alkyl$_{(C \leq 6)}$, or substituted alkyl$_{(C \leq 6)}$; and $R_j$ is hydrogen, halo, hydroxy, acyloxy$_{(C \leq 24)}$, or substituted acyloxy$_{(C \leq 24)}$;
$R_7$ is alkyl$_{(C6-24)}$, substituted alkyl$_{(C6-24)}$, alkenyl$_{(C6-24)}$, substituted alkenyl$_{(C6-24)}$;
or
$R_5$, $R_6$, and $X_1$ are each independently —$Z_3A''R_8$;
wherein:
$Z_3$ is alkanediyl$_{(C \leq 4)}$ or substituted alkanediyl$_{(C \leq 4)}$;
$A''$ is —CHR$_k$—, —C(O)O—, or —C(O)NR$_l$—;
$R_l$ is hydrogen, alkyl$_{(C \leq 6)}$, or substituted alkyl$_{(C \leq 6)}$; and
$R_k$ is hydrogen, halo, hydroxy, acyloxy$_{(C \leq 24)}$, or substituted acyloxy$_{(C \leq 24)}$; and
$R_8$ is alkyl$_{(C6-24)}$, substituted alkyl$_{(C6-24)}$, alkenyl$_{(C6-24)}$, substituted alkenyl$_{(C6-24)}$;
q is 1, 2, or 3; and
r is 1, 2, 3, or 4.
In some embodiments, $R_1$ is a group of the formula:

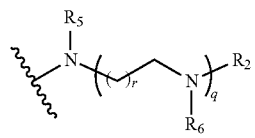

wherein:
$R_5$, $R_6$, and $R_2$ are each independently hydrogen or alkyl$_{(C \leq 8)}$, -alkanediyl$_{(C \leq 6)}$-NH$_2$, -alkanediyl$_{(C \leq 6)}$-alkylamino$_{(C \leq 8)}$, -alkanediyl$_{(C \leq 6)}$-dialkylamino$_{(C \leq 12)}$, -alkanediyl$_{(C \leq 6)}$-NR'R", or a substituted version of any of these groups wherein:
R' and R" are each independently hydrogen, alkyl$_{(C \leq 8)}$, substituted alkyl$_{(C \leq 8)}$, —(CH$_2$)$_s$CH(OH)R$_7$, —(CH$_2$)$_s$C(O)OR$_7$, or —(CH$_2$)$_s$C(O)(NR$_b$)R$_7$;
wherein:
s is 1, 2, 3, or 4;
$R_b$ is hydrogen, alkyl$_{(C \leq 6)}$, or substituted alkyl$_{(C \leq 6)}$; and
$R_7$ is alkyl$_{(C6-24)}$, substituted alkyl$_{(C6-24)}$, alkenyl$_{(C6-24)}$, substituted alkenyl$_{(C6-24)}$;
or
$R_5$, $R_6$, and $X_1$ are each independently —(CH$_2$)$_t$CH(OH)R$_8$, —(CH2)$_t$C(O)OR$_8$, —(CH$_2$)$_t$C(O)(NR$_c$)R$_8$;
wherein:
t is 1, 2, 3, or 4;
$R_c$ is hydrogen, alkyl$_{(C \leq 6)}$, or substituted alkyl$_{(C \leq 6)}$; and
$R_8$ is alkyl$_{(C6-24)}$, substituted alkyl$_{(C6-24)}$, alkenyl$_{(C6-24)}$, substituted alkenyl$_{(C6-24)}$; or
q is 1, 2, or 3; and
r is 1, 2, 3, or 4.
In some embodiments, q is 1 or 2. In one instance, q is 1. In another instance, q is 2. In some embodiments, r is 1 or 2. In one instance, r is 1. In another instance, r is 2. In some embodiments, $R_5$ is hydrogen. In other embodiments, $R_5$ is alkyl$_{(C \leq 8)}$ or substituted alkyl$_{(C \leq 8)}$. $R_5$ may be alkyl$_{(C \leq 8)}$ such as methyl or isopropyl.
In some embodiments, $R_5$ is further defined as —$Z_3A''R_8$ wherein:
$Z_3$ is alkanediyl$_{(C \leq 4)}$ or substituted alkanediyl$_{(C \leq 4)}$;
$A''$ is —CHR$_k$—, —C(O)O—, or —C(O)NR$_l$—;
$R_l$ is hydrogen, alkyl$_{(C \leq 6)}$, or substituted alkyl$_{(C \leq 6)}$; and
$R_k$ is hydrogen, halo, hydroxy, acyloxy$_{(C \leq 24)}$, or substituted acyloxy$_{(C \leq 24)}$; and
$R_8$ is alkyl$_{(C6-24)}$, substituted alkyl$_{(C6-24)}$, alkenyl$_{(C6-24)}$, substituted alkenyl$_{(C6-24)}$.

In some embodiments, $Z_3$ is alkanediyl$_{(C1-2)}$. In one instance, $Z_3$ is —CH$_2$—. In some embodiments, $Z_3$ is substituted alkanediyl$_{(C1-2)}$. In one instance, $Z_3$ is —CH$_2$CH(OH)—. In some embodiments, A" is —CHR$_k$—. In one instance, R$_k$ is hydroxy. In some embodiments, R$_k$ is acyloxy$_{(C\leq24)}$ or substituted acyloxy$_{(C\leq24)}$. In some embodiments, R$_k$ is acyloxy$_{(C1-8)}$ or substituted acyloxy$_{(C1-8)}$. In some embodiments, R$_k$ is acyloxy$_{(C\leq12-24)}$ or substituted acyloxy$_{(C\leq12-24)}$. In one instance, A" is —C(O)O—. In another instance, A" is —C(O)NH—.

In other embodiments, R$_5$ is —(CH$_2$)$_t$CH(OH)R$_8$, —(CH$_2$)$_t$C(O)OR$_8$, or —(CH$_2$)$_t$C(O)(NR$_c$)R$_8$; wherein:
t is 1, 2, 3, or 4;
R$_c$ is hydrogen, alkyl$_{(C\leq6)}$, or substituted alkyl$_{(C\leq6)}$; and
R$_8$ is alkyl$_{(C6-24)}$, substituted alkyl$_{(C6-24)}$, alkenyl$_{(C6-24)}$, substituted alkenyl$_{(C6-24)}$.

In some embodiments, R$_5$ is —(CH$_2$)$_t$CH(OH)R$_8$. In other embodiments, R$_5$ is —(CH$_2$)$_t$C(O)OR$_8$. In other embodiments, R$_5$ is —(CH$_2$)$_t$C(O)(NR$_c$)R$_8$. In some embodiments, t is 1 or 2. In one instance, t is 1. In another instance, t is 2. In some embodiments, R$_c$ is hydrogen. In other embodiments, R$_c$ is alkyl$_{(C\leq6)}$ or substituted alkyl$_{(C\leq6)}$. In some embodiments, R$_8$ is alkyl$_{(C6-24)}$ or substituted alkyl$_{(C6-24)}$. R$_8$ may be alkyl$_{(C6-24)}$ such as octyl, decyl, dodecyl, tetradecyl, hexadecyl, or octadecyl. In some embodiments, R$_8$ is alkenyl$_{(C6-24)}$ or substituted alkenyl$_{(C6-24)}$.

In some embodiments, R$_6$ is —Z$_3$A"R$_8$; wherein:
Z$_3$ is alkanediyl$_{(C\leq4)}$ or substituted alkanediyl$_{(C\leq4)}$;
A" is —CHR$_k$—, —C(O)O—, or —C(O)NR$_l$—;
R$_l$ is hydrogen, alkyl$_{(C\leq6)}$, or substituted alkyl$_{(C\leq6)}$; and
R$_k$ is hydrogen, halo, hydroxy, acyloxy$_{(C\leq24)}$, or substituted acyloxy$_{(C\leq24)}$; and
R$_8$ is alkyl$_{(C6-24)}$, substituted alkyl$_{(C6-24)}$, alkenyl$_{(C6-24)}$, substituted alkenyl$_{(C6-24)}$.

In some embodiments, Z$_3$ is alkanediyl$_{(C1-2)}$. In one instance, Z$_3$ is —CH$_2$—. In some embodiments, Z$_3$ is substituted alkanediyl$_{(C1-2)}$. In one instance, Z$_3$ is —CH$_2$CH(OH)—. In some embodiments, A" is —CHR$_k$—. In one instance, R$_k$ is hydroxy. In some embodiments, R$_k$ is acyloxy$_{(C\leq24)}$ or substituted acyloxy$_{(C\leq24)}$. In some embodiments, R$_k$ is acyloxy$_{(C1-8)}$ or substituted acyloxy$_{(C1-8)}$. In some embodiments, R$_k$ is acyloxy$_{(C\leq12-24)}$ or substituted acyloxy$_{(C\leq12-24)}$. In one instance, A" is —C(O)O—. In another instance, A" is —C(O)NH—. In some embodiments, R$_8$ is alkyl$_{(C6-24)}$ or substituted alkyl$_{(C6-24)}$. R$_8$ may be alkyl$_{(C6-24)}$ such as octyl, decyl, dodecyl, tetradecyl, hexadecyl, or octadecyl. In some embodiments, R$_8$ is alkenyl$_{(C6-24)}$ or substituted alkenyl$_{(C6-24)}$.

In some embodiments, R$_6$ is hydrogen. In other embodiments, R$_6$ is alkyl$_{(C\leq8)}$ or substituted alkyl$_{(C\leq8)}$. R$_6$ may be alkyl$_{(C\leq8)}$ such as methyl or isopropyl. In other embodiments, R$_6$ is —(CH$_2$)$_t$CH(OH)R$_8$, —(CH$_2$)$_t$C(O)OR$_8$, or —(CH$_2$)$_t$C(O)(NR$_c$)R$_8$; wherein:
t is 1, 2, 3, or 4;
R$_c$ is hydrogen, alkyl$_{(C\leq6)}$, or substituted alkyl$_{(C\leq6)}$; and
R$_8$ is alkyl$_{(C6-24)}$, substituted alkyl$_{(C6-24)}$, alkenyl$_{(C6-24)}$, substituted alkenyl$_{(C6-24)}$.

In some embodiments, R$_6$ is —(CH$_2$)$_t$CH(OH)R$_8$. In other embodiments, R$_6$ is —(CH$_2$)$_t$C(O)OR$_8$. In other embodiments, R$_6$ is —(CH$_2$)$_t$C(O)(NR$_c$)R$_8$. In some embodiments, t is 1 or 2. In one instance, t is 1. In another instance, t is 2. In some embodiments, R$_c$ is hydrogen. In some embodiments, R$_c$ is alkyl$_{(C\leq6)}$ or substituted alkyl$_{(C\leq6)}$. In some embodiments, R$_8$ is alkyl$_{(C6-24)}$ or substituted alkyl$_{(C6-24)}$. R$_8$ may be alkyl$_{(C6-24)}$ such as octyl, decyl, dodecyl, tetradecyl, hexadecyl, or octadecyl. In some embodiments, R$_8$ is alkenyl$_{(C6-24)}$ or substituted alkenyl$_{(C6-24)}$.

In some embodiments, R$_6$ is -alkanediyl$_{(C\leq6)}$-NH$_2$, -alkanediyl$_{(C\leq6)}$-alkylamino$_{(C\leq8)}$, -alkanediyl$_{(C\leq6)}$-dialkylamino$_{(C\leq12)}$, or a substituted version of any of these groups. In some embodiments, R$_6$ is -alkanediyl$_{(C\leq6)}$-NH$_2$ or a substituted version of this group such as —CH$_2$CH$_2$NH$_2$. In other embodiments, R$_6$ is -alkanediyl$_{(C\leq6)}$-alkylamino$_{(C\leq8)}$ or a substituted version of this group such as —CH$_2$CH$_2$NHMe or —CH$_2$CH$_2$NHiPr. In other embodiments, R$_6$ is -alkanediyl$_{(C\leq6)}$-dialkylamino$_{(C\leq8)}$ or a substituted version of this group.

In some embodiments, R$_2$ is hydrogen. In other embodiments, R$_2$ is alkyl$_{(C\leq8)}$ or substituted alkyl$_{(C\leq8)}$. R$_2$ may be alkyl$_{(C\leq8)}$ such as methyl or isopropyl.

In some embodiments, R$_2$ is —Z$_3$A"R$_8$; wherein:
Z$_3$ is alkanediyl$_{(C\leq4)}$ or substituted alkanediyl$_{(C\leq4)}$;
A" is —CHR$_k$—, —C(O)O—, or —C(O)NR$_l$—;
R$_l$ is hydrogen, alkyl$_{(C\leq6)}$, or substituted alkyl$_{(C\leq6)}$; and
R$_k$ is hydrogen, halo, hydroxy, acyloxy$_{(C\leq24)}$, or substituted acyloxy$_{(C\leq24)}$; and
R$_8$ is alkyl$_{(C6-24)}$, substituted alkyl$_{(C6-24)}$, alkenyl$_{(C6-24)}$, substituted alkenyl$_{(C6-24)}$.

In some embodiments, Z$_3$ is alkanediyl$_{(C1-2)}$. In one instance, Z$_3$ is —CH$_2$—. In some embodiments, Z$_3$ is substituted alkanediyl$_{(C1-2)}$. In one instance, Z$_3$ is —CH$_2$CH(OH)—. In some embodiments, A" is —CHR$_k$—. In one instance, R$_k$ is hydroxy. In some embodiments, R$_k$ is acyloxy$_{(C\leq24)}$ or substituted acyloxy$_{(C\leq24)}$. In some embodiments, R$_k$ is acyloxy$_{(C1-8)}$ or substituted acyloxy$_{(C1-8)}$. In some embodiments, R$_k$ is acyloxy$_{(C\leq12-24)}$ or substituted acyloxy$_{(C\leq12-24)}$. In one instance, A" is —C(O)O—. In another instance, A" is —C(O)NH—. In some embodiments, R$_8$ is alkyl$_{(C6-24)}$ or substituted alkyl$_{(C6-24)}$. R$_8$ may be alkyl$_{(C6-24)}$ such as octyl, decyl, dodecyl, tetradecyl, hexadecyl, or octadecyl. In some embodiments, R$_8$ is alkenyl$_{(C6-24)}$ or substituted alkenyl$_{(C6-24)}$.

In some embodiments, R$_2$ is -alkanediyl$_{(C\leq6)}$-NH$_2$, -alkanediyl$_{(C\leq6)}$alkylamino$_{(C\leq8)}$, -alkanediyl$_{(C\leq6)}$-dialkylamino$_{(C\leq12)}$, or a substituted version of any of these groups. In some embodiments, R$_2$ is -alkanediyl$_{(C\leq6)}$-NH$_2$ or a substituted version of this group such as —CH$_2$CH$_2$NH$_2$. In other embodiments, R$_2$ is -alkanediyl$_{(C\leq6)}$alkylamino$_{(C\leq8)}$ or a substituted version of this group such as —CH$_2$CH$_2$NHMe or —CH$_2$CH$_2$NHiPr. In other embodiments, R$_2$ is alkanediyl$_{(C\leq6)}$dialkylamino$_{(C\leq8)}$ or a substituted version of this group.

In other embodiments, R$_2$ is —(CH$_2$)$_t$CH(OH)R$_8$, —(CH$_2$)$_t$C(O)OR$_8$, or —(CH$_2$)$_t$C(O)(NR$_c$)R$_8$; wherein:
t is 1, 2, 3, or 4;
R$_c$ is hydrogen, alkyl$_{(C\leq6)}$, or substituted alkyl$_{(C\leq6)}$; and
R$_8$ is alkyl$_{(C6-24)}$, substituted alkyl$_{(C6-24)}$, alkenyl$_{(C6-24)}$, substituted alkenyl$_{(C6-24)}$.

In other embodiments, R$_2$ is —(CH$_2$)$_t$CH(OH)R$_8$. In other embodiments, R$_2$ is —(CH$_2$)$_t$C(O)OR$_8$. In other embodiments, R$_2$ is —(CH$_2$)$_t$C(O)(NR$_c$)R$_8$. In some embodiments, t is 1 or 2. In one instance, t is 1. In another instance, t is 2. In some embodiments, R$_c$ is hydrogen. In some embodiments, R$_c$ is alkyl$_{(C\leq6)}$ or substituted alkyl$_{(C\leq6)}$. In some embodiments, R$_8$ is alkyl$_{(C6-24)}$ or substituted alkyl$_{(C6-24)}$. R$_8$ may be alkyl$_{(C6-24)}$ such as octyl, decyl, dodecyl, tetradecyl, hexadecyl, or octadecyl. In some embodiments, R$_8$ is alkenyl$_{(C6-24)}$ or substituted alkenyl$_{(C6-24)}$.

In other embodiments, R$_2$ is -alkanediyl$_{(C\leq6)}$-NH$_2$, alkanediyl$_{(C\leq6)}$-alkylamino$_{(C\leq8)}$, -alkanediyl$_{(C\leq6)}$-dialkylamino$_{(C\leq12)}$, or a substituted version of any of these groups. In some embodiments, R$_2$ is -alkanediyl$_{(C\leq6)}$-NH$_2$ or a substituted version of this group such as —CH$_2$CH$_2$NH$_2$. In other embodiments, R$_2$ is -alkanediyl$_{(C\leq6)}$-alkylamino$_{(C\leq8)}$ or a substituted version of this group such as —CH$_2$CH$_2$NHMe or —CH$_2$CH$_2$NHiPr. In other embodiments, R$_2$ is -alkanediyl$_{(C \le 6)}$dialkylamino$_{(C \le 8)}$ or a substituted version of this group.

In some embodiments, R$_1$ is a group of the formula:

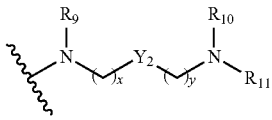

wherein:
Y$_2$ is arenediyl$_{(C \le 12)}$, heterocycloalkanediyl$_{(C \le 12)}$, heteroarenediyl$_{(C \le 12)}$, alkoxydiyl$_{(C \le 12)}$, or a substituted version of any of these groups;
R$_9$, R$_{10}$, and R$_{11}$ are each independently selected from hydrogen, alkyl$_{(C \le 8)}$, substituted alkyl$_{(C \le 8)}$, or —Z$_4$A'''R$_{12}$; wherein:
Z$_4$ is alkanediyl$_{(C \le 4)}$ or substituted alkanediyl$_{(C \le 4)}$;
A''' is —CHR$_k$—, —C(O)O—, or —C(O)NR$_l$—;
R$_l$ is hydrogen, alkyl$_{(C \le 6)}$, or substituted alkyl$_{(C \le 6)}$; and
R$_k$ is hydrogen, halo, hydroxy, acyloxy$_{(C \le 24)}$, or substituted acyloxy$_{(C \le 24)}$; and
R$_{12}$ is alkyl$_{(C6-24)}$, substituted alkyl$_{(C6-24)}$, alkenyl$_{(C6-24)}$, substituted alkenyl$_{(C6-24)}$; and
x and y are 1, 2, 3, or 4.

In some embodiments, R$_1$ is a group of the formula:

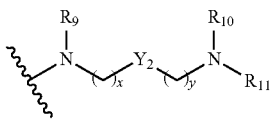

wherein:
Y$_2$ is arenediyl$_{(C \le 12)}$, heterocycloalkanediyl$_{(C \le 12)}$, heteroarenediyl$_{(C \le 12)}$, or a substituted version of any of these groups;
R$_9$, R$_{10}$, and R$_{11}$ are each independently selected from hydrogen, alkyl$_{(C \le 8)}$, substituted alkyl$_{(C \le 8)}$, —(CH$_2$)$_u$—CH(OH)R$_{12}$, —(CH$_2$)$_u$C(O)OR$_{12}$, —(CH$_2$)$_u$C(O)(NR$_d$)R$_{12}$; wherein:
u is 1, 2, 3, or 4;
R$_d$ is hydrogen, alkyl$_{(C \le 6)}$, or substituted alkyl$_{(C \le 6)}$; and
R$_{12}$ is alkyl$_{(C6-24)}$, substituted alkyl$_{(C6-24)}$, alkenyl$_{(C6-24)}$, substituted alkenyl$_{(C6-24)}$; and
x and y are 1, 2, 3, or 4.

In some embodiments, Y$_2$ is heterocycloalkanediyl$_{(C \le 12)}$ or substituted heterocycloalkanediyl$_{(C \le 12)}$. Y$_2$ may be heterocycloalkanediyl$_{(C \le 12)}$ such as piperazinediyl. In other embodiments, Y$_2$ is heteroarenediyl$_{(C \le 12)}$ or substituted heteroarenediyl$_{(C \le 12)}$. In other embodiments, Y$_2$ is arenediyl$_{(C \le 12)}$ or substituted arenediyl$_{(C \le 12)}$. In some embodiments, Y$_2$ is alkoxydiyl$_{(C \le 12)}$ or substituted alkoxydiyl$_{(C \le 12)}$. In some embodiments, x is 2 or 3. In one instance, x is 2. In another instance, x is 3. In some embodiments, y is 2 or 3. In one instance, y is 2. In another instance, y is 3.

In some embodiments, R$_9$ is —Z$_4$A'''R$_{12}$; wherein:
Z$_4$ is alkanediyl$_{(C \le 4)}$ or substituted alkanediyl$_{(C \le 4)}$;
A''' is —CHR$_k$—, —C(O)O—, or —C(O)NR$_l$—;
R$_l$ is hydrogen, alkyl$_{(C \le 6)}$, or substituted alkyl$_{(C \le 6)}$; and
R$_k$ is hydrogen, halo, hydroxy, acyloxy$_{(C \le 24)}$, or substituted acyloxy$_{(C \le 24)}$; and
R$_{12}$ is alkyl$_{(C6-24)}$, substituted alkyl$_{(C6-24)}$, alkenyl$_{(C6-24)}$, substituted alkenyl$_{(C6-24)}$.

In some embodiments, Z$_4$ is alkanediyl$_{(C1-2)}$. In one instance, Z$_4$ is —CH$_2$—. In some embodiments, Z$_4$ is substituted alkanediyl$_{(C1-2)}$. In one instance, Z$_4$ is —CH$_2$CH(OH). In some embodiments, A''' is —CHR$_k$—. In one instance, R$_k$ is hydroxy. In some embodiments, R$_k$ is acyloxy$_{(C \le 24)}$ or substituted acyloxy$_{(C \le 24)}$. In some embodiments, R$_k$ is acyloxy$_{(C1-8)}$ or substituted acyloxy$_{(C1-8)}$. In some embodiments, R$_k$ is acyloxy$_{(C \le 12-24)}$ or substituted acyloxy$_{(C \le 12-24)}$. In one instance, A''' is —C(O)O—. In another instance, A''' is —C(O)NH—. In some embodiments, R$_{12}$ is alkyl$_{(C6-24)}$ or substituted alkyl$_{(C6-24)}$. R$_{12}$ may be alkyl$_{(C6-24)}$ such as octyl, decyl, dodecyl, tetradecyl, hexadecyl, or octadecyl. In some embodiments, R$_{12}$ is alkenyl$_{(C6-24)}$ or substituted alkenyl$_{(C6-24)}$.

In some embodiments, R$_9$ is —(CH$_2$)$_u$CH(OH)R$_{12}$, —(CH$_2$)$_u$C(O)OR$_{12}$, —(CH$_2$)$_u$C(O)(NR$_d$)R$_{12}$; wherein:
u is 1, 2, 3, or 4;
R$_d$ is hydrogen, alkyl$_{(C \le 6)}$, or substituted alkyl$_{(C \le 6)}$; and
R$_{12}$ is alkyl$_{(C6-24)}$, substituted alkyl$_{(C6-24)}$, alkenyl$_{(C6-24)}$, substituted alkenyl$_{(C6-24)}$.

In some embodiments, R$_9$ is —(CH$_2$)$_u$CH(OH)R$_{12}$. In other embodiments, R$_9$ is —(CH$_2$)$_u$C(O)OR$_{12}$. In other embodiments, R$_9$ is —(CH$_2$)$_u$C(O)(NR$_d$)R$_{12}$. In some embodiments, u is 1, 2, or 3. In some embodiments, u is 1 or 2. In one instance, u is 1. In another instance, u is 2. In some embodiments, R$_d$ is hydrogen. In other embodiments, R$_d$ is alkyl$_{(C \le 6)}$ or substituted alkyl$_{(C \le 6)}$. In some embodiments, R$_{12}$ is alkyl$_{(C6-24)}$ or substituted alkyl$_{(C6-24)}$. R$_{12}$ may be alkyl$_{(C6-24)}$ such as octyl, decyl, dodecyl, tetradecyl, hexadecyl, or octadecyl. In other embodiments, R$_{12}$ is alkenyl$_{(C6-24)}$ or substituted alkenyl$_{(C6-24)}$.

In some embodiments, R$_{10}$ is —Z$_4$A'''R$_{12}$; wherein:
Z$_4$ is alkanediyl$_{(C \le 4)}$ or substituted alkanediyl$_{(C \le 4)}$;
A''' is —CHR$_k$—, —C(O)O—, or —C(O)NR$_l$—;
R$_l$ is hydrogen, alkyl$_{(C \le 6)}$, or substituted alkyl$_{(C \le 6)}$; and
R$_k$ is hydrogen, halo, hydroxy, acyloxy$_{(C \le 24)}$, or substituted acyloxy$_{(C \le 24)}$; and
R$_{12}$ is alkyl$_{(C6-24)}$, substituted alkyl$_{(C6-24)}$, alkenyl$_{(C6-24)}$, substituted alkenyl$_{(C6-24)}$.

In some embodiments, Z$_4$ is alkanediyl$_{(C1-2)}$. In one instance, Z$_4$ is —CH$_2$—. In some embodiments, Z$_4$ is substituted alkanediyl$_{(C1-2)}$. In one instance, Z$_4$ is —CH$_2$CH(OH). In some embodiments, A''' is —CHR$_k$—. In one instance, R$_k$ is hydroxy. In some embodiments, R$_k$ is acyloxy$_{(C \le 24)}$ or substituted acyloxy$_{(C \le 24)}$. In some embodiments, R$_k$ is acyloxy$_{(C1-8)}$ or substituted acyloxy$_{(C1-8)}$. In some embodiments, R$_k$ is acyloxy$_{(C \le 12-24)}$ or substituted acyloxy$_{(C \le 12-24)}$. In one instance, A''' is —C(O)O—. In another instance, A''' is —C(O)NH—. In some embodiments, R$_{12}$ is alkyl$_{(C6-24)}$ or substituted alkyl$_{(C6-24)}$. R$_{12}$ may be alkyl$_{(C6-24)}$ such as octyl, decyl, dodecyl, tetradecyl, hexadecyl, or octadecyl. In some embodiments, R$_{12}$ is alkenyl$_{(C6-24)}$ or substituted alkenyl$_{(C6-24)}$.

In some embodiments, R$_{10}$ is —(CH$_2$)$_u$CH(OH)R$_{12}$, —(CH$_2$)$_u$C(O)OR$_{12}$, —(CH$_2$)$_u$C(O)(NR$_d$)R$_{12}$; wherein:
u is 1, 2, 3, or 4;
R$_d$ is hydrogen, alkyl$_{(C \le 6)}$, or substituted alkyl$_{(C \le 6)}$; and
R$_{12}$ is alkyl$_{(C6-24)}$, substituted alkyl$_{(C6-24)}$, alkenyl$_{(C6-24)}$, substituted alkenyl$_{(C6-24)}$.

In some embodiments, R$_{10}$ is —(CH$_2$)$_u$CH(OH)R$_{12}$. In other embodiments, R$_{10}$ is —(CH$_2$)$_u$C(O)OR$_{12}$. In other embodiments, R$_{10}$ is —(CH$_2$)$_u$C(O)(NR$_d$)R$_{12}$. In some embodiments, u is 1, 2, or 3. In some embodiments, u is 1 or 2. In one instance, u is 1. In another instance, u is 2. In some embodiments, R$_d$ is hydrogen. In other embodiments, $R_d$ is alkyl$_{(C\leq6)}$ or substituted alkyl$_{(C\leq6)}$. In some embodiments, $R_{12}$ is alkyl$_{(C6-24)}$ or substituted alkyl$_{(C6-24)}$. $R_{12}$ may be alkyl$_{(C6-24)}$ such as octyl, decyl, dodecyl, tetradecyl, hexadecyl, or octadecyl. In other embodiments, $R_{12}$ is alkenyl$_{(C6-24)}$ or substituted alkenyl$_{(C6-24)}$.

In some embodiments, $R_{11}$ is —$Z_4A'''R_{12}$; wherein:
$Z_4$ is alkanediyl$_{(C\leq4)}$ or substituted alkanediyl$_{(C\leq4)}$;
$A'''$ is —CHR$_k$—, —C(O)O—, or —C(O)NR$_l$—;
$R_l$ is hydrogen, alkyl$_{(C\leq6)}$, or substituted alkyl$_{(C\leq6)}$; and
$R_k$ is hydrogen, halo, hydroxy, acyloxy$_{(C\leq24)}$, or substituted acyloxy$_{(C\leq24)}$; and
$R_{12}$ is alkyl$_{(C6-24)}$, substituted alkyl$_{(C6-24)}$, alkenyl$_{(C6-24)}$, substituted alkenyl$_{(C6-24)}$.

In some embodiments, $Z_4$ is alkanediyl$_{(C1-2)}$. In one instance, $Z_4$ is —CH$_2$—. In some embodiments, $Z_4$ is substituted alkanediyl$_{(C1-2)}$. In one instance, $Z_4$ is —CH$_2$CH(OH). In some embodiments, $A'''$ is —CHR$_k$—. In one instance, $R_k$ is hydroxy. In some embodiments, $R_k$ is acyloxy$_{(C\leq24)}$ or substituted acyloxy$_{(C\leq24)}$. In some embodiments, $R_k$ is acyloxy$_{(C1-8)}$ or substituted acyloxy$_{(C1-8)}$. In some embodiments, $R_k$ is acyloxy$_{(C\leq12-24)}$ or substituted acyloxy$_{(C\leq12-24)}$. In one instance, $A'''$ is —C(O)O—. In another instance, $A'''$ is —C(O)NH—. In some embodiments, $R_{12}$ is alkyl$_{(C6-24)}$ or substituted alkyl$_{(C6-24)}$. $R_{12}$ may be alkyl$_{(C6-24)}$ such as octyl, decyl, dodecyl, tetradecyl, hexadecyl, or octadecyl. In some embodiments, $R_{12}$ is alkenyl$_{(C6-24)}$ or substituted alkenyl$_{(C6-24)}$.

In some embodiments, $R_{11}$ is —(CH$_2$)$_u$CH(OH)R$_{12}$, —(CH$_2$)$_u$C(O)OR$_{12}$, —(CH$_2$)$_u$C(O)(NR$_d$)R$_{12}$; wherein:
u is 1, 2, 3, or 4;
$R_d$ is hydrogen, alkyl$_{(C\leq6)}$, or substituted alkyl$_{(C\leq6)}$; and
$R_{12}$ is alkyl$_{(C6-24)}$, substituted alkyl$_{(C6-24)}$, alkenyl$_{(C6-24)}$, substituted alkenyl$_{(C6-24)}$.

In some embodiments, $R_{11}$ is —(CH$_2$)$_u$CH(OH)R$_{12}$. In other embodiments, $R_{11}$ is —(CH$_2$)$_u$C(O)OR$_{12}$. In other embodiments, $R_{11}$ is —(CH$_2$)$_u$C(O)(NR$_d$)R$_{12}$. In some embodiments, u is 1, 2, or 3. In some embodiments, u is 1 or 2. In one instance, u is 1. In another instance, u is 2. In some embodiments, $R_d$ is hydrogen. In other embodiments, $R_d$ is alkyl$_{(C\leq6)}$ or substituted alkyl$_{(C\leq6)}$. In some embodiments, $R_{12}$ is alkyl$_{(C6-24)}$ or substituted alkyl$_{(C6-24)}$. $R_{12}$ may be alkyl$_{(C6-24)}$ such as octyl, decyl, dodecyl, tetradecyl, hexadecyl, or octadecyl. In other embodiments, $R_{12}$ is alkenyl$_{(C6-24)}$ or substituted alkenyl$_{(C6-24)}$.

In yet another aspect, the present disclosure provides compounds of the formula:

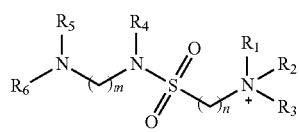

(IV)

wherein:
$R_1$, $R_2$, and $R_3$ are each independently hydrogen, alkyl$_{(C\leq6)}$, substituted alkyl$_{(C\leq6)}$, or a group of the formula:

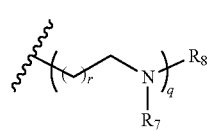

wherein:
$R_7$ and $R_8$ are each independently hydrogen, alkyl$_{(C\leq6)}$, substituted alkyl$_{(C\leq6)}$, or a group of the formula:

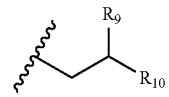

wherein:
$R_9$ is hydrogen, halo, or hydroxy, or alkoxy$_{(C\leq8)}$, acyloxy$_{(C\leq8)}$, or a substituted version of either of these groups; and
$R_{10}$ is alkyl$_{(C\leq24)}$, alkenyl$_{(C\leq24)}$, or a substituted version of either group;
q is 1, 2, or 3; and
r is 0, 1, 2, 3, or 4;
$R_4$, $R_5$, and $R_6$ are each independently hydrogen, alkyl$_{(C\leq6)}$, or substituted alkyl$_{(C\leq6)}$, or $R_4$ is taken together with either $R_5$ or $R_6$ and is alkanediyl$_{(C\leq12)}$, alkoxydiyl$_{(C\leq12)}$, alkylaminodiyl$_{(C\leq12)}$, or a substituted version of any of these groups; and
m and n are each independently 1, 2, 3, 4, or 5;
or a pharmaceutically acceptable salt thereof. In some embodiments, the compounds are further defined as:

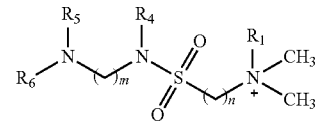

(V)

wherein:
$R_1$ is hydrogen, alkyl$_{(C\leq6)}$, substituted alkyl$_{(C\leq6)}$, or a group of the formula:

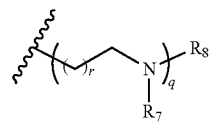

wherein:
$R_7$ and $R_8$ are each independently hydrogen, alkyl$_{(C\leq6)}$, substituted alkyl$_{(C\leq6)}$, or a group of the formula:

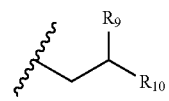

wherein:
$R_9$ is hydrogen, halo, or hydroxy, or alkoxy$_{(C\leq8)}$, acyloxy$_{(C\leq8)}$, or a substituted version of either of these groups; and
$R_{10}$ is alkyl$_{(C\leq24)}$, alkenyl$_{(C\leq24)}$, or a substituted version of either group;
q is 1, 2, or 3; and
r is 0, 1, 2, 3, or 4;
$R_4$, $R_5$, and $R_6$ are each independently hydrogen, alkyl$_{(C\leq6)}$, or substituted alkyl$_{(C\leq6)}$, or $R_4$ is taken together with either $R_5$ or $R_6$ and is alkanediyl$_{(C\leq12)}$, alkoxydiyl$_{(C\leq12)}$, alkylaminodiyl$_{(C\leq12)}$, or a substituted version of any of these groups; and
m and n are each independently 1, 2, 3, 4, or 5;

or a pharmaceutically acceptable salt thereof. In some embodiments, the compounds are further defined as:

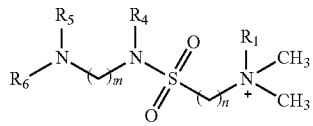
(V)

wherein:
R$_1$, R$_2$, and R$_3$ are each independently hydrogen, alkyl$_{(C\le6)}$, substituted alkyl$_{(C\le6)}$, or a group of the formula:

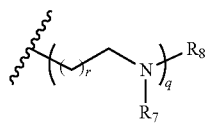

wherein:
R$_7$ and R$_8$ are each independently hydrogen, alkyl$_{(C\le6)}$, substituted alkyl$_{(C\le6)}$, or a group of the formula:

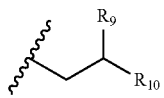

wherein:
R$_9$ is hydrogen, halo, or hydroxy, or alkoxy$_{(C\le8)}$, acyloxy$_{(C\le8)}$, or a substituted version of either of these groups; and
R$_{10}$ is alkyl$_{(C\le24)}$, alkenyl$_{(C\le24)}$, or a substituted version of either group;
q is 1, 2, or 3; and
r is 0, 1, 2, 3, or 4;
R$_5$ and R$_6$ are each independently hydrogen, alkyl$_{(C\le6)}$, or substituted alkyl$_{(C\le6)}$; and
m and n are each independently 1, 2, 3, 4, or 5;
or a pharmaceutically acceptable salt thereof. In some embodiments, the compounds are further defined as:

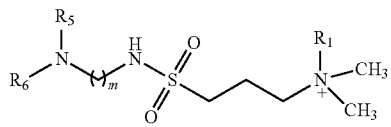
(VI)

wherein:
R$_1$, R$_2$, and R$_3$ are each independently hydrogen, alkyl$_{(C\le6)}$, substituted alkyl$_{(C\le6)}$, or a group of the formula:

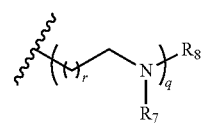

wherein:
R$_7$ and R$_8$ are each independently hydrogen, alkyl$_{(C\le6)}$, substituted alkyl$_{(C\le6)}$, or a group of the formula:

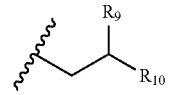

wherein:
R$_9$ is hydrogen, halo, or hydroxy, or alkoxy$_{(C\le8)}$, acyloxy$_{(C\le8)}$, or a substituted version of either of these groups; and
R$_{10}$ is alkyl$_{(C\le24)}$, alkenyl$_{(C\le24)}$, or a substituted version of either group;
q is 1, 2, or 3; and
r is 0, 1, 2, 3, or 4;
R$_5$ and R$_6$ are each independently hydrogen, alkyl$_{(C\le6)}$, or substituted alkyl$_{(C\le6)}$; and
m is 1, 2, 3, 4, or 5;
or a pharmaceutically acceptable salt thereof.

In some embodiments, R$_2$ is hydrogen. In other embodiments, R$_2$ is alkyl$_{(C\le6)}$ or substituted alkyl$_{(C\le6)}$. R$_2$ may be alkyl$_{(C\le6)}$ such as methyl or ethyl. In other embodiments, R$_2$ is a group of the formula:

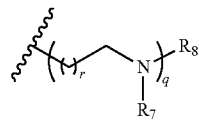

wherein:
R$_7$ and R$_8$ are each independently hydrogen, alkyl$_{(C\le6)}$, substituted alkyl$_{(C\le6)}$, or a group of the formula:

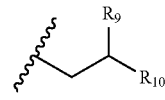

wherein:
R$_9$ is hydrogen, halo, or hydroxy, or alkoxy$_{(C\le8)}$, acyloxy$_{(C\le8)}$, or a substituted version of either of these groups; and
R$_{10}$ is alkyl$_{(C\le24)}$, alkenyl$_{(C\le24)}$, or a substituted version of either group;
q is 1, 2, or 3; and
r is 0, 1, 2, 3, or 4.

In some embodiments, R$_7$ is hydrogen. In other embodiments, R$_7$ is alkyl$_{(C\le6)}$ or substituted alkyl$_{(C\le6)}$. R$_7$ may be alkyl$_{(C\le6)}$ such as methyl or ethyl. In other embodiments, R$_7$ is

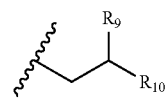

wherein:
R$_9$ is hydrogen, halo, or hydroxy, or alkoxy$_{(C\le8)}$, acyloxy$_{(C\le8)}$, or a substituted version of either of these groups; and $R_{10}$ is alkyl$_{(C≤24)}$, alkenyl$_{(C≤24)}$, or a substituted version of either group.

In some embodiments, $R_9$ is halo such as chloro or bromo. In other embodiments, $R_9$ is hydroxy. In other embodiments, $R_9$ is alkoxy$_{(C≤8)}$ or substituted alkoxy$_{(C≤8)}$. $R_9$ may be alkoxy$_{(C≤8)}$ such as methoxy. In some embodiments, $R_9$ is acyloxy$_{(C≤8)}$ or substituted acyloxy$_{(C≤8)}$. $R_9$ may be acyloxy$_{(C≤8)}$ such as acetoxy or pivaloyloxy. In some embodiments, $R_{10}$ is alkyl$_{(C≤24)}$ or substituted alkyl$_{(C≤24)}$ such as octyl, decyl, dodecyl, tetradecyl, hexadecyl, or octadecyl. In other embodiments, $R_{10}$ is alkenyl$_{(C≤24)}$ or substituted alkenyl$_{(C≤24)}$.

In some embodiments, $R_8$ is hydrogen. In other embodiments, $R_8$ is alkyl$_{(C≤6)}$ or substituted alkyl$_{(C≤6)}$. $R_8$ may be alkyl$_{(C≤6)}$ such as methyl or ethyl. In some embodiments, $R_8$ is

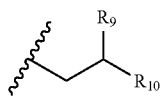

wherein:
$R_9$ is hydrogen, halo, or hydroxy, or alkoxy$_{(C≤8)}$, acyloxy$_{(C≤8)}$, or a substituted version of either of these groups; and
$R_{10}$ is alkyl$_{(C≤24)}$, alkenyl$_{(C≤24)}$, or a substituted version of either group.

In some embodiments, $R_9$ is halo such as chloro or bromo. In other embodiments, $R_9$ is hydroxy. In other embodiments, $R_9$ is alkoxy$_{(C≤8)}$ or substituted alkoxy$_{(C≤8)}$. $R_9$ may be alkoxy$_{(C≤8)}$ such as methoxy. In some embodiments, $R_9$ is acyloxy$_{(C≤8)}$ or substituted acyloxy$_{(C≤8)}$. $R_9$ may be acyloxy$_{(C≤8)}$ such as acetoxy or pivaloyloxy. In some embodiments, $R_{10}$ is alkyl$_{(C≤24)}$ or substituted alkyl$_{(C≤24)}$ such as octyl, decyl, dodecyl, tetradecyl, hexadecyl, or octadecyl. In other embodiments, $R_{10}$ is alkenyl$_{(C≤24)}$ or substituted alkenyl$_{(C≤24)}$.

In some embodiments, q is 1 or 2. In one instance, q is 1. In another instance, q is 2. In some embodiments, r is 1, 2, or 3. In one instance, r is 1. In another instance, r is 2. In another instance, r is 3.

In some embodiments, $R_3$ is hydrogen. In other embodiments, $R_3$ is alkyl$_{(C≤6)}$ or substituted alkyl$_{(C≤6)}$. $R_3$ may be alkyl$_{(C≤6)}$ such as methyl or ethyl. In some embodiments, $R_4$ is hydrogen. In other embodiments, $R_4$ is alkyl$_{(C≤6)}$ or substituted alkyl$_{(C≤6)}$. In some embodiments, $R_5$ is hydrogen. In other embodiments, $R_5$ is alkyl$_{(C≤6)}$ or substituted alkyl$_{(C≤6)}$. $R_5$ may be alkyl$_{(C≤6)}$ such as methyl or ethyl. In some embodiments, $R_6$ is hydrogen. In other embodiments, $R_6$ is alkyl$_{(C≤6)}$ or substituted alkyl$_{(C≤6)}$. $R_6$ may be alkyl$_{(C≤6)}$ such as methyl or ethyl. In some embodiments, m is 2, 3, or 4. In one instance, m is 2. In another instance, m is 3. In another instance, m is 4. In some embodiments, n is 2, 3, or 4. In one instance, n is 2. In another instance, n is 3. In yet another instance, n is 4.

In some embodiments, $R_1$ is hydrogen. In other embodiments, $R_1$ is alkyl$_{(C≤6)}$ or substituted alkyl$_{(C≤6)}$. $R_1$ may be alkyl$_{(C≤6)}$ such as methyl or ethyl. In other embodiments, $R_1$ is a group of the formula:

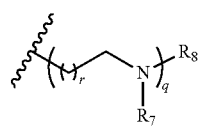

wherein:
$R_7$ and $R_8$ are each independently hydrogen, alkyl$_{(C≤6)}$, substituted alkyl$_{(C≤6)}$, or a group of the formula:

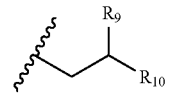

wherein:
$R_9$ is hydrogen, halo, or hydroxy, or alkoxy$_{(C≤8)}$, acyloxy$_{(C≤8)}$, or a substituted version of either of these groups; and
$R_{10}$ is alkyl$_{(C≤24)}$, alkenyl$_{(C≤24)}$, or a substituted version of either group;
q is 1, 2, or 3; and
r is 0, 1, 2, 3, or 4.

In some embodiments, $R_7$ is hydrogen. In other embodiments, $R_7$ is alkyl$_{(C≤6)}$ or substituted alkyl$_{(C≤6)}$. $R_7$ may be alkyl$_{(C≤6)}$ such as methyl or ethyl. In other embodiments, $R_7$ is

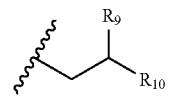

wherein:
$R_9$ is hydrogen, halo, or hydroxy, or alkoxy$_{(C≤8)}$, acyloxy$_{(C≤8)}$, or a substituted version of either of these groups; and
$R_{10}$ is alkyl$_{(C≤24)}$, alkenyl$_{(C≤24)}$, or a substituted version of either group.

In some embodiments, $R_9$ is halo such as chloro or bromo. In other embodiments, $R_9$ is hydroxy. In other embodiments, $R_9$ is alkoxy$_{(C≤8)}$ or substituted alkoxy$_{(C≤8)}$. $R_9$ may be alkoxy$_{(C≤8)}$ such as methoxy. In some embodiments, $R_9$ is acyloxy$_{(C≤8)}$ or substituted acyloxy$_{(C≤8)}$. $R_9$ may be acyloxy$_{(C≤8)}$ such as acetoxy or pivaloyloxy. In some embodiments, $R_{10}$ is alkyl$_{(C≤24)}$ or substituted alkyl$_{(C≤24)}$ such as octyl, decyl, dodecyl, tetradecyl, hexadecyl, or octadecyl. In other embodiments, $R_{10}$ is alkenyl$_{(C≤24)}$ or substituted alkenyl$_{(C≤24)}$.

In some embodiments, $R_8$ is hydrogen. In other embodiments, $R_8$ is alkyl$_{(C≤6)}$ or substituted alkyl$_{(C≤6)}$. $R_8$ may be alkyl$_{(C≤6)}$ such as methyl or ethyl. In other embodiments, $R_8$ is

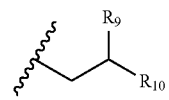

wherein:
$R_9$ is hydrogen, halo, or hydroxy, or alkoxy$_{(C≤8)}$, acyloxy$_{(C≤8)}$, or a substituted version of either of these groups; and
$R_{10}$ is alkyl$_{(C≤24)}$, alkenyl$_{(C≤24)}$, or a substituted version of either group.

In some embodiments, $R_9$ is halo such as chloro or bromo. In other embodiments, $R_9$ is hydroxy. In other embodiments, $R_9$ is alkoxy$_{(C≤8)}$ or substituted alkoxy$_{(C≤8)}$. $R_9$ may be alkoxy$_{(C≤8)}$ such as methoxy. In some embodiments, $R_9$ is acyloxy$_{(C≤8)}$ or substituted acyloxy$_{(C≤8)}$. $R_9$ may be acyloxy$_{(C≤8)}$ such as acetoxy or pivaloyloxy. In some embodiments, $R_{10}$ is alkyl$_{(C≤24)}$ or substituted alkyl$_{(C≤24)}$ such as octyl, decyl, dodecyl, tetradecyl, hexadecyl, or octadecyl. In other embodiments, $R_{10}$ is alkenyl$_{(C≤24)}$ or substituted alkenyl$_{(C≤24)}$.

In some embodiments, q is 1 or 2. In one instance, q is 1. In another aspect, q is 2. In some embodiments, r is 1, 2, or 3. In one instance, r is 1. In another instance, r is 2. In another instance, r is 3. In some embodiments, the compounds are further defined as:

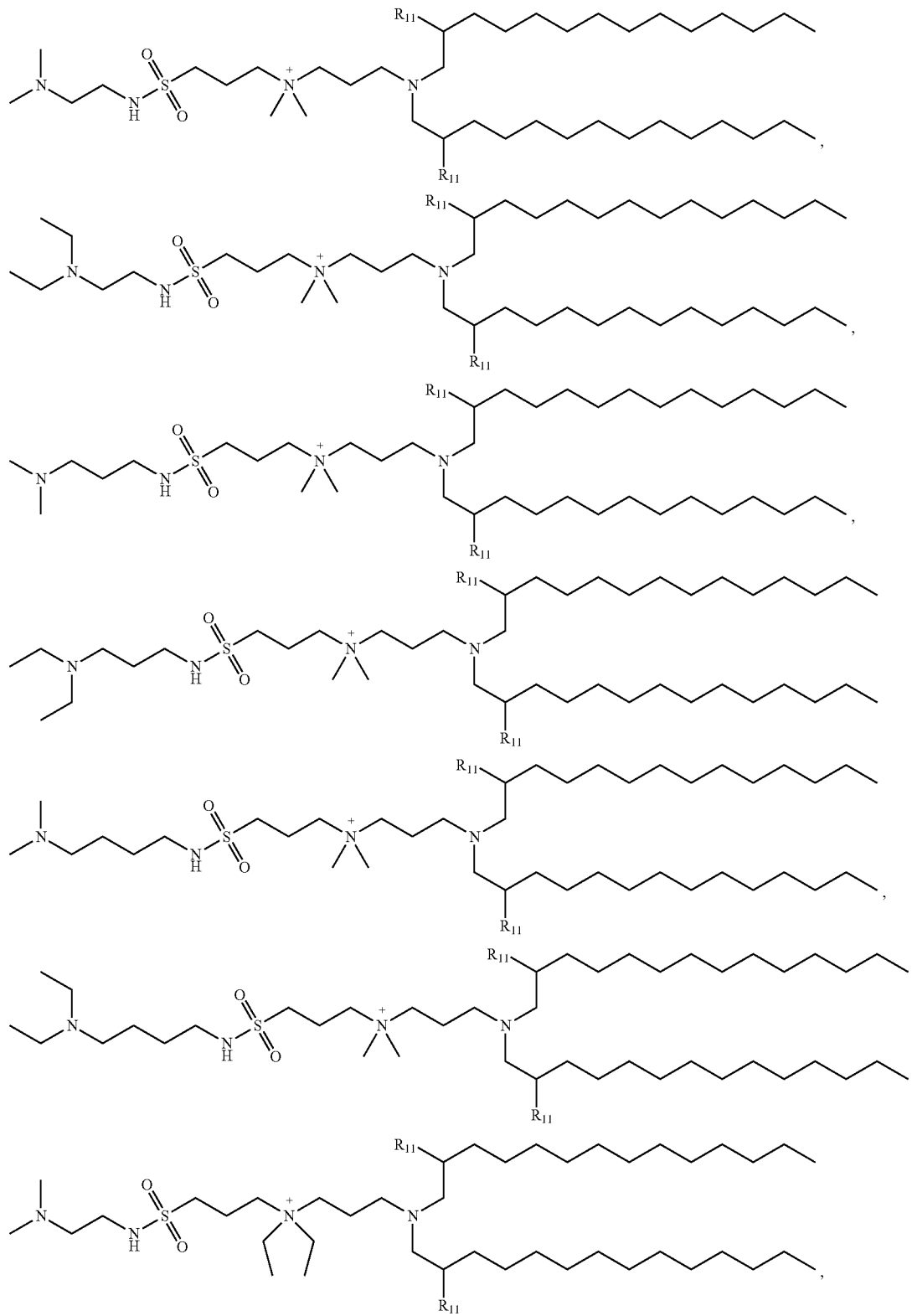

-continued
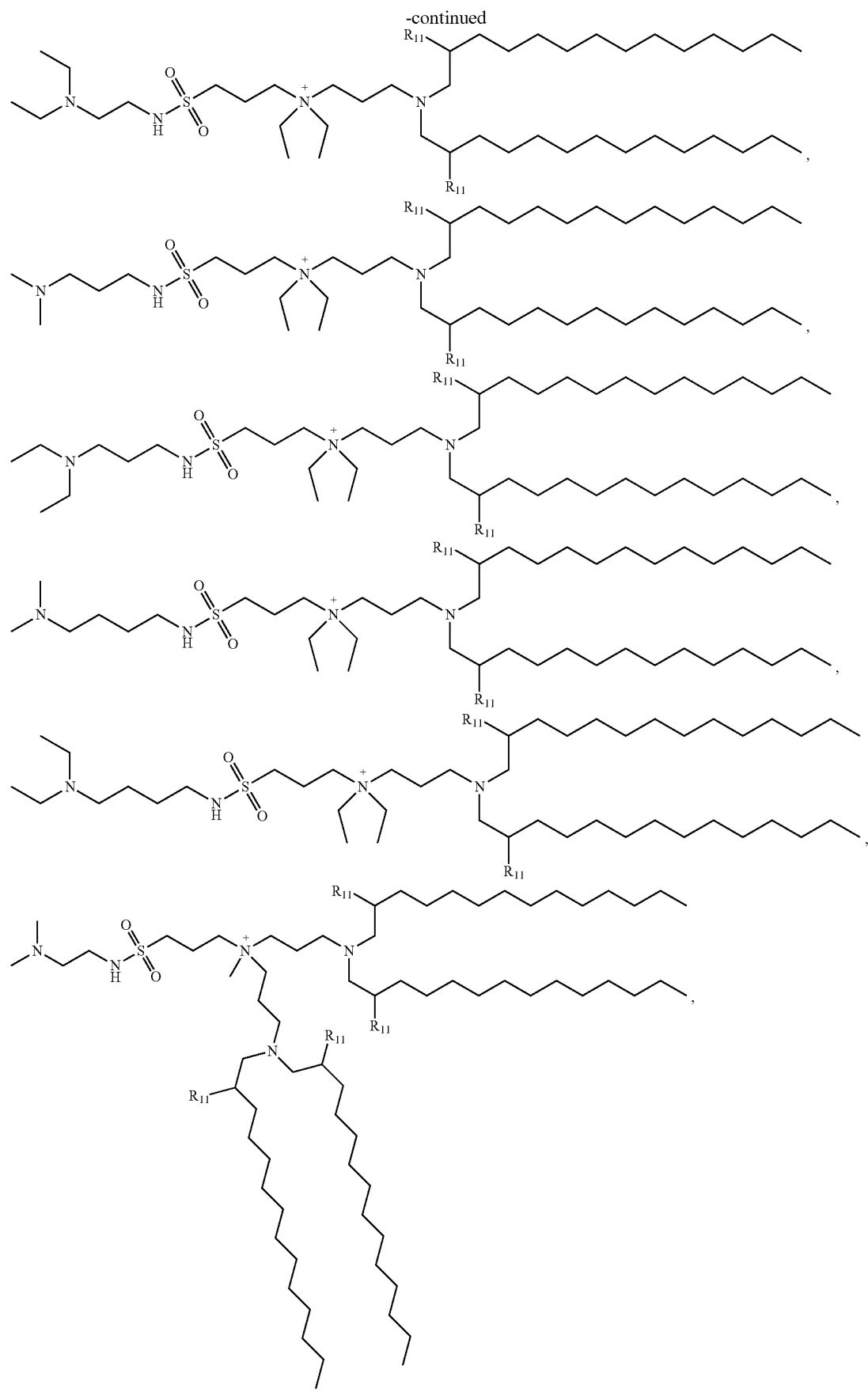

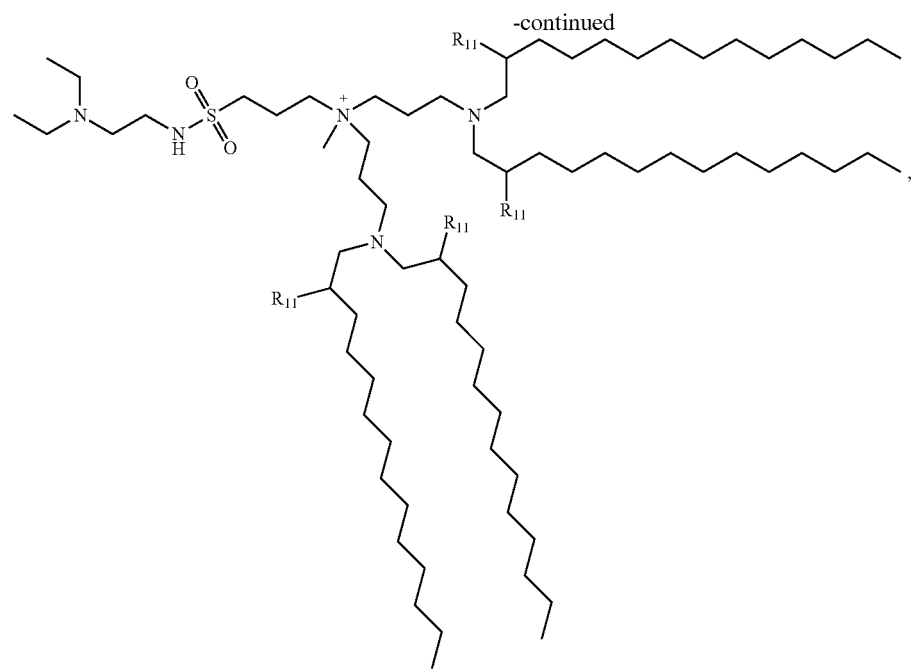
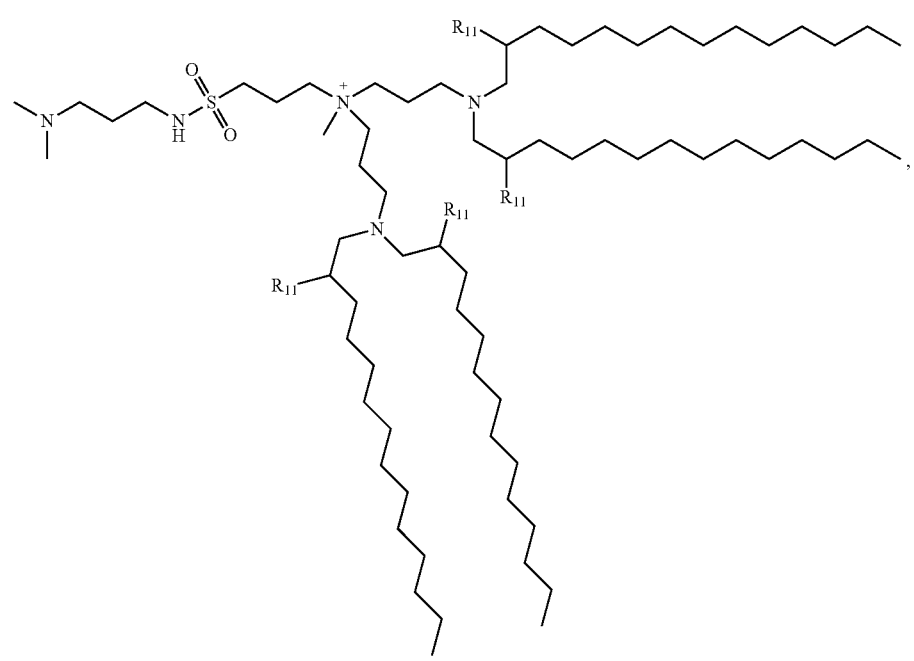

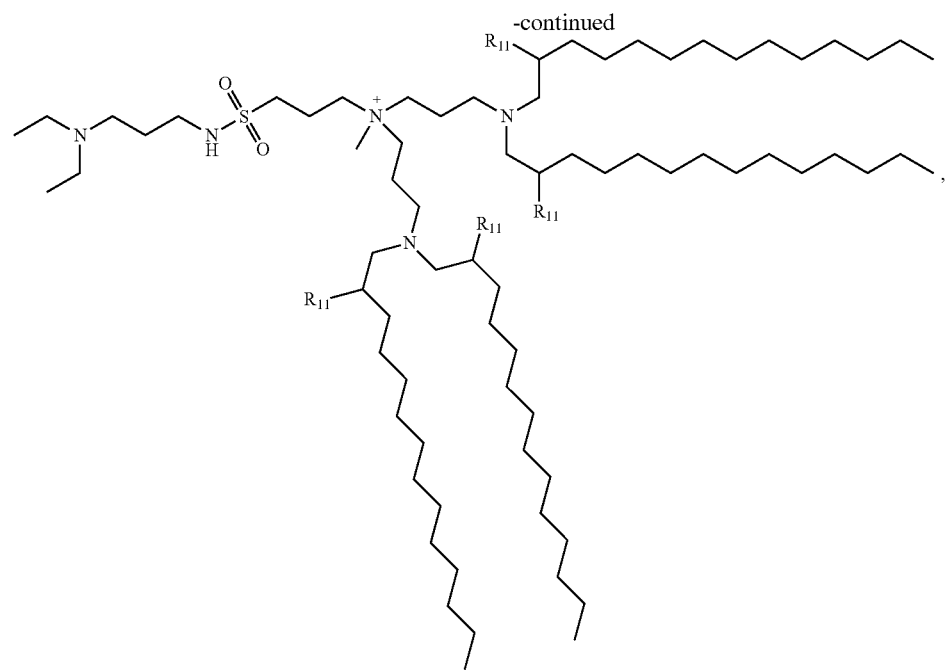

-continued

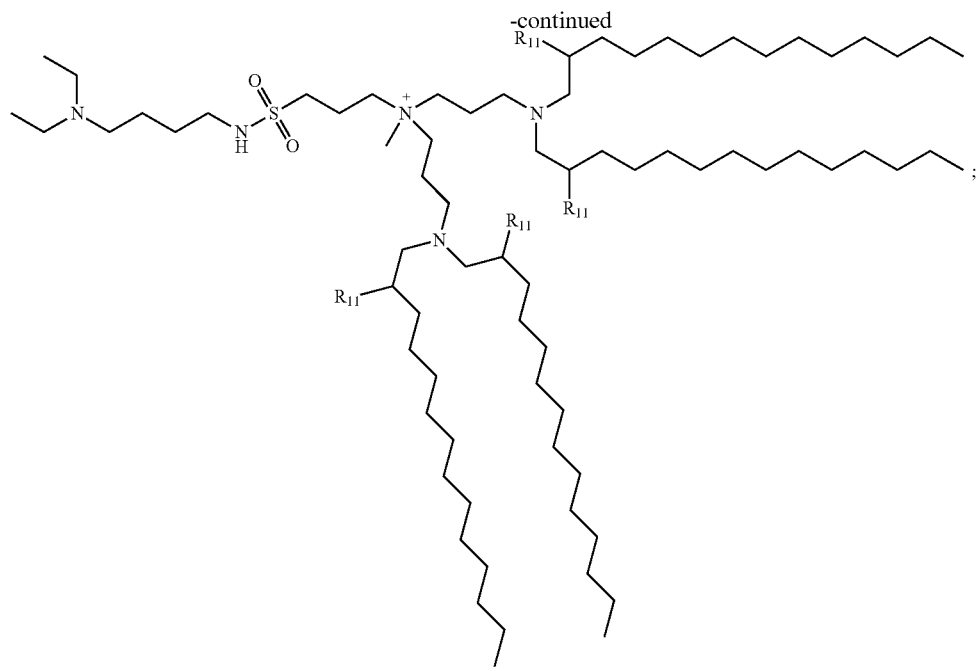

wherein:

$R_{11}$ is hydrogen, halo, hydroxy, or alkoxy$_{(C\leq 8)}$, acyloxy$_{(C\leq 8)}$, or a substituted version of either of these groups; or a pharmaceutically acceptable salt thereof.

In still another aspect, the present disclosure provides compositions comprising:

(A) a compound described herein; and
(B) a nucleic acid.

In some embodiments, the nucleic acid is a therapeutic nucleic acid. In some embodiments, the nucleic acid is a short (small) interfering RNA (siRNA), a microRNA (miRNA), a messenger RNA (mRNA), a cluster regularly interspaced short palindromic repeats (CRISPR) RNA (crRNA), a trans-activating crRNA (tracrRNA), a single guide RNA (sgRNA), a transfer RNA (tRNA), a plasmid DNA (pDNA), a double stranded DNA (dsDNA), a single stranded DNA (ssDNA), a single stranded RNA (ssRNA), a double stranded RNA (dsRNA), a locked nucleic acid (LNA), a peptide nucleic acid (PNA), a miRNA mimic, or a anti-miRNA.

In some embodiments, the nucleic acid is a siRNA such as a siRNA useful in the treatment of cancer. In other embodiments, the nucleic acid is a tRNA such as a tRNA useful for correcting a nonsense mutation. In other embodiments, the nucleic acid is an mRNA. In other embodiments, the nucleic acid is a sgRNA.

In some embodiments, the compositions further comprise a steroid or steroid derivative. In some embodiments, the steroid or steroid derivative is a sterol such as cholesterol. In some embodiments, the compositions further comprise a phospholipid. In some embodiments, the phospholipid is a phosphatidylcholine. In other embodiments, the phospholipid is distearoylphosphatidyl-choline. In some embodiments, the compositions further comprise a PEG lipid. In some embodiments, the PEG lipid is a PEGylated diacylglycerol such as PEGylated dimyristoyl-sn-glycerol. In other embodiments, the PEG lipid is:

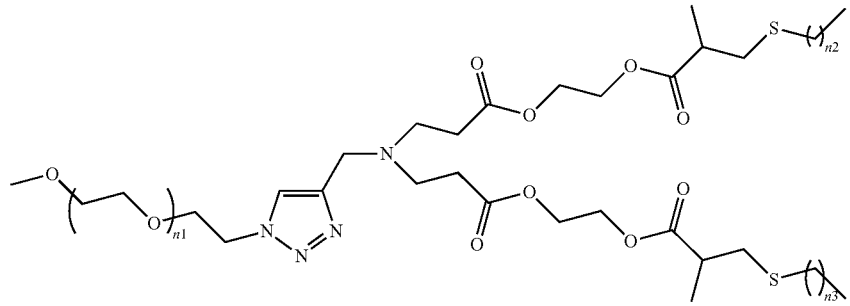

wherein:

$n_1$ is an integer from 1 to 250; and $n_2$ and $n_3$ are each independently selected from 5, 6, 7, 8, 9, 10, 11, 12, 13, 14, 15, 16, 17, 18, 19, 20, 21, 22, or 23.

In some embodiments, $n_1$ is 5 to 100. In some embodiments, $n_1$ is 45. In some embodiments, $n_2$ is 11, 12, 13, 14, 15, 16, or 17. In some embodiments, $n_2$ is 15. In some embodiments, $n_3$ is 11, 12, 13, 14, 15, 16, or 17. In some embodiments, $n_3$ is 15.

In some embodiments, the compositions comprise a mole ratio of the compound to the nucleic acid from about 5:1 to about 1000:1. In some embodiments, the mole ratio of the compound to the nucleic acid is from about 100:1 to about 1000:1. In some embodiments, the mole ratio is about 166:1. In other embodiments, the mole ratio is from about 250:1 to about 750:1 such as about 333:1 or about 666:1. In some embodiments, the compositions comprise a ratio of the compound to the steroid or steroid derivative from about 1:1 to about 20:1 such as from about 1:1 to about 6:1. In some embodiments, the ratio is from about 1.3:1. In some embodiments, the compositions comprise a ratio of the compound to the phospholipid is from about 1:1 to about 9:1 such as from about 2.5:1 to about 7.5:1. In some embodiments, the ratio is about 5:1. In some embodiments, the compositions comprise a ratio of the compound to the PEG-lipid is from about 2.5:1 to about 100:1 such as from about 7.5:1 to about 50:1. In some embodiments, the ratio is about 100:3. In some embodiments, the compositions comprise a ratio of the compound to the steroid or steroid derivative to the phospholipid to the PEG lipid is from about 25:57:15:3 to about 75:19:5:1 such as about 50:38.5:10:1.5.

In some embodiments, the compositions further comprise a pharmaceutically acceptable carrier. In some embodiments, the compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the compositions are formulated for aerosol, intravenous, intraperitoneal, subcutaneous, topical, or oral administration. In other embodiments, the compositions are formulated for injection such as for intraperitoneal injection or intravenous injection. In some embodiments, the compositions are formulated for inhalation.

In still yet another aspect, the present disclosure provides methods of treating a disease or disorder in a patient in need thereof comprising administering to the patient a therapeutically effective amount of a compound or composition described herein.

In some embodiments, the disease or disorder is a genetic disease such as a disease associated with a nonsense mutation. In some embodiments, the disease or disorder is cystic fibrosis, NGLY1 deficiency, Duchene muscular dystrophy, thalassemia, Hurler syndrome, or Dravet syndrome.

In some embodiments, the disease or disorder is cystic fibrosis. In some embodiments, the methods further comprise a second therapeutic agent. In some embodiments, the second therapeutic agent is another cystic fibrosis therapy. In some embodiments, the second therapeutic agent is a therapeutic agent useful for the management of cystic fibrosis. In some embodiments, the second therapeutic agent is an antibiotic, an agent useful for maximizing organ function, or an agent useful for reducing or altering the mucosal layer of the lungs. In some embodiments, the second therapeutic agent is an inhaled antibiotic, an oral antibiotic, ivacaftor, dornase alfa, hypertonic saline, denufosol, or a corticosteroid. In some embodiments, the methods further comprise a second therapeutic modality. In some embodiments, the second therapeutic modality is mechanical method of removing or reducing sputum.

In other embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is liver cancer, lung cancer, ovarian cancer, pancreatic cancer, breast cancer, leukemia cancer, or bone cancer. In some embodiments, the cancer is lung cancer or colorectal cancer. In some embodiments, the cancer has a nonsense mutation in a tumor suppressor gene such as a mutation in the p53 gene. In some embodiments, the nonsense mutation is a mutation in the p53 gene in a lung cancer. In other embodiments, the nonsense mutation is in the APC gene such as a mutation in the APC gene in a colorectal cancer. In other embodiments, the nonsense mutation is in the LKB1, ERCC3, WRN, BRCA2, IDH1, or ARID1A gene. In some embodiments, the cancer is a hepatitis B driven hepatocellular carcinoma.

In some embodiments, the methods further comprise a second cancer therapy. In some embodiments, the second cancer therapy is a second chemotherapeutic agent, an immunotherapy, a genetic therapy, or surgery. In some embodiments, the patient is a mammal such as a human. In some embodiments, the methods comprise administering the composition once. In other embodiments, the methods comprise administering the composition two or more times.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

As used in this application, the term "average molecular weight" refers to the relationship between the number of moles of each polymer species and the molar mass of that species. In particular, each polymer molecule may have different levels of polymerization and thus a different molar mass. The average molecular weight can be used to represent the molecular weight of a plurality of polymer molecules. Average molecular weight is typically synonymous with average molar mass. In particular, there are three major types of average molecular weight: number average molar mass, weight (mass) average molar mass, and Z-average molar mass. In the context of this application, unless otherwise specified, the average molecular weight represents either the number average molar mass or weight average molar mass of the formula. In some embodiments, the average molecular weight is the number average molar mass. In some embodiments, the average molecular weight may be used to describe a PEG component present in a lipid.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the description presented herein.

(FIG. 43A) Blotting with tx-FLAG antibody in the pool of cells after Blasticidin S selection. (FIG. 43B) Luciferase expression of single cell clones as evaluated by the One-Glo assay (5,000 cells, 48 h growth). (FIG. 43C) Cas9 expression of single cell clone 2 of HeLa-Luc-Cas9 blotted with α-Cas9.

FIG. 49 shows the optimization of the ZA3-Ep10 ZNPs for mRNA delivery was performed in IGROV1 cells. The weight ratio of the ZAL:mRNA was set at 20:1, 10:1, 7.5:1 and 5:1. The lipid mix was prepared with a relative molar ratio of 50:38.5:n, ZAL:cholesterol:PEG-lipid, where n=5, 2, 1 or 0.5. Cells were treated in 96-well plates with 100 ng mRNA and incubated for the indicted time (18 h light gray, 26 h gray, 45 h dark gray) prior to evaluation of cell viability (dots) and luciferase expression (bars) using the One-Glo+ Tox assay. Cell viability was determined compared to untreated cells and luminescence was normalized to viability to determine relative luminescence. Values are plotted as a mean+/−standard deviation, N=4.

Figure 50:
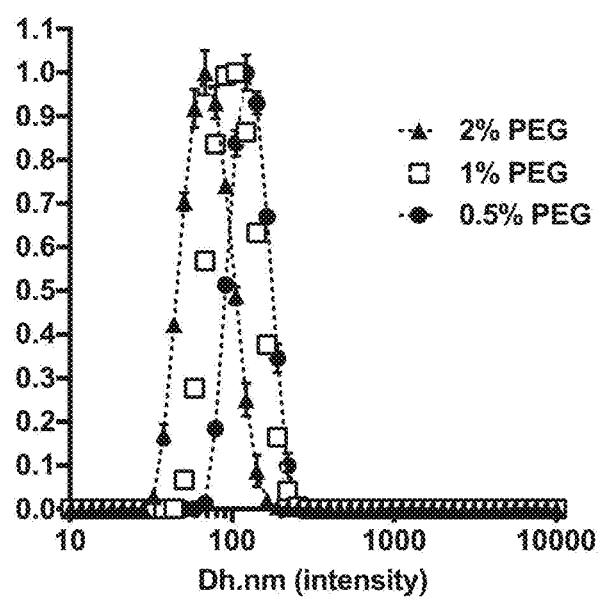

FIG. 50 shows the effect of PEG lipid composition of ZA3-Ep10 Luc mRNA NPs formulated for in vivo assays. The ZAL:cholesterol ratio was fixed at 50:38.5 molar ratio while PEG-lipid was included at the indicated percentage. As expected increased PEG leads to smaller particle size, but poorer expression of mRNA.

Figure 51:
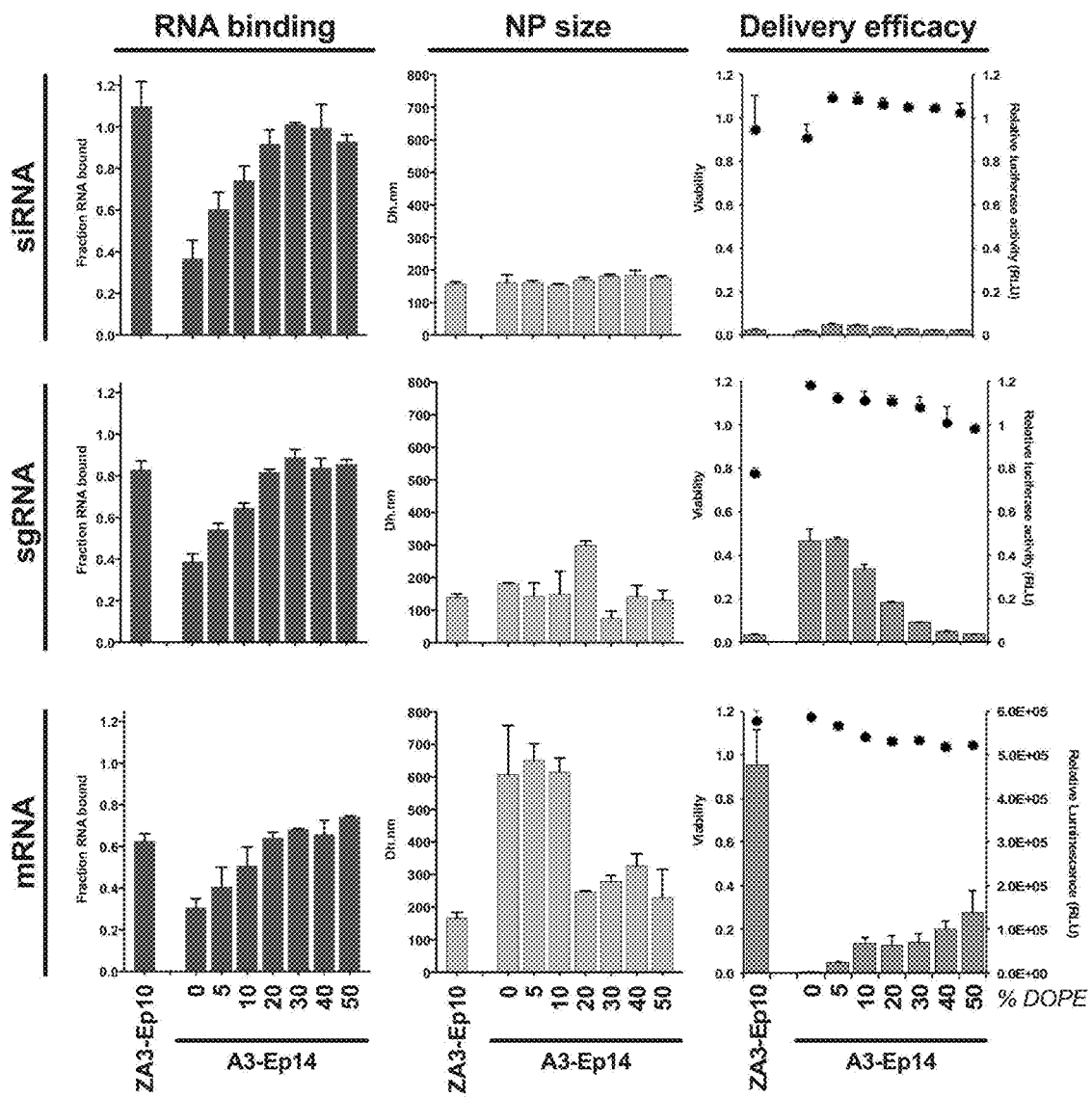

FIG. 51 shows that comparing the RNA encapsulation, nanoparticle size, and delivery efficacy of ZA3-Ep10 and a cationic structural analogue (A3-Ep14, also referred to as C14-110 in the literature (Love et al., 2010)), which is known to deliver small RNA. The ZNP or LNP formulation was fixed at 7.5:1 weight ratio ZAL or Cationic analogue to RNA. The lipid mixture for the NPs was 50:38.5:0.5 ZAL or cationic analogue: cholesterol: PEG-lipid, while for the A3-Ep14 NPs the zwitterionic phospholipid was titrated from 0 to 50% in the lipid mix. The nanoparticles were formulated by manual mixing using the in vitro formulation protocol. RNA binding was determined by the Ribogreen assay (N=3+/−standard deviation), while nanoparticle size was determined by dynamic light scattering (N=3+/−standard deviation). Luciferase silencing or editing of siLuc and sgLuc NPs was assayed in HeLa-Luc-Cas9 cells (7.35 nM sgRNA, 17.9 nM siRNA), while luciferase expression by Luc mRNA NPs was evaluated in IGROV1 cells (0.77 nM mRNA). Cells were assays after 40 h incubation time by the One-Glo+Tox assay and plotted with viability (dots) and luciferase expression (bars) as mean+/−standard deviation (N=4).

Figure 52:
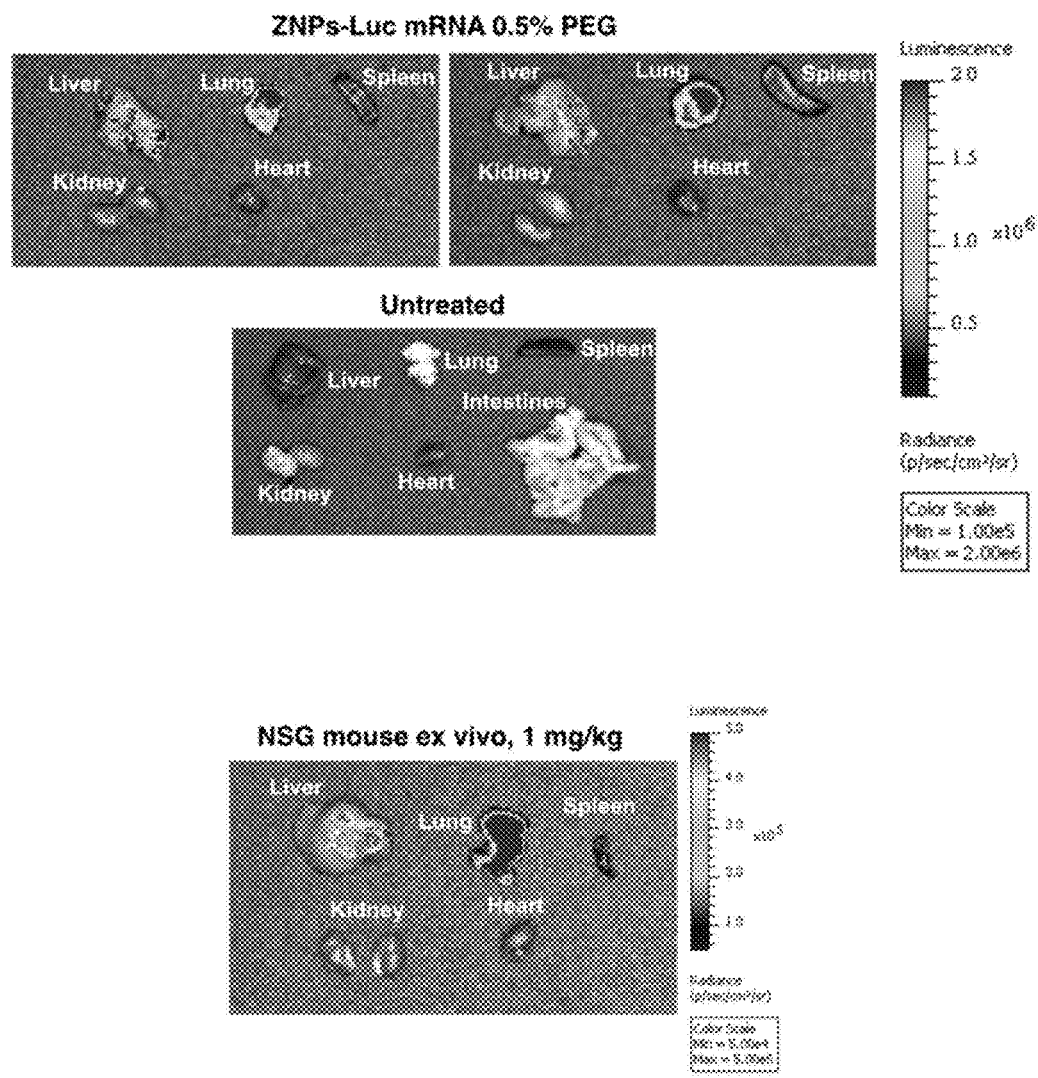

FIG. 52 shows bioluminescence imaging shows that in vivo expression of luciferase after Luc-mRNA administration by i.v. injection correlates with in vitro activity. Mice were injected with 1 mg/kg Luc mRNA and imaged 24 h after treatment. An untreated mouse was used as a negative control. The top right panel shows the ex vivo expression of the animal shown in FIG. 65E.

FIGS. 53A & 53B show quantitation of the ex vivo images by ROI analysis. (FIG. 53A) Quantitation of the athymic nude mice images shown in FIG. 52 (top) and (FIG. 53B) quantitation images of the images in FIG. 51 (bottom, NSG) and FIG. 65F (C57BL/6). A minimum of 5 ROIs per organ was measured and plotted as mean+/−S.E.M.

FIG. 54 shows co-delivery of Cas9 mRNA and sgLuc leads to editing in staged delivery at 2 µg per well Cas9 mRNA and 1 µg sgLuc in a 6-well plate in both A549-Luc and HeLa-Luc. Meanwhile, unguided Cas9, Cas9-sgCtrl, or sgLuc alone do not show edited bands. The expected genomic DNA amplicon was 510 bp while the expected cut bands indicating editing are 233 bp and 277 bp (arrows).

Figure 55:
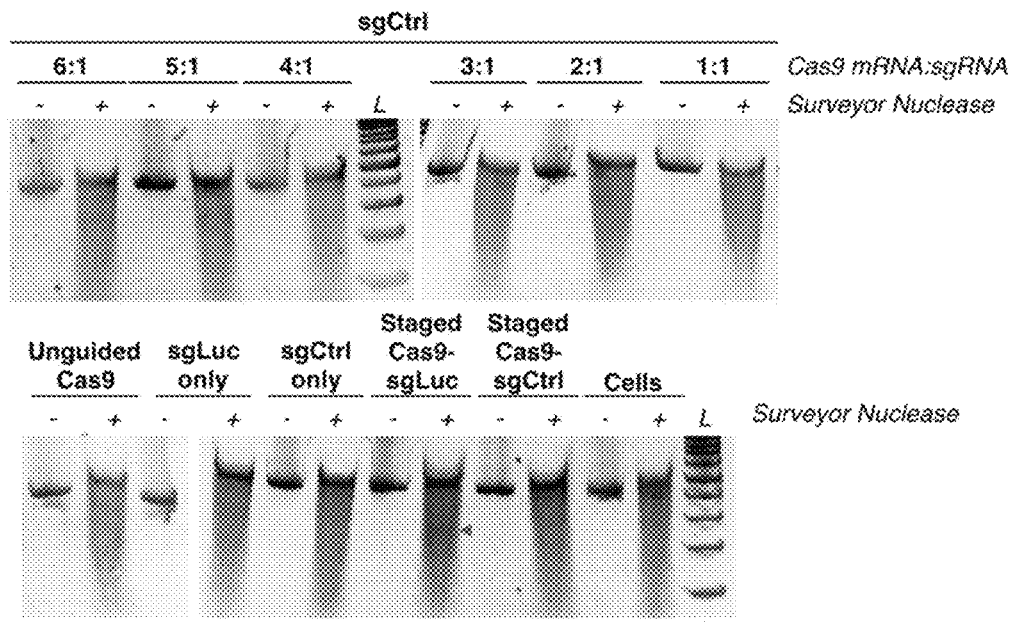

FIG. 55 shows control ZNPs (Cas9+sgCtrl, unguided Cas9, sgLuc only and sgCtrl only) did not show editing of luciferase target in A549-Luc cells. Staged co-delivery shows editing with sgLuc under similar conditions with 2:1 Cas9 mRNA:sgLuc wr.

Figure 56:
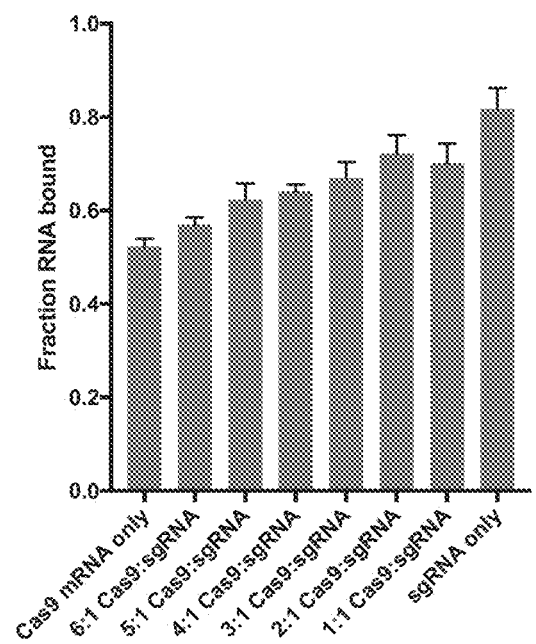

FIG. 56 shows the encapsulation of Cas9 mRNA and sgRNA in co-delivery ZNPs. ZAL: total RNA was fixed at 7.5:1, with a lipid mixture of 50:38.5:0.5 ZA3-Ep10: cholesterol: PEG-lipid. Data are plotted as mean+/−standard deviation (N=4).

Figure 57:
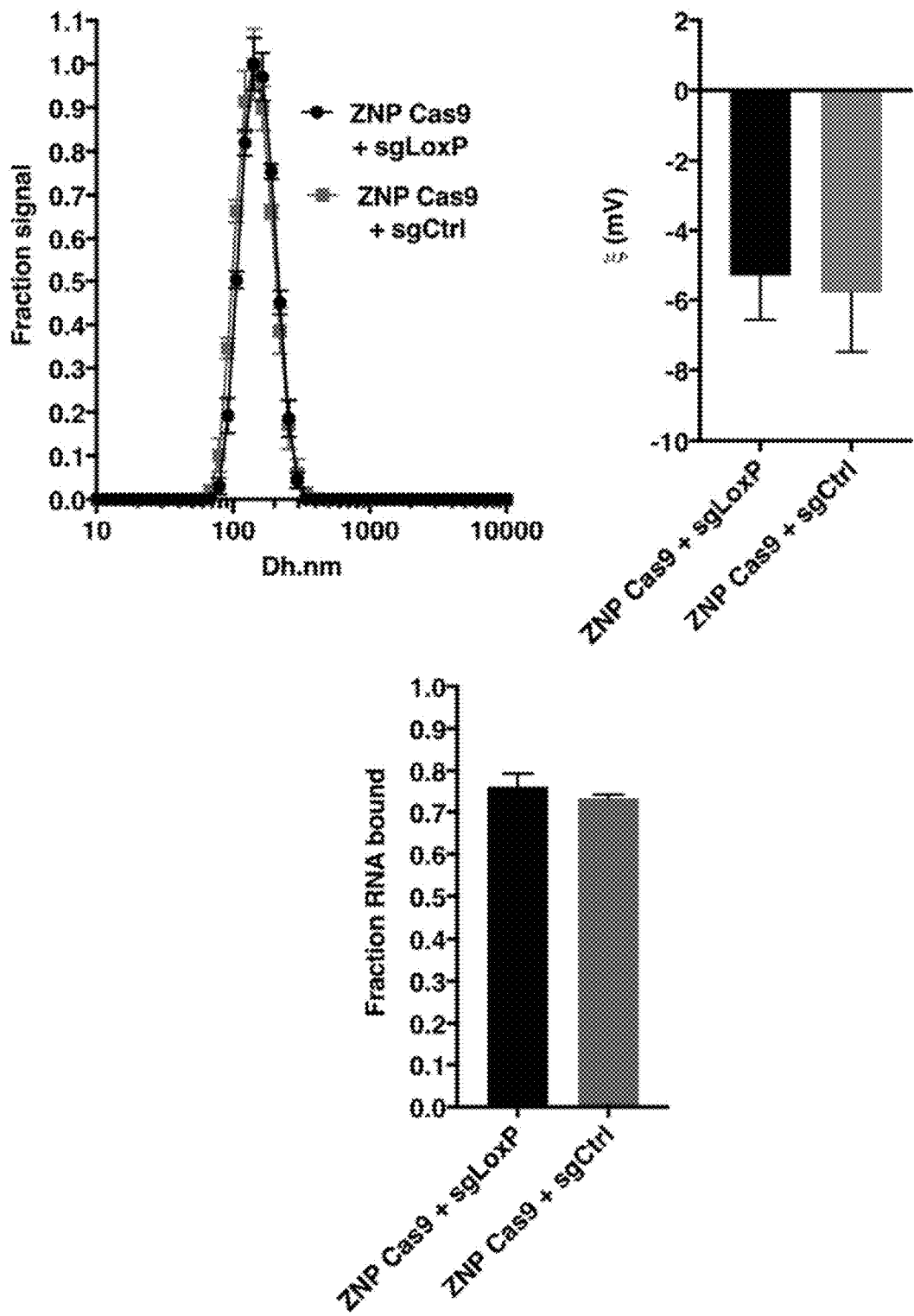

FIG. 57 shows particle properties of in vivo administered ZNPs encapsulating Cas9 mRNA and sgRNA. For size and zeta potential measurements, N=5 for RNA encapsulation N=4. Data are plotted as mean+/−standard deviation.

FIG. 58 shows the Cre recombinase AAV positive control demonstrates expression of tdTomato in liver ex vivo at the whole organ level and in cells from tissue sections.

Figure 59:
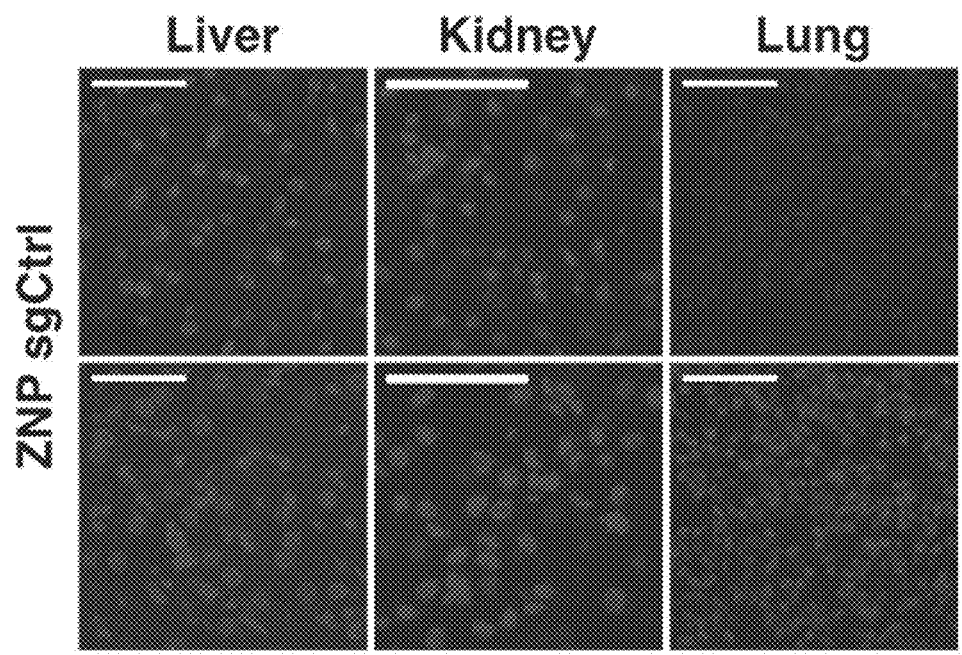

FIG. 59 shows the delivery of ZA3-Ep10 ZNPs encapsulating Cas9 mRNA and sgCtrl does not show any tdTomato positive cells in sectioned tissue slides.

Figure 60:
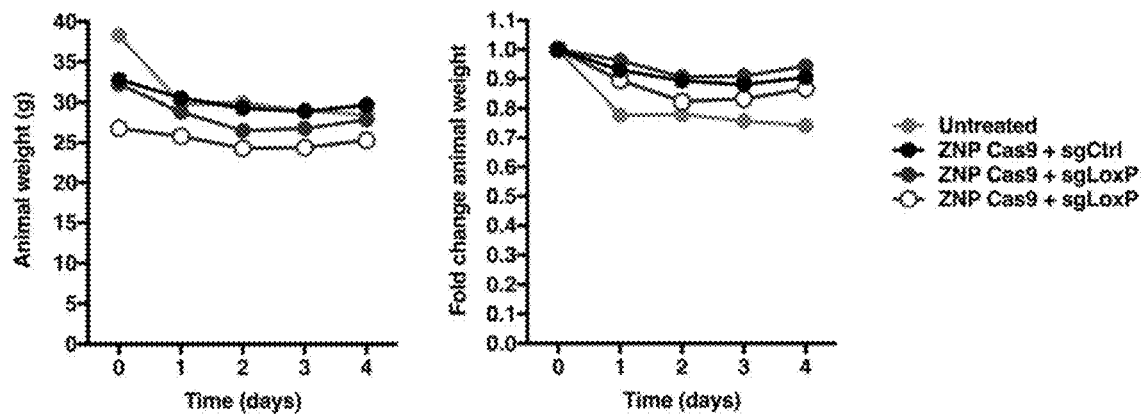

FIG. 60 shows the measurement of animal body weight after systemic administration of ZA3-Ep10 ZNPs encapsulating Cas9 mRNA and sgRNA at 5 mg/kg total RNA dose.

FIG. 61 shows the quantification of tdTomato positive hepatocytes in animals treated with ZNPs as determined by flow cytometry of isolated primary hepatocytes. The left panel shows representative plots of samples from an untreated LSL-tdTO mouse and a ZNP-Cas9 mRNA-sgLoxP treated mouse. Mouse 1 and mouse 2 were treated at 2 mg/kg total RNA 2 times on consecutive days, while mouse 3 received a single dose at 5 mg/kg total RNA and all animals were harvested ~1 week after ZNP administration. Each sample was run four times and values are plotted as mean+/−standard deviation.

Figure 62:
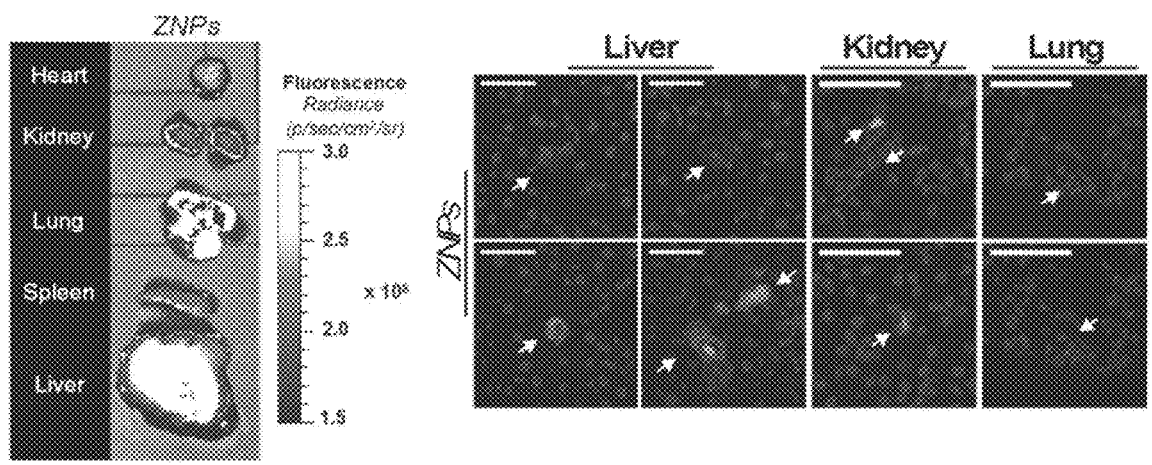

FIG. 62 shows that a ZNP treated tdTomato mouse shows significant fluorescent signal in the liver and kidneys 2 months after editing by ZA3-Ep10 ZNPs encapsulating Cas9 mRNA and sgLoxP (5 mg/kg).

FIGS. 63A-63D shows that ZNPs enable permanent CRISPR/Cas-mediated DNA editing. (FIG. 63A) Sequence specific silencing of luciferase by siRNA (9 nM) and editing by sgRNA (7 nM) in HeLa-Luc-Cas9 cells. N=4±stdev, ****p<0.0001 (FIG. 63B) Kinetically, silencing with siRNA is transient while sgRNA delivery results in permanent loss of luciferase signal after 2 days. (FIG. 63C) Sequence specific editing of luciferase was confirmed by the Surveyor assay. (FIG. 63D) The chemical structure of ZA3-Ep10.

Figure 64:
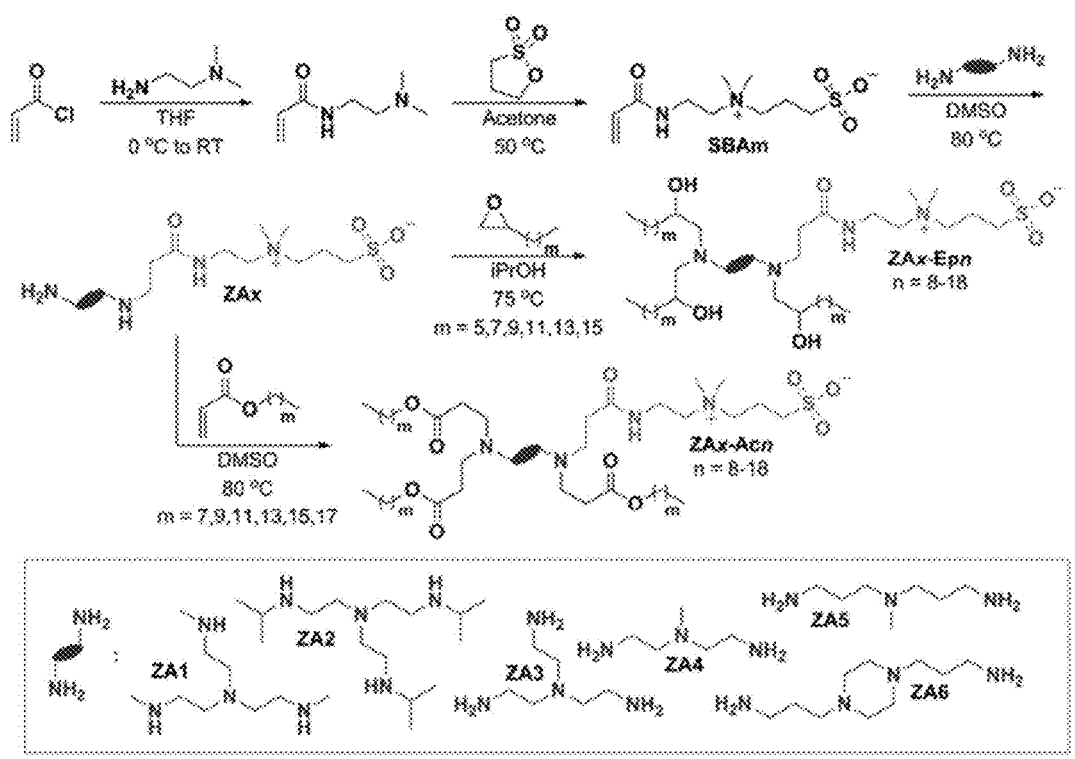

FIG. 64 shows ZALs were designed to increase molecular interactions with longer RNAs by combining the chemical and structural roles of zwitterionic lipids and cationic lipids into a single lipid compound. High efficiency reactions provided access to a library of unique charge unbalanced lipids.

FIGS. 65A-65F show ZNPs enable delivery of long RNAs both in vitro and in vivo. (FIG. 65A) ZA3-Ep10 ZNPs (ZAL:cholesterol:PEG-lipid=100:77:1 (mol); ZAL: RNA=7.5:1 (wt)) are uniform for both sgRNA and mRNA. (FIG. 65B) ZA3-Ep10 sgRNA ZNPs show dose-responsive Luc editing in HeLa-Luc-Cas9 cells. ZA3-Ep10 ZNPs can also deliver (FIG. 65C) mCherry mRNA (18 h) and (FIG. 65D) luciferase mRNA (24 h) to IGROV1 cells. (FIG. 65E) In vivo luciferase expression was achieved by systemic i.v. administration of ZA3-Ep10 Luc mRNA ZNPs (24 h). Bioluminescence imaging both in vivo (FIG. 65E, athymic nude mice, 1 mg/kg) and ex vivo (FIG. 65F, C57BL/6 mice, 4 mg/kg) revealed expression of luciferase in liver, lung and spleen tissue.

FIGS. 66A-66D show ZNPs enable co-delivery of Cas9 mRNA and sgRNA for CRISPR/Cas editing. (FIG. 66A) The kinetics of mRNA and protein expression after ZNP delivery of Cas9 mRNA (0.48 ng/mL mRNA) to A549-Luc cells. Cas9 mRNA levels (A light gray curve) and protein expression (A black curve, FIG. 66B) were measured over time. (FIG. 66C) ZNPs enable dose responsive expression of Cas9, detectable as low as 0.05 μg/mL delivered mRNA. (FIG. 66D) Surveyor confirmed editing of the luciferase target at mRNA:sgRNA ratios of 3:1 or higher (wt). Co-delivery of Cas9 mRNA and sgCtrl showed no editing (FIG. 55).

Figures 67A, 67B, 67C:
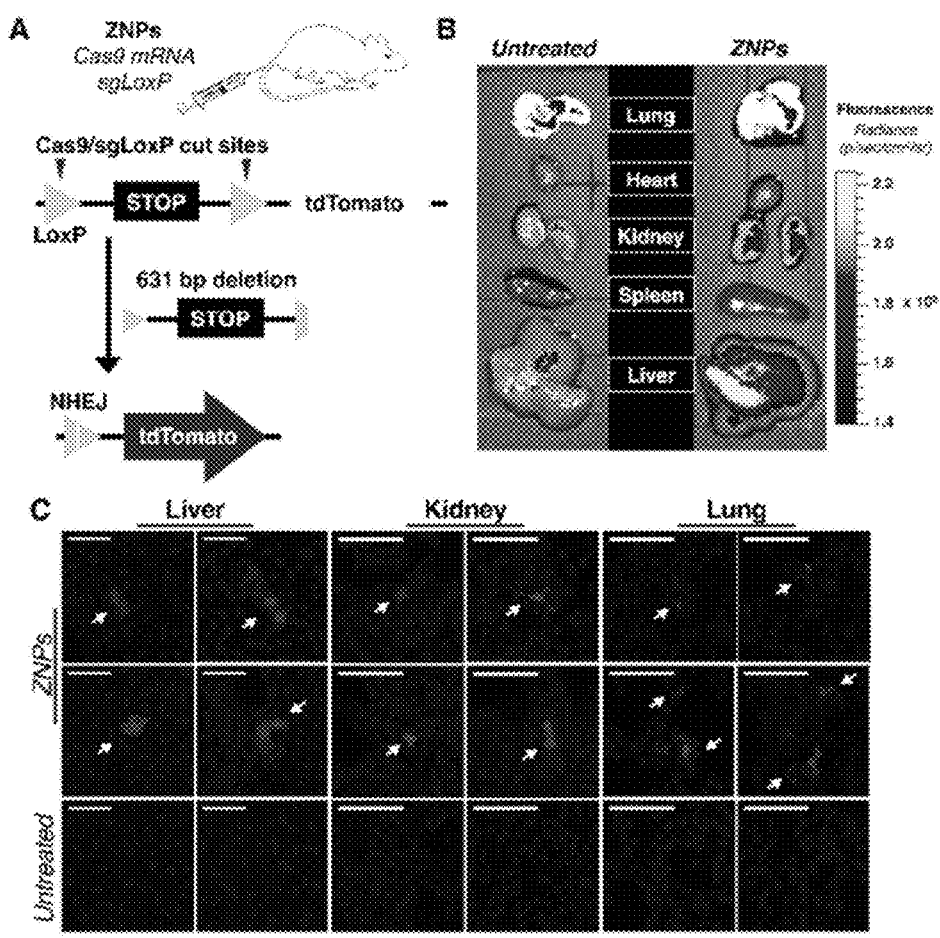

FIGS. 67A-67C show ZNPs enabled non-viral CRISPR/Cas editing in vivo. (FIG. 67A) Schematic representation shows that co-delivery of Cas9 mRNA and sgLoxP deletes the stop cassette and activates downstream tdTomato protein. (FIG. 67B) After administration of ZNPs encapsulating Cas9 mRNA:sgRNA (4:1, wt) at 5 mg/kg total RNA, tdTomato fluorescence was detected in the liver and kidney upon whole organ ex vivo imaging. (FIG. 67C) Confocal fluorescence microscopy of tissue sections showed tdTomato positive cells in liver, lung, and kidneys. Scale bars=50 μm).

Figure 68:
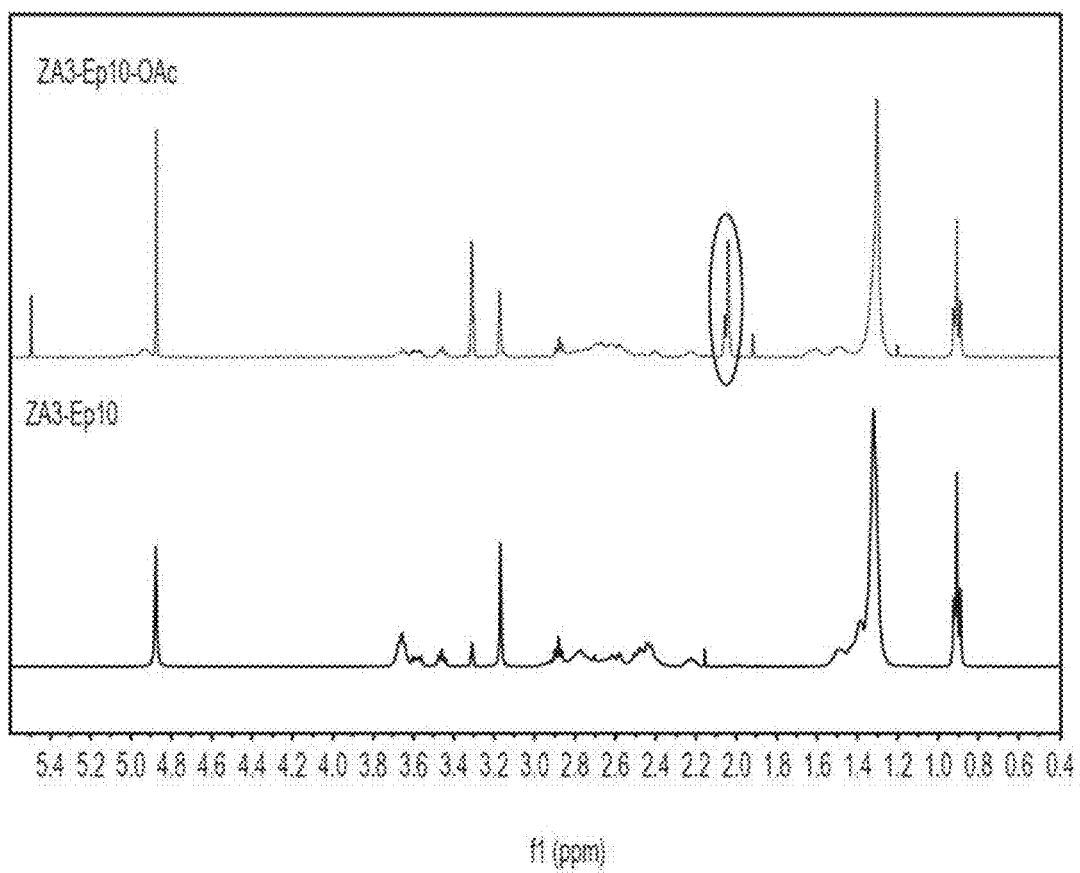

FIG. 68 shows the $^1$H NMR of ZA3-Ep10-OAc (top) relative to ZA3-Ep10 (bottom). The spectrum at the top shows the presence of the methyl group on the acetyl moiety (circle) at about 2 ppm.

Figure 69:
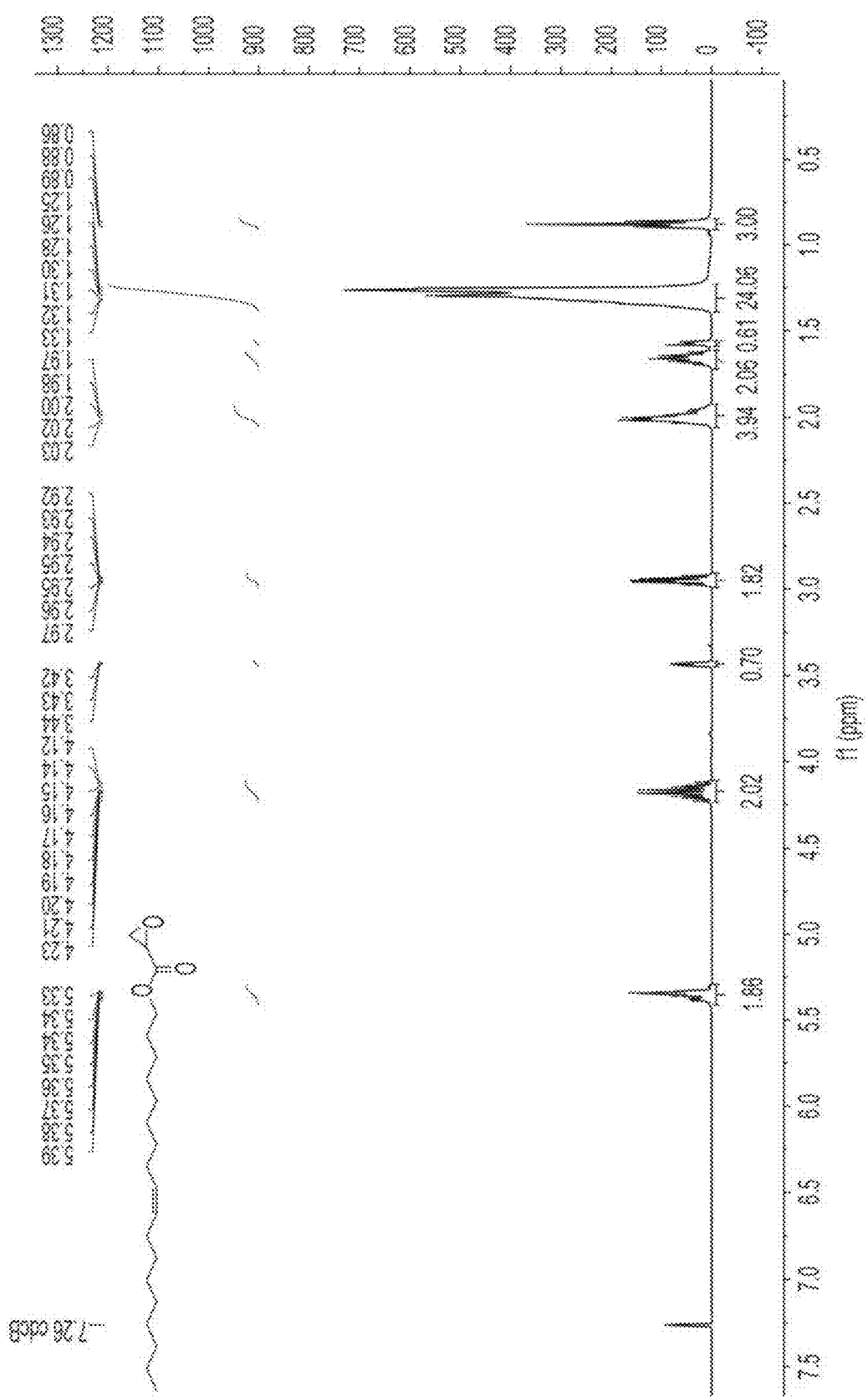

FIG. 69 show the $^1$H NMR spectra for the glycidic ester of oleoyl.

Figure 70A:
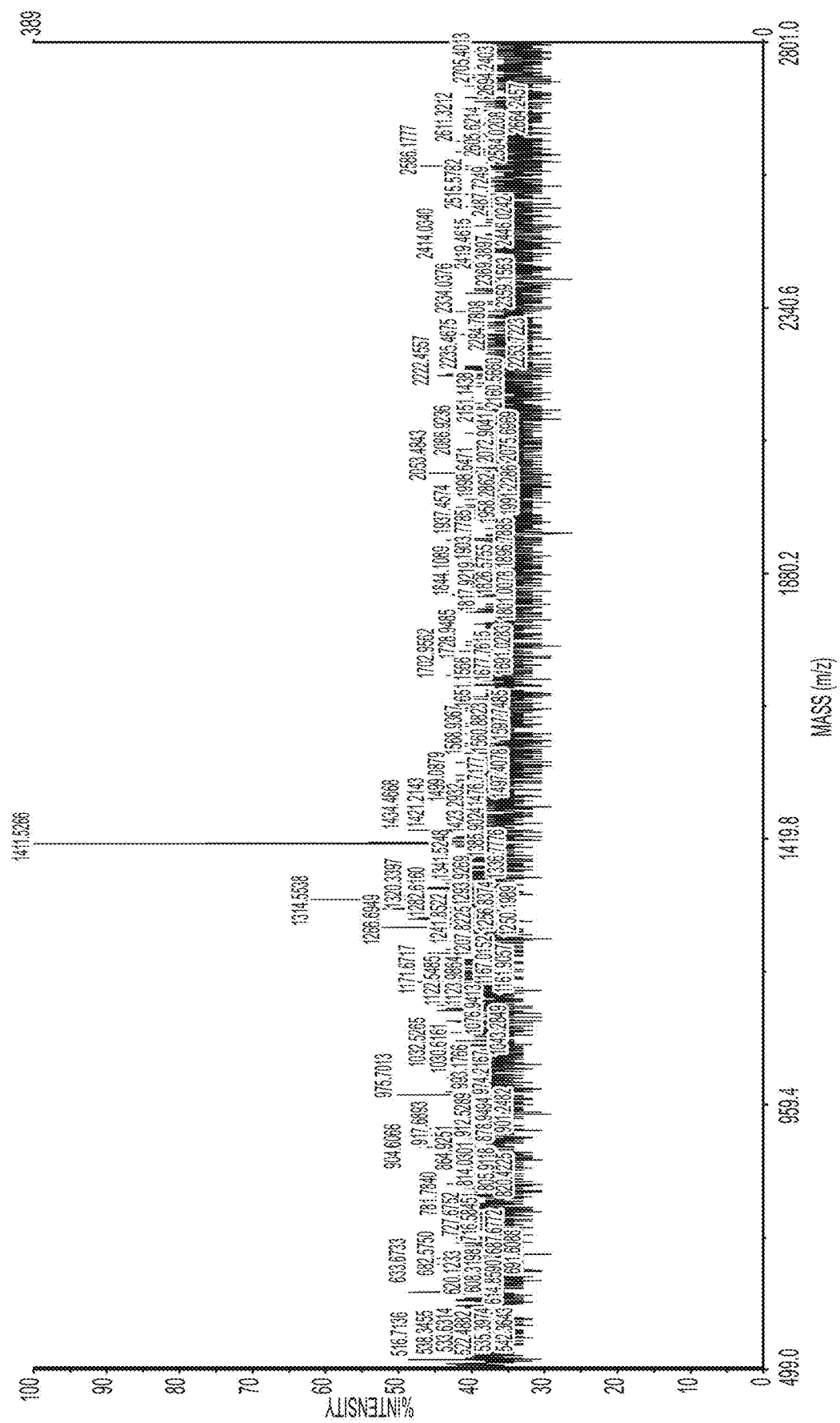
Figure 70B:
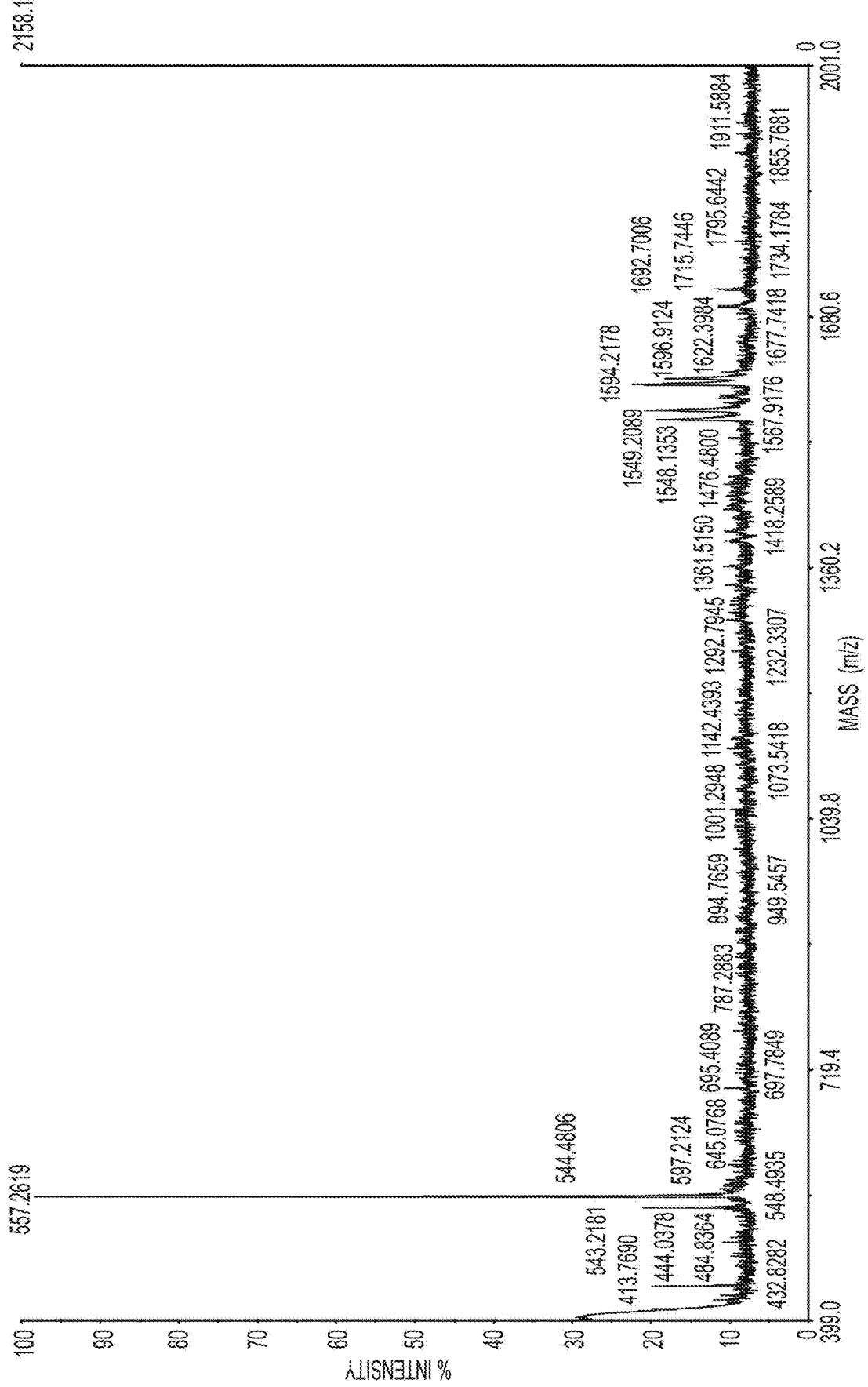
Figure 70C:
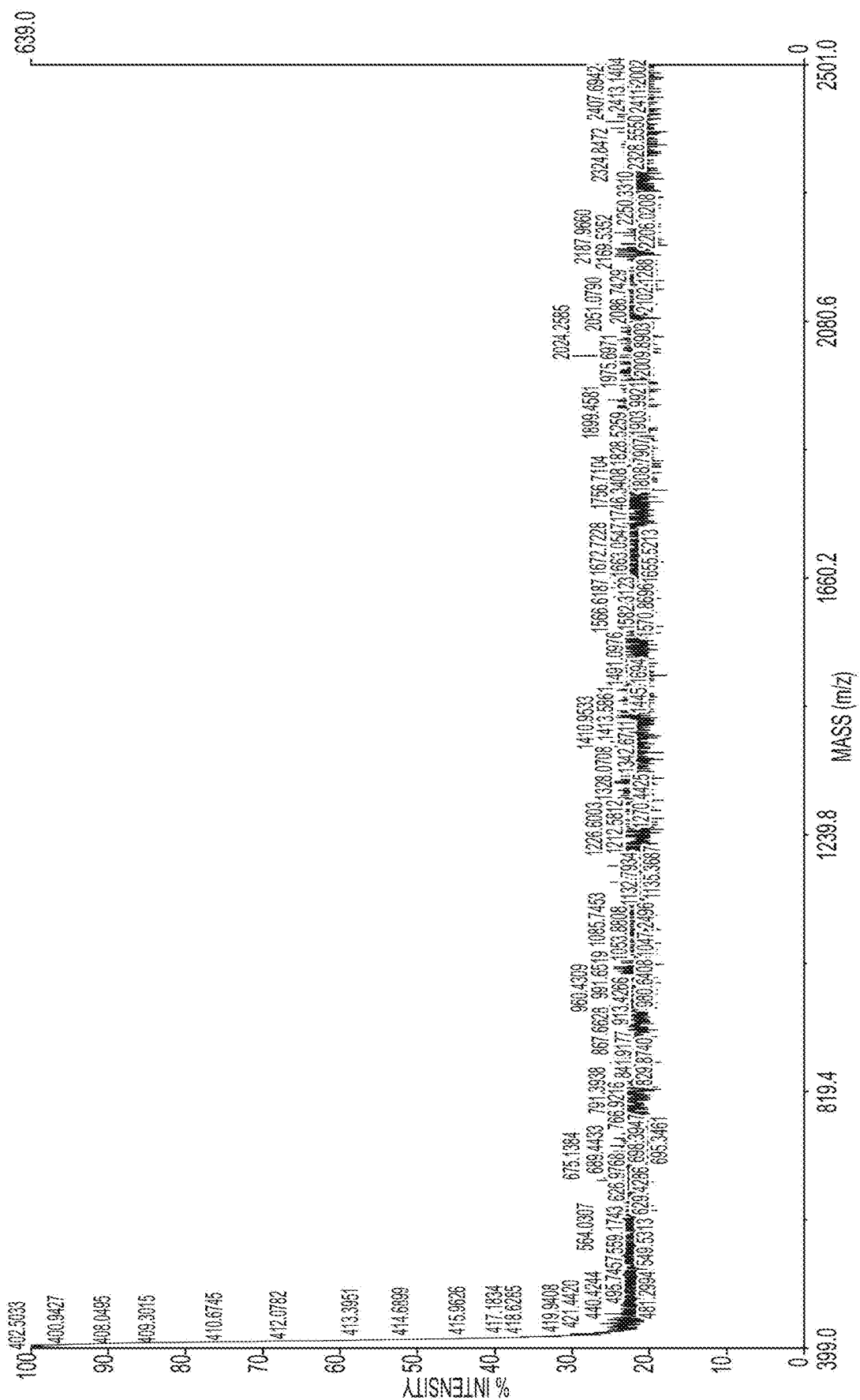
Figure 70D:
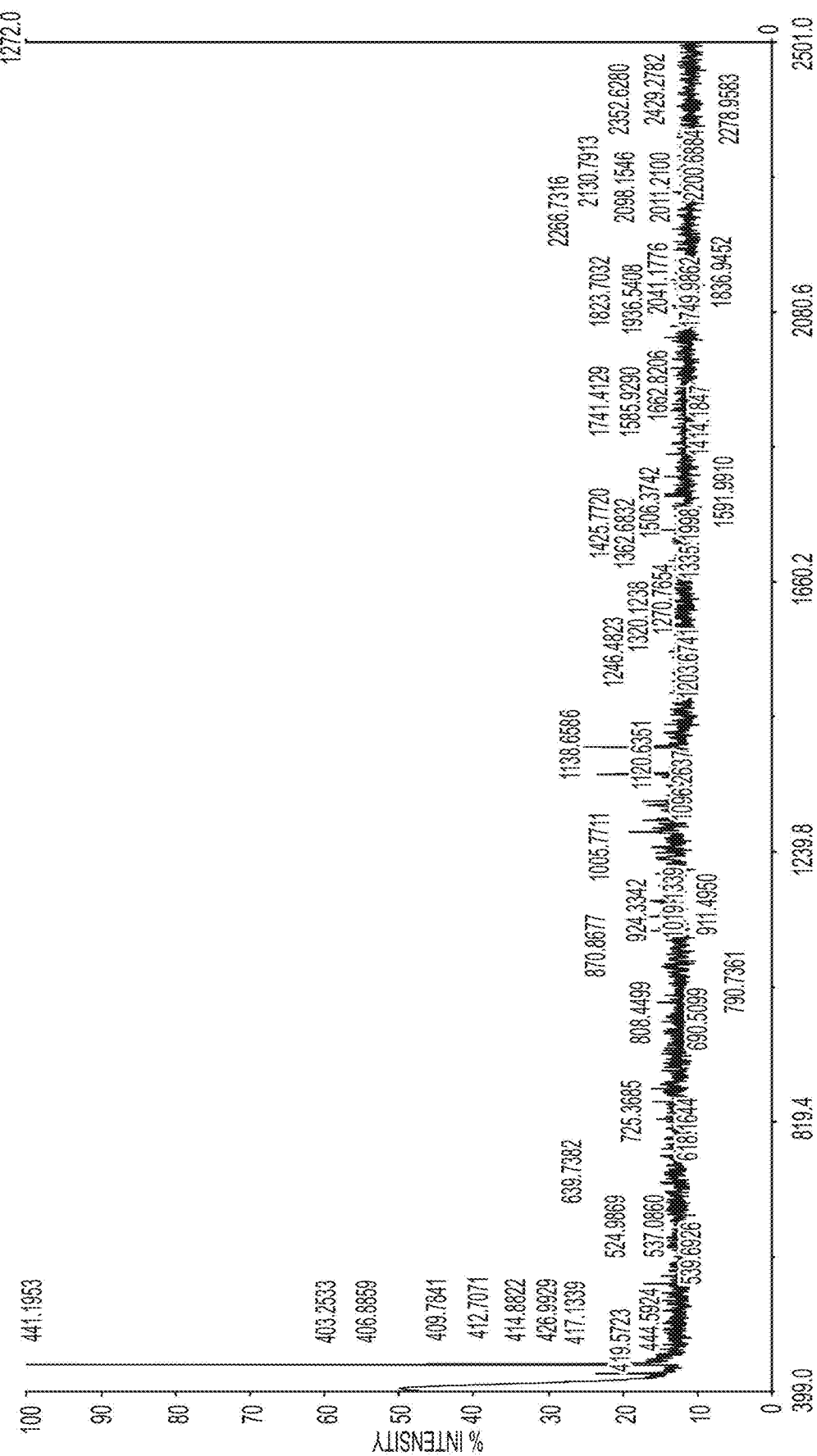
Figure 70E:
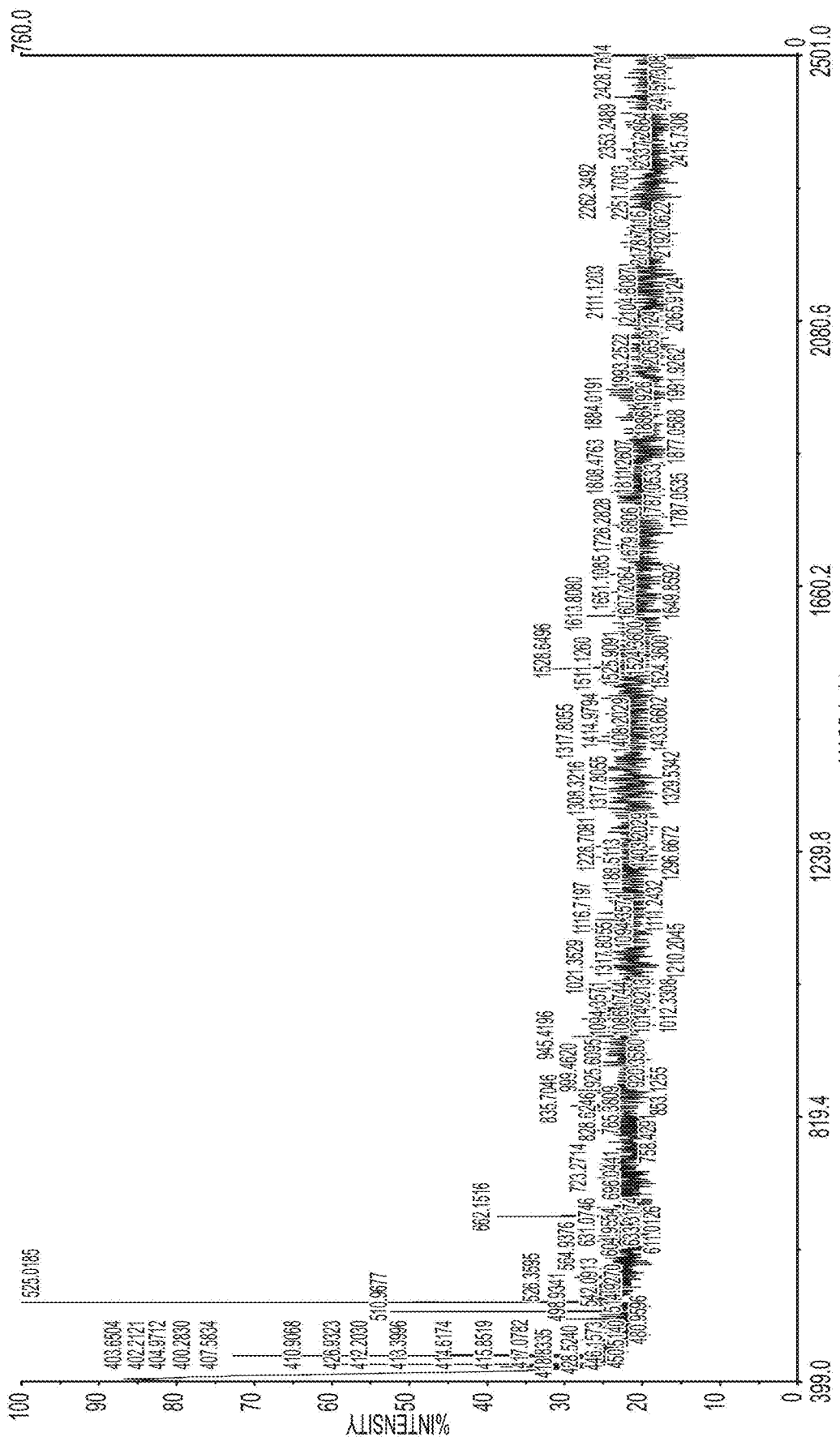
Figure 70F:
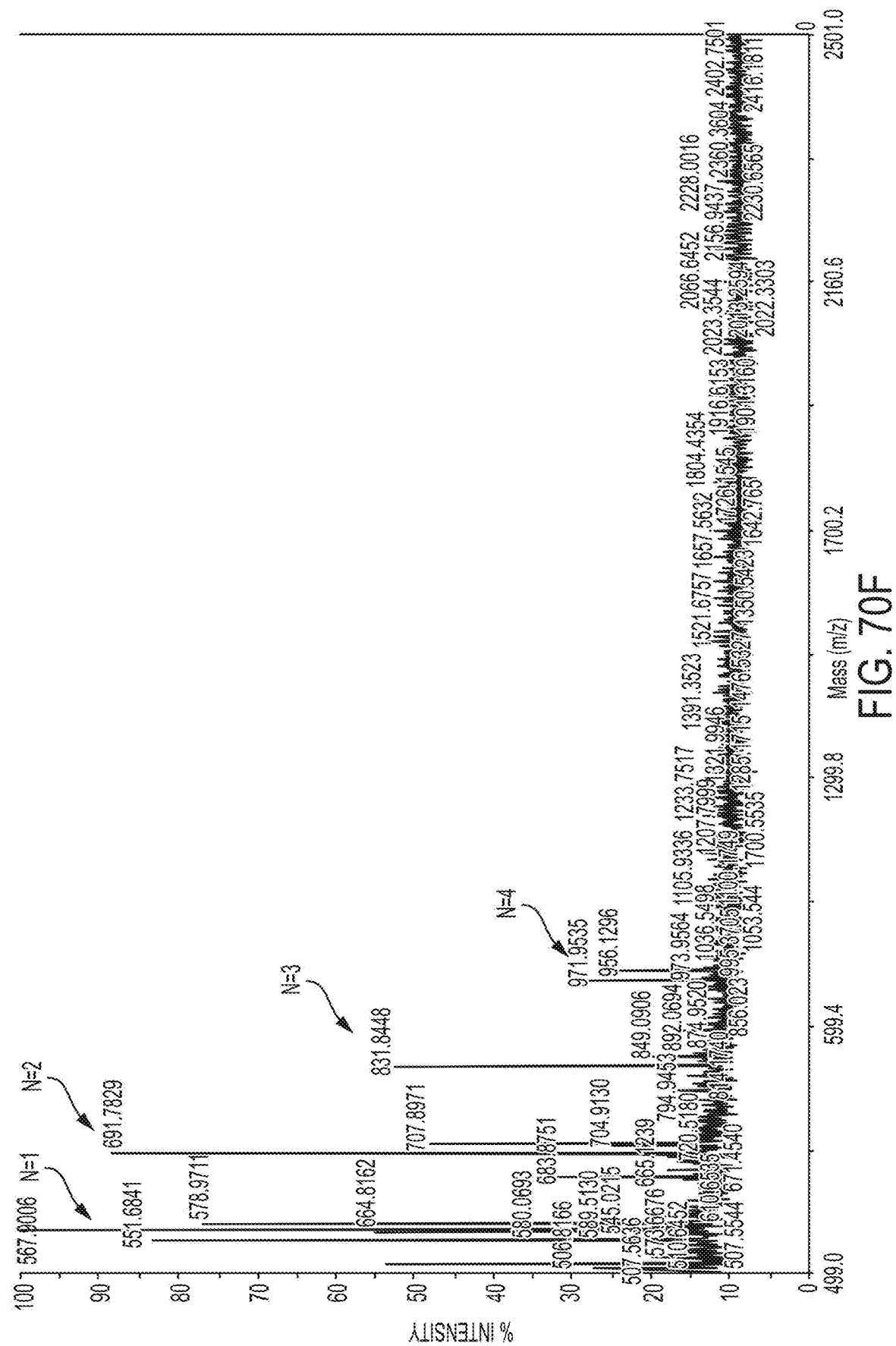
Figure 70G:
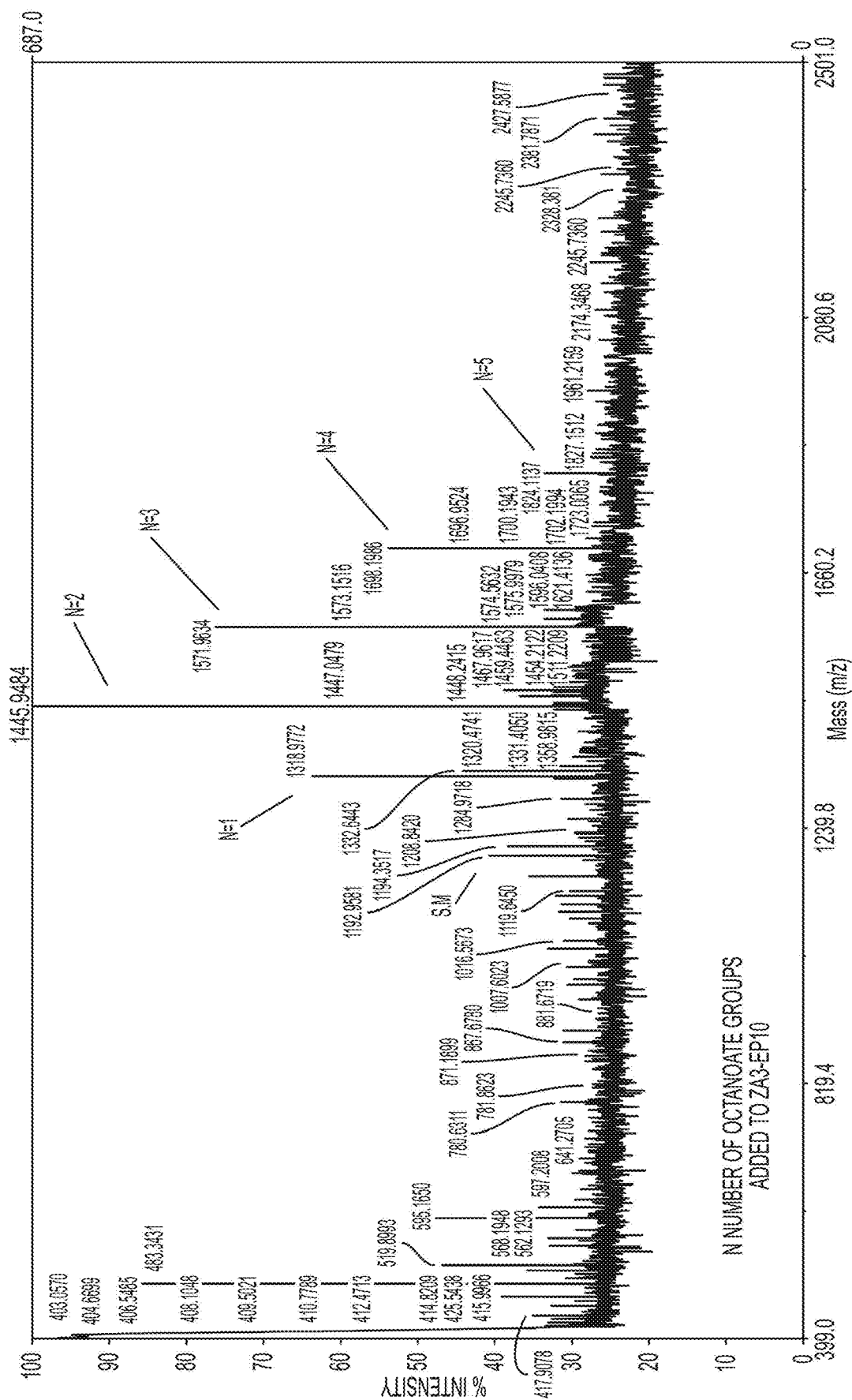
Figure 70H:
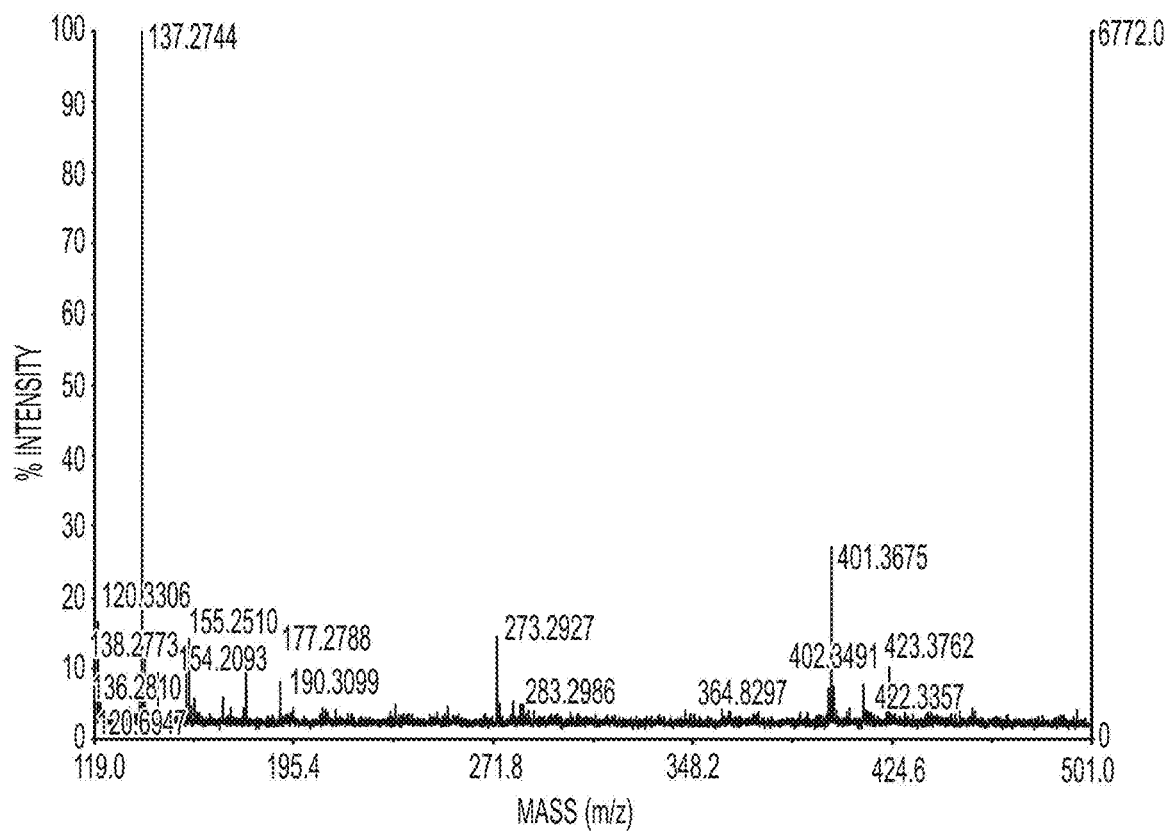
Figure 70I:
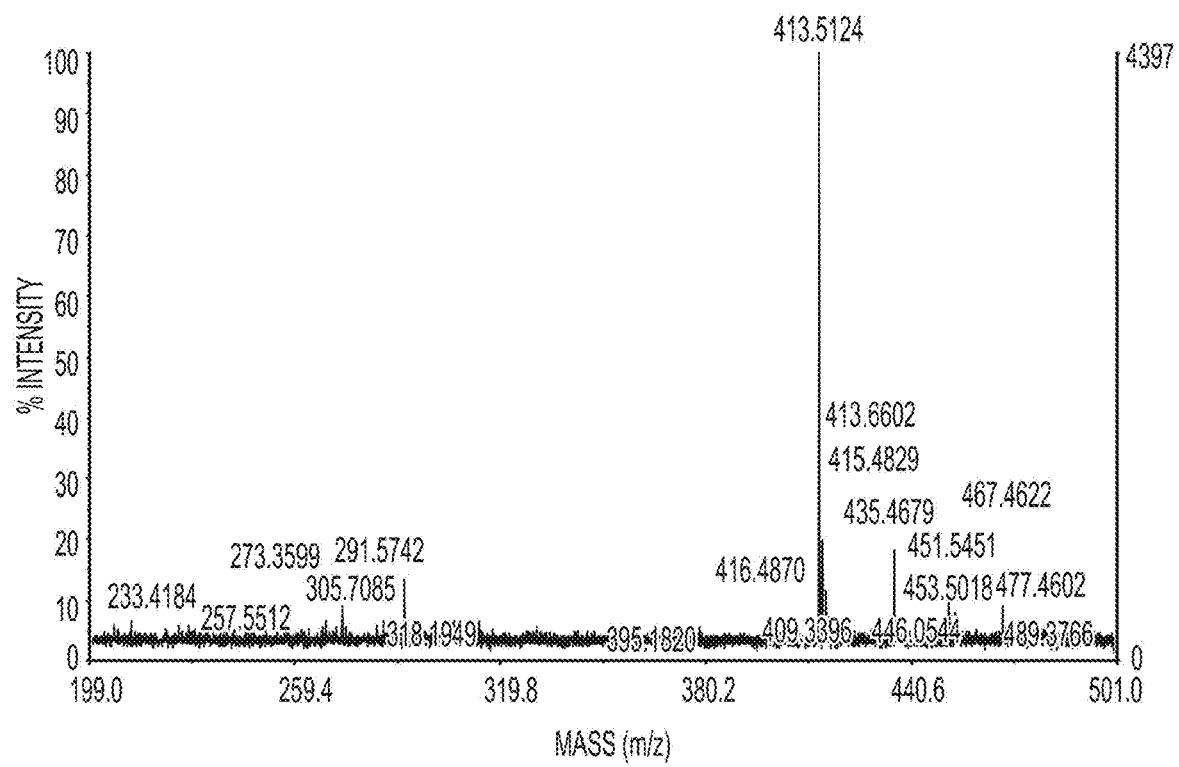
Figure 70J:
Figure 70K:
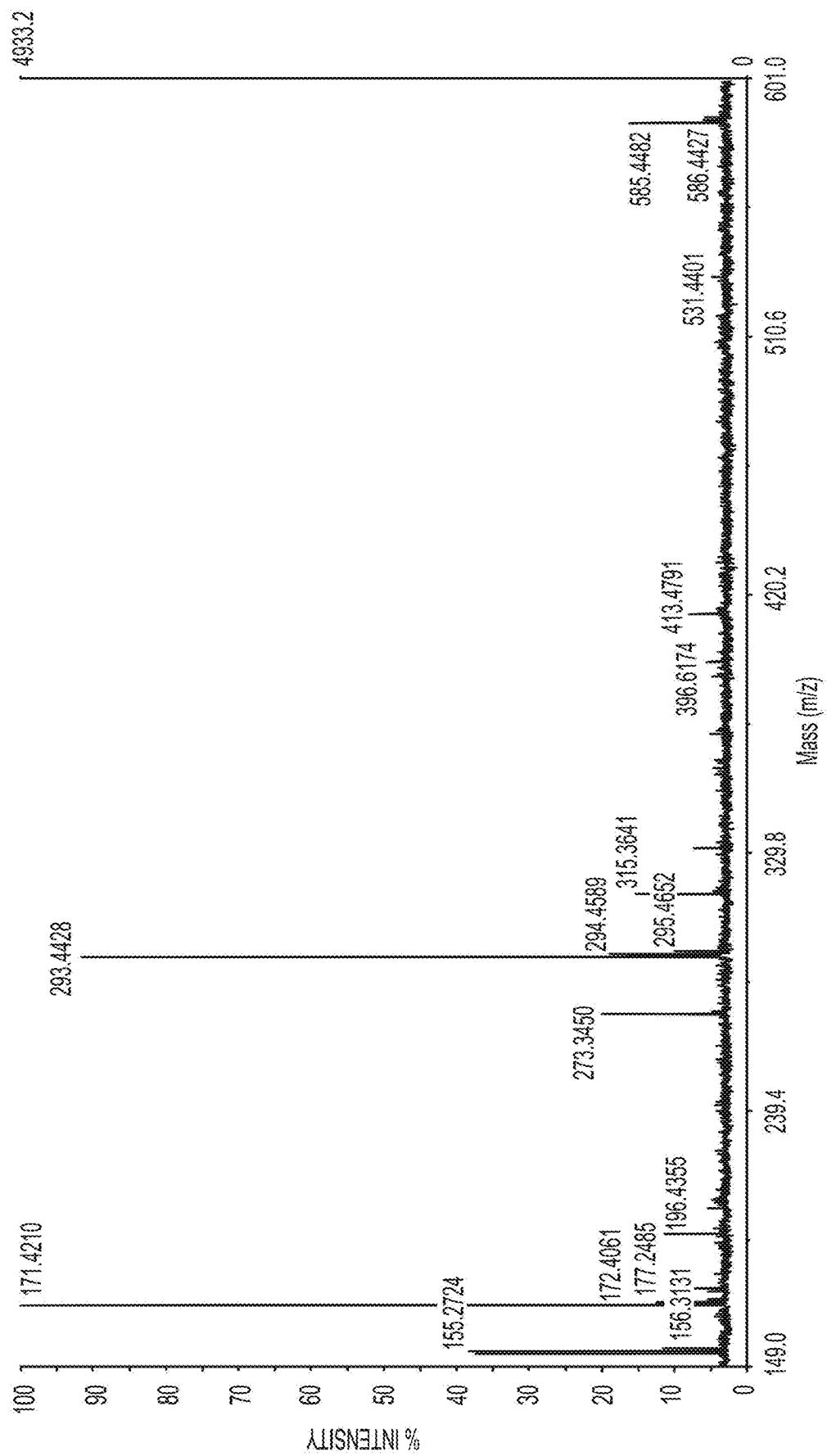
Figure 70L:
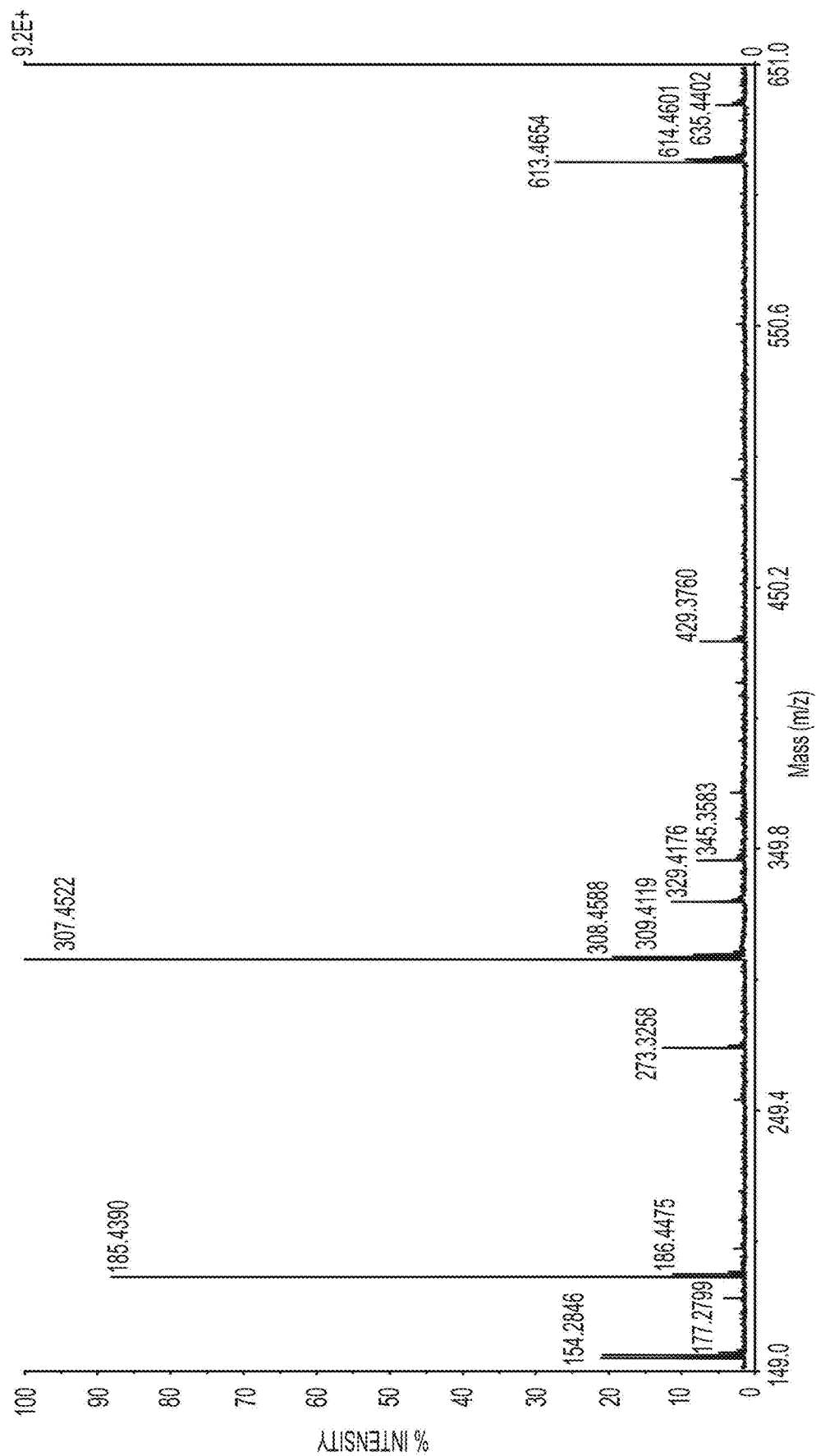
Figure 70M:
Figure 70N:
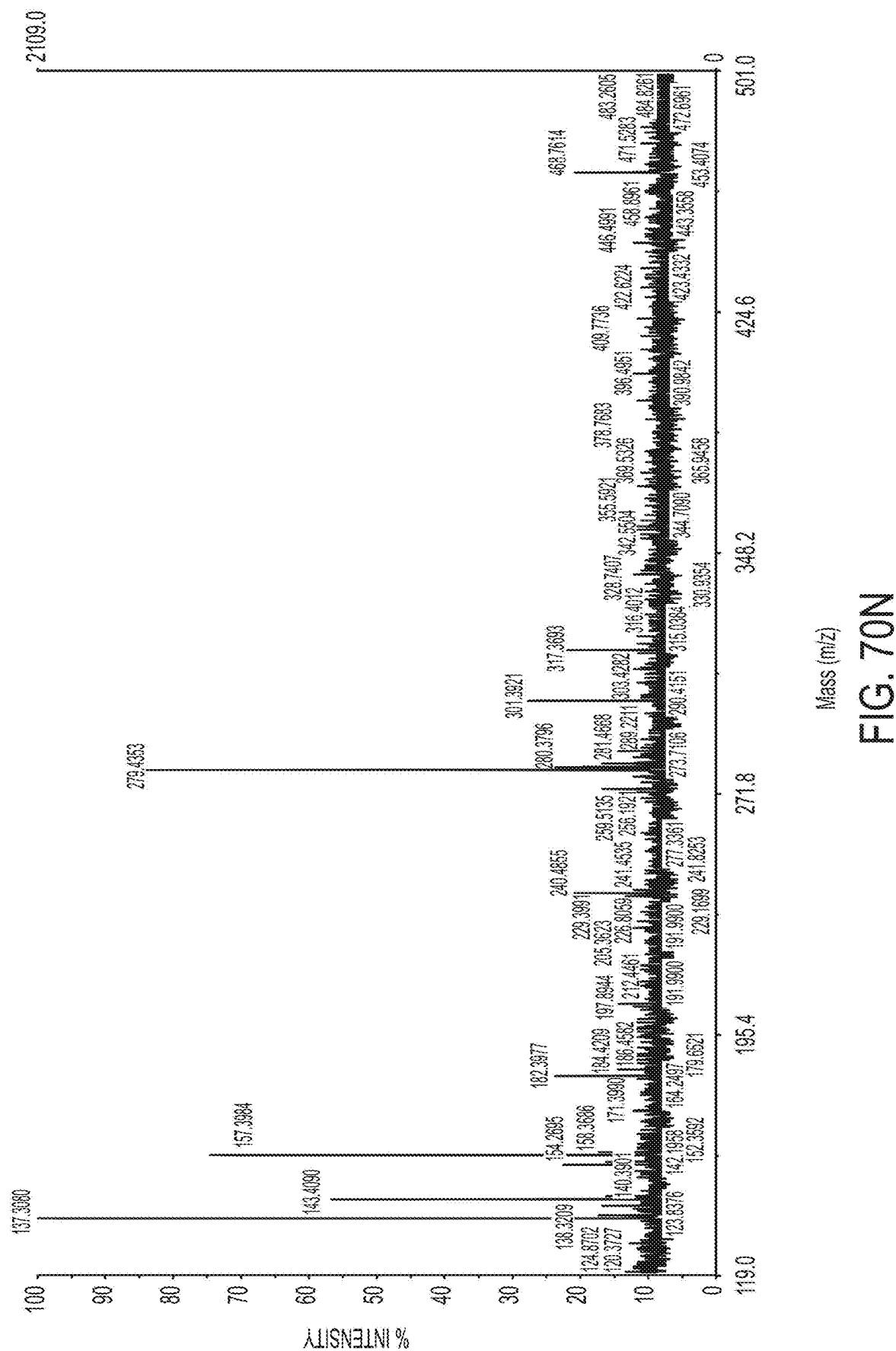
Figure 700:
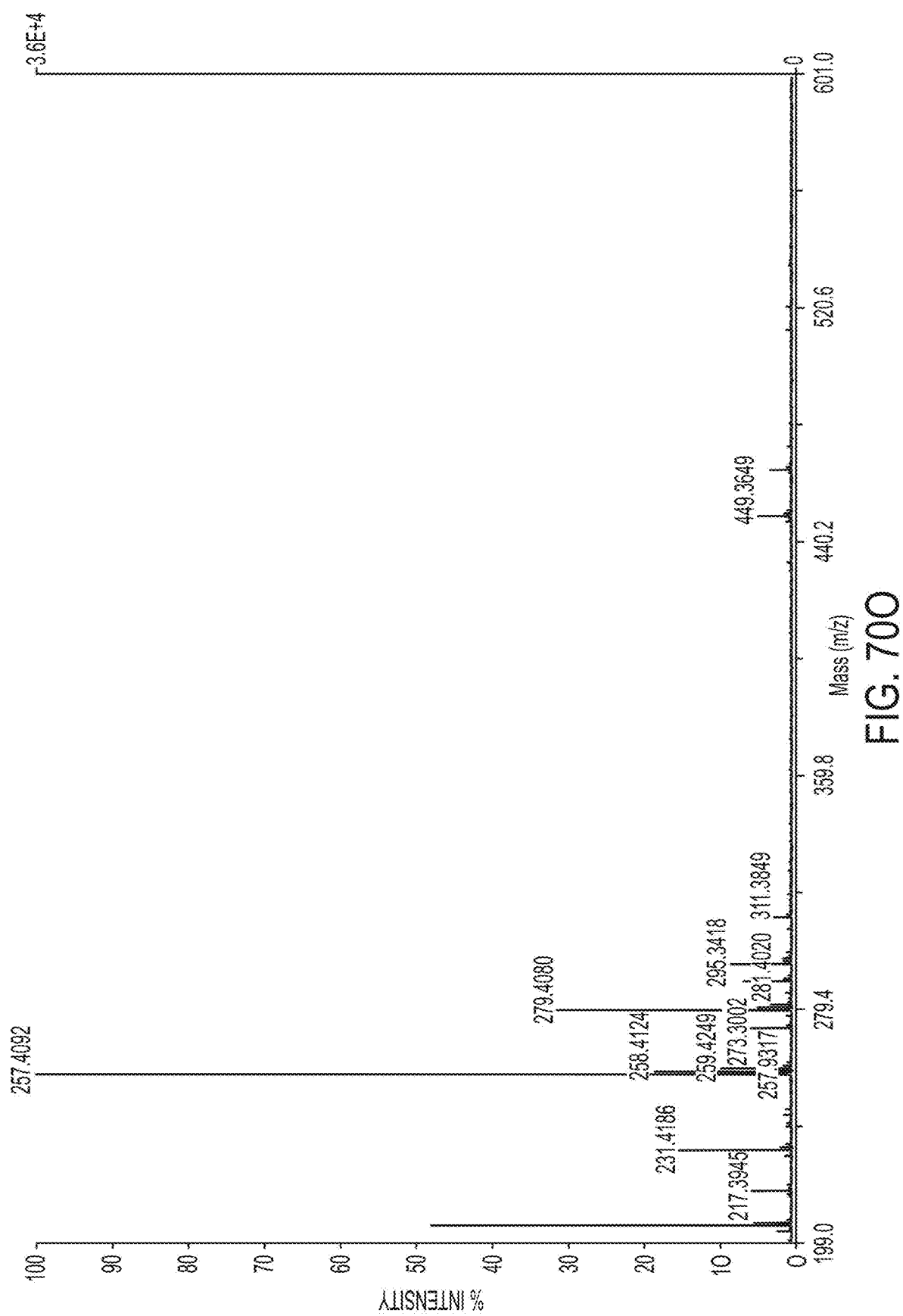

FIGS. 70A-70O show the mass spectra of modified ZAL compounds: ZA3-GE8 (FIG. 70A), ZA3-GE12 (FIG. 70B), ZA3-Ac-oleyl (FIG. 70C), ZA3-Ep10-OAc (FIG. 70D), ZA3-Ep10-OPiv (FIG. 70E), ZA3-Ep10-alkyl (FIG. 70F), ZA3-Ep10-Octanoate (FIG. 70G), 4A2SBAm (FIG. 70H), 4A4SBAm (FIG. 70I), SBAm-C3Me (FIG. 70J), SBAm-C2Et (FIG. 70K), SBAm-C3Et (FIG. 70L), CBAm-C2Me (FIG. 70M), C4SBAm-C2Me (FIG. 70N), and iPCAm-C2Me (FIG. 70O).

Figure 71A:
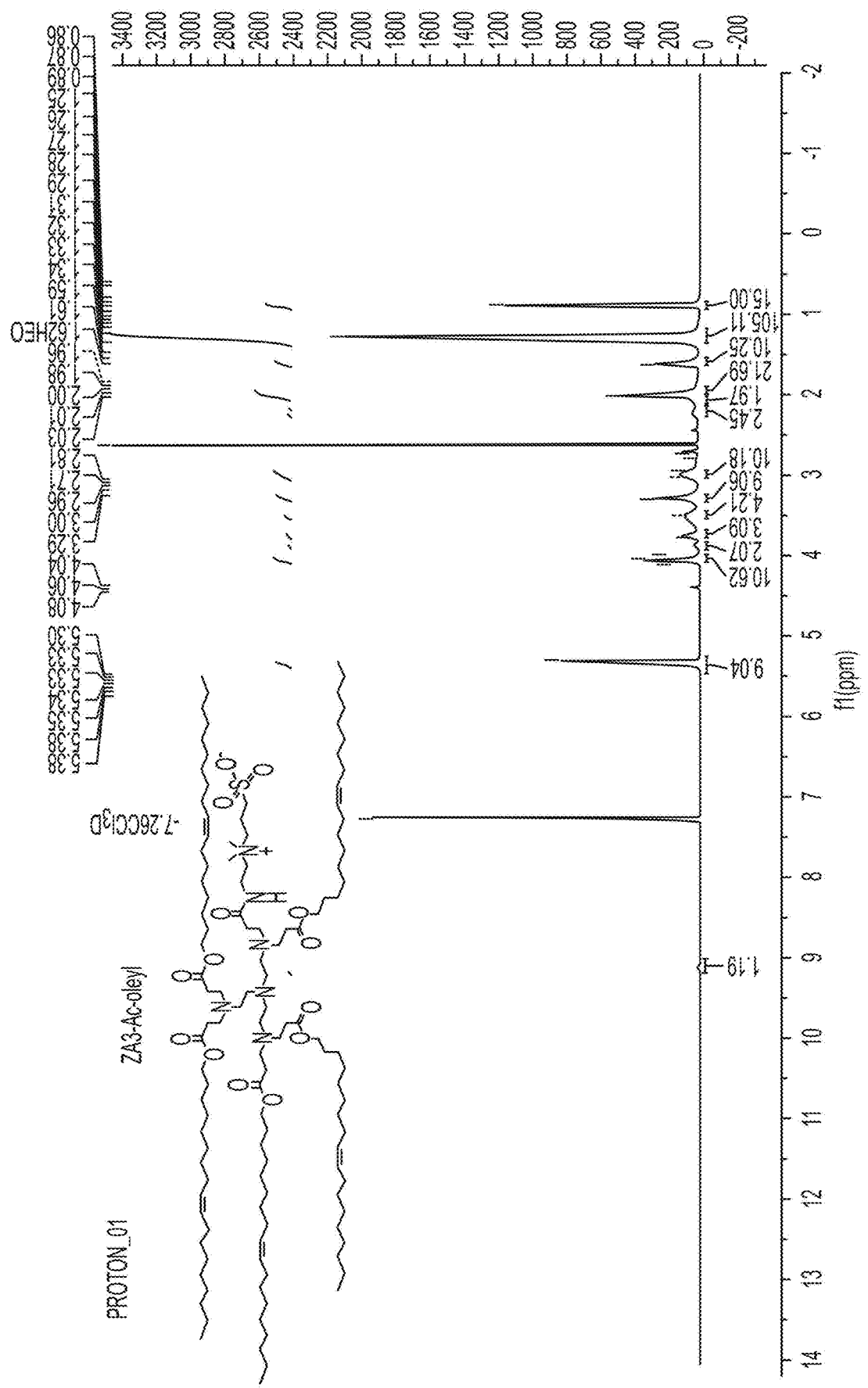
Figure 71B:
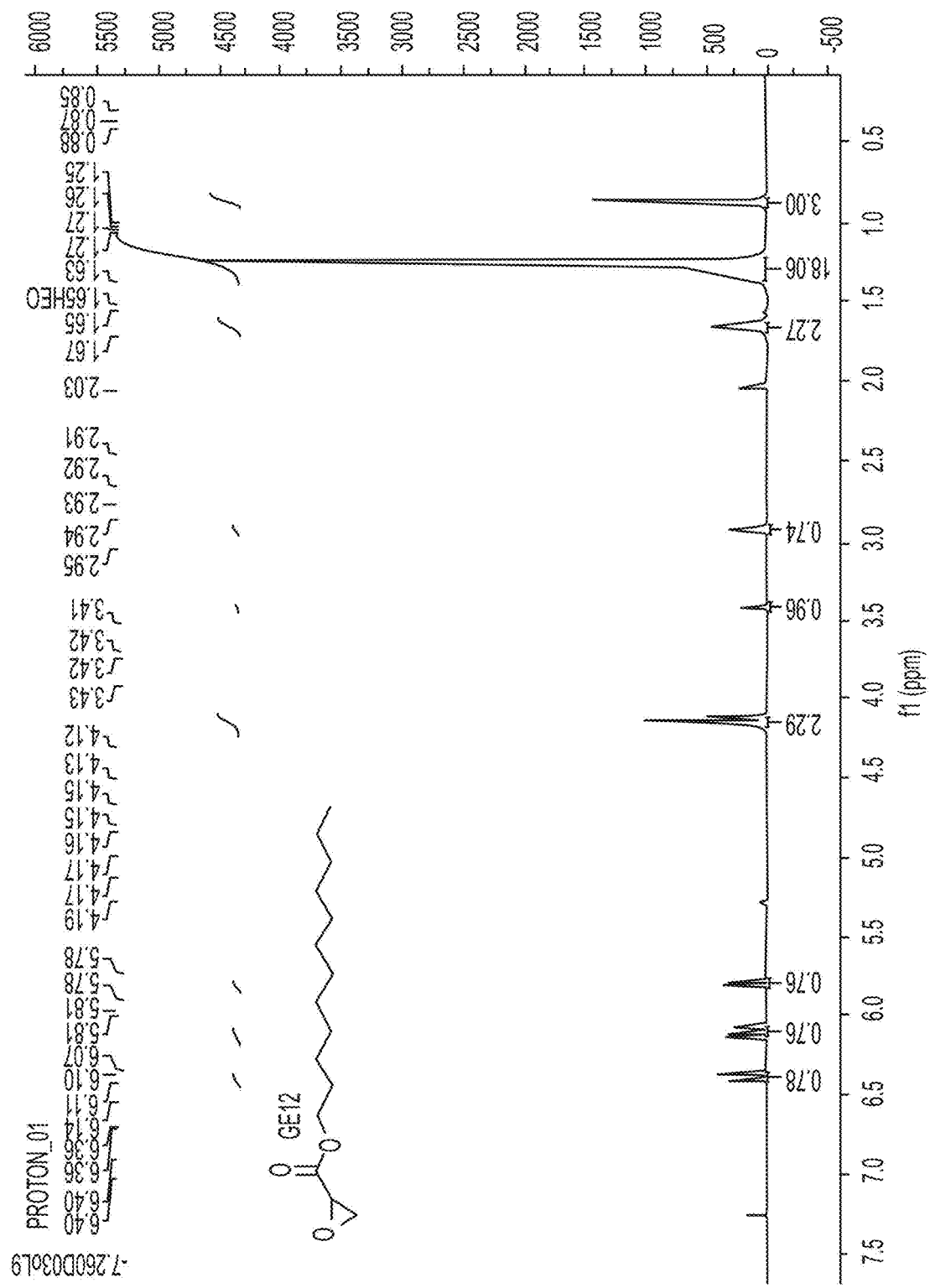
Figure 71C:
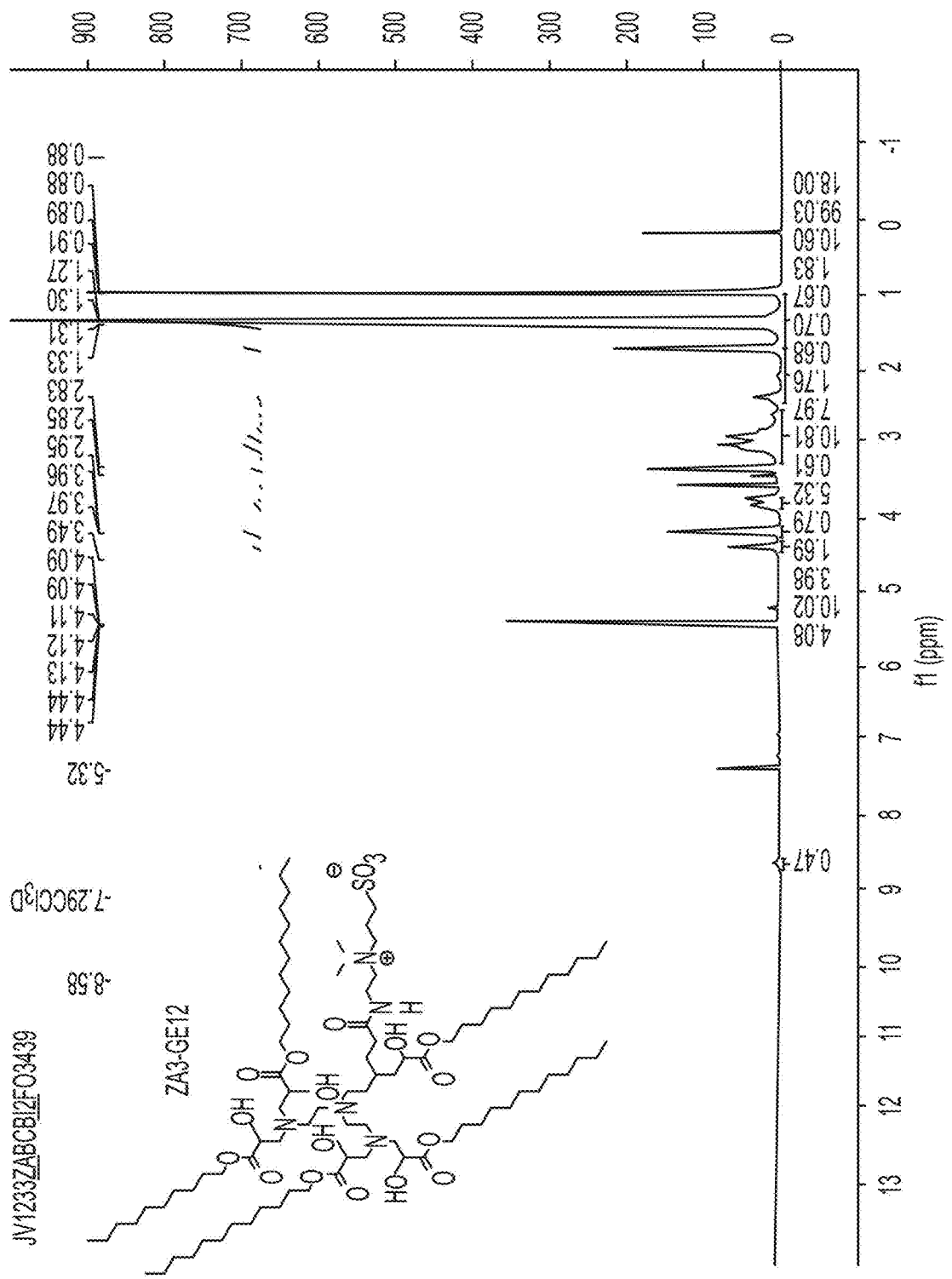
Figure 71D:
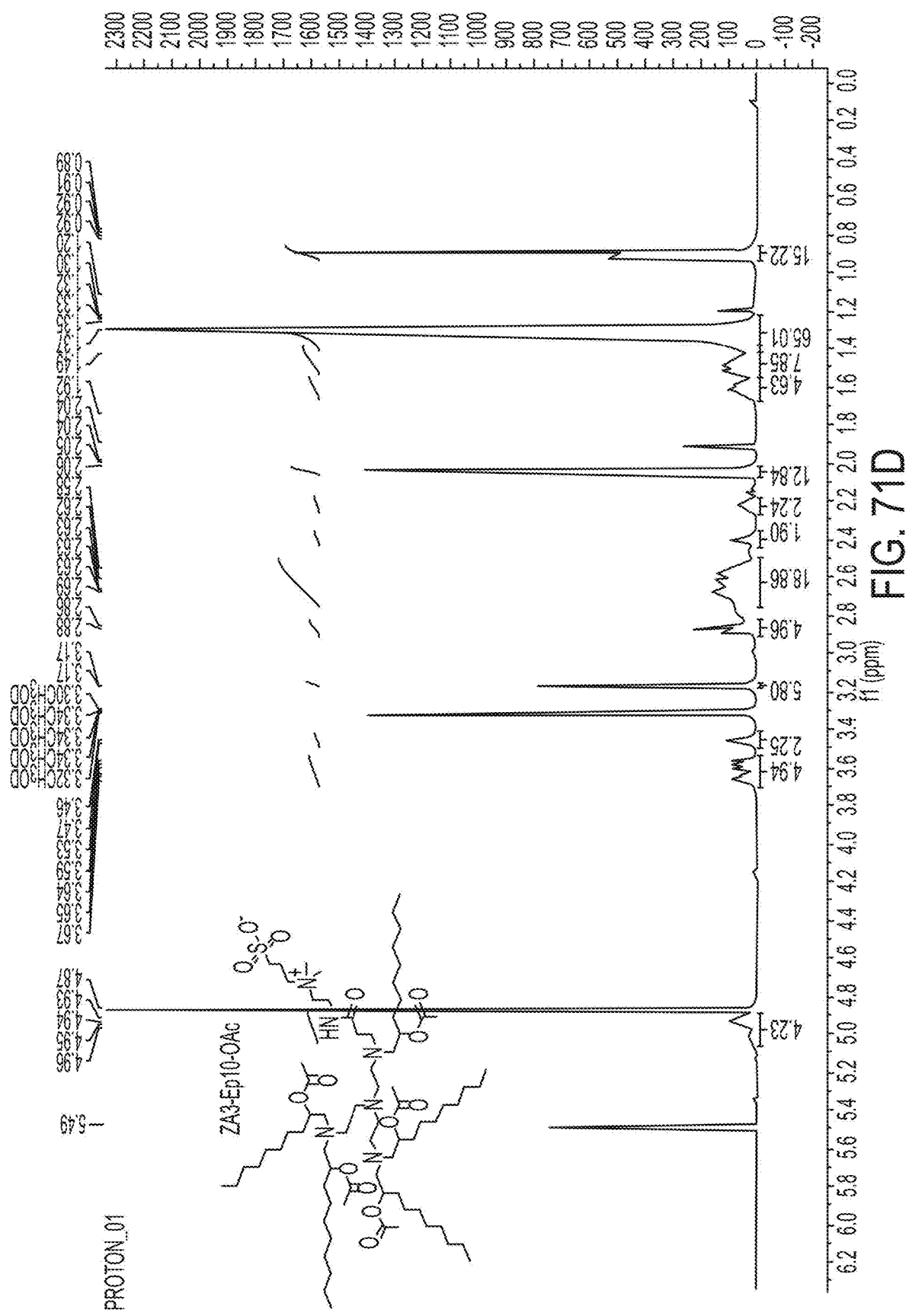
Figure 71E:
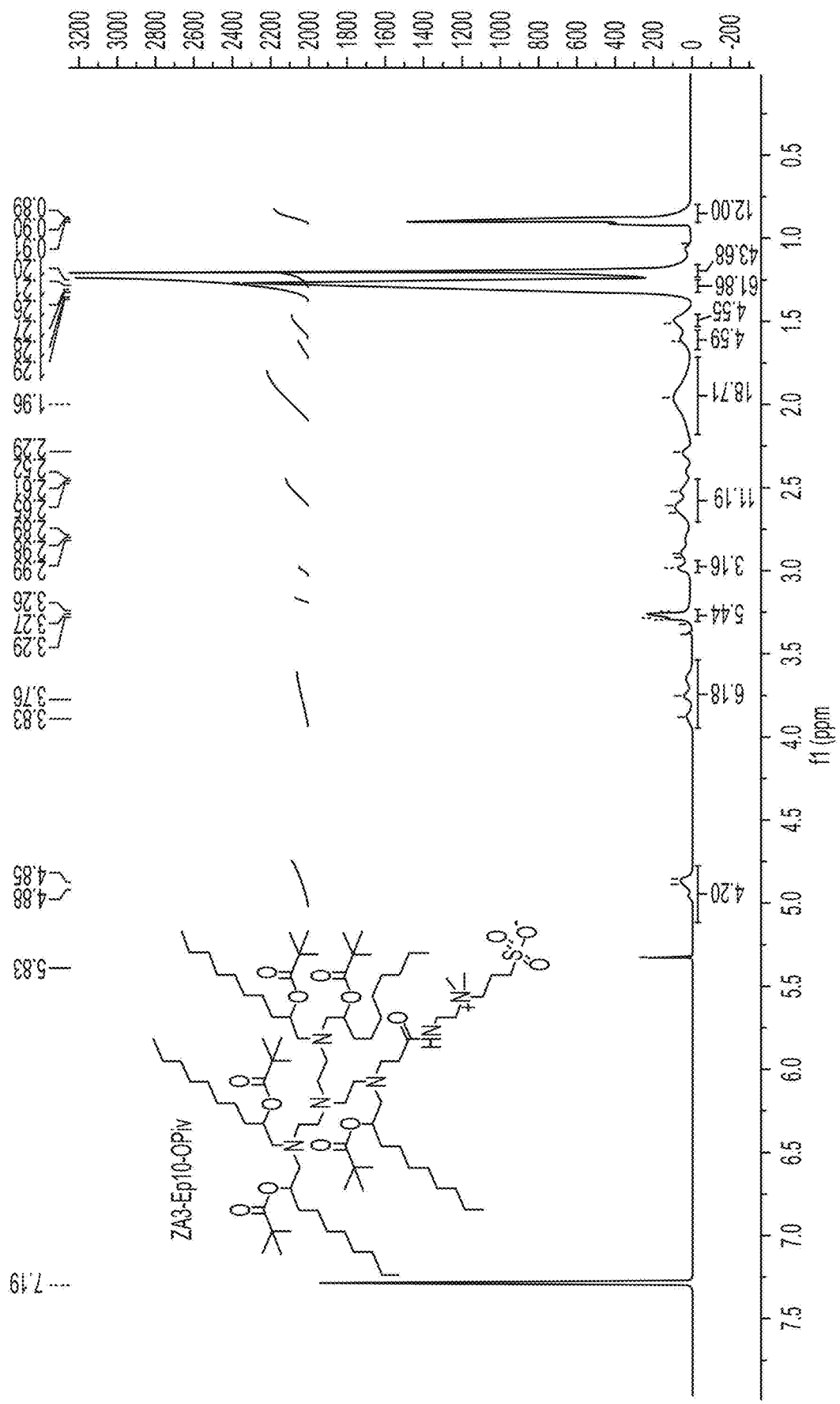

FIGS. 71A-E show the $^1$H NMR spectra of the modified ZAL compounds: ZA3-Ac-oleyl (FIG. 71A), GE12 (FIG. 71B), ZA3-GE12 (FIG. 71C), Z A3-Ep10-OAc (FIG. 71D), and ZA3-Ep10-OPiv (FIG. 71E).

DESCRIPTION OF ILLUSTRATIVE EMBODIMENTS

The present disclosure provides amino lipid composition containing one or more sulfonic acid or a sulfonic acid derivative such as a sulfonamide. These compounds may be combined with one or more helper lipids to form nanoparticles in aqueous solution which may be used to transport nucleic acid based therapeutic agents. In some embodiments, the present compositions may be used to transport siRNA, sgRNA, mRNA, or tRNA therapeutics to treating a disease or disorder such as cancer, cystic fibrosis, or other genetic disorders.

A. Definitions

The compounds (also described as an amino lipid, a compound, or a compound of the present disclosure herein) provided by the present disclosure are shown, for example, above in the summary section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the present disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent compounds of the disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the present disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol " - - - " represents an optional bond, which if present is either single or double. The symbol "====" represents a single bond or a double bond. Thus, for example, the formula

includes

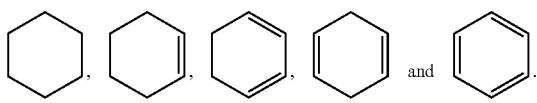

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿", when drawn perpendicularly across a bond (e.g.

or methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "▪▪▪▌" means a single bond where the group attached to the thick end of the wedge is "into the page". The symbol "∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

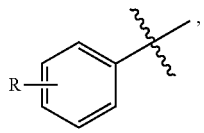

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

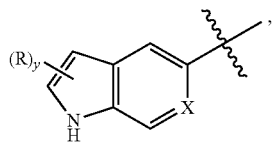

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in a moiety replacing a hydrogen atom is not counted. Thus methoxyhexyl is an example of a substituted alkyl$_{(C1-6)}$.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

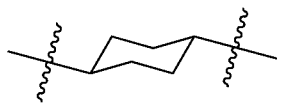 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

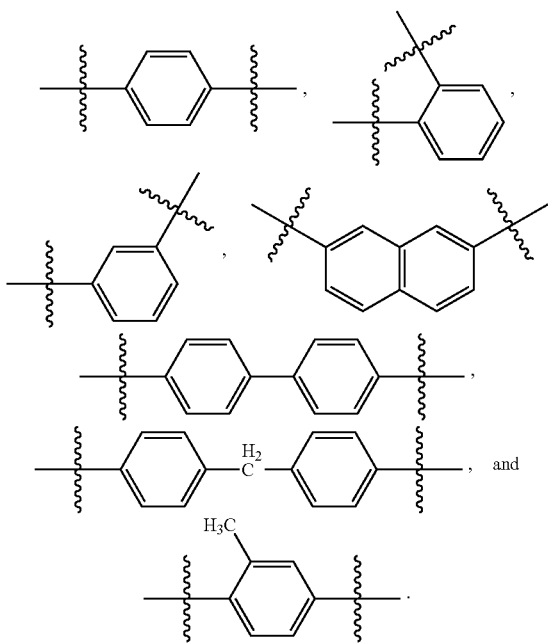

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group alkanediylaryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

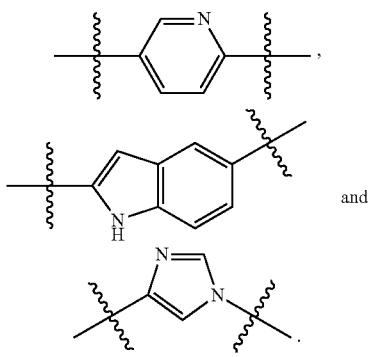

The term "N-heteroaryl" refers to a heteroaryl group with a nitrogen atom as the point of attachment. A "heteroarene"

refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

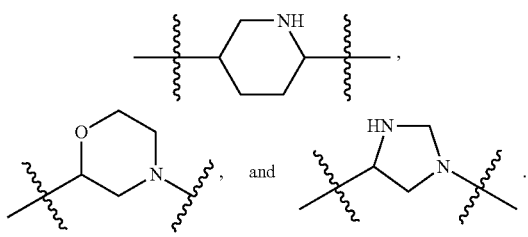

The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples include: —OCH₃ (methoxy), —OCH₂CH₃ (ethoxy), —OCH₂CH₂CH₃, —OCH(CH₃)₂ (isopropoxy), —OC(CH₃)₃ (tert-butoxy), —OCH(CH₂)₂, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkylamino" when used without the "substituted" modifier refers to the group —NHR, in which R is an alkyl, as that term is defined above. Non-limiting examples include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂ and —N(CH₃)(CH₂CH₃). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomotology of the disease, and/or (2) slowing the onset of the pathology or symptomotology of a disease in a subject or patient which may be at risk and/or predisposed to the disease but does not yet experience or display any or all of the pathology or symptomotology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomotology of the disease (e.g., arresting further development of the pathology and/or symptomotology), (2) ameliorating a disease in a subject or patient that is experiencing or displaying the pathology or symptomotology of the disease (e.g., reversing the pathology and/or symptomotology), and/or (3) effecting any measurable decrease in a disease in a subject or patient that is experiencing or displaying the pathology or symptomotology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

B. Amino Lipids

In some aspects, the present disclosure provides one or more amino lipid compounds containing two or more nitrogen atoms and a sulfonic acid or sulfonic acid derivative such as a sulfonamide. In some embodiments, one class of amino lipids is a cationic sulfonamide amino lipid which contains two or more nitrogen atoms wherein at least one of the nitrogen atoms is an amine which is protonated at physiological pH, two or more lipid groups, and a sulfonamide group. This class of amino lipids contains two or more lipid groups wherein the lipid group is a C6-C24 aliphatic group including alkyl, alkenyl, alkynyl groups or a substituted version of these groups. These lipid groups are connected to the rest of the amino lipid groups through an ester, an amide, or an epoxide. In some embodiments, the lipid group is a C6-C24 alkyl or substituted alkyl group.

In other embodiments, another class of amino lipids described herein is a zwitterionic amino lipid which contains two or more nitrogen atoms wherein at least one of the nitrogen atoms is a quaternary ammonium atom, a negatively charged group, and two or more lipid groups. The negatively charged group may be a phosphonic acid group or a sulfonic group. In some embodiments, the negatively charged group is a sulfonic group. As described above, the lipid groups are a C6-C24 aliphatic group including alkyl, alkenyl, alkynyl groups or a substituted version of these groups. These lipid groups are connected to the rest of the amino lipid groups through an ester, an amide, or an epoxide. In some embodiments, the lipid group is a C6-C24 alkyl or substituted alkyl group.

In some embodiments, the present composition comprises a ratio of the compound or amino lipids to the nucleic acid from about 1:1 to about 1500:1 or from about 5:1 to about 1000:1. The ratio may be from about 100:1-1000:1 or from about 250:1 to about 750:1 such as a ratio of about 166:1, 333:1, or 666:1. In some embodiments, the ratio is from about 1:1, 5:1, 25:1, 50:1, 75:1, 100:1, 200:1, 300:1, 350:1, 400:1, 500:1, 600:1, 650:1, 700:1, 750:1, 800:1, 900:1, to about 1000:1, or any range derivable therein.

C. Helper Lipids

In some aspects of the present disclosure, one or more lipids are mixed with the amino lipids of the instant disclosure to create a nanoparticle composition. In some embodiments, the amino lipids are mixed with 1, 2, 3, 4, or 5 different types of lipids. It is contemplated that the amino lipids can be mixed with multiple different lipids of a single type. In some embodiments, the lipid could be a steroid or a steroid derivative. In other embodiments, the lipid is a PEG lipid. In other embodiments, the lipid is a phospholipid. In other embodiments, the nanoparticle composition comprises a steroid or a steroid derivative, a PEG lipid, a phospholipid, or any combination thereof.

1. Steroids and Steroid Derivatives

In some aspects of the present disclosure, the amino lipids are mixed with one or more steroid or a steroid derivative to create a nanoparticle composition. In some embodiments, the steroid or steroid derivative comprises any steroid or steroid derivative. As used herein, in some embodiments, the term "steroid" is a class of compounds with a four ring 17 carbon cyclic structure which can further comprises one or more substitutions including alkyl groups, alkoxy groups, hydroxy groups, oxo groups, acyl groups, or a double bond between two or more carbon atoms. In one aspect, the ring structure of a steroid comprises three fused cyclohexyl rings and a fused cyclopentyl ring as shown in the formula below:

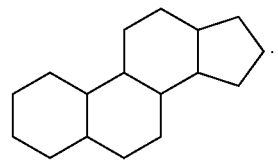 [SMILES: C1CCC2C(C1)CCC1C3CCCC3CCC21]

In some embodiments, a steroid derivative comprises the ring structure above with one or more non-alkyl substitutions. In some embodiments, the steroid or steroid derivative is a sterol wherein the formula is further defined as:

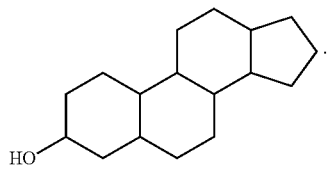 [SMILES: OC1CCC2C(CCC3C4CCCC4CCC23)C1]

In some embodiments of the present disclosure, the steroid or steroid derivative is a cholestane or cholestane derivative. In a cholestane, the ring structure is further defined by the formula:

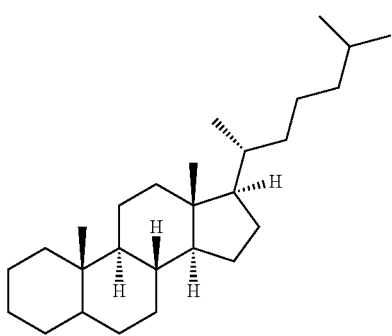

As described above, a cholestane derivative includes one or more non-alkyl substitution of the above ring system. In some embodiments, the cholestane or cholestane derivative is a cholestene or cholestene derivative or a sterol or a sterol derivative. In other embodiments, the cholestane or cholestane derivative is both a cholestere and a sterol or a derivative thereof.

In some embodiments, the present composition comprises a ratio of the compound or amino lipids to the steroid or steroid derivative from about 1:3 to about 30:1 or from about 1:1 to about 20:1. The ratio may be from about 1:1-6:1 such as a ratio of about 1.3:1. In some embodiments, the ratio is from about 1:3, 1:2, 1:1, 1.25:1, 1.5:1, 2:1, 3:1, 5:1, 8:1, 10:1, 12.5:1, 15:1, 17.5:1, 20:1, 25:1, to about 30:1, or any range derivable therein.

2. PEG or PEGylated Lipid

In some aspects of the present disclosure, the amino lipids (or compounds) are mixed with one or more PEGylated lipids (or PEG lipid) to create a nanoparticle composition. In some embodiments, the present disclosure comprises using any lipid to which a PEG group has been attached. In some embodiments, the PEG lipid is a diglyceride which also comprises a PEG chain attached to the glycerol group. In other embodiments, the PEG lipid is a compound which contains one or more C6-C24 long chain alkyl or alkenyl group or a C6-C24 fatty acid group attached to a linker group with a PEG chain Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 5,000. In some embodiments, the molecular weight is from about 200 to about 500 or from about 1,200 to about 3,000. Some non-limiting examples of lipids that may be used in the present disclosure are taught by U.S. Pat. No. 5,820,873, WO 2010/141069, or U.S. Pat. No. 8,450,298, which is incorporated herein by reference.

In another aspect, the PEG lipid has the formula:

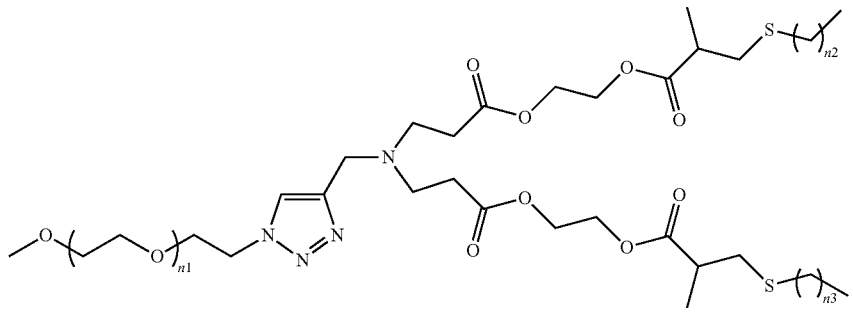

wherein: $n_1$ is an integer between 1 and 100 and $n_2$ and $n_3$ are each independently selected from an integer between 1 and 29. In some embodiments, $n_1$ is 5, 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, or any range derivable therein. In some embodiments, $n_1$ is from about 30 to about 50. In some embodiments, $n_2$ is from 5 to 23. In some embodiments, $n_2$ is 11 to about 17. In some embodiments, $n_3$ is from 5 to 23. In some embodiments, $n_3$ is 11 to about 17.

In some embodiments, the present composition comprises a ratio of the compound or amino lipids to the PEG lipid from about 1:1 to about 150:1 or from about 2.5:1 to about 100:1. The ratio may be from about 7.5:1-50:1 such as a ratio of about 33.3:1. In some embodiments, the ratio is from about 5:1, 10:1, 20:1, 25:1, 30:1, 35:1, 40:1, 50:1, 60:1, 70:1, 80:1, 90:1, 100:1, 120:1, 140:1, to about 150:1, or any range derivable therein.

3. Phospholipid

In some aspects of the present disclosure, the amino lipids are mixed with one or more phospholipids to create a nanoparticle composition. In some embodiments, any lipid which also comprises a phosphate group. In some embodiments, the phospholipid is a structure which contains one or two long chain C6-C24 alkyl or alkenyl groups, a glycerol or a sphingosine, one or two phosphate groups, and, optionally, a small organic molecule. In some embodiments, the small organic molecule is an amino acid, a sugar, or an amino substituted alkoxy group, such as choline or ethanolamine. In some embodiments, the phospholipid is a phosphatidylcholine. In some embodiments, the phospholipid is distearoylphosphatidylcholine.

In some embodiments, the present composition comprises a ratio of the compound or amino lipids to the phospholipid from about 1:1 to about 15:1 or from about 1:1 to about 9:1. The ratio may be from about 2.5:1-7.5:1 such as a ratio of about 5:1. In some embodiments, the ratio is from about 1:1, 2:1, 3:1, 4:1, 4.5:1, 5:1, 5.5:1, 6:1, 7:1, 8:1, 9:1, 10:1, 12:1, 14:1, to about 15:1, or any range derivable therein.

D. Nucleic Acids and Nucleic Acid Based Therapeutic Agents

1. Nucleic Acids

In some aspects of the present disclosure, the nanoparticle compositions comprise one or more nucleic acids. In addition, it should be clear that the present disclosure is not limited to the specific nucleic acids disclosed herein. The present disclosure is not limited in scope to any particular source, sequence, or type of nucleic acid, however, as one of ordinary skill in the art could readily identify related homologs in various other sources of the nucleic acid including nucleic acids from non-human species (e.g., mouse, rat, rabbit, dog, monkey, gibbon, chimp, ape, baboon, cow, pig, horse, sheep, cat and other species). It is contemplated that the nucleic acid used in the present disclosure can comprises a sequence based upon a naturally-occurring sequence. Allowing for the degeneracy of the genetic code, sequences that have at least about 50%, usually at least about 60%, more usually about 70%, most usually about 80%, preferably at least about 90% and most preferably about 95% of nucleotides that are identical to the nucleotide sequence of the naturally-occurring sequence. In another embodiment, the nucleic acid is a complementary sequence to a naturally occurring sequence, or complementary to 75%, 80%, 85%, 90%, 95% and 100%.

In some aspects, the nucleic acid is a sequence which silences, is complimentary to, or replaces another sequence present in vivo. Sequences of 17 bases in length should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or longer are contemplated as well.

The nucleic acid used herein may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present disclosure may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

In some embodiments, the nucleic acid comprises one or more antisense segments which inhibits expression of a gene or gene product. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to form a siRNA or to generate specific constructs. For example, where an intron is desired in the ultimate construct, a genomic clone will need to be used. The cDNA, siRNA, or a synthesized polynucleotide may provide more convenient restriction sites for the remaining portion of the construct and, therefore, would be used for the rest of the sequence. Other embodiments include dsRNA or ssRNA, which may be used to target genomic sequences or coding/non-coding transcripts.

In other embodiments, the nanoparticles may comprise a nucleic acid which comprises one or more expression vectors are used in a gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

2. siRNA

As mentioned above, the present disclosure contemplates the use of one or more inhibitory nucleic acid for reducing expression and/or activation of a gene or gene product. Examples of an inhibitory nucleic acid include but are not limited to molecules targeted to an nucleic acid sequence, such as an siRNA (small interfering RNA), short hairpin RNA (shRNA), double-stranded RNA, an antisense oligonucleotide, a ribozyme and molecules targeted to a gene or gene product such as an aptamer.

An inhibitory nucleic acid may inhibit the transcription of a gene or prevent the translation of the gene transcript in a cell. An inhibitory nucleic acid may be from 16 to 1000 nucleotides long, and in certain embodiments from 18 to 100 nucleotides long.

Inhibitory nucleic acids are well known in the art. For example, siRNA, shRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Since the discovery of RNAi by Fire and colleagues in 1998, the biochemical mechanisms have been rapidly characterized. Double stranded RNA (dsRNA) is cleaved by Dicer, which is an RNAase III family ribonuclease. This process yields siRNAs of 21 nucleotides in length. These siRNAs are incorporated into a multiprotein RNA-induced silencing complex (RISC) that is guided to target mRNA. RISC cleaves the target mRNA in the middle of the complementary region. In mammalian cells, the related microRNAs (miRNAs) are found that are short RNA fragments (~22 nucleotides). miRNAs are generated after Dicer-mediated cleavage of longer (~70 nucleotide) precursors with imperfect hairpin RNA structures. The miRNA is incorporated into a miRNA-protein complex (miRNP), which leads to translational repression of target mRNA.

In designing a nucleic acid capable of generating an RNAi effect, there are several factors that need to be considered such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Particularly the siRNA exhibits greater than 80, 85, 90, 95, 98% or even 100% identity between the sequence of the siRNA and a portion of a EphA nucleotide sequence. Sequences less than about 80% identical to the target gene are substantially less effective. Thus, the greater identity between the siRNA and the gene to be inhibited, the less likely expression of unrelated genes will be affected.

In addition, the size of the siRNA is an important consideration. In some embodiments, the present disclosure relates to siRNA molecules that include at least about 19-25 nucleotides, and are able to modulate gene expression. In the context of the present disclosure, the siRNA is particularly less than 500, 200, 100, 50, 25, or 20 nucleotides in length. In some embodiments, the siRNA is from about 25 nucleotides to about 35 nucleotides or from about 19 nucleotides to about 25 nucleotides in length.

To improve the effectiveness of siRNA-mediated gene silencing, guidelines for selection of target sites on mRNA have been developed for optimal design of siRNA (Soutschek et al., 2004; Wadhwa et al., 2004). These strategies may allow for rational approaches for selecting siRNA sequences to achieve maximal gene knockdown. To facilitate the entry of siRNA into cells and tissues, a variety of vectors including plasmids and viral vectors such as adenovirus, lentivirus, and retrovirus have been used (Wadhwa et al., 2004).

Within an inhibitory nucleic acid, the components of a nucleic acid need not be of the same type or homogenous throughout (e.g., an inhibitory nucleic acid may comprise a nucleotide and a nucleic acid or nucleotide analog). Typically, an inhibitory nucleic acid form a double-stranded structure; the double-stranded structure may result from two separate nucleic acids that are partially or completely complementary. In certain embodiments of the present disclosure, the inhibitory nucleic acid may comprise only a single nucleic acid (polynucleotide) or nucleic acid analog and form a double-stranded structure by complementing with itself (e.g., forming a hairpin loop). The double-stranded structure of the inhibitory nucleic acid may comprise 16-500 or more contiguous nucleobases, including all ranges derivable thereof. The inhibitory nucleic acid may comprise 17 to 35 contiguous nucleobases, more particularly 18 to 30 contiguous nucleobases, more particularly 19 to 25 nucleobases, more particularly 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

siRNA can be obtained from commercial sources, natural sources, or can be synthesized using any of a number of techniques well-known to those of ordinary skill in the art. For example, commercial sources of predesigned siRNA include Invitrogen's Stealth™ Select technology (Carlsbad, Calif.), Ambion® (Austin, Tex.), and Qiagen® (Valencia, Calif.). An inhibitory nucleic acid that can be applied in the compositions and methods of the present disclosure may be any nucleic acid sequence that has been found by any source to be a validated downregulator of the gene or gene product.

In some embodiments, the disclosure features an isolated siRNA molecule of at least 19 nucleotides, having at least one strand that is substantially complementary to at least ten but no more than thirty consecutive nucleotides of a nucleic acid that encodes a gene, and that reduces the expression of a gene or gene product. In one embodiments of the present disclosure, the siRNA molecule has at least one strand that is substantially complementary to at least ten but no more than thirty consecutive nucleotides of the mRNA that encodes a gene or a gene product.

In one embodiments, the siRNA molecule is at least 75, 80, 85, or 90% homologous, particularly at least 95%, 99%, or 100% similar or identical, or any percentages in between the foregoing (e.g., the disclosure contemplates 75% and greater, 80% and greater, 85% and greater, and so on, and said ranges are intended to include all whole numbers in between), to at least 10 contiguous nucleotides of any of the nucleic acid sequences encoding a target therapeutic protein.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present disclosure can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication 2004/0019001 and U.S. Pat. No. 6,673,611 (each of which is incorporated by reference in its entirety). Collectively, all such altered nucleic acids or RNAs described above are referred to as modified siRNAs.

In one embodiment, siRNA is capable of decreasing the expression of a particular genetic product by at least 10%, at least 20%, at least 30%, or at least 40%, at least 50%, at least 60%, or at least 70%, at least 75%, at least 80%, at least 90%, at least 95% or more or any ranges in between the foregoing.

3. tRNA

In some aspects, the present composition comprises a transfer RNA (known as a tRNA). As used herein, the term transfer RNA or tRNA refers to both traditional tRNA molecules as well as tRNA molecules with one or more modifications unless specifically noted otherwise. Transfer RNA is an RNA polymer that is about 70 to 100 nucleotides in length. During protein synthesis, a tRNA delivers an amino acid to the ribosome for addition to the growing peptide chain Active tRNAs have a 3' CCA tail that may be transcribed into the tRNA during its synthesis or may be added later during post-transcriptional processing. The amino acid is covalently attached to the 2' or 3' hydroxyl group of the 3'-terminal ribose to form an aminoacyl-tRNA (aa-tRNA); an amino acid can spontaneously migrate from the 2'-OH to the 3'-OH and vice versa, but it is incorporated into a growing protein chain at the ribosome from the 3'-OH position. A loop at the other end of the folded aa-tRNA molecule contains a sequence of three bases known as the anticodon. When this anticodon sequence base-pairs with a three-base codon sequence in a ribosome-bound messenger RNA (mRNA), the aa-tRNA binds to the ribosome and its amino acid is incorporated into the nascent protein chain. Since all tRNAs that base-pair with a specific codon are aminoacylated with a single specific amino acid, the translation of the genetic code is effected by tRNAs: each of the 61 non-termination codons in an mRNA directs the binding of its cognate aa-tRNA and the addition of a single specific amino acid to the growing protein polymer. In some embodiments, the tRNA may comprise a mutation in the anticodon region of the tRNA such that the aa-tRNA base-pairs with a different codon on the mRNA. In certain embodiments, the mutated tRNA introduces a different amino acid into the growing protein chain than the amino acid encoded by the mRNA. In other embodiments, the mutated tRNA base-pairs with a stop codon and introduces an amino acid instead of terminating protein synthesis, thereby allowing the nascent peptide to continue to grow. In some embodiments, a tRNA, wild-type or mutated, may read through a stop codon and introduce an amino acid instead of terminating protein synthesis. In some embodiments, the tRNA may comprise a full-length tRNA with the 3'-terminal-CCA nucleotides included. In other embodiments, tRNAs lacking the 3'-terminal -A, —CA, or —CCA are made full-length in vivo by the CCA-adding enzyme.

In other aspects, the present compositions may further comprise one or more modified tRNA molecules including: acylated tRNA; alkylated tRNA; a tRNA containing one or more bases other than adenine, cytosine, guanine, or uracil; a tRNA covalently modified by the attachment of a fluorescent, affinity, reactive, spectral, or other probe moiety; a tRNA containing one or more ribose moieties that are methylated or otherwise modified; aa-tRNAs that are aminoacylated with an amino acid other than the 20 natural amino acids, including non-natural amino acids that function as a carrier for reagents or as a fluorescent, reactive, affinity, spectral, or other probe; or any combination of these compositions. Some examples of modified tRNA molecules are taught by Soll, et al., 1995; El Yacoubi, et al., 2012; Grosjean and Benne, et al., 1998; Hendrickson, et al., 2004; Ibba and Soll, 2000; Johnson, et al., 1995; Johnson, et al., 1982; Crowley, et al., 1994; Beier and Grimm, 2001; Torres, et al., 2014; and Björk, et al., 1987, all of which are incorporated herein by reference.

4. mRNA

In some aspects, the present compounds and compositions may be used in the delivery of an mRNA to a cell. Messenger RNA or mRNA are short RNA strands which transfer the genetic code from the DNA to the ribosomes so it may be translated into a functional protein or peptide. The mRNA's described herein may be unprocessed or have undergone processing to add a poly(A) tail, be edited in vivo, or have a 5' cap added. The present compositions are contemplated in the delivery of a variety of different mRNA including those which have not undergone processing or have been further processed. Additionally, these nucleic acids may be used therapeutically, used to produce an antibody in vivo, or in a vaccine formulation.

5. CRISPR Related RNAs

In some aspects, the present compound and compositions may be used to deliver nucleic acid sequences for use in CRISPR gene editing. The CRISPR/Cas nuclease or CRISPR/Cas nuclease systems that may be used herein can include a non-coding RNA molecule (guide) RNA (sgRNA), which sequence-specifically binds to DNA, and a Cas protein (e.g., Cas9), with nuclease functionality (e.g., two nuclease domains).

In some aspects, a Cas nuclease and sgRNA (including a fusion of crRNA specific for the target sequence and fixed tracrRNA) are introduced into the cell. In general, target sites at the 5' end of the sgRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the sgRNA is targeted to the desired sequence by modifying the first 20 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex. In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, it is contemplated that the compositions described herein may be used to delivery to one or more cells the CRISPR nucleic acids and the nuclease or may be used to direct the delivery of only the nucleic acid.

6. Modified Nucleobases

In some embodiments, the nucleic acids of the present disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In some embodiments, modified sugar moieties are substituted sugar moieties. In some embodiments, modified sugar moieties are sugar surrogates. Such sugar surrogates may comprise one or more substitutions corresponding to those of substituted sugar moieties.

In some embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C1-C10 alkyl. Examples of sugar substituents at the 5'-position, include, but are not limited to: 5'-methyl (R or S); 5'-vinyl, and 5'-methoxy. In some embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In some embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(R$_m$)(R$_n$) or O—CH$_2$—C(=O)—N(R$_m$) (R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In some embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)

($R_n$) where each $R_m$ and $R_n$ is, independently, H, an amino protecting group or substituted or unsubstituted $C_1$-$C_{10}$ alkyl.

In some embodiments, a 2'-substituted nucleoside comprises a sugar moiety comprising a 2'-substituent group selected from F, $OCF_3$, O—$CH_3$, $OCH_2CH_2OCH_3$, $O(CH_2)_2$ $SCH_3$, $O(CH_2)_2$—O—$N(CH_3)_2$, —$O(CH_2)_2O$ $(CH_2)_2N(CH_3)_2$, and O—$CH_2$—C(=O)—N(H)$CH_3$.

In some embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In some such embodiments, the bicyclic sugar moiety comprises a bridge between the 4' and the 2' furanose ring atoms. Examples of such 4' to 2' sugar substituents, include, but are not limited to: —[C($R_a$)($R_b$)]$_n$—, —[C($R_a$)($R_b$)]$_n$—O—, —C($R_aR_b$)—N(R)—O— or, —C($R_aR_b$)—O—N(R)—; 4'-$CH_2$-2', 4'-$(CH_2)_2$-2', 4'-$(CH_2)$—O-2' (LNA); 4'-$(CH_2)$—S-2'; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845); 4'-C($CH_3$)($CH_3$)—O-2' and analogs thereof, (see, e.g., WO 2009/006478); 4'-$CH_2$—N(O$CH_3$)-2' and analogs thereof (see, e.g., WO2008/150729); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672); 4'-$CH_2$—C(H)($CH_3$)-2' (see, e.g., Chattopadhyaya et al., J. Org. Chem., 2009, 74, 118-134); and 4'-$CH_2$—C(=$CH_2$)-2' and analogs thereof (see, PCT International Application WO 2008/154401).

In some embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=$NR_a$)—, —C(=O)—, —C(=S)—, —Si($R_a$)$_2$—, —S(=O)$_x$—, and —N($R_a$)—; wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, (J) propylene carbocyclic (4'-$(CH_2)_3$-2') BNA, and (K) Methoxy(ethyleneoxy) (4'-CH($CH_2OMe$)-O-2') BNA (also referred to as constrained MOE or cMOE).

Additional bicyclic sugar moieties are known in the art, for example Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 5561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US 2004/0171570, US 2007/0287831, and US 2008/0039618; U.S. Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In some embodiments, bicyclic sugar moieties and nucleosides incorporating such bicyclic sugar moieties are further defined by isomeric configuration. For example, a nucleoside comprising a 4'-2' methylene-oxy bridge, may be in the .alpha.-L configuration or in the .beta.-D configuration. Previously, α-L-methyleneoxy (4'-$CH_2$—O-2) bicyclic nucleosides have been incorporated into antisense oligonucleotides that showed antisense activity (Frieden et al., Nucleic Acids Research, 2003, 21, 6365-6372).

In some embodiments, substituted sugar moieties comprise one or more non-bridging sugar substituent and one or more bridging sugar substituent (e.g., 5'-substituted and 4'-2' bridged sugars; PCT International Application WO 2007/134181, wherein LNA is substituted with, for example, a 5'-methyl or a 5'-vinyl group).

In some embodiments, modified sugar moieties are sugar surrogates. In some such embodiments, the oxygen atom of the naturally occurring sugar is substituted, e.g., with a sulfer, carbon or nitrogen atom. In some such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US 2005/0130923) and/or the 5' position. By way of additional example, carbocyclic bicyclic nucleosides having a 4'-2' bridge have been described (see, e.g., Freier et al., Nucleic Acids Research, 1997, 25(22), 4429-4443 and Albaek et al., J. Org. Chem., 2006, 71, 7731-7740).

In some embodiments, sugar surrogates comprise rings having other than 5-atoms. For example, in some embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10:841-854), and fluoro HNA (F-HNA).

In some embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In some embodiments, at least one of $q_1$, $q_2$, $q_3$, $q_4$, $q_5$, $q_6$ and $q_7$ is methyl. In some embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J C, Bioorganic & Medicinal Chemistry, 2002, 10, 841-854).

Combinations of modifications are also provided without limitation, such as 2'-F-5'-methyl substituted nucleosides (see PCT International Application WO 2008/101157 for other disclosed 5',2'-bis substituted nucleosides) and replacement of the ribosyl ring oxygen atom with S and further substitution at the 2'-position (see U.S. Patent Publication US 2005/0130923) or alternatively 5'-substitution of a bicyclic nucleic acid (see PCT International Application WO 2007/134181 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In some embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In some embodiments, oligonucleotides comprise one or more RNA-like nucleosides. In some embodiments, oligonucleotides comprise one or more DNA-like nucleotides.

In some embodiments, nucleosides of the present disclosure comprise one or more unmodified nucleobases. In certain embodiments, nucleosides of the present disclosure comprise one or more modified nucleobases.

In some embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2(3H)-one), carbazole cytidine (²H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., Angewandte Chemie, International Edition, 1991, 30, 613; and those disclosed by Sanghvi, Y. S., Chapter 15, Antisense Research and Applications, Crooke, S. T. and Lebleu, B., Eds., CRC Press, 1993, 273-288.

Representative United States Patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, each of which is herein incorporated by reference in its entirety.

In some embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In some embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)'O-5), amide-3 (3'-CH$_2$—C(=O)—N(H)-5'), amide-4 (3'-CH$_2$—N(H)—C(=O)-5'), formacetal (3'-O—CH$_2$—O-5), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-5-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylaminocarbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

E. Kits

The present disclosure also provides kits. Any of the components disclosed herein may be combined in the form of a kit. In some embodiments, the kits comprise a polyester polymer or a composition as described above or in the claims.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. In some embodiments, all of the nucleic acid delivery components are combined in a single container. In other embodiments, some or all of the nucleic acid delivery components with the instant compounds or compositions are provided in separate containers.

The kits of the present disclosure also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

F. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Materials and Instrumentation

Cell Culture:

Calu-6 and Calu-3 cells were obtained from the American Type Culture Collection and cultured in RMP1 1640 (Corning) medium with L-Glutamine and 25 mM HEPES supplemented with 5% FBS (Gemini Bio-Products). IB3-1 cells were kindly provided by Harvey Pollard and cultured in serum free LHC-8 (Invitrogen) medium. HEK 293 cells were obtained from the American Type Culture Collection and cultured in DMEM (Invitrogen) supplemented with 10% FBS (Gemini Bio-Products). HeLa-Luc cells and A549-Luc cells were cultured in phenol red free DMEM high glucose medium (Hyclone) supplemented with 5% FBS (Sigma-Aldrich). IGROV1 cells were cultured in RPMI 1640 (Sigma-Aldrich) with sodium bicarbonate and L-glutamine, supplemented with 5% FBS.

Antibodies and Reagents:

p53 DO-1(#sc-126) and GFP C2 (#sc-390394) antibodies were purchased from Santa Cruz Biotechnology, Inc. Actin antibody (MAB1501) was purchased from EMD Millipore. CFTR 596 antibody was purchased from the UNC Antibody Distribution Program. Unacylated $E.\ coli$ tRNA$^{Phe}$-Fl$^8$ (P05) was purchased from tRNA Probes, Inc. RNAiMax and Lipofectamine 2000 were purchased from Invitrogen and used following the supplier's recommended protocols. G418 (sc-29065) was purchased from Santa Cruz. PTC124 (S6003) and VX-770 (S1144) were purchased from Selleck Chemicals. 3-Isobutyl-1-methylxanthine (IBMX) (15879) and Forskolin (F3917) were purchased from Sigma-Aldrich. CFTR-Inh172 was obtained from CFFT (Cystic Fibrosis Foundation Therapeutics, Inc)

Plasmids and Site-Directed Mutagenesis of CFTR:

An expression plasmid of full-length, wild-type CFTR (pBI-CFTR) was purchased from Clontech and was mutagenized using standard protocols for site-directed mutagenesis (Sambrook et al., 1989). Site-directed mutagenesis was performed by PCR techniques using PfuUltra High-Fidelity DNA Polymerase (Stratagene, Santa Clara, Calif.). All mutations were confirmed by DNA sequencing. Sup-tRNA$^{Arg}$ was a gift from Carla Oliveira (Institute of Molecular Pathology and Immunology of the University of Porto (IPATIMUP), Porto, Portugal.

Quantification Methods of Mature CFTR:

HEK293 cells were seeded ($9 \times 10^5$ cells) and transfected with CFTR plasmids. 2 μg of CFTR plasmid and 500 ng of Sup-tRNA$^{Arg}$ were co-transfected using 4 μl of Lipofectamine 2000 in a 6-well format. G418 (200 μg) or PTC124 (40 μM) was added to the media 24 hr post-transfection and remained for 48 hr. IB3-1 cells were seeded and G418 (0-400 μG) or PTC124 (0-20 μM) was added 24 hr later. After 48 hr, cells were lysed directly in 2× Sample Buffer ((Tris-HCL 250 mM, pH 6.8, 20% Glycerol, 2.5% SDS, 0.1% Bromophenol blue). Cell lysate proteins were separated by electrophoresis on 7%/10% step (wt/vol) polyacrylamide gels using a Tris-glycine buffering system and transferred to polyvinylidene fluoride immobilon membranes (EMD Millipore) Western blot analysis was performed using primary CFTR antibody (596) (University of North Carolina School of Medicine, Chapel Hill, N.C.), actin antibody (EMD Millipore), and secondary antibody IRdye-680RD (Li-Cor) and imaged/quantified using a Li-Cor Odyssey CLx (Li-Cor). Data was plotted using Prism 6 (Graphpad).

CFTR-Dependent Whole-Cell Current in HEK293 Cells:

HEK293 cells were transfected with the plasmids used for the CFTR maturation experiments. 2 μg of CFTR plasmid and 500 ng of Sup-tRNA$^{Arg}$ were cotransfected using 4 μl of Lipofectamine 2000 in a 6-well format. 24 hr post-transfection, the whole-cell configuration of the patch-clamp technique was used to measure the Cl-current. The pipette solution contained 145 mM NMDG+—Cl—, 1 mM MgCl2, 2 mM EGTA, 5 mM ATP, and 10 mM HEPES (pH 7.3 with Tris). The bath solution was 145 mM NMDG+—Cl—, 1 mM $MgCl_2$, 1 mM $CaCl_2$, 10 mM HEPES and 10 mM glucose (pH 7.4 with Tris). The current was recorded with an Axopatch 200B patch-clamp amplifier and digitized at 2 kHz. The membrane conductance was probed by stepping the membrane potential from a holding potential of 0 mV to membrane potentials −40 and +40 mV steps for 200 ms. Whole-cell current responses were measured in response to 10 μM forskolin plus 100 μM IBMX and 10 μM CFTRInh-172 (Inh-172). Pipettes had resistances between 3 and 5 MΩ when filled with pipette solution and seal resistance exceeded 8 GU. Current recording and analysis was performed with pClamp 9.2 software and analyzed with Origin 8 software.

In Vitro ZAL Nanoparticle Formulations:

Lipid nanoparticles were prepared by the ethanol dilution method. The RNA (whether an siRNA, tRNA, sgRNA, or mRNA) was diluted in acidic aqueous buffer (unless otherwise indicated, 10 mM citric acid/sodium citrate buffer pH 3). The lipid mix was prepared in ethanol, with the appropriate molar ratios of ZAL, cholesterol, PEG-lipid, DSPC, and or DOPE from ethanol stock solutions of each component. Via pipette, the lipid dilution was added to the RNA dilution at a final volumetric ratio of 1:3, rapidly mixed by pipette, and incubated for 15-20 minutes. After this incubation period, the particles were either diluted 3-fold in, or dialyzed against 1× Dulbecco's Modified PBS without calcium and magnesium (Sigma-Aldrich). Dialyses were performed in Pur-A-Lyzer Midi dialysis chambers (Sigma-Aldrich) for 1 hour per 200 μL sample per chamber.

ZAL siRNA Delivery Library Screen:

The library of ZALs functionalized with epoxide and acrylate hydrophobic tails was screened for siRNA delivery efficacy in HeLa-Luc cells. In a white opaque 96-well plate tissue culture plate, HeLa cells were seeded at a density of $10 \times 10^3$ cells per well in 100 μL growth medium (DMEM without phenol red, 5% FBS), and allowed to attach overnight. The medium was exchanged for 200 μL fresh growth medium the day of the assay. Crude ZALs products were using a formulation lipid mixture of 50:38.5 ZAL: cholesterol, and a ZAL:siRNA such that the number of hydrophobic tails in the ZAL times the ZAL:siRNA mole ratio in the formulation is ~1000, which resulted in a weight ratio range across the library of 16:1 ZAL:siRNA for the largest ZAL and 45:1 ZAL:siRNA, with an average of 29.5+/−6.3 weight ratio across the library. ZAL NP formulations were performed in a 96-well plate by rapid mixing of ZAL lipid mix (20 μL) and siLuc dilution (60 μL, 13.33 ng/μL in 10 mM citric acid-sodium citrate buffer, pH 5) at 3:1 aqueous:EtOH v:v ratio with a multichannel pipette. After a 15-20 minute incubation period, the formulations were diluted in 12 volumes (240 μL) PBS. The nanoparticles (40 μL) were added to the HeLa-Luc cells at a dose of 100 ng siRNA per well. The nanoparticles were incubated with the cells for 24 h after which time the cell viability and luciferase expression were evaluated with the ONE-Glo+Tox Assay cell viability and luciferase assay (Promega).

sgRNA Delivery to HeLa-Luc-Cas9 Cells:

Select ZALs were evaluated in the delivery of single guide RNA (sgRNA) to HeLa-Luc-Cas9 cells. In a white opaque 96-well plate tissue culture plate, HeLa-Luc-Cas9 cells were seeded at a density of $5 \times 10^3$ cells per well in 100 μL growth medium (DMEM without phenol red, 5% FBS), and allowed to attach overnight and then supplemented with an additional 100 μL DMEM. ZALs-sgRNA nanoparticles were formulated using the in vitro nanoparticle formulation protocol at the indicated lipid composition and weight ratio (maintaining 50:38.5 ZAL: cholesterol mole ratio, tuning-PEG-lipid additive from 5% to 0.5%, and tuning weight ratio from 20:1 ZAL:sgRNA to 5:1 ZAL:sgRNA). Luciferase deletion was evaluated using a single guide RNA designed against luciferase using the CRISPR.mit.edu algorithm, while non-targeting control sgRNA (sgScr) was used as a negative control. The nanoparticles were added to the cells at a dose of 50 ng sgRNA per well and incubated with the cells for 24 h or 48 h. RNAiMax (Invitrogen) formulated according to the manufacturer's protocol with sgLuc or sgScr was used as a positive control. After 24 h or 48 h, the cell viability and luciferase expression were evaluated with the ONE-Glo+Tox Assay cell viability and luciferase assay (Promega).

Co-Delivery of Cas9 mRNA and sgRNA A549 and HeLa-Luc Cells:

ZA3 ZAL were evaluated in the co-delivery of Cas9 mRNA (Tri-Link biotechnologies) and single guide RNA (sgRNA) to luciferase expressing cancer cells. In a white opaque 96-well plate tissue culture plate, A549-Luc or HeLa-Luc cells were seeded at a density of $5 \times 10^3$ cells per well in 100 μL growth medium (DMEM without phenol red, 5% FBS), and allowed to attach overnight and then supplemented with an additional 100 μL DMEM. ZALs-Cas9mRNA nanoparticles were formulated using the in vitro nanoparticle formulation protocol at the indicated lipid composition and weight ratio (maintaining 50:38.5 ZAL: cholesterol mole ratio, tuning PEG-lipid additive from 5% to 0.5%, and tuning weight ratio from 20:1 ZAL:sgRNA to 5:1 ZAL:sgRNA).

Different dosing regiments were evaluated including sgRNA and Cas9 mRNA in the same nanoparticle (where the sgRNA and Cas9 mRNA were diluted in the acidic buffer dilution prior to the addition of the lipid mixture) sgRNA and Cas9 mRNA formulated in different ZAL particles but added simultaneously, or Cas9 mRNA added 24 h prior to the addition of sgRNA. As a negative control, sgRNA delivery in the absence of Cas9 mRNA was also included for all ZAL NPs tested. The nanoparticles were added to the cells at a dose of 100 ng Cas9 mRNA or 50 ng sgRNA per well and incubated with the cells for 48 h. As a positive control Lipofectamine 3000 (Invitrogen) was used to deliver Cas9 mRNA while RNAiMax (Invitrogen) formulated according to the manufacturer's protocol. 48 h after the sgRNA deliver, the cell viability and luciferase expression were evaluated with the ONE-Glo+Tox Assay cell viability and luciferase assay (Promega).

CSAL In Vitro siRNA Delivery Efficacy:

In a white opaque 96-well plate tissue culture plate, HeLa-Luc or A549-Luc cells were seeded at a density of $10 \times 10^3$ cells per well in 100 μL growth medium (DMEM without phenol red, 5% FBS), and allowed to attach overnight. The medium was exchanged for 200 μL fresh growth medium the day of the assay. CSAL products were using a formulation lipid mixture of 50:38.5:10:1.5 ZAL:cholesterol:DSPC:PEG-lipid, and screened at a mole ratio CSAL:siRNA of 666:1, 333:1 and 167:1. ZAL NP formulations were performed in a 96-well plate by rapid mixing of CSAL lipid mix (10 μL) and siLuc dilution (20 μL, 40 ng/μL in 10 mM citrate phosphate buffer, pH 3) at 2:1 aqueous:EtOH v:v ratio with a multichannel pipette. After a 15-20 minute incubation period, the formulations were diluted in 12 volumes (120 μL) PBS. The nanoparticles (18.75 μL) were added to the HeLa-Luc cells at a dose of 100 ng siRNA per well. The nanoparticles were incubated with the cells for 24 h after which time the cell viability and luciferase expression were evaluated with the ONE-Glo+Tox Assay cell viability and luciferase assay (Promega) and normalized to untreated cells (N=3 or 4+/− standard deviation).

siRNA Uptake Studies:

Cellular uptake studies were performed using CSALs NPs with the same formulation as the in vitro delivery efficacy screen in HeLa-Luc cells and A549-Luc cells. Cells were seeded at a density of 30,000 cells per well in 8-chambered coverglass slides (Nunc) and allowed to attached for 24 hours. The nanoparticles were added to the cells at a final siRNA concentration of 34 nM. After 4 h or 24 h incubation, the medium was aspirated, washed with PBS, and cell membrane staining was performed (Cell Mask Green, Molecular Probes) using the manufacturer's protocol. Cells were fixed with 4% paraformaldehyde (15 minutes RT), washed with PBS 2 times 5 minutes, the cell nuclei were stained with DAPI (Sigma-Aldrich) and washed with PBS. Confocal microscopy imaging was performed using a Zeiss LSM 700 microscope and images were analyzed using ImageJ (NIH).

Nucleic Acid Binding Experiments:

Nucleic acid binding was evaluated using the Ribogreen assay (Molecular Probes). In short, nanoparticles were prepared using the in vitro or in vivo formulation protocols. The nanoparticle formulations (5 μL) were added to a black 96-well opaque microplate (Corning). A standard curve of the appropriate nucleic acid was prepared in the same medium as the nanoparticles. Ribogreen reagent was diluted 1:1000 in 1×PBS and 50 μL was added to each well via multichannel pipette. The mixture was stirred on an orbital mixer for 10 minutes, and the fluorescence of each well was read using a plate reader ($\lambda_{Ex}$ 485 nm, $\lambda_{Em}$ 535 nm). The amount of free nucleic acid was determined by fitting the signal from each nanoparticle sample to the nucleic acid standard curve, and the fraction bound determined by the following formula: Fraction nucleic acid bound=(total nucleic acid input-free nucleic acid)/total nucleic acid input) (N=3 or 4+/− standard deviation).

ZAL mRNA Delivery In Vitro Assay:

ZAL nanoparticles with firefly luciferase mRNA (Tri-Link Biotechnologies) were prepared using the in vitro nanoparticle formulation method outlined above. IGROV1 cells were seed in white opaque 96-well tissue culture plates at a seeding density of $5 \times 10^3$ cells per well in 100 μL RPMI 1640 medium supplemented with 5% FBS, and allowed to attach overnight. After overnight incubation, and additional 100 μL medium was added to the wells. The ZAL:mRNA nanoparticles were prepared at a ZAL:mRNA weight ratio of 20:1, 10:1, 7.5:1 and 5:1, and lipid mixture molar compositions of 50:38.5 ZAL:cholesterol, with PEG lipid supplemented at a molar ratio of 5%, 2%, 1% or 0.5% at each weight ratio. The ZAL-mRNA nanoparticles were added to the cells at a dose of 100 ng mRNA per well and incubated for the indicated time (ranging from 6 h to 48 h), after which time cell viability and luciferase expression were evaluated with the ONE-Glo+Tox Assay cell viability and luciferase assay (Promega) and normalized to untreated cells (N=4+/− standard deviation)

In Vivo Nanoparticle Formulations:

In vivo nanoparticle formulations were performed using the NanoAssemblr microfluidic mixing system (Precision Nanosystems). Lipids were dissolved in ethanol and nucleic acids (mRNA or siRNA) were diluted in 10 mM citric acid-sodium citrate buffer pH 3. The lipid mixture and nucleic acid dilution were combined at a volumetric ratio of 3:1 nucleic acid: lipid mix at a total flow rate of 12 mL per minute, and a waste collection of 0.1 mL in the beginning and end of each formulation. The nanoparticles were dialyzed against 1×PBS in Pur-A-Lyzer midi dialysis chambers (Sigma-Aldrich) for 1 hour per 200 μL volume in each chamber, and diluted in 1× PBS to the appropriate nucleic acid concentration.

In Vivo siRNA Nanoparticle Biodistribution:

All experiments were approved by the Institutional Animal Care & Use Committee (IACUC) of The University of Texas Southwestern Medical Center and were consistent with local, state and federal regulations as applicable. CSAL nanoparticles were prepared using the in vivo nanoparticle formulation method at a lipid mixture mole ratio of 50:38.5:10:1.5 CSAL: cholesterol: DSPC: PEG-lipid, and weight ratio ranging from 20:1 to 45:1 total lipid:siRNA weight ratio. For the siRNA dilution, the siRNA was spiked with 50% Cy5.5 labeled siRNA, and formulation performed as normal. After dialysis, the nanoparticles were diluted to a concentration of 1 μg per 10 μL formulation. This formulation was injected at a dose of 1 mg/kg siRNA by tail vein injection into Black 6 mice. After 2 h or 24 h time, the animals were anesthetized under isofluorane, sacrificed by cervical dislocation, and the organs resected. Fluorescence imaging of the organs was performed on an IVIS Lumina system (PerkinElmer) using the Cy5 excitation and emission filter set, and the images processed using Living Image analysis software (PerkinElmer).

In Vivo Luciferase mRNA Delivery:

All experiments were approved by the Institutional Animal Care & Use Committee (IACUC) of The University of Texas Southwestern Medical Center and were consistent with local, state and federal regulations as applicable. ZA3-Ep10 ZAL was formulated with in vivo formulation at 50 ZAL:38.5 cholesterol: 2 or 0.5 PEG-lipid mole ratio in the lipid mix, and 7.5:1 ZAL:mRNA weight ratio. Athymic Nude-Foxn1$^{nu}$ mice (Harlan Laboratories) were injected with ZAL-mRNA NPs at a dose of 1 mg/kg via tail vein injection or intraperiotneal injection. After 24 h and 48 h the luciferase expression was evaluated by live animal bioluminescence imaging Animals were anesthetized under isofluorane, and D-luciferin monosodium hydrate (GoldBio) substrate was injected IP. After 10-12 minute incubation, the luciferase activity by imaged on an IVIS Lumina system (PerkinELmer), and the images processed using Living Image analysis software (PerkinElmer). Ex vivo imaging was performed on systemic organs after resection, and the tissue frozen on dry ice for ex vivo luciferase expression analysis.

In Vivo Luciferase Silencing in A549 Xenografts:

All experiments were approved by the Institutional Animal Care & Use Committee (IACUC) of The University of Texas Southwestern Medical Center and were consistent with local, state and federal regulations as applicable. Athymic Nude-Foxn1$^{nu}$ mice (Harlan Laboratories) were implanted with xenografts in each hind flank with firefly luciferase expressing A549 ($5 \times 10^6$ cells suspended in 100 μL of 1:1 v:v PBS: Matrigel (Corning)). After the tumors reached adequate size, each tumor on the same animal was injected with in vivo formulated NPs (~50 μL per tumor) of CSAL A3OAcC2Me, with a lipid molar ratio of 50 CSAL: 38.5 cholesterol: 10 DSPC: 1.5 PEG-lipid, and total lipid: siRNA weight ratio of 30:1, and final siRNA dose of 1 mg/kg siLuc or siCtrl. After 24 h and 48 h the luciferase expression was evaluated by live animal bioluminescence imaging Animals were anesthetized under isofluorane, and D-luciferin monosodium hydrate (GoldBio) substrate was injected IP. After 10-12 minute incubation, the luciferase activity by imaged on an IVIS Lumina system (PerkinELmer), and the images processed using Living Image analysis software (PerkinElmer).

Ex Vivo Luciferase Expression Analysis in A549 Xenografts:

48 h post injection of A3OAcC2Me siLuc or siCtrl the mice were euthanized by cervical dislocation and the A549 xenografts were resected and frozen on dry ice. The tumors were weighed on a balance, cut into strips with a straight razor and diluted at 1:3 tumor mass:volume (mg:μL) of 1× reporter lysis buffer (Promega) supplemented with protease inhibitor mini tablets (Pierce) and kept on ice. The tissue was homogenized and the luciferase expression evaluated by the Luciferase assay system.

Nanoparticle Property Characterization:

Physical properties were measured using a Zetasizer Nano ZS (Malvern) with an He—Ne laser ($\lambda$=632 nm). Particle sizes were measured by dynamic light scattering (BLS) (5 measurements, 3 runs×10 seconds, automatic attenuator setting) by 173° back scattering. Zeta potential was measured in a folded capillary cell (Malvern) with samples diluted in PBS for ZAL NPs or citrate phosphate buffer pH 7.4 for CSAL NPs.

tRNA Uptake Studies:

Cellular uptake studies were performed using the top performing materials from the screen. Calu6 cells were seeded at a density of 30,000 cells per well in 8-chambered coverglass slides (Nunc) and allowed to attached for 24 hours. NP formulations were prepared using the in vitro nanoparticle formulation procedure. The nanoparticles were added to the cells at a final tRNA concentration of 0.9 μg/well. After 6 h incubation, the medium was aspirated, washed with PBS, and cell membrane staining was performed (Cell Mask Orange, Molecular Probes) using the manufacturer's protocol. Cells were fixed with 4% paraformaldehyde (15 minutes RT), washed with PBS 2 times 5 minutes, the cell nuclei were stained with DAPI (Sigma-Aldrich) and washed with PBS. Confocal microscopy imaging was performed using a Zeiss LSM 700 microscope and images were analyzed using ImageJ (NIH).

Nanoparticle Carrier Screen in Calu6 Cells:

Calu6 cells were seeded at a density of 500,000 cells per well in a 6-well format and allowed to attach overnight. For plasmid DNA; 1 μg was transfected using 3 μl of Lipofectamine 2000 using manufacturer recommend protocols. For tRNA$^{ArgOp}$-RNAiMax, 4 μg was transfected using 3 μl of RNAiMax using manufacturer recommended protocols. Particles were diluted in Opti-MEM (Invitrogen). G418 (50 μg) and PTC124 (10 μl M) was added directly to the media. Nanoparticles were formulated as follows. Functional polyester-RNA polyplexes were prepared using a weight ratio of 30:1 polymer:RNA by adding 10 μL polymer stock (15 g/L in DMSO) to a dilution of tRNA (5 μg tRNA in 490 μL 10 mM citrate buffer pH 4.2) and incubating for 20 minutes. Deudrimer, ZAL, and CSAL nanoparticles were prepared using the in vitro nanoparticle formulation method detailed above. Dendrimers were formulated with a lipid mixture of 50:38:10:2 dendrimer:cholesterol:DSPC:PEG-lipid, and a dendrimer:tRNA mole ratio of 200:1 unless otherwise indicated. ZAL-tRNA NPs were formulated with a lipid mixture of 50:38.5 ZAL:cholesterol and a total lipid:tRNA weight ratio of 25:1. CSAL-tRNA NPs were formulated with a CSAL:tRNA weight ratio of 20:1. For all nanoparticles, 400 μL of each formulation was added to the cells in 2 mL medium for a dose of 4 μg tRNA per well. After 48 hr, cells were lysed directly in 2× Sample Buffer ((Tris-HCL 250 mM, pH 6.8, 20% Glycerol, 2.5% SDS, 0.1% Bromophenol blue). Cell lysate proteins were separated by electrophoresis on 10% (wt/vol) polyacrylamide gels using a Tris-glycine buffering system and transferred to polyvinylidene fluoride Immobilon membranes (EMD Millipore). Western blot analysis was performed using primary p53 antibody (Santa Cruz Biotechnology, True) actin antibody (EMI) Millipore), and secondary antibody IRdye-680RD (Li-Cor) and imaged/ quantified using a Li-Cor Odyssey CLx (Li-Cor).

Example 2: Synthesis and Characterization of the Amino Lipids

Figure 1:
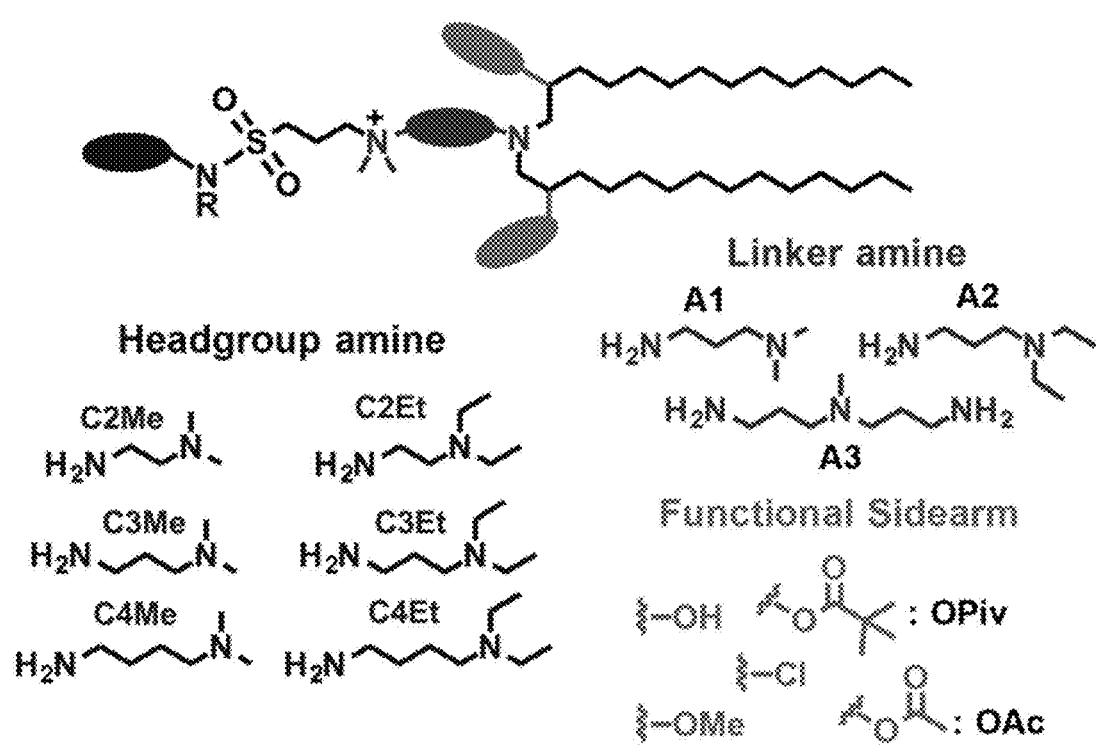
FIG. 1 shows non-limiting examples of components of the cationic sulfonamide amino lipids of the present disclosure as a new class of lipids with properties enabling nucleic acid therapeutic delivery. The modular design enabled systematic changes to the linker amine region (red), the headgroup amine (blue) and a functional sidearm (green) to determine their relative contributions to biophysical properties. Steric interactions around the quaternary amine, the number of lipid tails, and sidearm functionality were evaluated.
Figure 2:
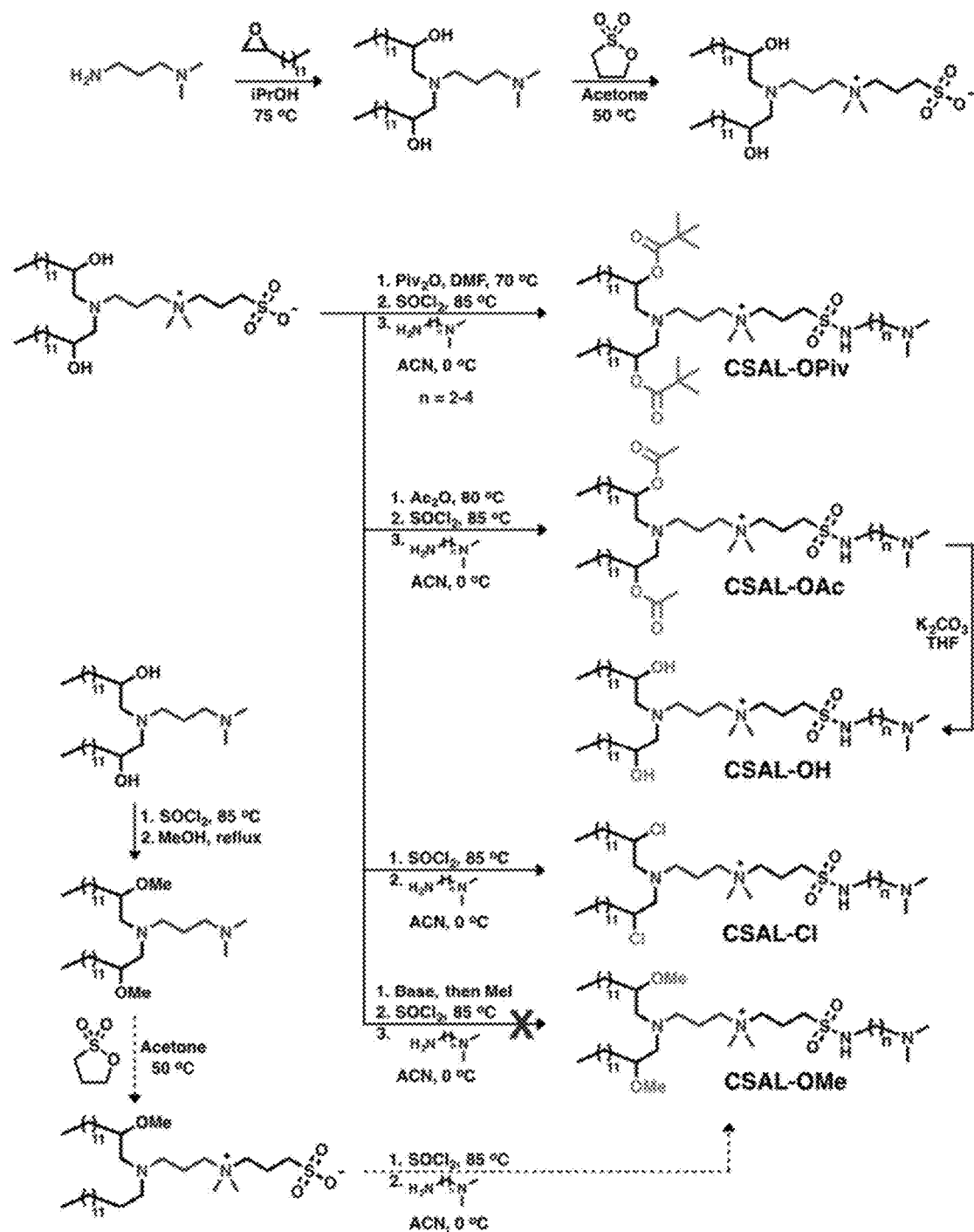
FIG. 2 shows an exemplary synthesis of CSALs based on the A1 linker amine were performed from a common sulfobetaine zwitterionic precursor.
Figure 40:
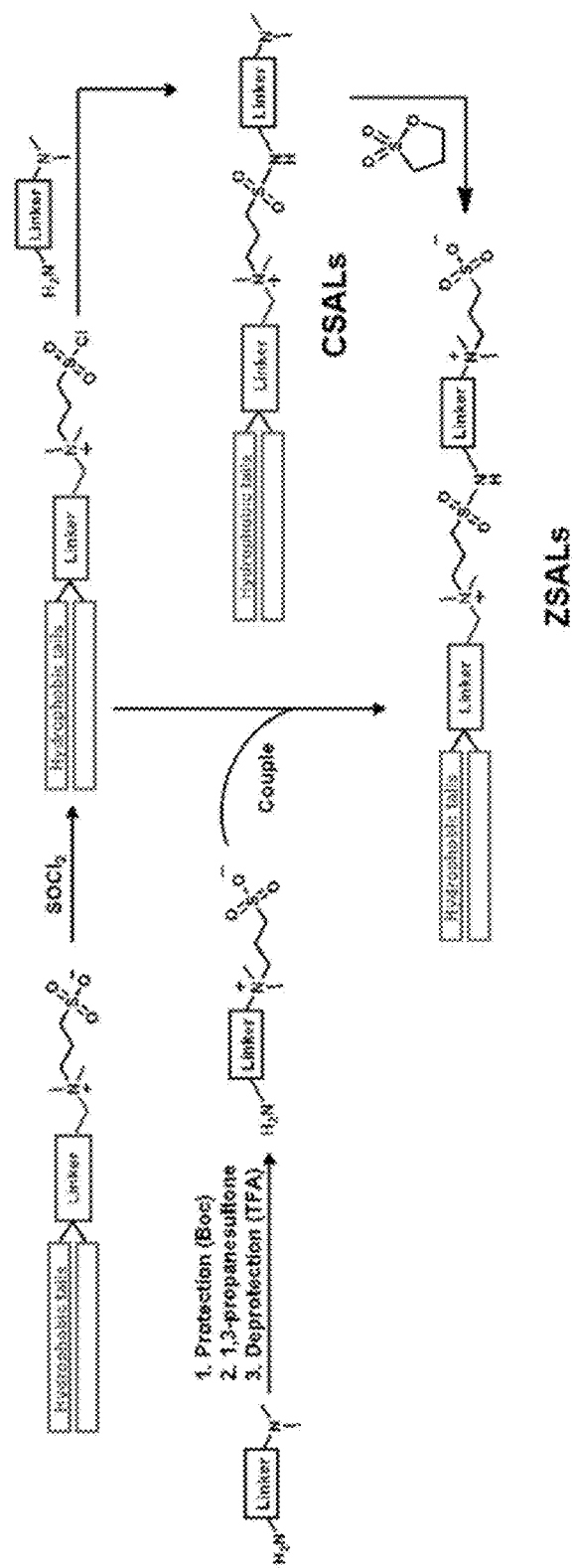
FIG. 40 shows alternative synthesis methods for the preparation of the CSALs and ZALs.
Figure 41A:
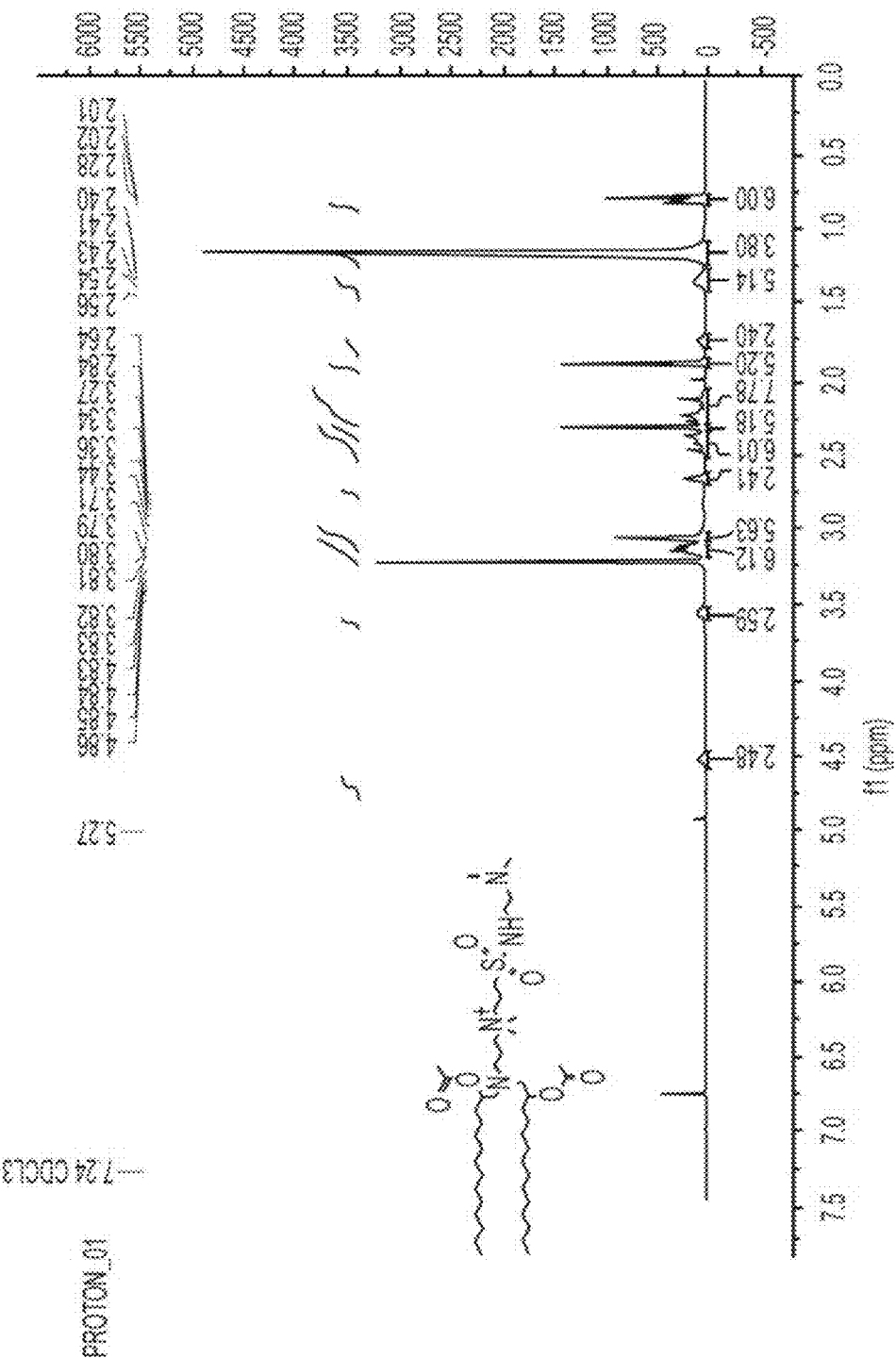
FIGS. 41A-41D show $^1$H NMR spectra of CSALs: A1OAcC2Me (FIG. 41A), A1OAcC3Me (FIG. 41B), A1OAcC4Me (FIG. 41C), and ZA (FIG. 41D).
Figure 41B:
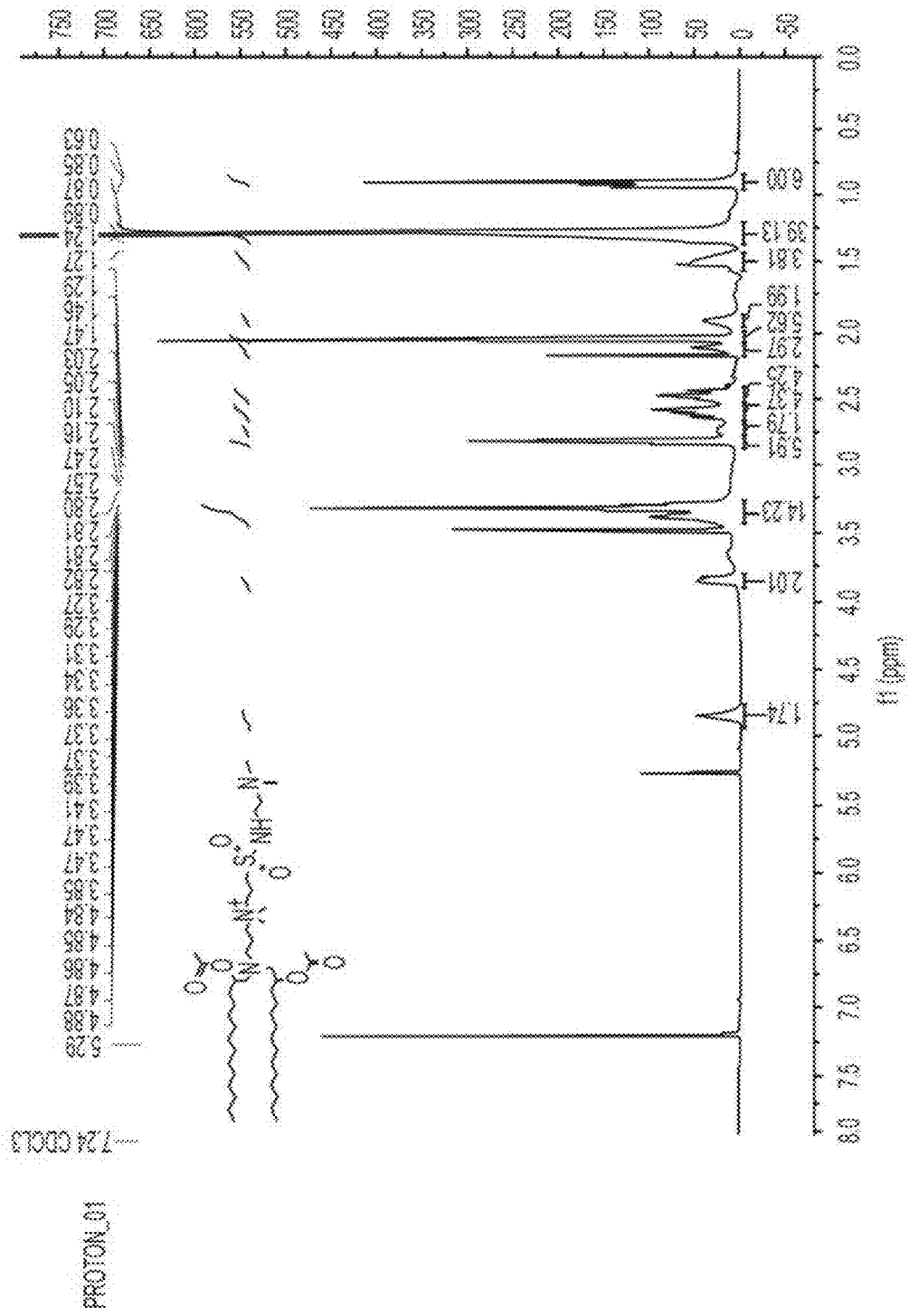
Figure 41C:
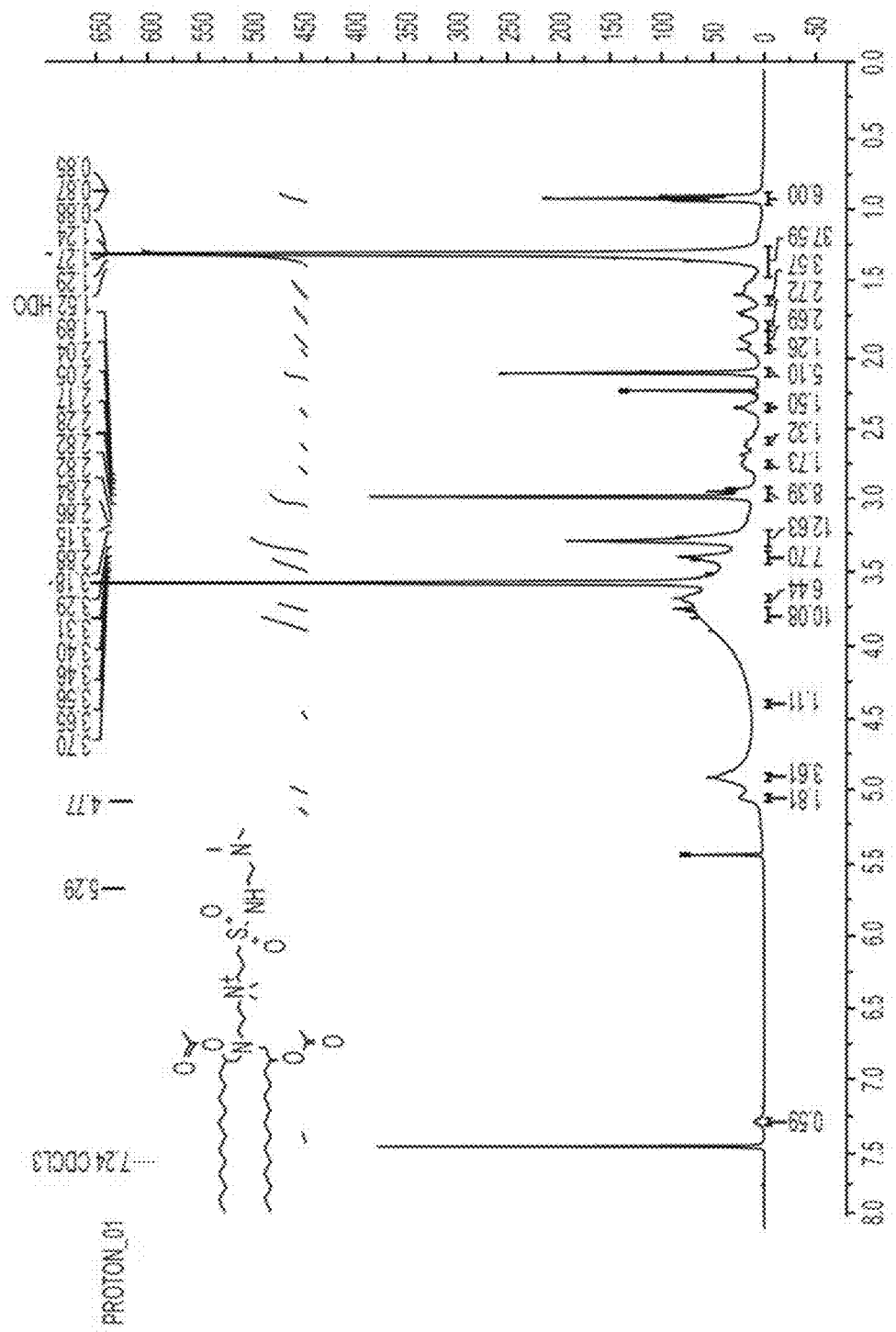
Figure 41D:
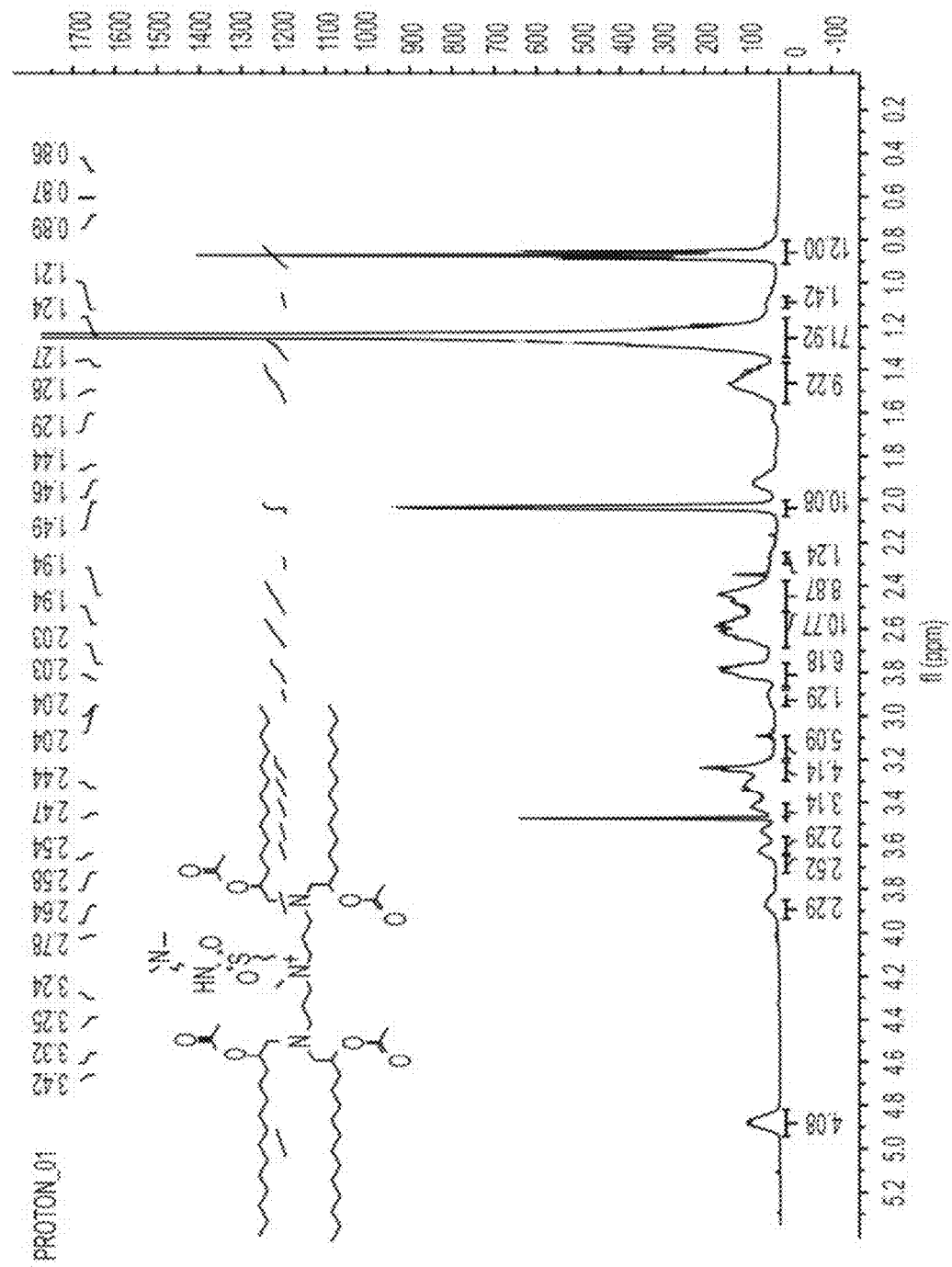
Figure 42A:
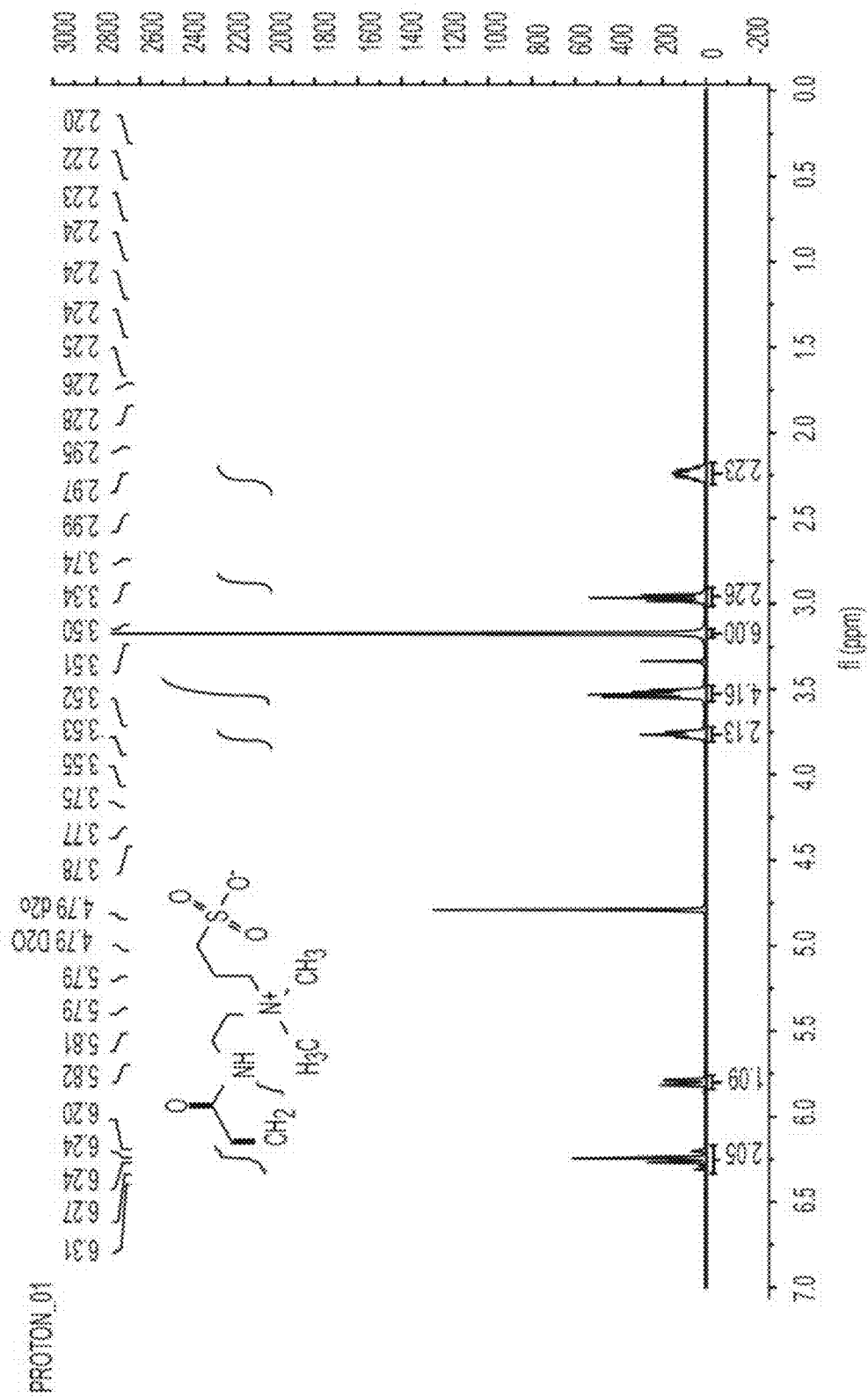
FIGS. 42A-42F show $^{11}$H NMR spectra of ZALs: ZA (FIG. 42A), ZA3-Ep10 (FIG. 42B), A1-OH (FIG. 42C), A3-OH (FIG. 42D), A3-OAc (FIG. 42E), and A1-OPiv (FIG. 42F).
Figure 42B:
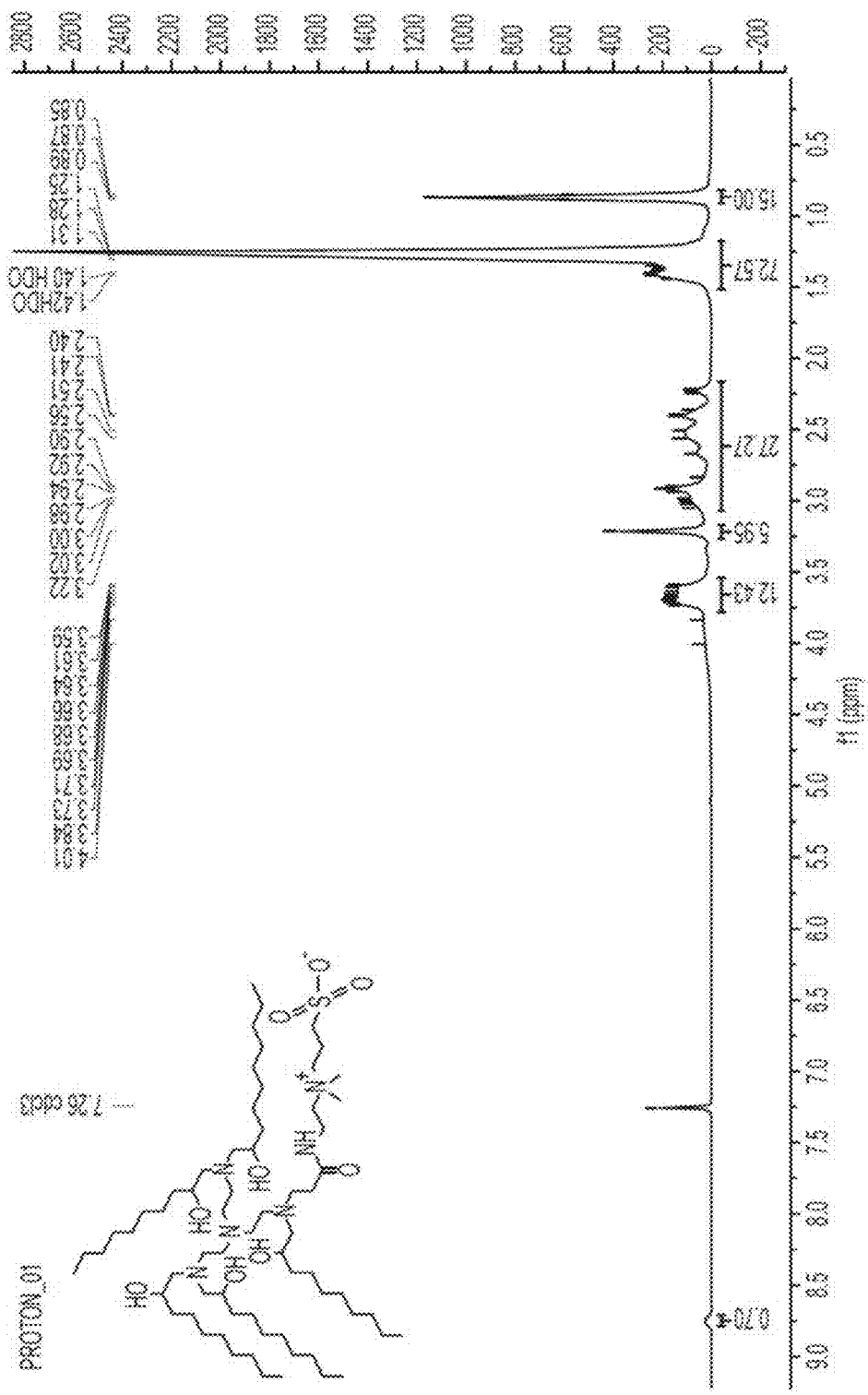
Figure 42C:
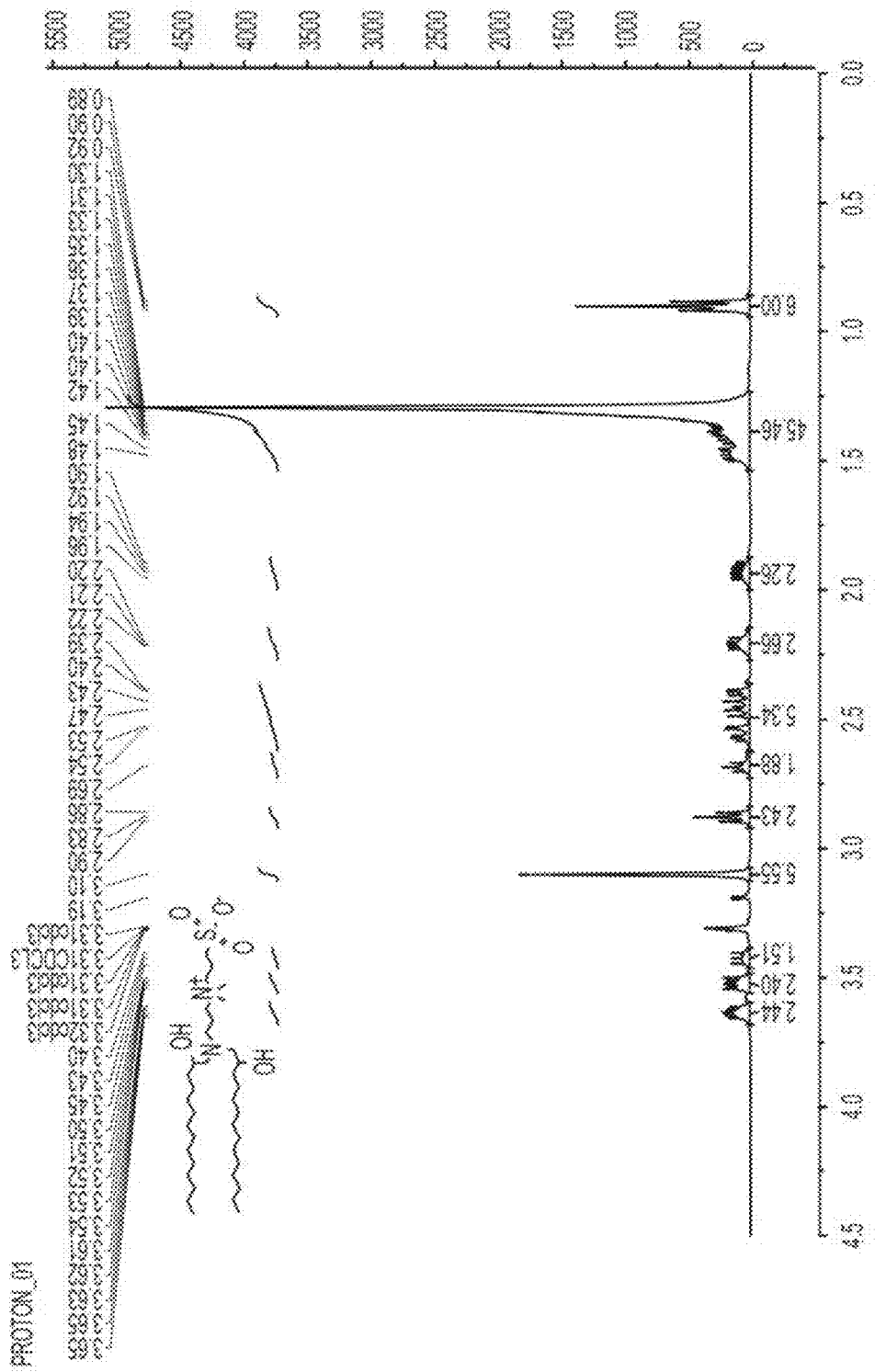
Figure 42D:
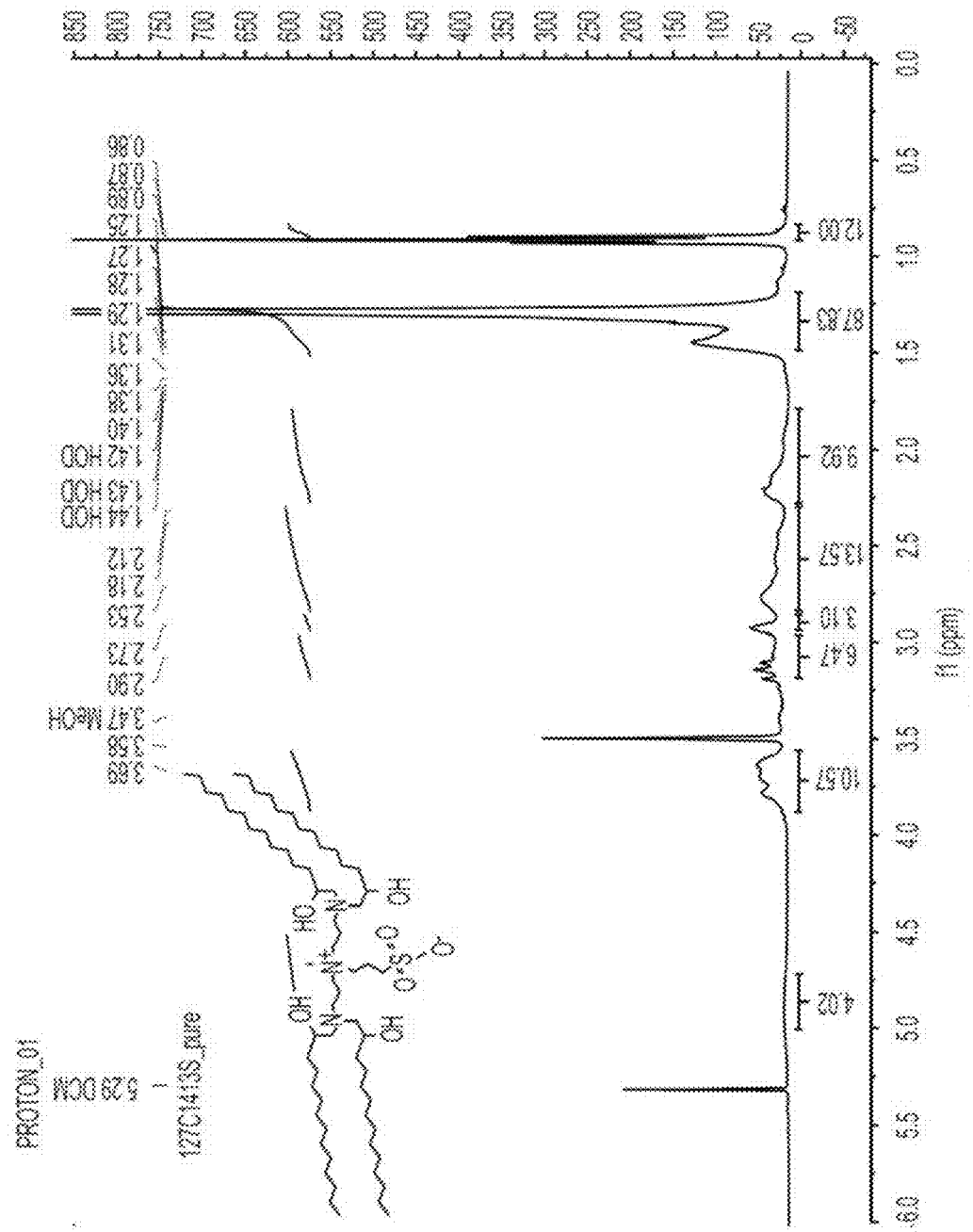
Figure 42E:
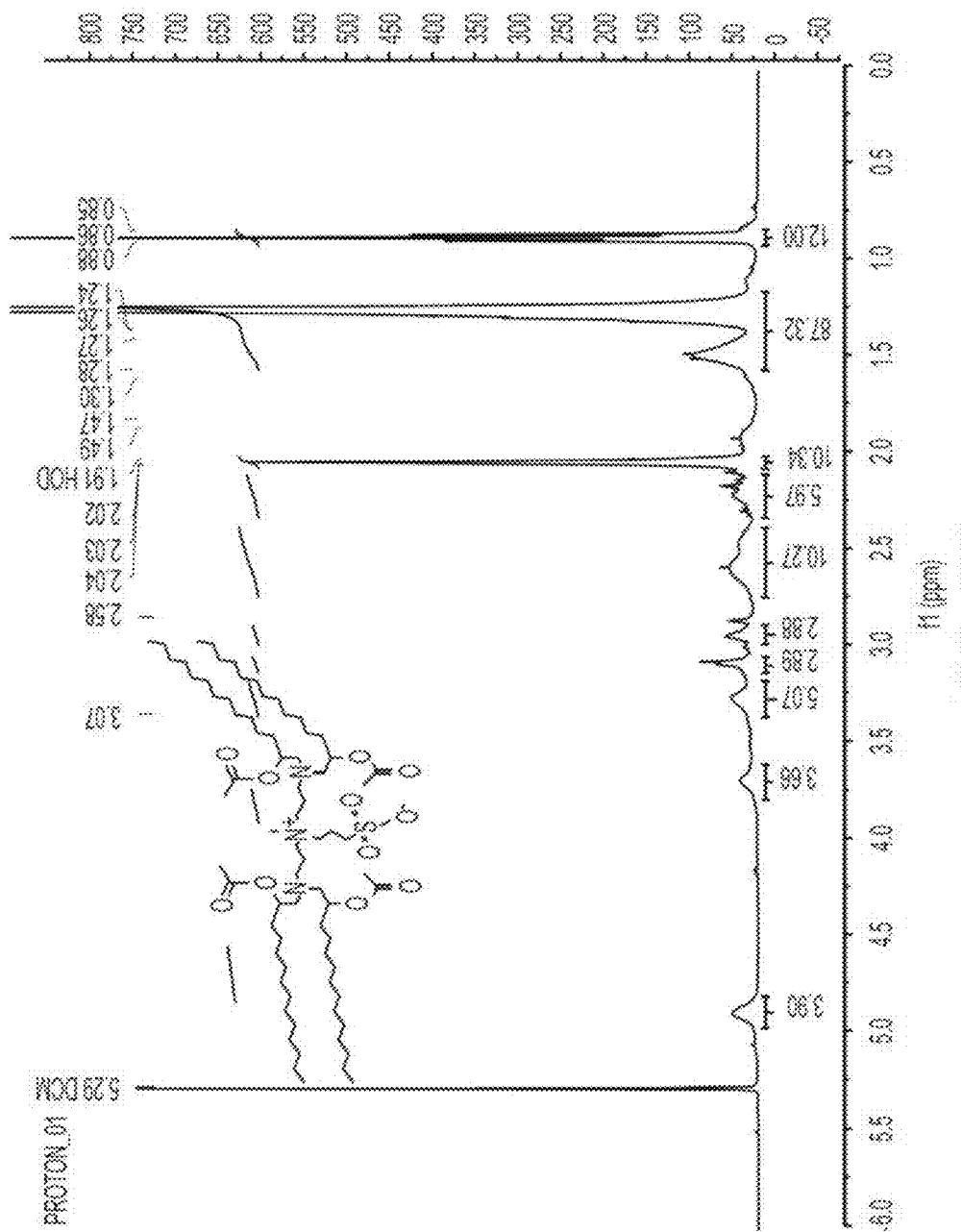
Figure 42F:
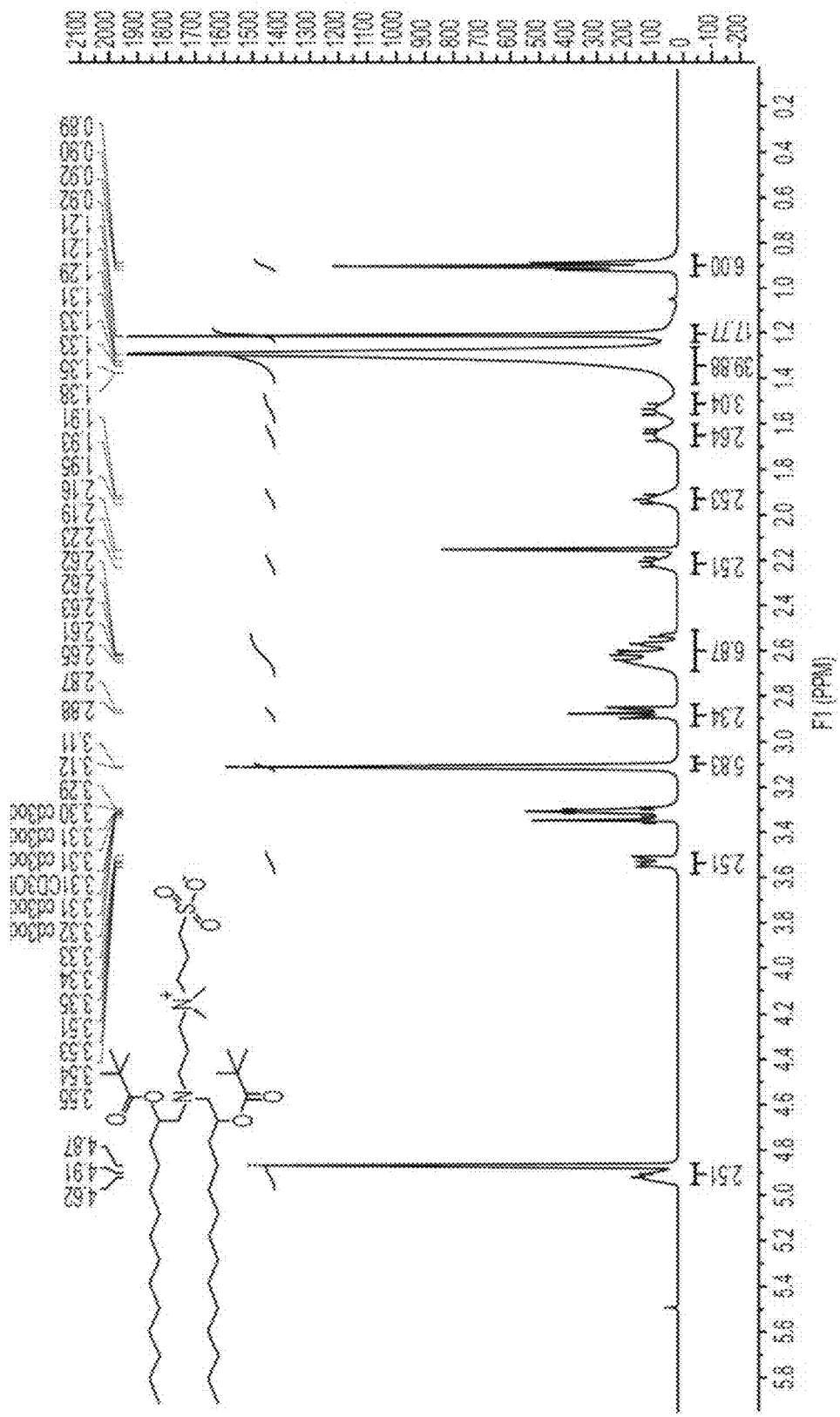

The cationic sulfonamide amino lipids (CSALs) were prepared using different headgroups, linker amides, with a variety of functional sidearms for the lipid groups as shown in FIG. 1. An exemplary synthetic route for preparing the cationic sulfonamide amino lipids is shown in FIG. 2. Some exemplary characterization information for CSAL A3OAcC2Me is shown in FIG. 40. Alternative synthesis methods are described in FIG. 42.

Synthesis of A1-OAc-Cn-Me/Et and A2-OAc-Cn-Me/Et CSALs:

In a 20 mL vial equipped with a stir bar was dissolved A1-OAc propanesulfonate (100 mg, 0.136 mmol) or A2-OAc propanesulfonate (in 2 mL thionyl chloride. The vial was sealed and the reaction mixture heated to 85° C. for 30 minutes. The reaction was cooled to room temperature, diluted in 5 mL freshly distilled toluene and concentrated under reduced pressure. The crude sulfonyl chloride intermediate was cooled on ice and to this was added the appropriate N,N-dimethyl diamine or N,N-diethyl diamine (5 equiv) dissolved in 5 mL dry acetonitrile. The reaction mixture was stirred on ice for 15 minutes, and the reaction mixture concentrated under reduced pressure. The crude product was purified on silica gel with a solvent gradient of 5% MeOH in DCM to 20% MeOH, 1% sat. NH$_4$OH in DCM to yield the product as a sticky yellow or brown solid.

A1OAcC2Me Mass calculated m/z 803.6654, observed (MALDI-TOF ms) m/z 803.3930

A1OAcC3Me Mass calculated m/z 817.6810, observed (MALDI-TOF ms) m/z 817.5598

A1OAcC4Me Mass calculated m/z 831.6967, observed (MALDI-TOF ms) m/z 831.5186

A1OAcC2Et Mass calculated m/z 831.6967, observed (MALDI-TOF ms) m/z 831.80

A1OAcC3Et Mass calculated m/z 845.7123, observed (MALDI-TOF ms) m/z 846.51

A2OAcC2Me Mass calculated m/z 831.6967, observed $M^{+1}$ (MALDI-TOF ms) m/z 832.62

A2OAcC2Et Mass calculated m/z 859.7280, observed $M^{+1}$ (MALDI-TOF ms) m/z 860.66 thionyl chloride. The vial was sealed and the reaction mixture heated to 85° C. for 30 minutes. The reaction was cooled to room temperature, diluted in 5 mL freshly distilled toluene and concentrated under reduced pressure. The crude sulfonyl chloride intermediate was cooled on ice and to this was added the appropriate N,N-dimethyl diamine (5 equiv) dissolved in 5 mL dry acetonitrile. The reaction mixture was stirred on ice for 15 minutes, and the reaction mixture concentrated under reduced pressure. The crude product was purified on silica gel with a solvent gradient of 5% methanol in DCM to 75% DCM, 20% methanol, 5% saturated ammonium hydroxide in water to yield the product as a sticky yellow or brown solid.

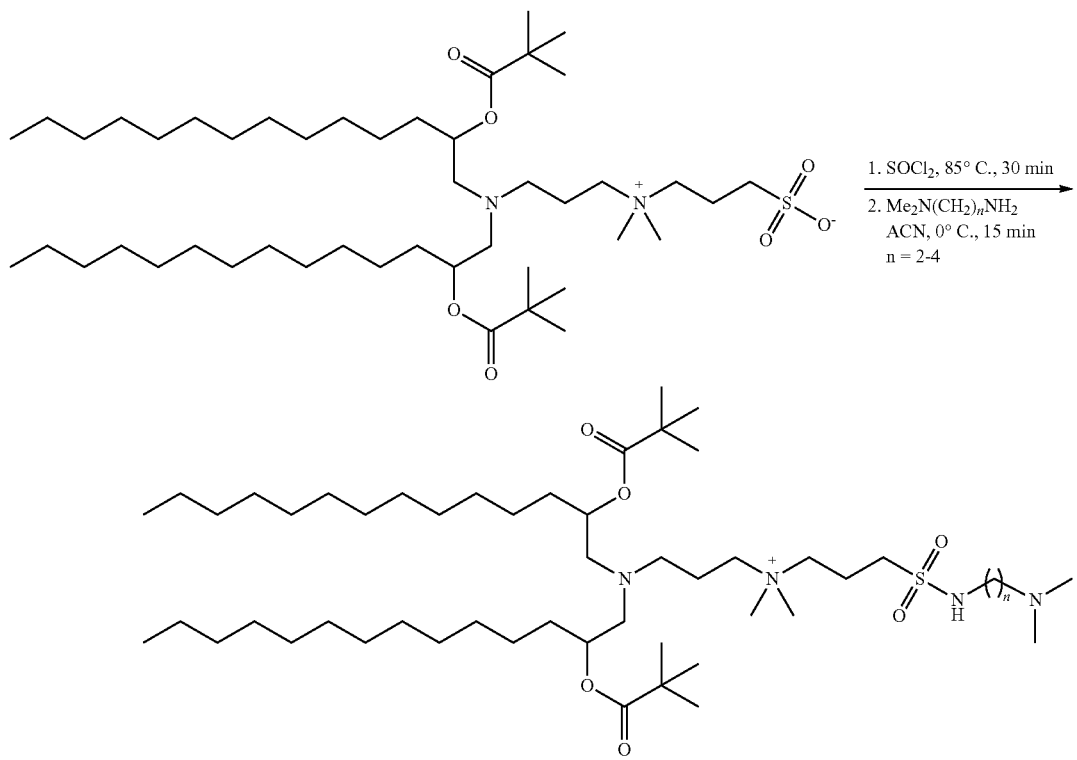

Synthesis of A3-OAc-C2Me:

In a 20 mL vial equipped with a stir bar was dissolved A3-OAc propanesulfonate (200 mg, 0.155 mmol) in 2 mL thionyl chloride. The vial was sealed and the reaction mixture heated to 85° C. for 30 minutes. The reaction was cooled to room temperature, diluted in 5 mL freshly distilled toluene and concentrated under reduced pressure. The crude sulfonyl chloride intermediate was cooled on ice and to this was added the appropriate N,N-dimethyl ethylenediamine (0.775 mmol, 85 µL, 5 equiv) dissolved in 5 mL dry acetonitrile. The reaction mixture was stirred on ice for 15 minutes, and the reaction mixture concentrated under reduced pressure. The crude product was purified on silica gel with a solvent gradient of 5% MeOH in DCM to 20% MeOH, 1% sat. $NH_4OH$ in DCM to yield the product as a sticky brown solid (79.8 mg, 38.0% yield). Mass calculated m/z 1355.1567, observed $M^{+1}$ (MALDI-TOF ms) m/z 1355.18.

Synthesis of A1-OPiv-CnMe CSALs:

In a 20 mL vial equipped with a stir bar was dissolved A1-OPiv propanesulfonate (100 mg, 0.122 mmol) in 2 mL A1OPivC2Me Mass calculated m/z 887.7593, observed $M^{+1}$ (MALDI-TOF ms) m/z 887.7920

A1OPivC3Me Mass calculated m/z 901.7749, observed $M^{+1}$ (MALDI-TOF ms) m/z 901.4854

A1OPivC4Me Mass calculated m/z 915.7906, observed $M^{+1}$ (MALDI-TOF ms) m/z 915.6368

Synthesis of A1-Cl-CnMe CSALs:

In a 20 mL vial equipped with a stir bar was dissolved A1-OH propanesulfonate (100 mg, 0.154 mmol) in 2 mL thionyl chloride. The vial was sealed and the reaction mixture heated to 85° C. for 1 hour. The reaction was cooled to room temperature, diluted in 5 mL freshly distilled toluene and concentrated under reduced pressure. The crude sulfonyl chloride intermediate was cooled on ice and to this was added the appropriate N,N-dimethyl diamine (5 equiv) dissolved in 5 mL dry acetonitrile. The reaction mixture was stirred on ice for 15 minutes, and the reaction mixture concentrated under reduced pressure, and dried under vacuum.

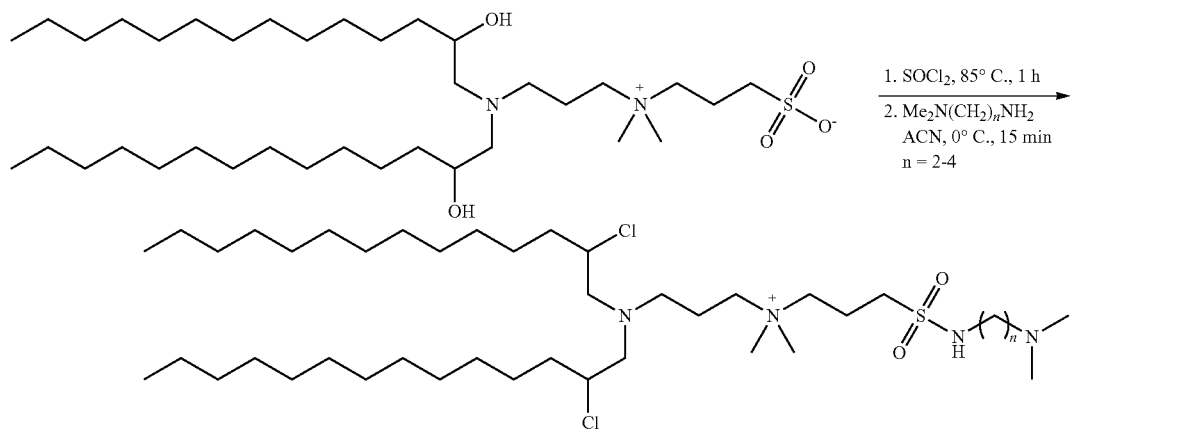

A1ClC2Me Mass calculated m/z 755.5765, observed M$^{+1}$ (MALDI-TOF ms) m/z 755.7258

A1ClC3Me Mass calculated m/z 769.5921, observed M$^{+1}$ (MALDI-TOF ms) m/z 769.6628

A1ClC4Me Mass calculated m/z 783.6078, observed M$^{+1}$ (MALDI-TOF ms) m/z 783.7239

Synthesis of A1OHC2Me:

In a 20 mL vial equipped with a stir bar was dissolved A1-OAc propanesulfonate (100 mg, 0.136 mmol) in 2 mL thionyl chloride. The vial was sealed and the reaction mixture heated to 85° C. for 30 minutes. The reaction was cooled to room temperature, diluted in 5 mL freshly distilled toluene and concentrated under reduced pressure. The crude sulfonyl chloride intermediate was cooled on ice and to this was added the appropriate N,N-dimethyl-ethylenediamine (85.6 µL, 0.68 mmol, 5 equiv) dissolved in 5 mL dry acetonitrile. The reaction mixture was stirred on ice for 15 minutes, and the reaction mixture concentrated under reduced pressure. The reaction mixture was redissolved in 5 mL methanol and potassium carbonate (0.93 g, 0.68 mmol, 5 equiv) was added and the reaction mixture stirred at 40° C. for 4 days. After reaction, the mixture was cooled, filtered, and concentrated under reduced pressure. The concentrate was dissolved in acetone and additional precipitate was removed by filtration to yield the crude product as a yellow sticky solid. The product was purified over silica gel (5% methanol in DCM to 20% methanol, 2% saturated ammonium hydroxide in dichloromethane to yield the product as a sticky yellow solid (17.5 mg, 17.9% yield). Mass calculated m/z 719.6443, observed M$^{+1}$ (MALDI-TOF ms) m/z 719.8963.

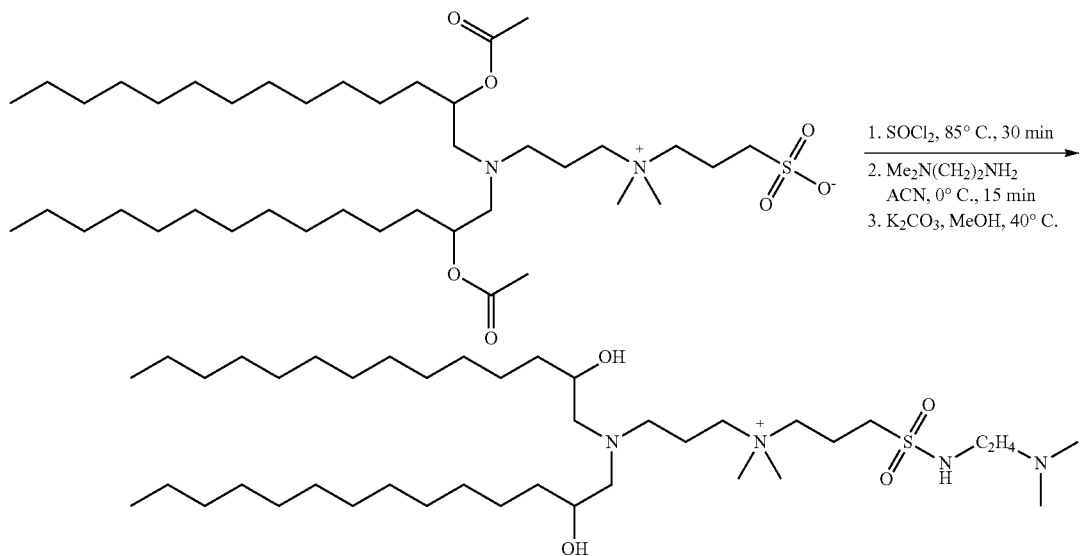

Figure 9:
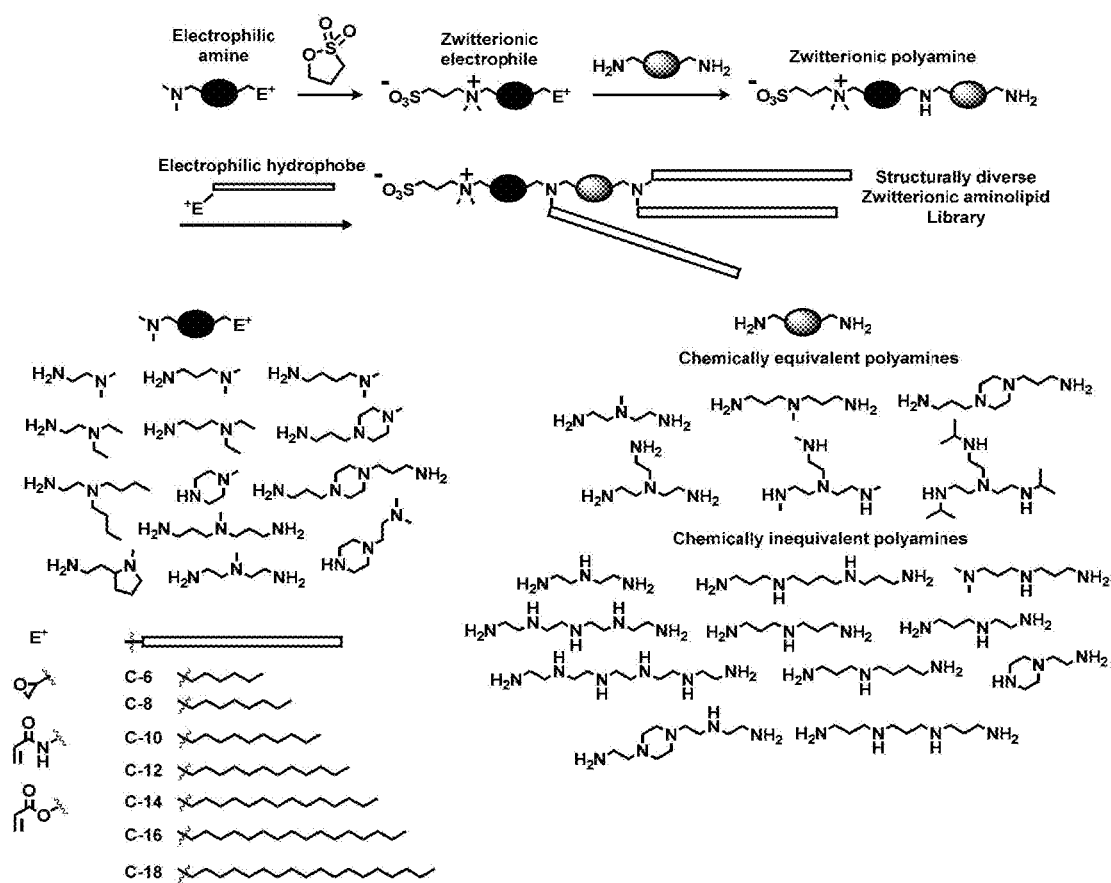
FIG. 9 shows non-limiting examples of some of the modular components from which the zwitterionic amino lipids may be prepared. The green molecules represent the electrophilic amine with the appropriate cationic amine group, red represents the core polyamine, and blue is the hydrophobic tails.
Figure 10:
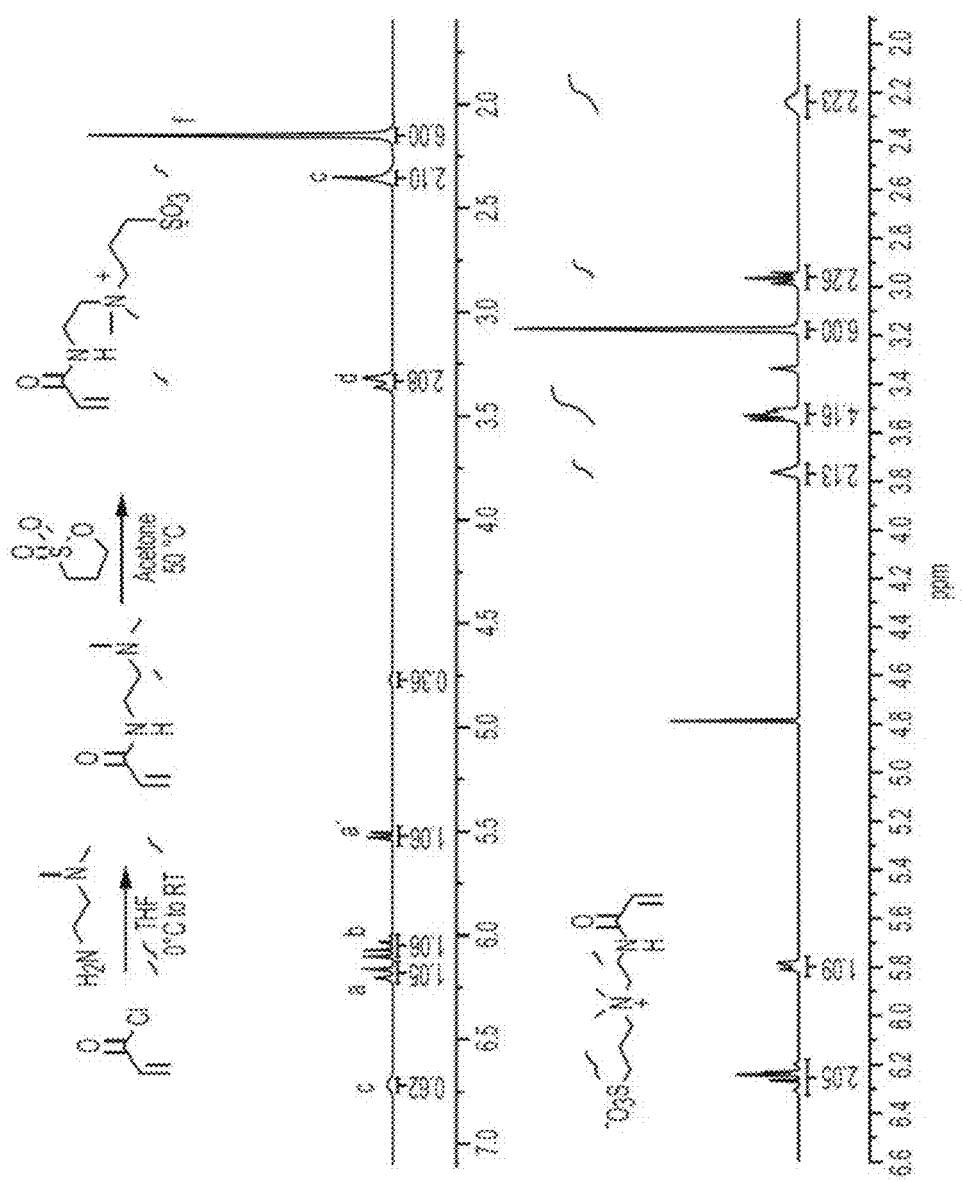
FIG. 10 shows the $^1$H NMR spectra of the zwitterionic electrophile component and an exemplary synthesis of that component.
Figure 11:
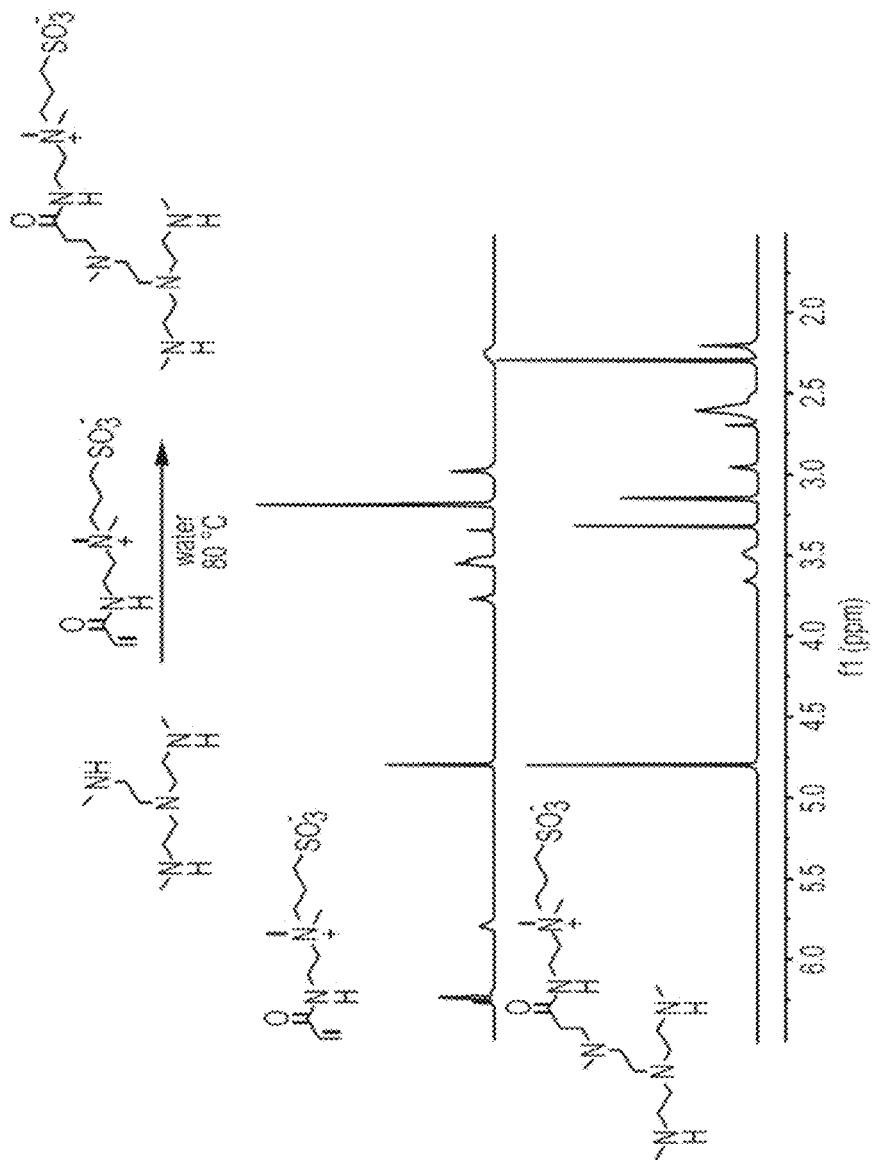
FIG. 11 shows the $^1$H NMR spectra of the zwitterionic electrophile component coupled to the poly amine and an exemplary synthesis of this joint component.
Figure 12:
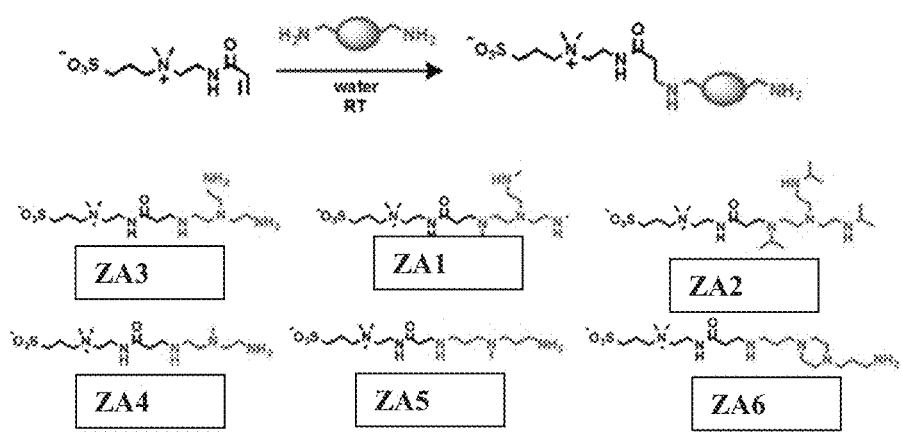
FIG. 12 shows the variety of zwitterionic components with different polyamines
Figure 13:
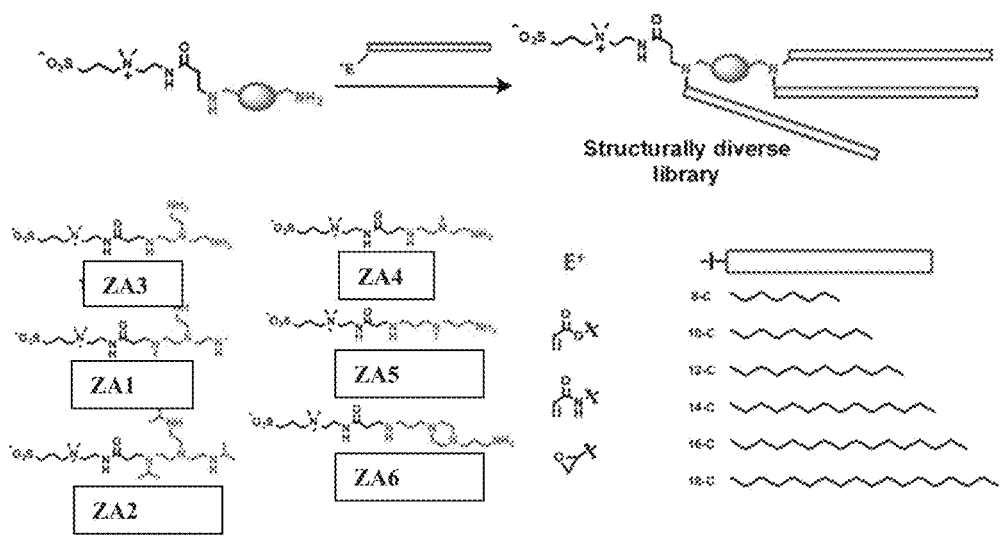
FIG. 13 shows the reaction of the components described in FIG. 12 with a variety of different hydrophobic components.
Figure 14:
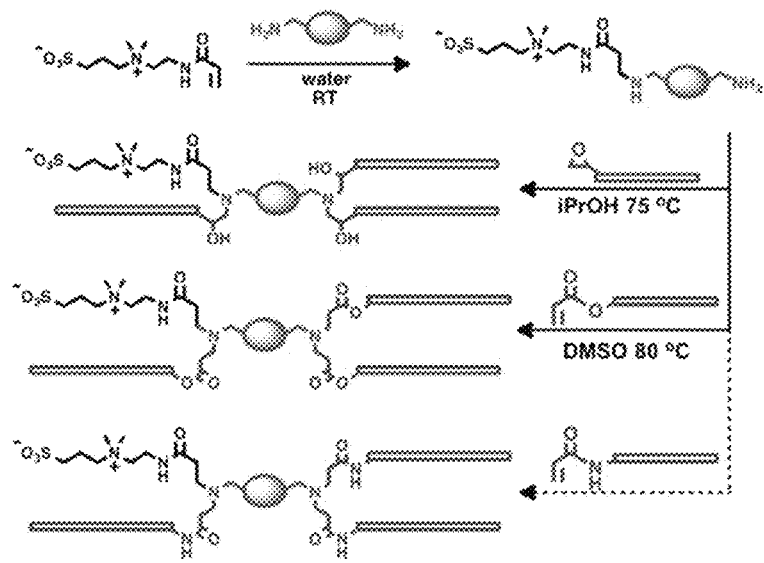
FIG. 14 shows the resultant zwitterionic amino lipids (ZALs) from the reaction shown in FIG. 11.
Figure 15A:
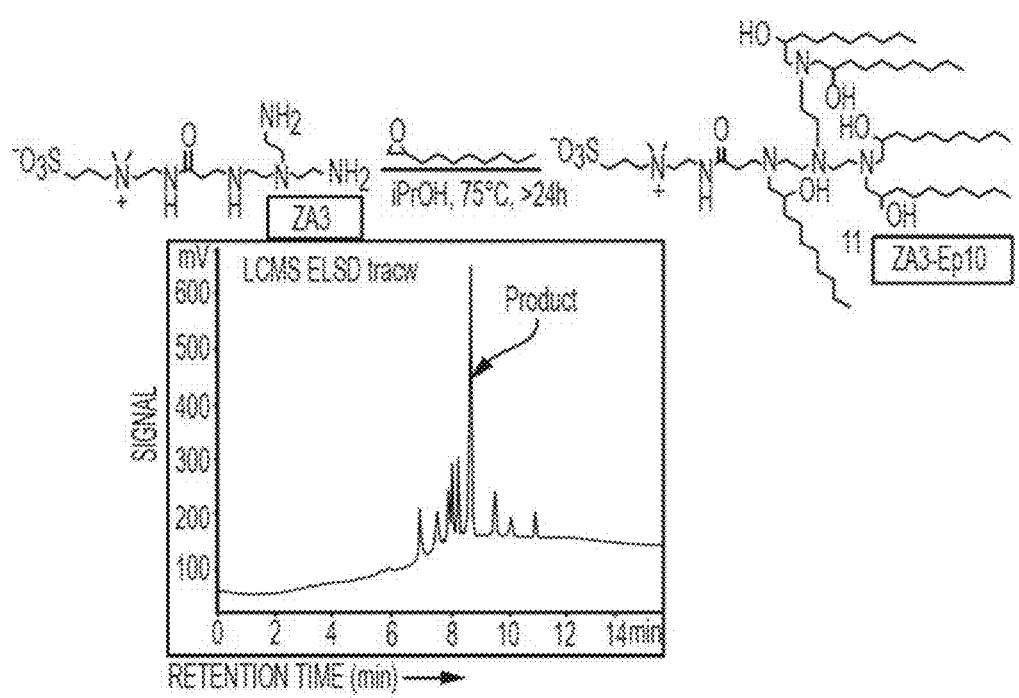
FIGS. 15A-15C show the HPLC traces of ZA3-Ep10 (FIG. 15A), 12SBAmO10 (FIG. 15B), and ZA1-Am10 (FIG. 15C).
Figure 15B:
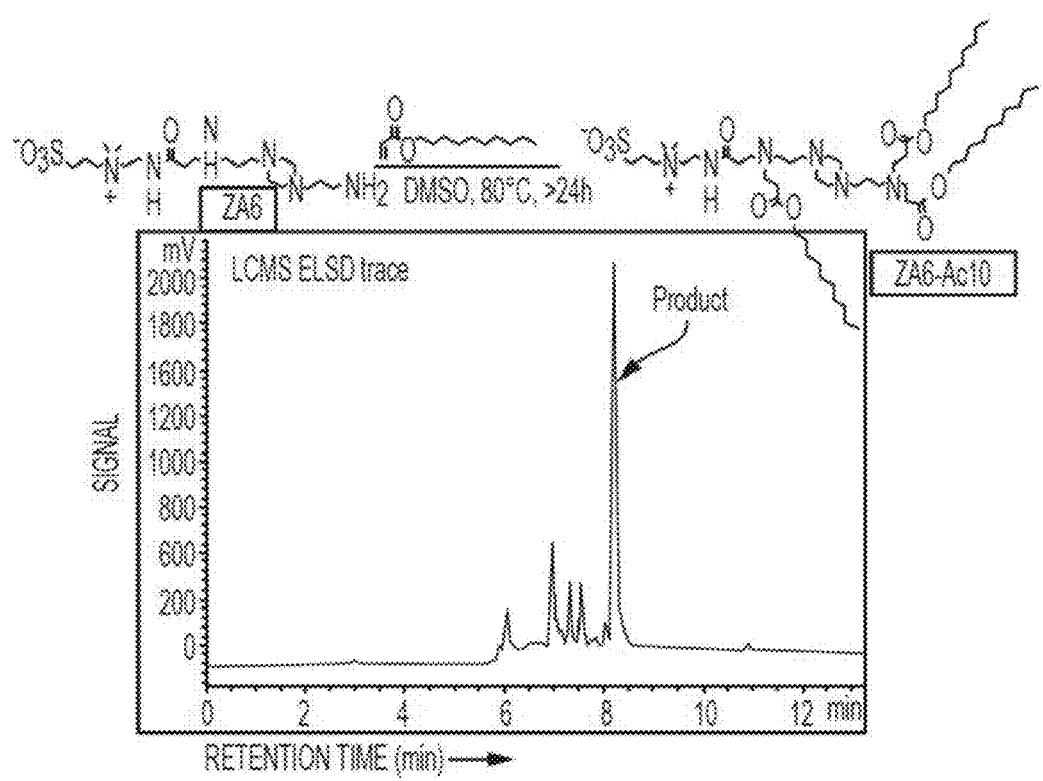
Figure 15C:
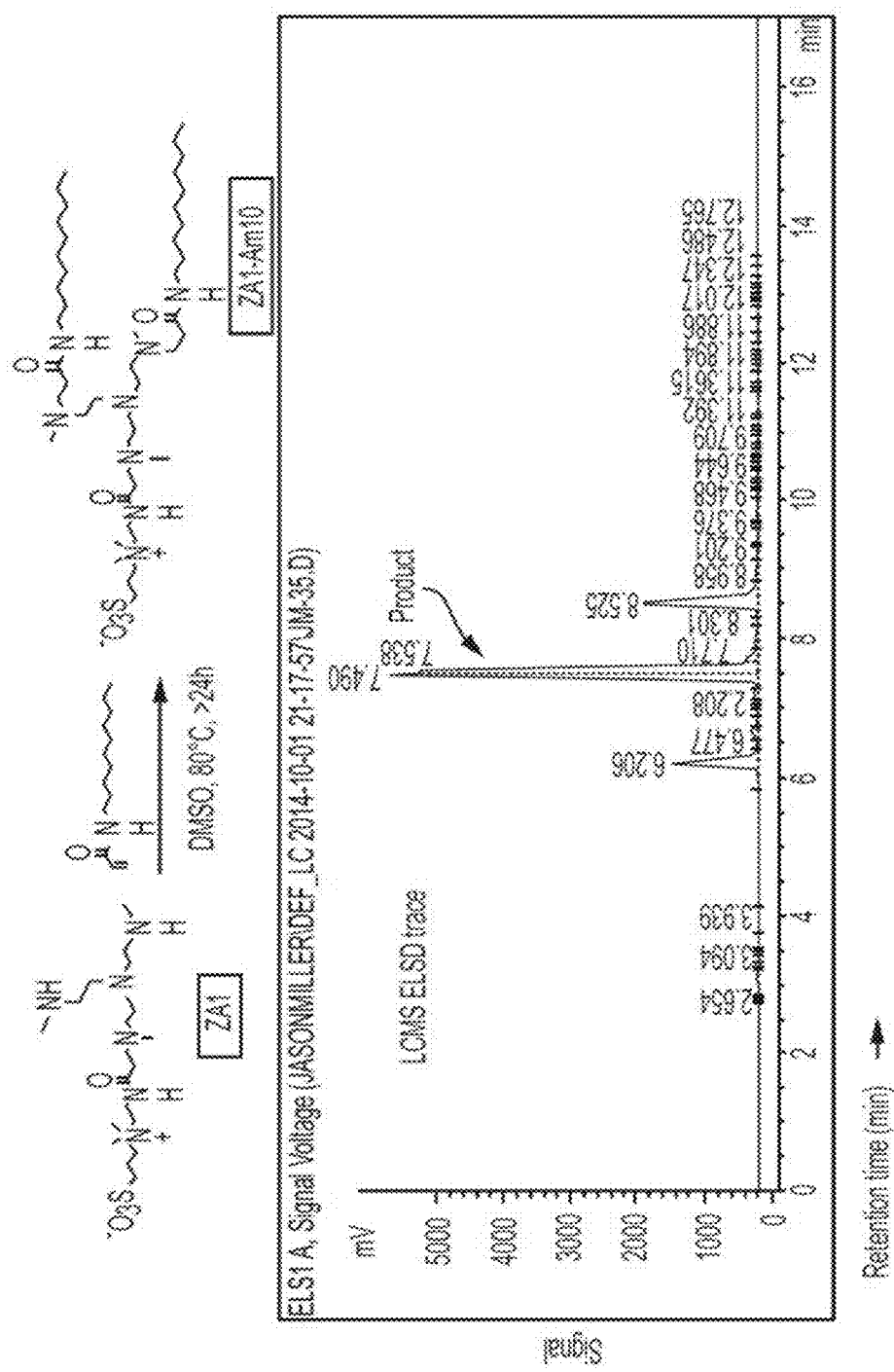
Figure 36:
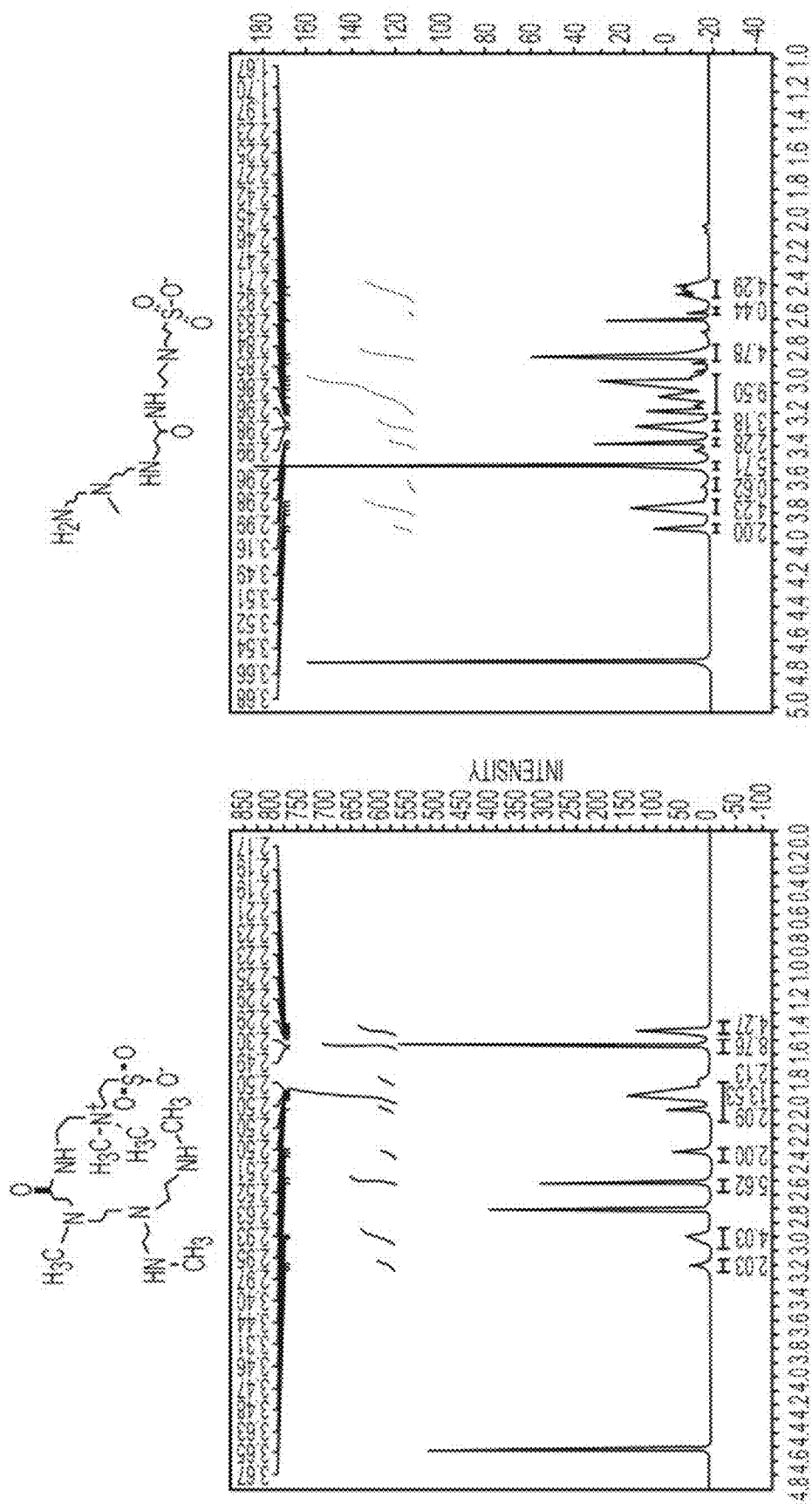
FIG. 36 shows the $^1$H NMR spectrum of 6 different ZALs with amino ZAs.
Figure 36:
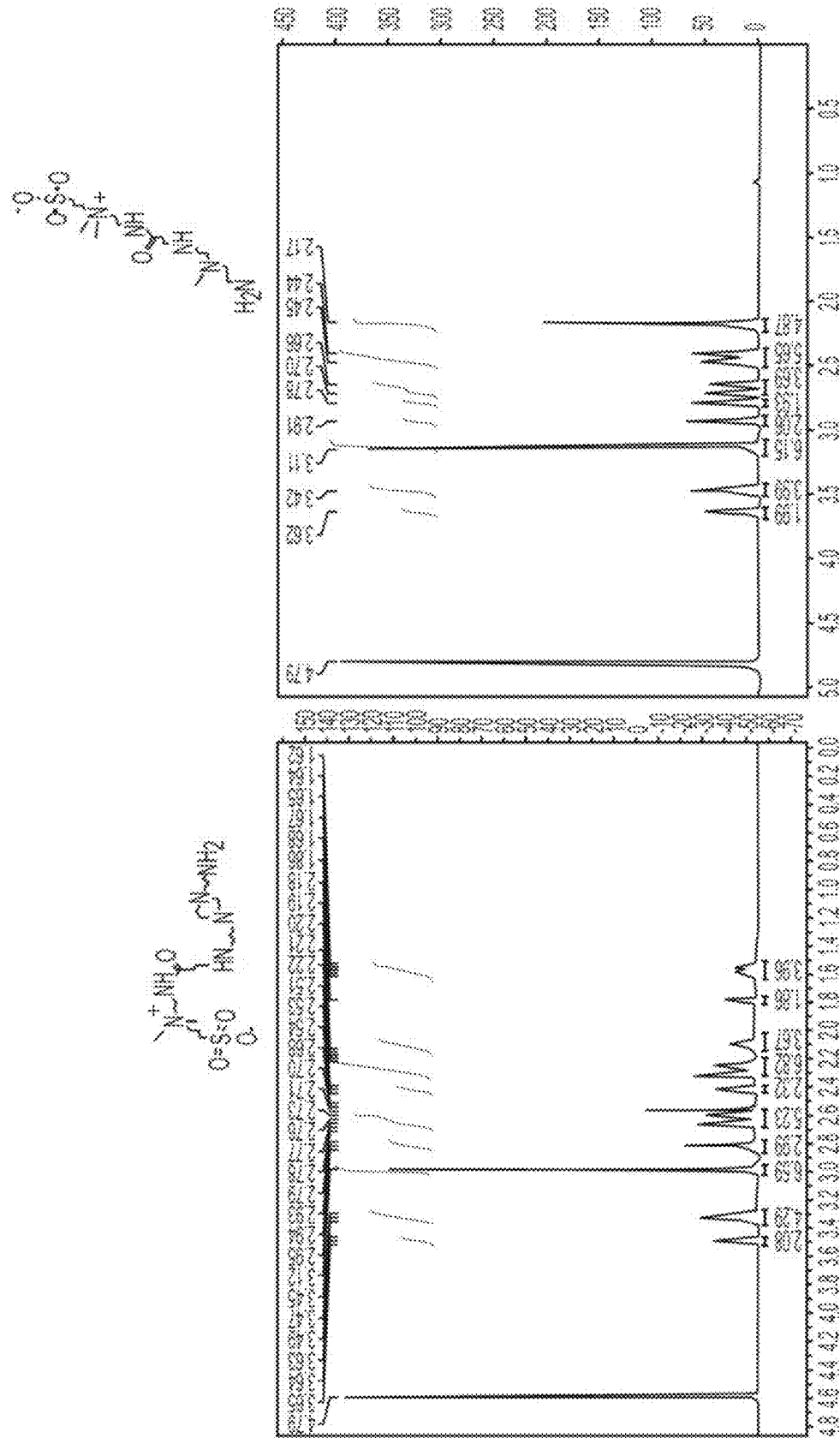
Figure 36:
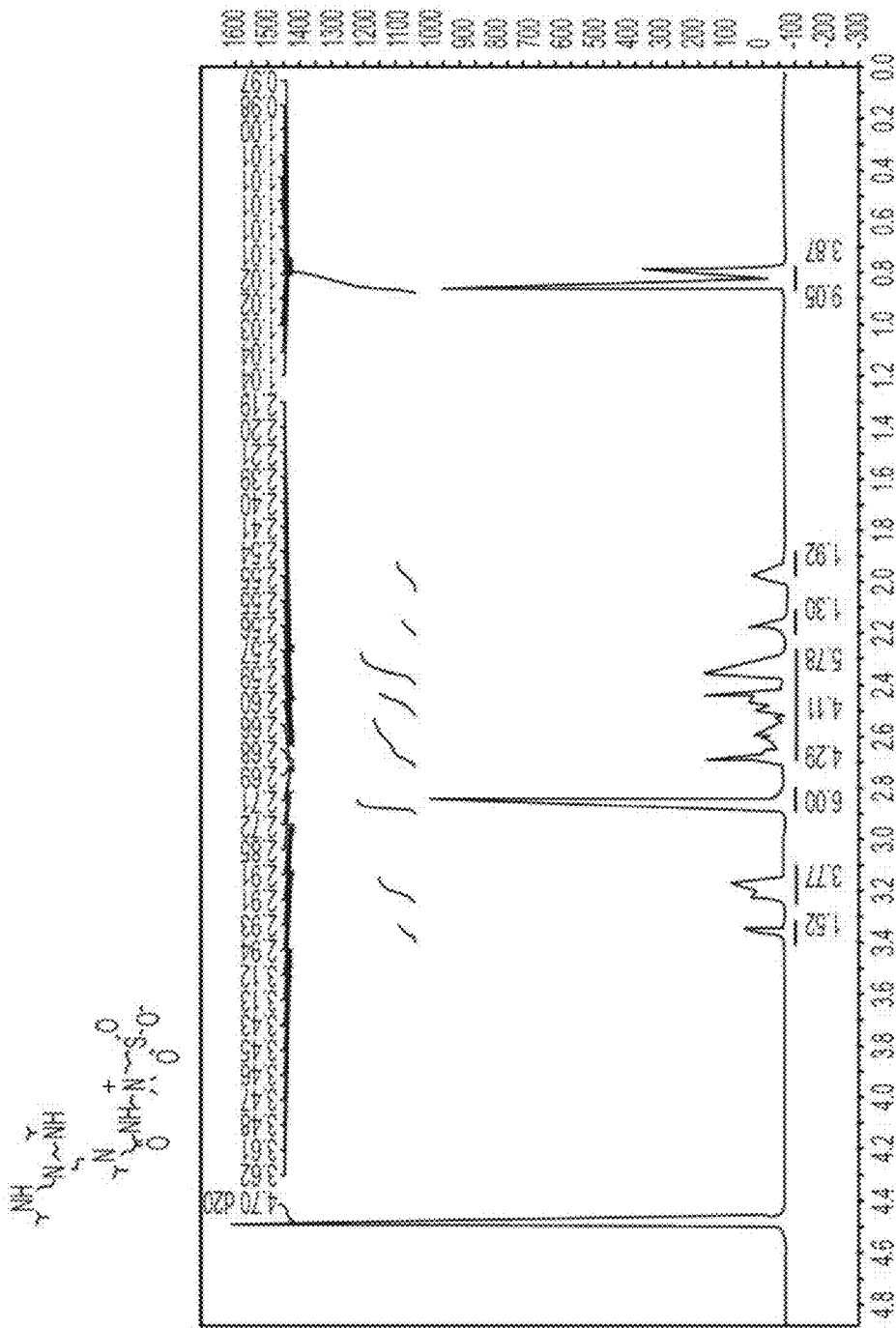
Figure 36:
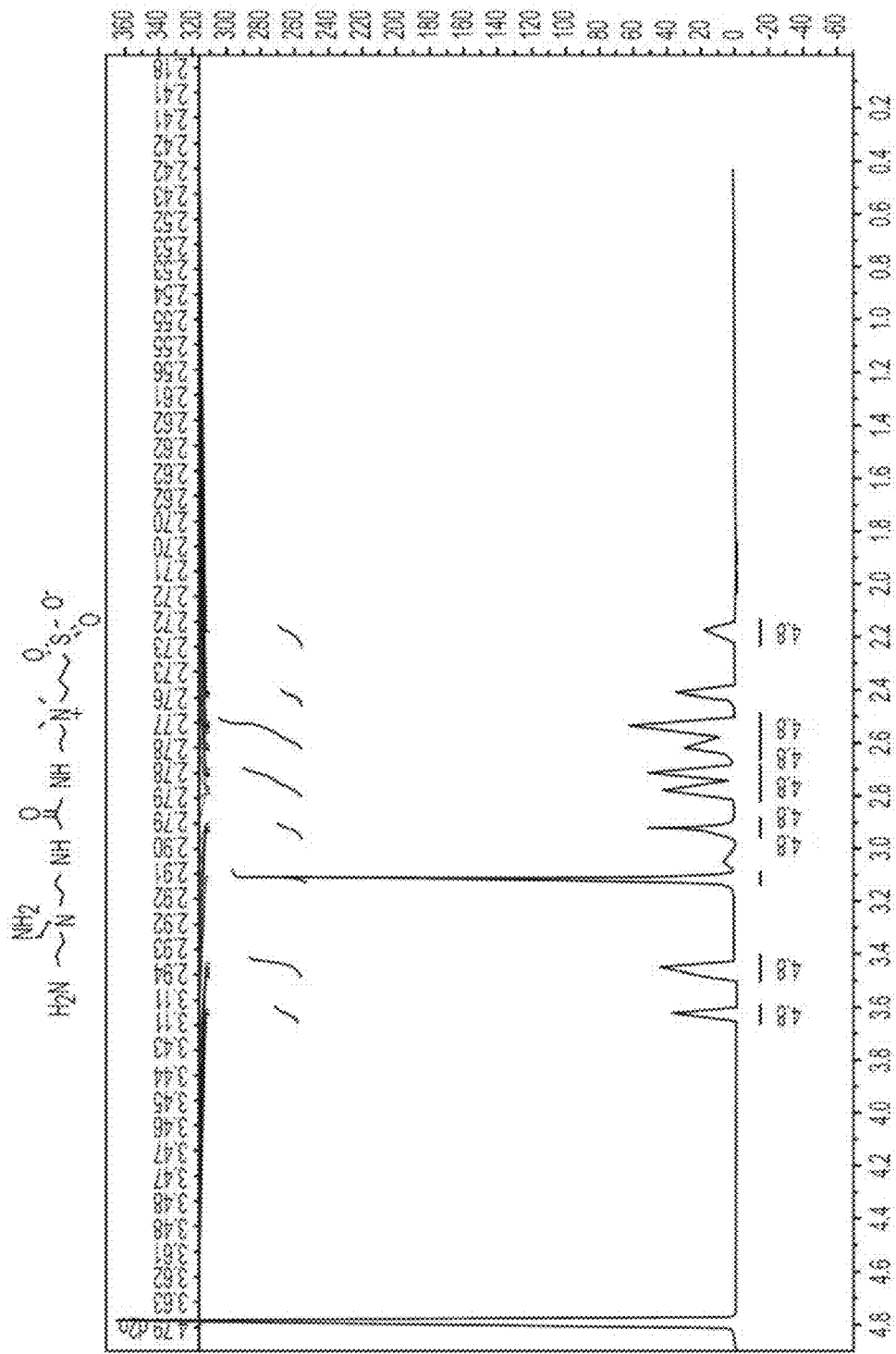
Figure 37:
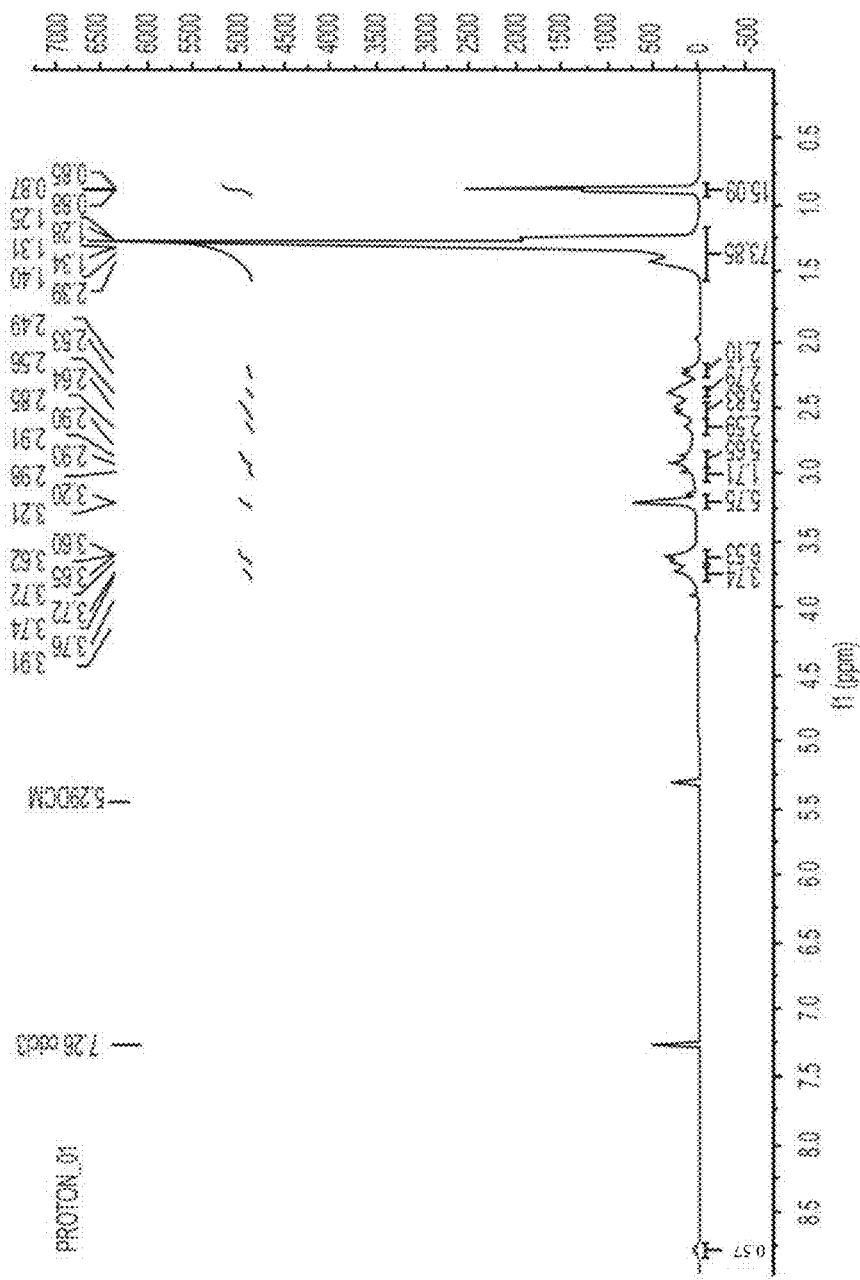
FIG. 37 shows the characterization of the purified ZA3-Ep10 ZAL including ELDS, mass spectroscopy, and $^{13}$C NMR.
Figure 38:
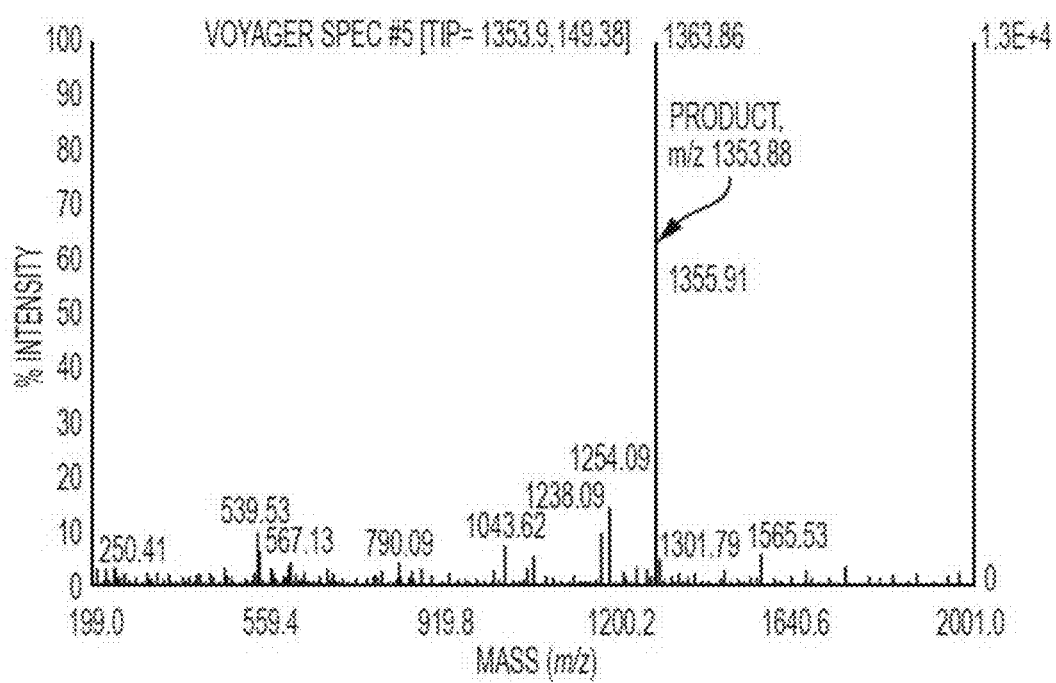
FIG. 38 shows the characterization of CSAL A3OAcC2Me via mass spectroscopy and $^{13}$C NMR.
Figure 38:
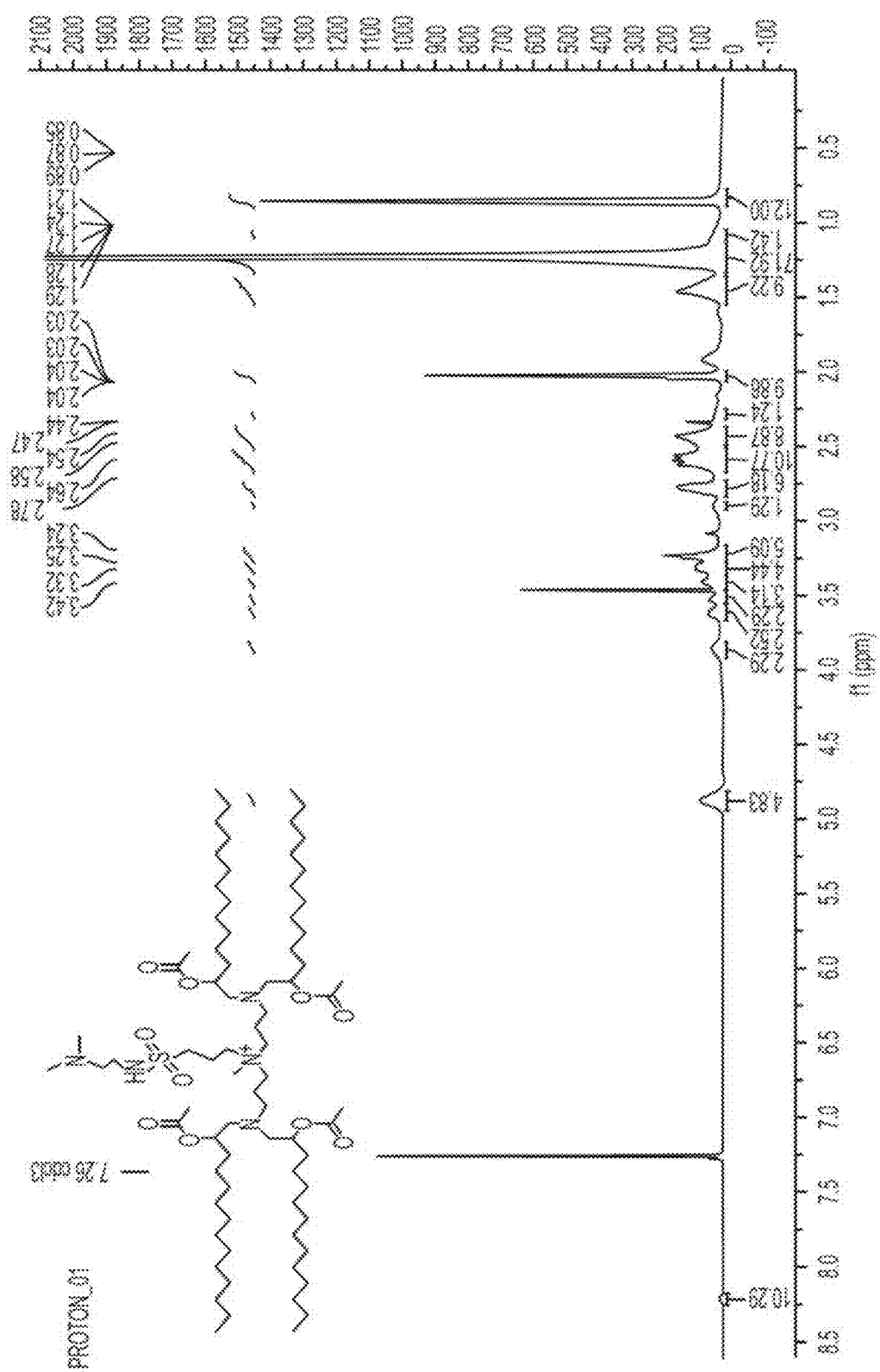
Figure 39:
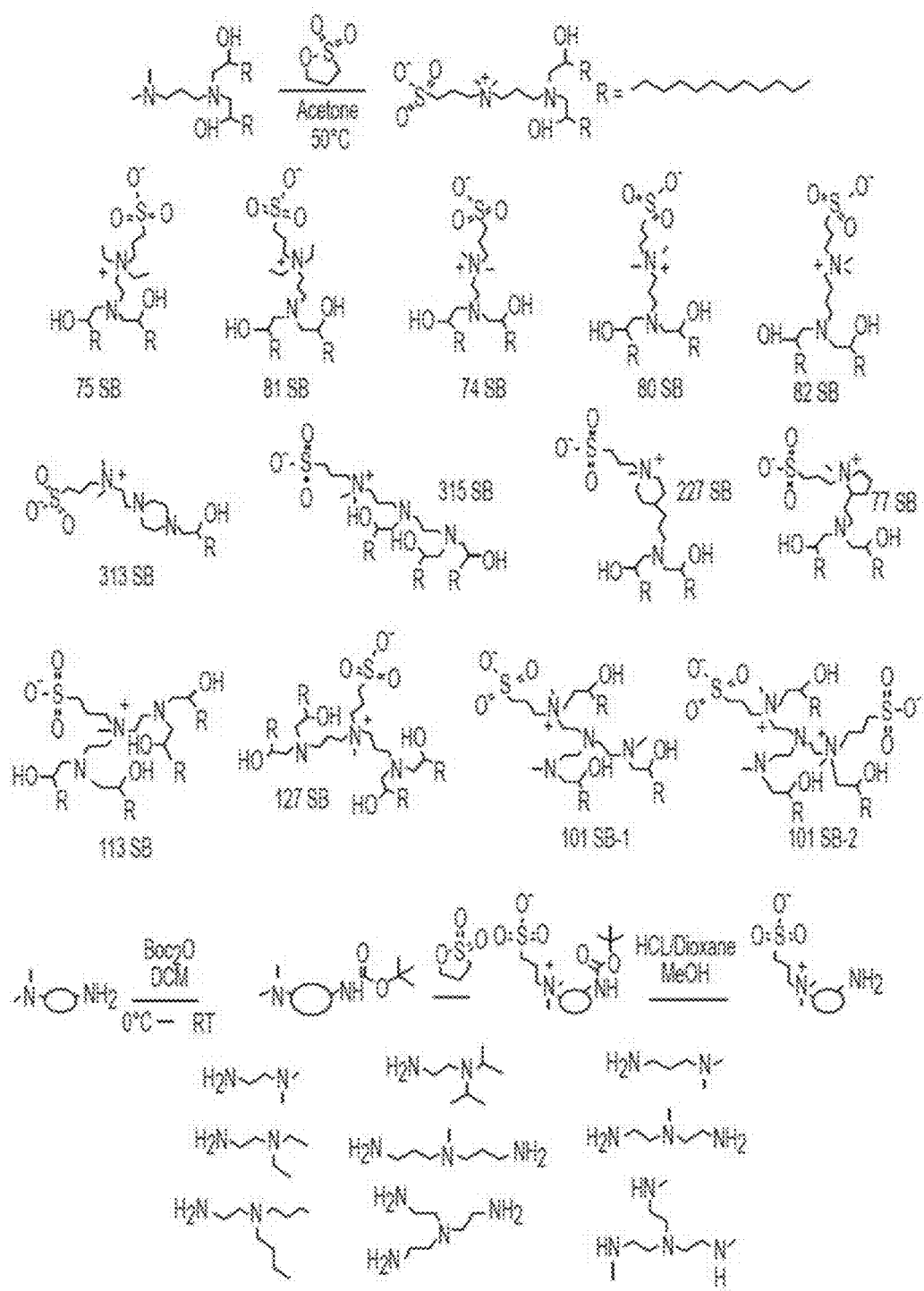
FIG. 39 shows alternative synthesis methods for preparation of the ZALs.

Similarly, the zwitterionic amino lipids (ZALs) were prepared from the starting components shown in FIG. 9. As shown in FIG. 10, the zwitterionic head group was synthesized and the appropriate $^1$H NMR spectra for the starting material and the zwitterionic head group are shown. The zwitterionic head group was reacted with the poly amine core to obtain the compound shown in FIG. 11 with the corresponding $^1$H NMR spectra. Several of the compounds with different polyamine core and the zwitterionic head group are shown in FIG. 12. The reaction of these head group and cores is shown in FIG. 13 and with the appropriate reaction conditions for the three different lipid reactive groups in FIG. 14. LCMS analysis of three compounds is shown in FIGS. 15A-15C. Some exemplary characterization informations for several ZALs including FIGS. 36 & 37. Alternative synthesis methods are described in FIGS. 39 & 40.

Synthesis of 3-((2-acrylamidoethyl)dimethylammonio)propane-1-sulfonate (SBAm):

A flame-dried 500 mL round-bottom flask equipped with a stir bar, and an addition funnel under a nitrogen atmosphere was charged with N,N-dimethyl ethenediamine (20 g, 226.9 mmol) and triethylamine (1 equiv, 227 mmol, 31.6 mL) in 250 mL dry THF, and cooled to 0° C. Acryloyl chloride (0.9 equiv, 204.2 mmol, 16.6 mL) was dissolved separately in 50 mL dry THF and added dropwise via the addition funnel to the stirring amine solution. The reaction was allowed to warm to room temperature overnight which resulted in a yellow solution with white precipitate. The precipitate was filtered off and the filtrate was concentrated in vacuo. The crude product was purified by silica gel column (20% MeOH in DCM). The product was dried with anhydrous sodium sulfate and concentrated under reduced pressure to yield the dimethylamino acrylamide intermediate as an orange liquid (9.36 g, 32.2% yield for step 1).

In a 250 mL round-bottom flask equipped with a stir bar, the dimethylamino acrylamide intermediate (9.36 g, 65.8 mmol) was dissolved in 100 mL acetone. In one portion, 1,3-propanesultone (1.1 equiv, 72.4 mmol, 8.85 g) was added. A rubber stopper with a needle vent was installed and the reaction mixture was heated to 50° C. overnight, yielding the formation of an off white solid precipitate. The precipitate was collected by vacuum filtration, washed with copious amounts of acetone, and dried under vacuum overnight yielding the SBAm product as an light yellow solid (14.77 g, 84.9% yield for step 2). Mass calculated m/z 264.11, observed $M^{+1}$ (LCMS direct inject) m/z 265.1.

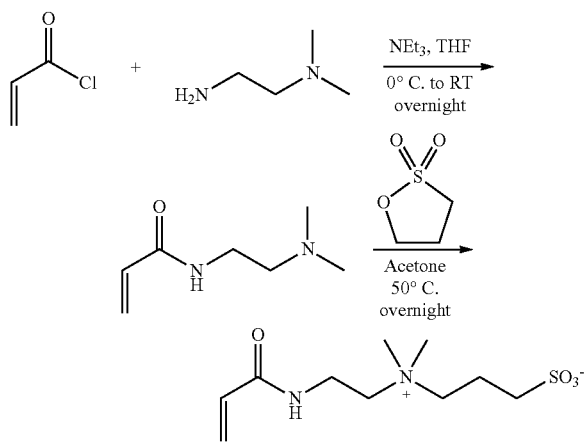

Amino SBAm Syntheses for Library Preparation:

General synthesis of propanesulfonate amide-bearing zwitterionic amines (Amino SBAms) In a 20 mL vial equipped with a stir bar, 3-((2-acrylamidoethyl)dimethylammonio)propane-1-sulfonate (SBAm, 1.5 g, 5.67 mmol, 1 equiv) was dissolved in 5.67 mL deionized water to a concentration of 1M. The corresponding amine (28.35 mmol, 5 equiv) was added via pipette in one portion, the vial covered and stirred at room temperature overnight. After overnight reaction, the amino SBAm reaction mixture was transferred to several 50 mL polypropylene conical tubes, was precipitated in >10 volumes acetone to remove the residual amine starting material, collected by centrifugation (4000×g, 10 minutes). The supernatant was decanted, the pellet washed with acetone, and dried under vacuum to yield the amino SBAms.

ZA1: Light yellow sticky solid (2.40 g, 93.6% yield). Mass calculated m/z 452.31, observed $M^{+1}$ (LCMS direct inject) m/z 453.3. $^1$H NMR (400 MHz, D$_2$O) δ 3.65 (t, J=6.8 Hz, 2H), 3.48 (ddd, J=13.7, 9.5, 5.7 Hz, 4H), 3.14 (s, 6H), 2.95 (t, J=7.2 Hz, 2H), 2.68 (s, 2H), 2.65-2.54 (m, 14H), 2.54-2.48 (m, 2H), 2.29 (d, J=1.0 Hz, 9H), 2.22-2.16 (m, 4H).

ZA2: Reaction done on a 0.776 g SBAm scale. Viscous yellow oil (0.36 g, 24.8% yield). Mass calculated m/z 536.41, observed $M^{+1}$ (LCMS direct inject) m/z 537.4. $^1$H NMR (500 MHz, D$_2$O) δ 3.50 (t, J=7.0 Hz, 2H), 3.33 (ddd, J=22.0, 11.2, 5.7 Hz, 4H), 2.98 (s, 6H), 2.83-2.62 (m, 4H), 2.57 (dt, J=21.3, 7.3 Hz, 4H), 2.44 (p, J=7.1 Hz, 6H), 2.30-2.23 (m, 1H), 2.11-2.01 (m, 2H), 0.92-0.86 (m, 9H), 0.84 (d, J=6.5 Hz, 4H).

ZA3: Brown sticky solid (2.61 g, quantitative yield). Mass calculated m/z 410.58, observed $M^{+1}$ (LCMS direct inject) m/z 411.3. $^1$H NMR (500 MHz, D$_2$O) δ 3.62 (t, J=6.7 Hz, 2H), 3.50-3.40 (m, 4H), 3.11 (d, J=1.4 Hz, 6H), 2.92 (td, J=7.2, 1.3 Hz, 2H), 2.82-2.68 (m, 5H), 2.66-2.49 (m, 8H), 2.41 (ddd, J=8.2, 5.9, 1.3 Hz, 2H), 2.23-2.14 (m, 2H).

ZA4: Light yellow sticky solid (2.01 g, 92.9% yield) Mass calculated m/z 381.24, observed $M^{+1}$ (LCMS direct inject) m/z 382.2. $^1$H NMR (400 MHz, D$_2$O) δ 3.66 (t, J=6.8 Hz, 2H), 3.49 (ddd, J=13.7, 8.7, 5.8 Hz, 4H), 3.14 (s, 6H), 2.96 (t, J=7.2 Hz, 2H), 2.86-2.64 (m, 6H), 2.57-2.40 (m, 5H), 2.28-2.14 (m, 6H).

ZA5: Sticky yellow solid (2.32 g, 84.1% yield). Mass calculated m/z 409.27, observed $M^{+1}$ (LCMS direct inject) m/z 410.2. $^1$H NMR (400 MHz, D$_2$O) δ 3.52 (t, J=6.8 Hz, 3H), 3.35 (ddd, J=13.8, 9.0, 5.6 Hz, 5H), 3.00 (s, 7H), 2.82 (t, J=7.2 Hz, 3H), 2.65 (t, J=7.1 Hz, 3H), 2.49 (q, J=6.4, 5.5 Hz, 1H), 2.39 (t, J=7.4 Hz, 2H), 2.26 (dq, J=15.4, 5.4, 3.7 Hz, 7H), 2.14-1.99 (m, 7H), 1.55-1.41 (m, 4H).

ZA6: Sticky yellow solid (2.71 g, quantitative yield). Mass calculated m/z 464.31, observed $M^{+1}$ (LCMS direct inject) m/z 465.3. $^1$H NMR (500 MHz, D$_2$O) δ 3.64 (t, J=6.9 Hz, 2H), 3.52-3.42 (m, 4H), 3.12 (s, 7H), 2.94 (t, J=7.2 Hz, 3H), 2.82-2.68 (m, 5H), 2.53 (t, J=7.4 Hz, 2H), 2.45-2.30 (m, 7H), 2.26-2.15 (m, 4H), 1.64 (tdd, J=15.5, 12.1, 7.6 Hz, 4H).

Synthesis of Amino SBAm Epoxide and Acrylate Libraries of Zwitterionic Amino Lipids (ZALs):

A zwitterionic amino lipid (ZAL) library of all previously described amino SBAms functionalized was prepared by introduction of hydrophobic tails through reaction with with 1,2-epoxy alkanes and hydrophobic acrylates. The epoxides (1,2-epoxyoctane, 1,2-epoxydecane, 1,2-epoxydodecane, 1,2-epoxytetradecane, 1,2-epoxyhexadecane, and 1,2-epoxyoctadecane) were purchased commercially and encoded to include the total number of carbon atoms in the molecule (Cn, 8-18). The hydrophobic acrylates (were either purchased commercially (O12, O18) or synthesized by the reaction of the appropriate primary alcohol with acryloyl chloride (O8, O10, O14, O16), and encoded to include the number of carbon atoms in the hydrophobic tail, but not including the acrylate moiety. To prepare the library, in a 4 mL vial equipped with a stir bar, the zwitterionic amines (0.1 mmol or 0.05 mmol) were weighed out by balance, and dissolved to a concentration of 1 M in iPrOH for epoxide ZALs or in DMSO for acrylate ZALs. The appropriate hydrophobic electrophile was added with N equivalents, where N is the number of amine reactive sites that would yield complete conversion of primary and secondary amines to tertiary amines The vials were sealed and the reactions stirred for several days at 75° C. for epoxides and 80° C. for acrylates. After reaction, the reactions were precipitated in acetone to yield the zwitterionic aminolipids.

Alternative Synthesis of ZA3:

A 20 mL vial equipped with a stir bar was charged with 3-((2-acrylamidoethyl)dimethylammonio)propane-1-sulfonate (SBAm, 0.8111 g, 3.068 mmol) and dissolved in 3 mL DMSO. Via syringe, tris(2-aminoethyl) amine (5 equiv, 15.32 mmol, 2.24 g) was added yielding a cloudy yellow/brown suspension. The reaction mixture was sealed and stirred at 80° C. overnight, yielding an orange cloudy suspension. The reaction mixture was further diluted in DMSO, transferred to several 50 mL conical tubes and precipitated in 10 volumes ethyl acetate. The precipitate collected by centrifugation (4,000×g, 10 minutes), and the supernatant decanted to yield a sticky yellow/brown. The product was reprecipitated in DMSO/EtOAc several times to remove any residual tris(2-aminoethyl) amine, and finally dissolved in MeOH transferred to round-bottom flask and concentrated under reduced pressure. The product was dried overnight under vacuum to remove residual solvent, redissolved in methanol and precipitated in ethyl acetate, and dried under vacuum to yield ZA3 as an orange/brown oil (1.4058 g, 100%).

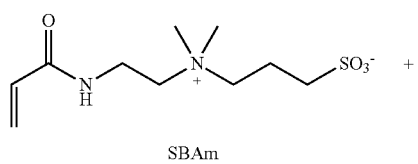

SBAm

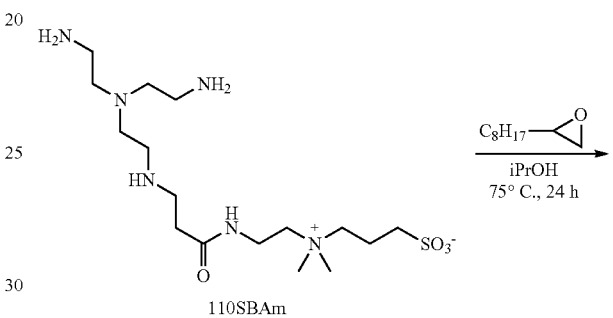

μL, 1M SBAm) and stirred briefly at RT to yield a yellow/brown suspension. 1,2-epoxydecane (4.384 mmol, 685 mg, 6 equiv) was added, the vial was sealed and stirred overnight at 75° C. for approximately 24 h resulting in a clear yellow/brown solution. The iPrOH was removed under reduced pressure to yield a yellow/brown oil. The crude product was dissolved in minimal 5% MeOH in DCM and purification was carried out on a silica gel column (24 g) using the CombiFlash® system (Teledyne Isco). The product was eluted and fractionated with a solvent gradient of 5% MeOH in DCM to 20% MeOH, 2% saturated ammonium hydroxide in DCM and the product elution tracked by ELSD. The product containing fractions were concentrated under reduced pressure, and dried under vacuum overnight to yield the product as a sticky yellow solid (192.5 mg, 22.1% yield). Mass calculated m/z 1191.0246, observed $M^{+1}$ (LCMS direct inject) m/z 1192.8.

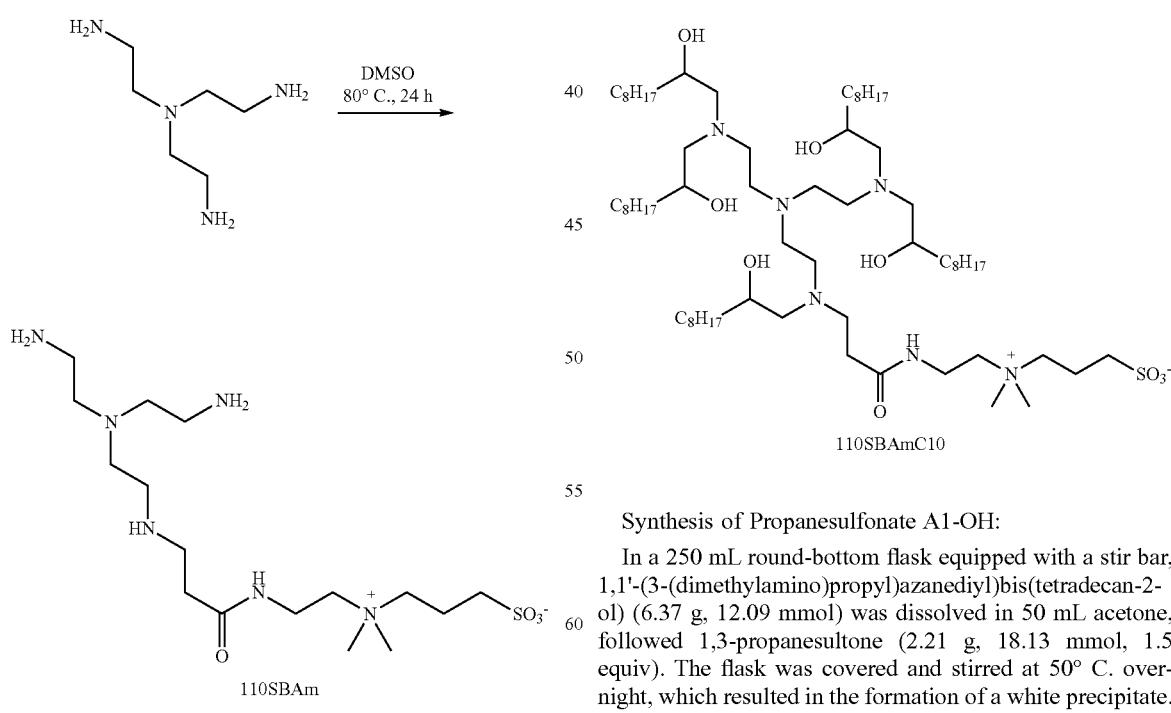

Synthesis of ZA3-Ep10:

A 20 mL scintillation vial equipped with a stir bar was charged with ZA3 (300 mg, 0.7307 mmol) and iPrOH (730

Synthesis of Propanesulfonate A1-OH:

In a 250 mL round-bottom flask equipped with a stir bar, 1,1'-(3-(dimethylamino)propyl)azanediyl)bis(tetradecan-2-ol) (6.37 g, 12.09 mmol) was dissolved in 50 mL acetone, followed 1,3-propanesultone (2.21 g, 18.13 mmol, 1.5 equiv). The flask was covered and stirred at 50° C. overnight, which resulted in the formation of a white precipitate. The white precipitate was collected by filtration, and dried under vacuum to yield the propanesulfonate product as a white solid (7.46 g, 95.0%). Mass calculated m/z 648.5475, observed $M^{+1}$ (MALDI-TOF ms) m/z 649.8078.

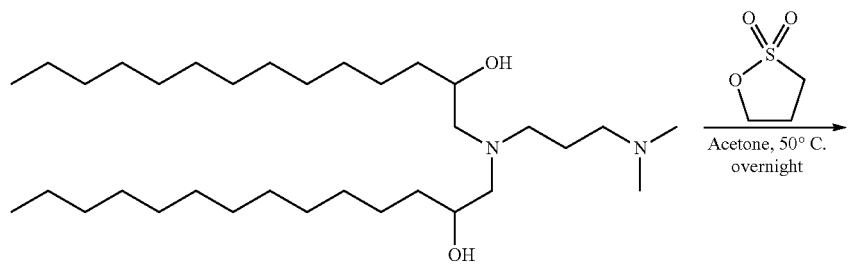

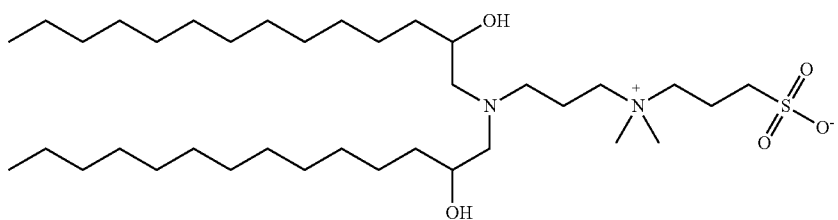

Synthesis of Propanesulfonate A2-OH:

In a 20 mL vial equipped with a stir bar, A2-OH (0.5 g, 0.901 mmol) was dissolved in 4 mL acetone, followed by the addition of 1,3-propanesultone (165 mg, 1.35 mmol, 1.5 equiv). The vial was sealed and stirred overnight at 50° C. After overnight reaction, an additional 1.5 equiv 1,3-propanesultone was added and stirred for an additional day. The reaction mixture was concentrated, dissolved in minimal dichloromethane, and purified over silica gel (gradient 10% MeOH in DCM to 10% MeOH, 1% sat. NH$_4$OH in DCM) to yield the product as a sticky pale yellow solid (310 mg, 50.8% yield). Mass calculated m/z 676.5788, observed M$^{+1}$ (MALDI-TOF ms) m/z 678.22

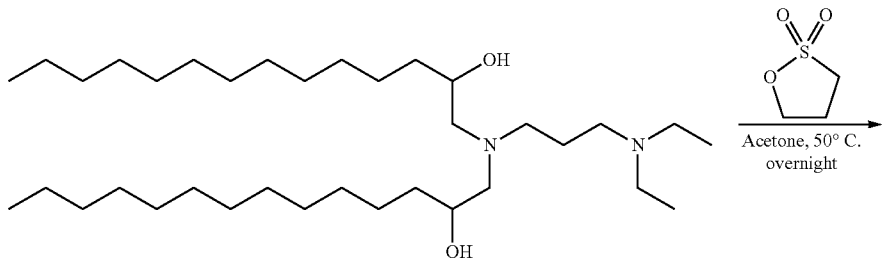

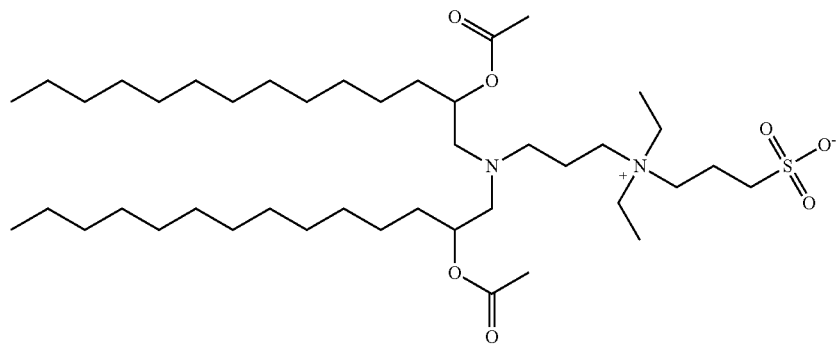

Synthesis of Propanesulfonate A3-OH:
Same protocol as propanesulfonate A2-OH sticky pale yellow solid (2.864 g, 85.0% yield) Mass calculated m/z 1116.0177, observed M$^{+1}$ (MALDI-TOF ms) m/z 1117.34

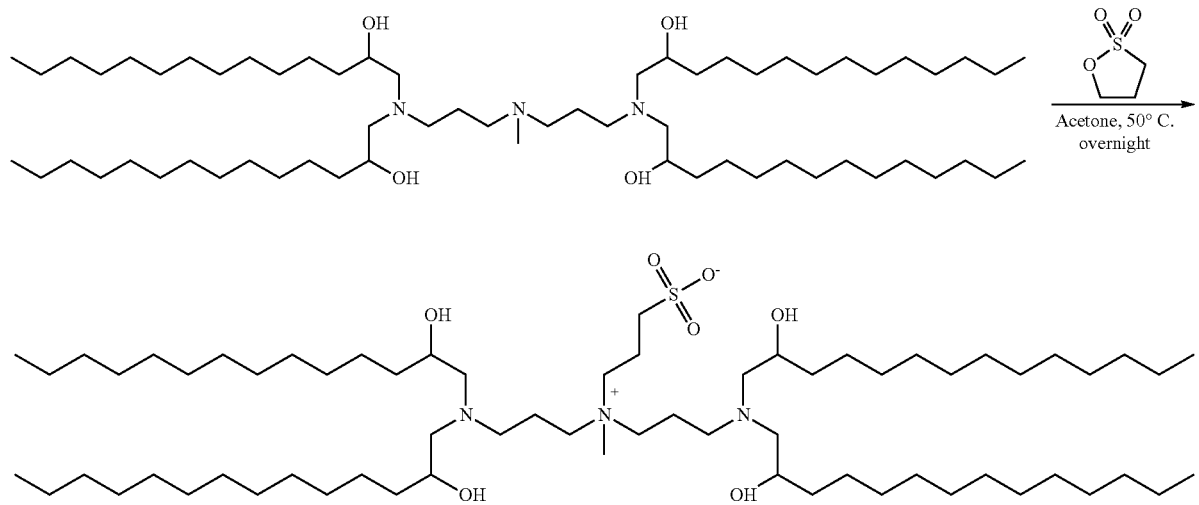

Synthesis of Propanesulfonate A1-OAc:

In a 20 mL vial equipped with a stir bar, propanesulfonate A1-OH (1.25 g, 1.93 mmol) was dissolved in 5 mL dichloromethane, followed by the addition acetic anhydride (10 mL, excess). The reaction mixture was stirred at room temperature for 3 days until the consumption of starting material by TLC. The reaction mixture was diluted in acetone and concentrated under reduced pressure to form a clear oil, which formed a colorless precipitate on standing. This precipitate was collected by filtration, and dried under vacuum to yield the product as a colorless crystalline solid (0.795 g, 56.3% yield). Mass calculated m/z 732.5686, observed M$^{+1}$ (MALDI-TOF ms) m/z 733.8095

Synthesis of Propanesulfonate A2-OAc:

In a 100 mL round-bottom flask equipped with a stir bar and reflux condenser, propanesulfonate A2-OH (0.28 g, 0.414 mmol) was dissolved in acetic anhydride (10 mL). The reaction was heated to 100° C. for 18 h yielding a clear orange solution, after which time the reaction concentrated in vacuo, and purified over silica gel (gradient 10% MeOH in DCM to 10% MeOH, 1% sat. NH$_4$OH in DCM). The product was isolated as an orange sticky solid (211.1 mg, 67.0% yield) Mass calculated m/z 760.5999, observed M$^{+1}$ (MALDI-TOF ms) m/z 762.62

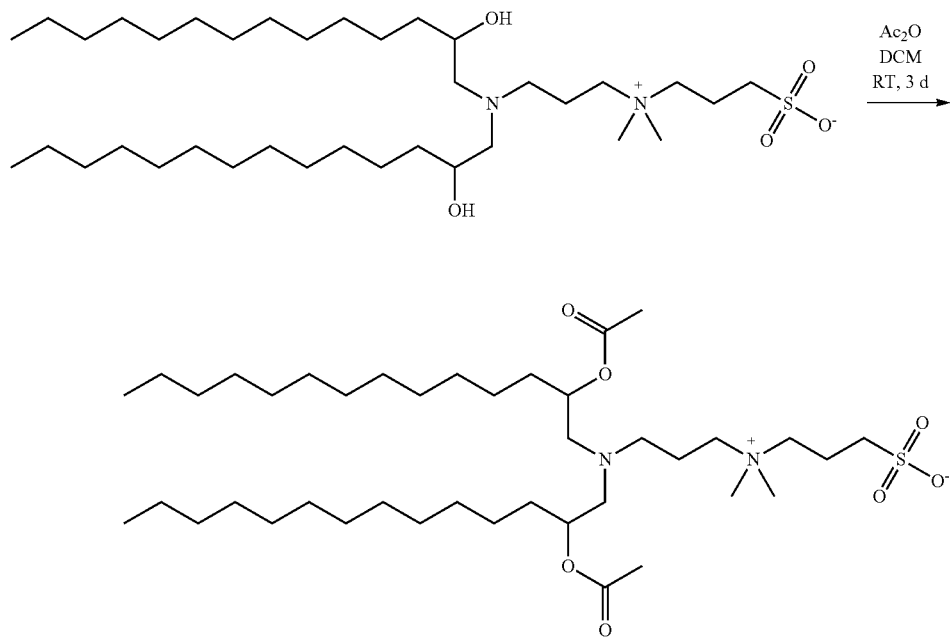

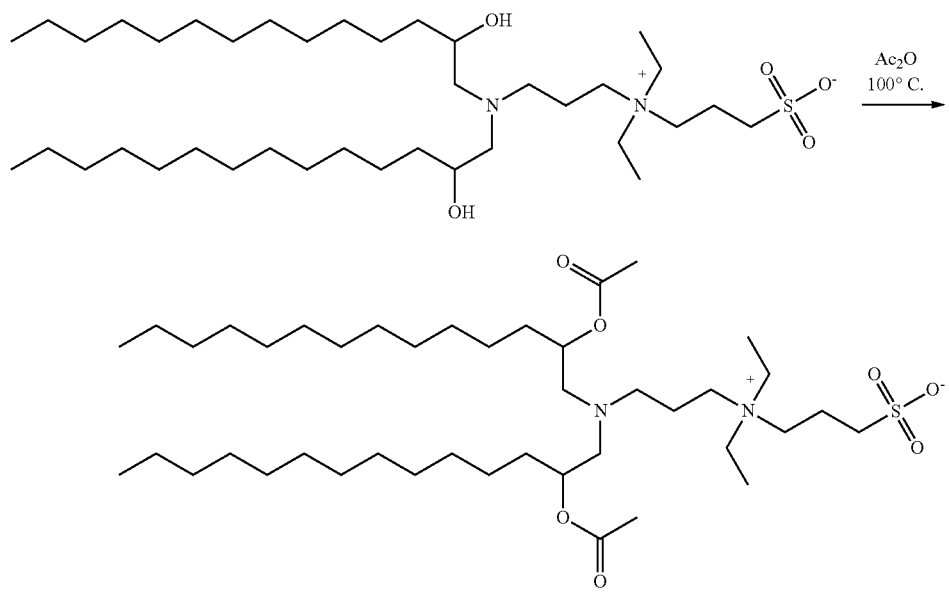

Synthesis of Propanesulfonate A3-OAc:

To a 20 mL vial equipped with a stir bar, propanesulfonate A3-OH (0.752 g, 0.673 mmol) and acetic anhydride (10 mL) were added. The vial was sealed and the reaction mixture stirred at 100° C. for 23 h. The reaction mixture was acetone and concentrated under reduced pressure to yield the crude product as an orange oil (0.91 g, quantitative yield). The crude product was used without further purification. Mass calculated m/z 1283.0516, observed M$^{+1}$ (MALDI-TOF ms) m/z 1284.74 dimethylformamide (5 mL), followed by the addition triethylamine (0.96 mL, 6.86 mmol, 5 equiv), 4-dimethylamino pyridine (1.7 mg, 0.014 mmol, 0.1 equiv) and pivalic anhydride (1.67 mL, 8.23 mmol, 6 equiv). After 14 h reaction at 90° C. with stirring, and additional 6 equiv. of pivalic anhydride, 5 equiv. triethylamine, and 0.1 equiv of DMAP was added and the reaction continued for an additional 26 h, at which point the starting A1-OH propanesulfonate had disappeared by TLC. The reaction mixture was diluted in dichloromethane, concentrated under reduced

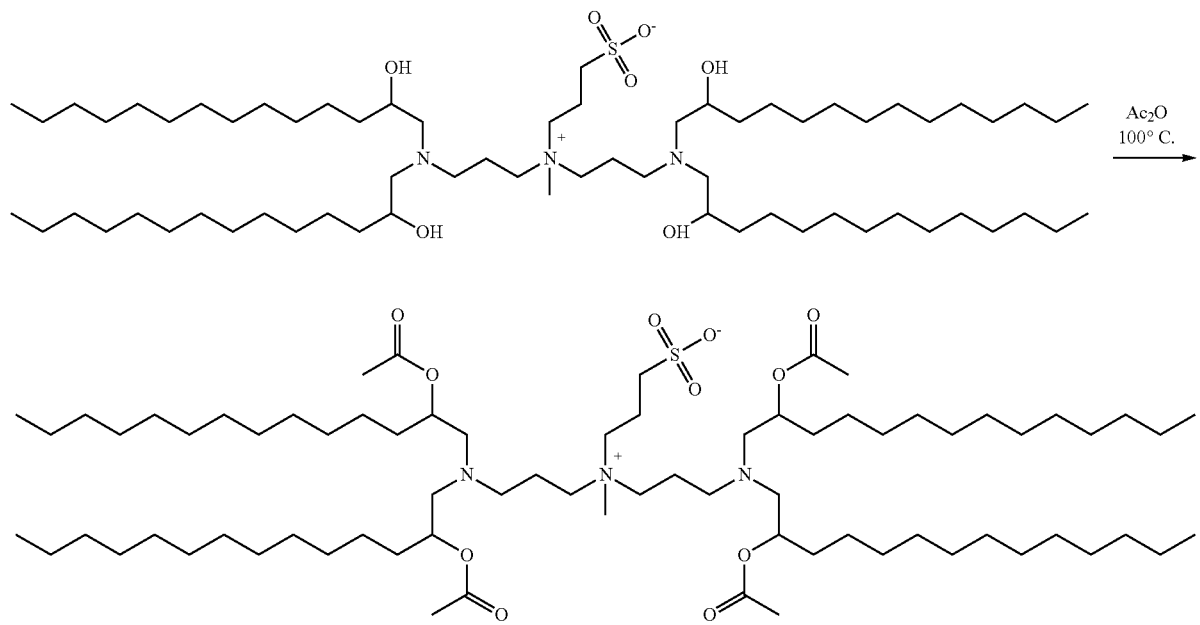

Synthesis of Propanesulfonate A1-OPiv:

In a dry 50-mL round bottom flask equipped with a stir bar and reflux condenser under nitrogen atmosphere, was dissolved A1-OH propanesulfonate (0.89 g, 1.37 mmol) in pressure, and purified by silica gel chromatography (gravity column) with 10% methanol in dichloromethane to yield the product A1-OPiv propanesulfonate as a sticky brown solid (0.585 g, 52.2%). Mass calculated m/z 817.6625, observed M$^{+1}$ (MALDI-TOF ms) m/z 817.4124.

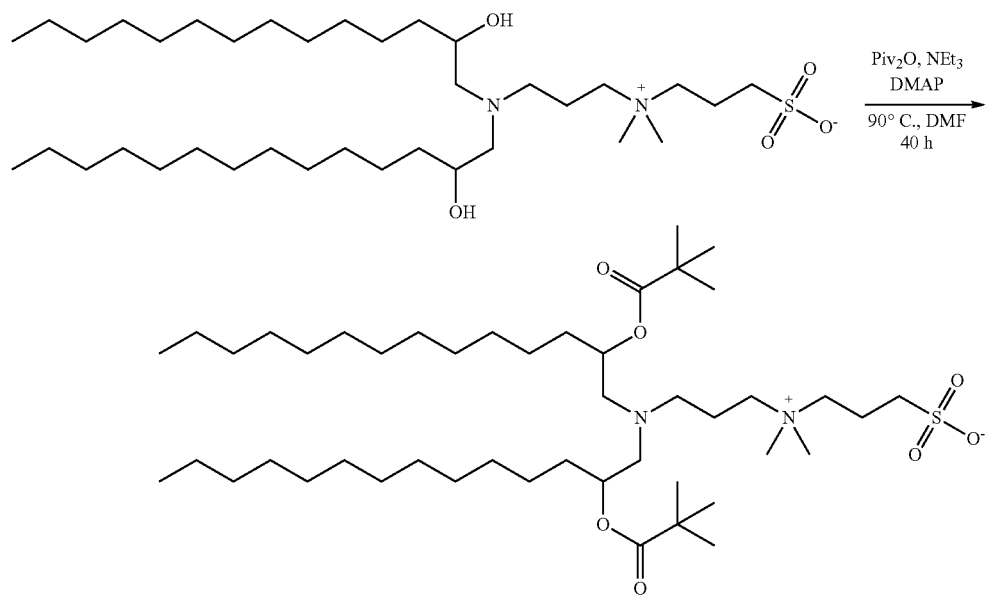

25

Example 3: Activity of the Compositions

Figure 3:
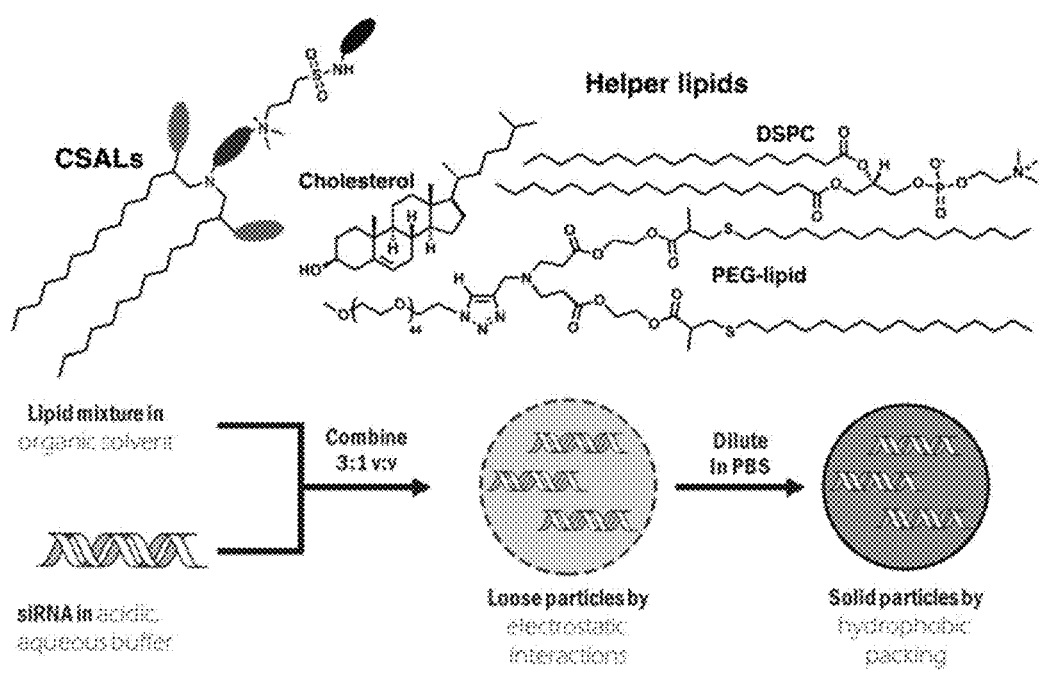
FIG. 3 shows CSAL nanoparticles are formed by the ethanol dilution method, where combining a lipid mixture containing CSALs, cholesterol, DSPC, and PEG in ethanol at a mole ratio of 50:38.5:10:1.5 respectively, with a solution of siRNA in citrate phosphate buffer followed by dilution in PBS.
Figures 4A, 4B, 4C, 4D:
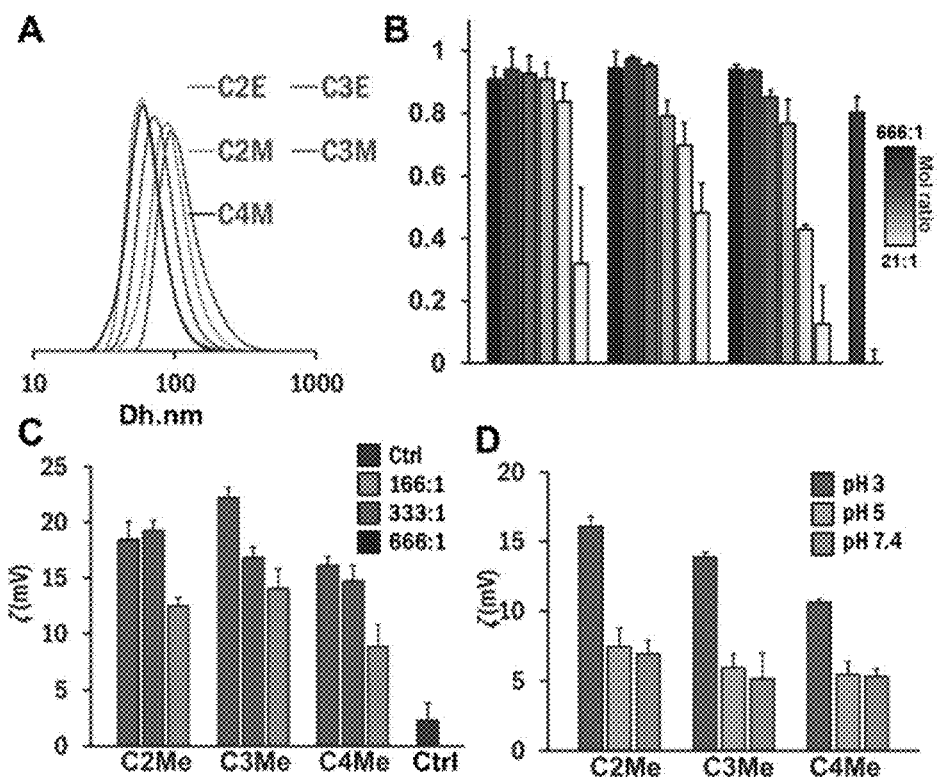
FIGS. 4A-4D show the biophysical characterization of A1-OAc CSAL, NPs show structurally independent size ~100 nm (FIG. 4A), siRNA binding decreases with increased headgroup linker length (FIG. 4B). Increased charge at a higher mole ratio indicates CSALs are present at the nanoparticle surface (FIG. 4C). Higher surface charge at pH 3 suggest changes in protonation states of surface CSALs (FIG. 4D).
Figure 5:
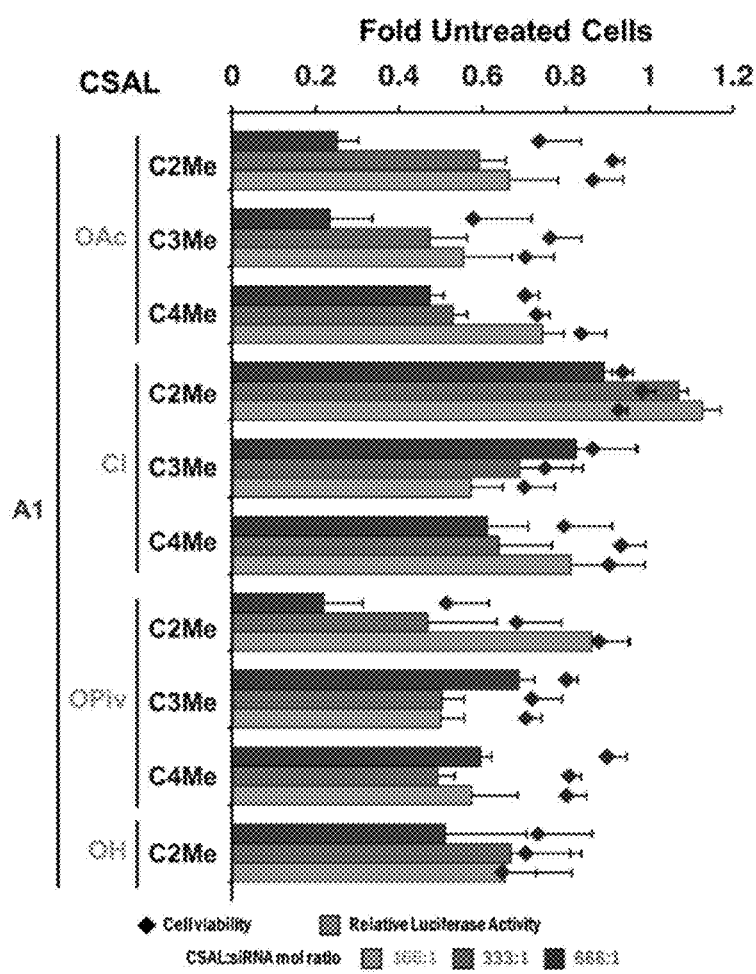
FIG. 5 shows siRNA delivery efficacy of A1-based CSALs was evaluated in HeLa luciferase reporter cells. NPs encapsulating siRNA against the luciferase reporter were dosed at 34 nM siRNA and incubated for 24 h. Relative luciferase activity (bars) and cell viability (dots) were evaluated at different CSAL:siRNA molar ratio. C2Me headgroups and acetate sidearms at higher mole ratios showed greater efficacy.
Figure 6:
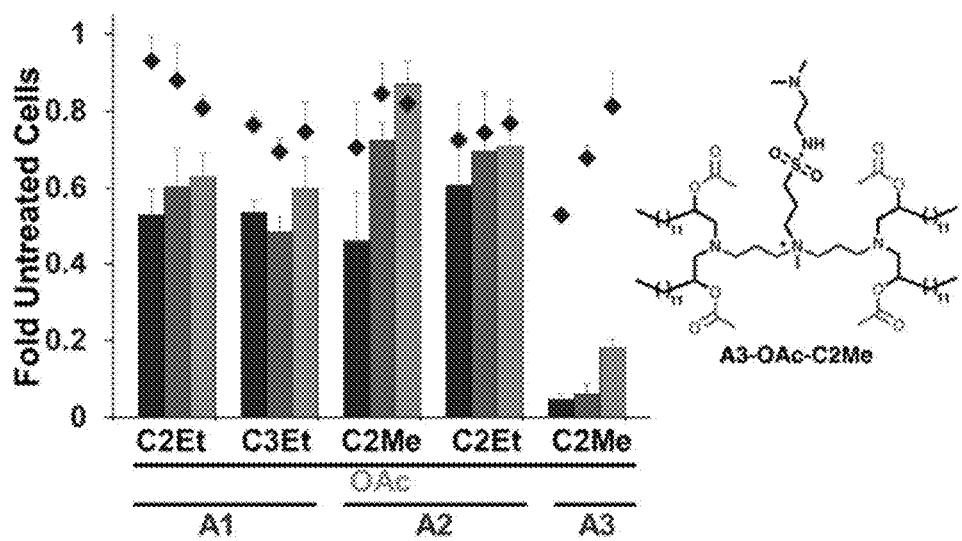
FIG. 6 shows the design of new CSALs examined the effects of sterics on the quaternary ammonium in the linker amine and in the head group amine. The C2Me head group shows the most activity. The four-tailed species highlights the importance tertiary amine content and hydrophobicity in delivery efficacy.
Figure 7:
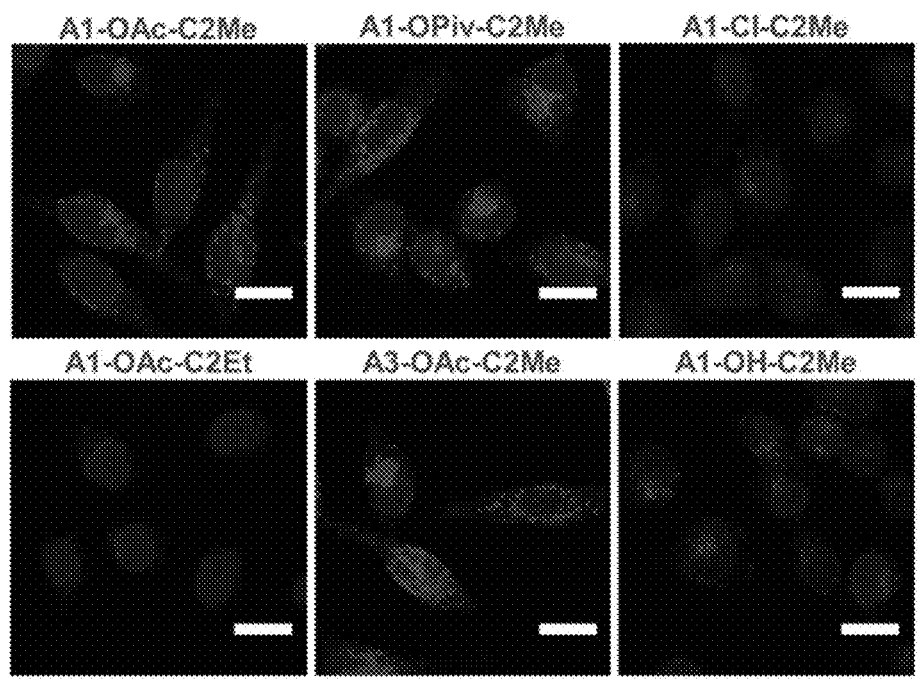
FIG. 7 shows uptake studies of CSAL-NPs in HeLa cells. Nanoparticles were formulated with Cy5.5-labeled siRNA (red) at 333:1 CSAL:siRNA mole ratio and incubated at 17.1 nM siRNA for 24 h. Cells were counterstained with DAPI (blue) overlayed with siRNA signal.
Figure 8:
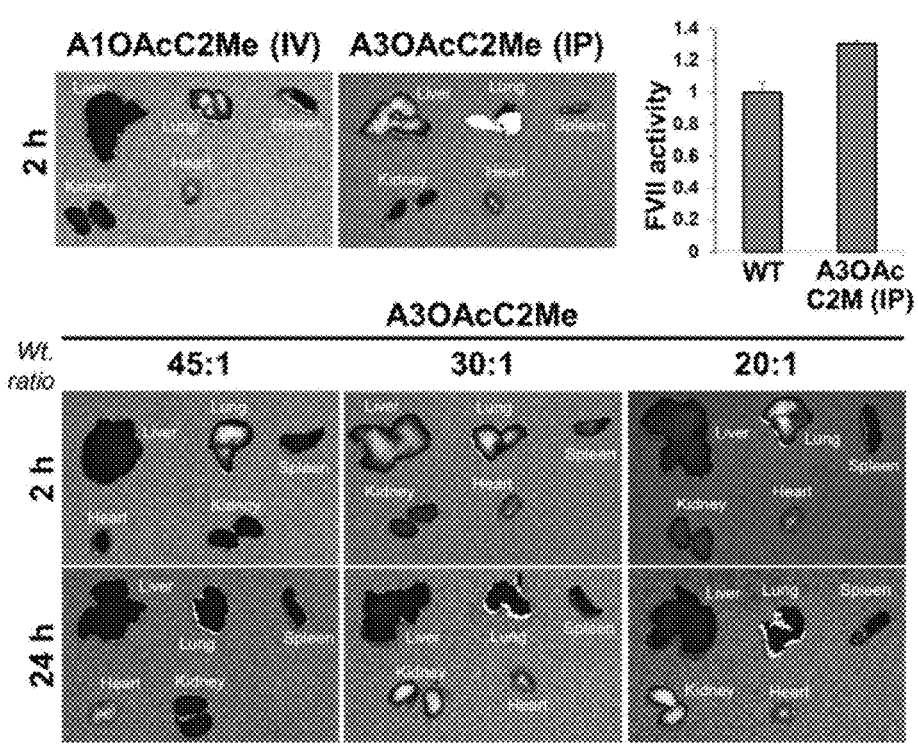
FIG. 8 shows the biodistribution of CSAL NPs in vivo. Cy5.5-labeled siRNA was encapsulated in CSAL NPs and injected systemically (1 mg/kg siRNA dose). A1OAcC2Me and A3OAcC2Me localize to lung after IV administration, A3OAcC2Me localizes to liver after IP administration. The effect of total lipid:siRNA weight ratio on A3OAcC2Me biodistribution was examined. All weight ratios resulted in lung accumulation at 2 h, while significant clearance to kidney was observed after 24 h at lower weight ratio suggesting better stability at higher weight ratio.
Figure 16:
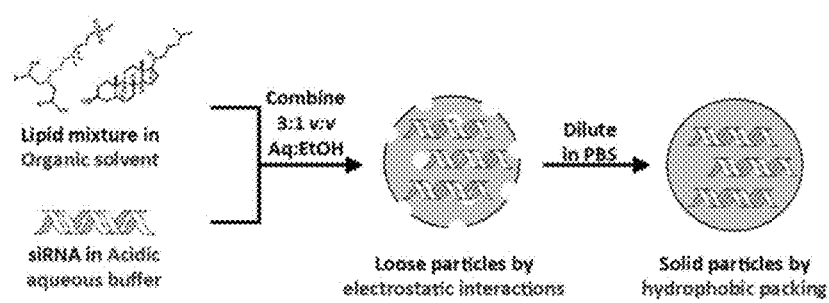
FIG. 16 shows the formation of nanoparticles comprising siRNA and ZALs in the presence of one or more helper lipids such as cholesterol.
Figure 17:
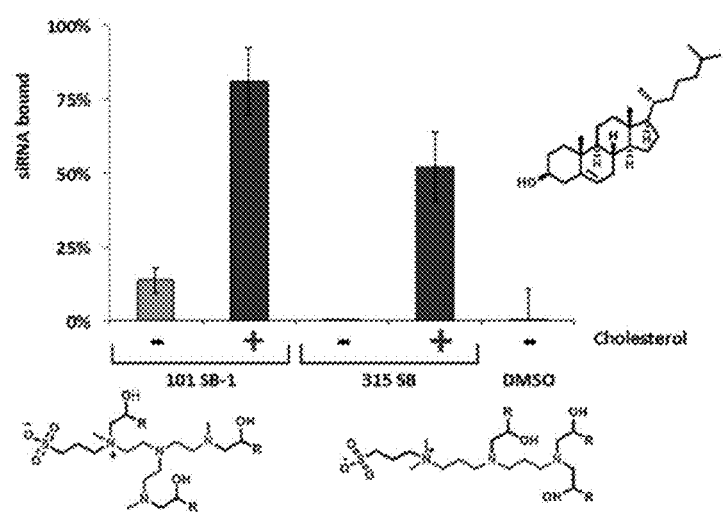
FIG. 17 shows that ZALs in the presence of cholesterol are able to encapsulate and bind siRNA.
Figure 21:
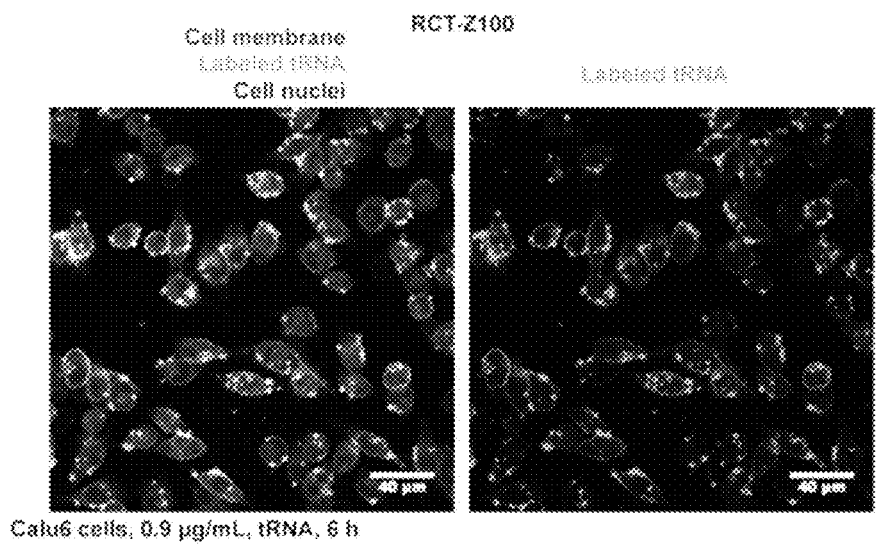
FIG. 21 shows that ZAL nanoparticles containing tRNA are internalized into Calu6 cells. These particles have been shown to taken up by multiple different cell lines.
Figure 22:
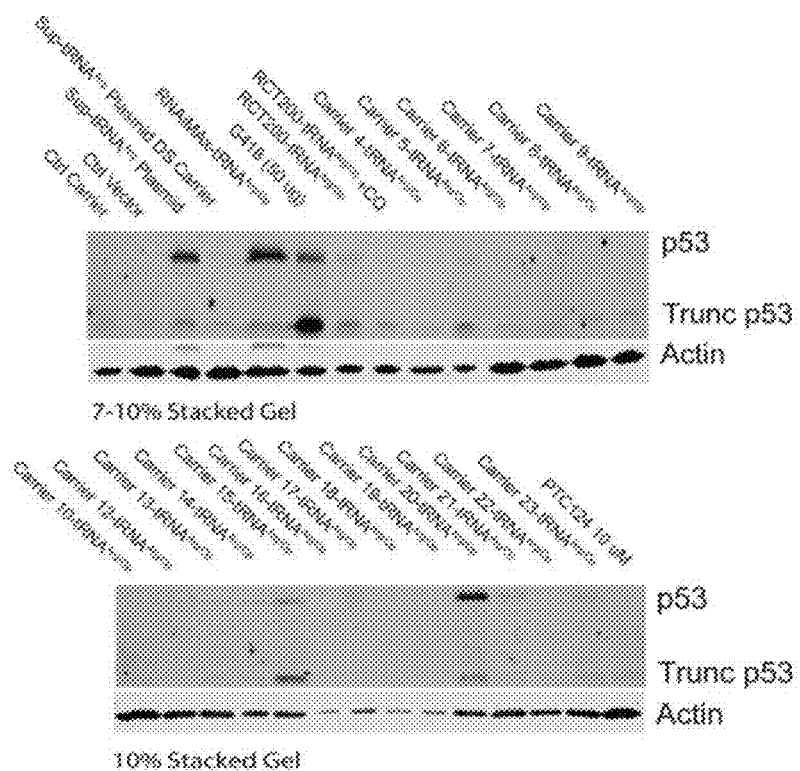
FIG. 22 shows restoration of p53 synthesis after delivery of the tRNA using different delivery composition.
Figure 23:
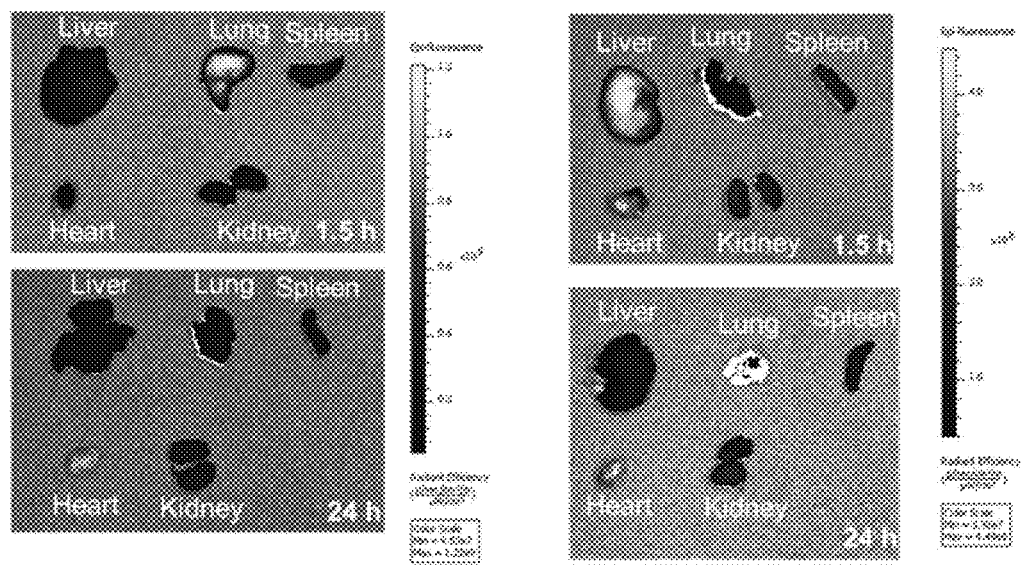
FIG. 23 shows distribution of a cationic sulfonamide and a zwitterionic amino lipid to different organs in vivo.
Figure 24:
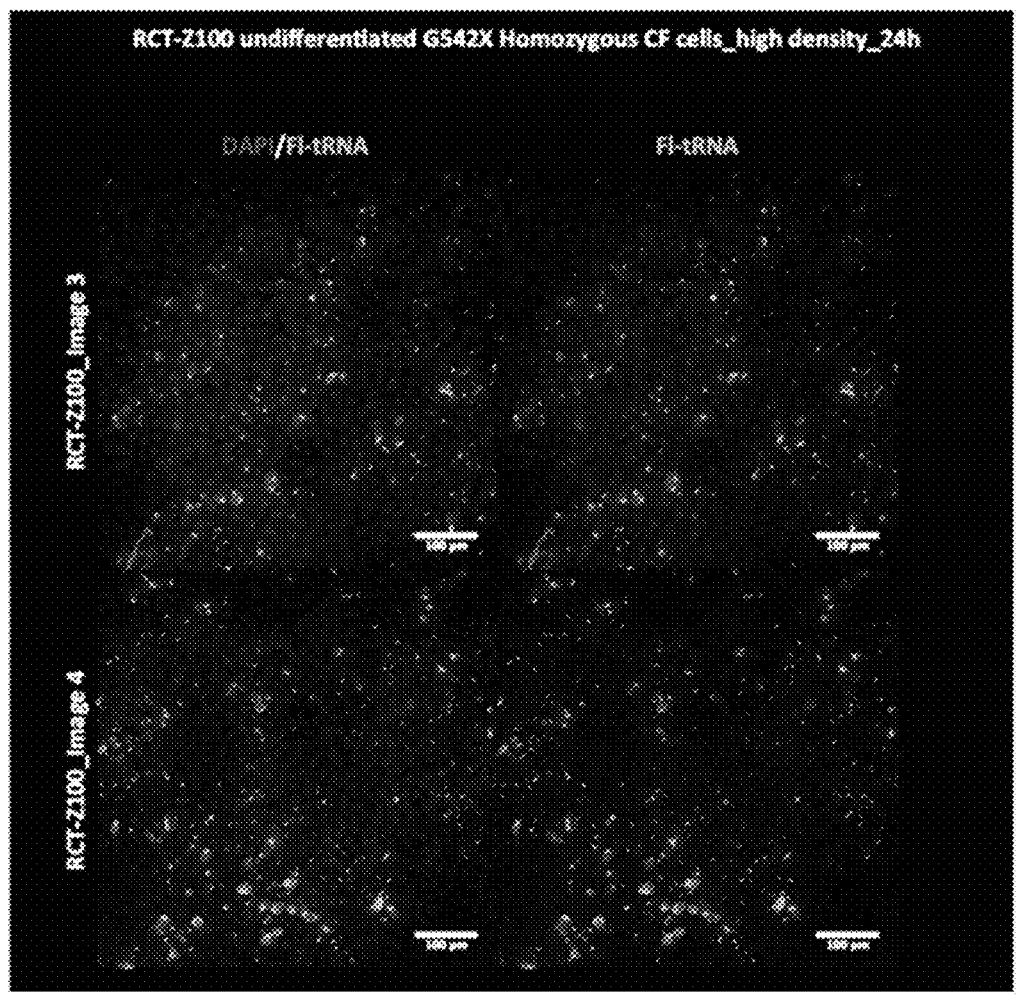
FIG. 24 shows delivery of tRNA into primary HBE cells using a zwitterionic amino lipid.

The CSALs (FIG. 3) and ZALs (FIG. 16) were formulated into nanoparticles in the presence of one or more helper lipids such as cholesterol. As shown in FIG. 17, cholesterol is an important component to allowing the nanoparticles to bind siRNA. In compositions without cholesterol, the amount of siRNA bound was significantly reduced. CSALs nanoparticles show an average size of about 100 nm (FIG. 4A). Additionally, the compositions with increased head group length then the siRNA binding decreased (FIG. 4B). Higher mole ratio of CSALs resulted in an increased charge (FIG. 4C) and decreased solution pH resulted in higher surface particularly at pH 3 (FIG. 4D). As shown in FIGS. 5 & 6, the CSALs showed activity in delivering siRNA and thus reducing luciferase activity. Additionally, the CSAL containing nanoparticles were tested for cell viability as well (FIG. 5). Similarly, the ZAL containing nanoparticles were also tested for luciferase activity. (See FIGS. 18-20B). Cellular imaging of CSALs and ZALs was carried out to determine if the compositions localized to cells. As shown in FIGS. 7, 21, and 24, the compositions localized to different cells. tRNA delivery was shown in FIG. 22 with a variety of different compositions as delivery of a modified tRNA resulted in restoration of p53 production from a genome which contained a nonsense mutation (FIG. 22). Finally, the distribution of the CSALs and ZALs containing nanoparticles in vivo was determined (FIGS. 8 & 23).

The compositions were tested for activity in delivering mRNA and the nucleic acids associated with the CRISPR process such as sgRNA. The composition of the nanoparticles used in these studies is shown below in Tables 1A & 1B.

TABLE 1A

Zwitterionic Amino Lipid Nanoparticle Molar Compositions

| Formulation code | ZAL in formulation | Mol. Wt. | ZAL | Cholesterol | DSPC | DOPE | PEG Lipid | ZAL:nucleic acid wt ratio |
|---|---|---|---|---|---|---|---|---|
| Z100 | ZA3-Ep10 | 1191.92 | 50 | 38.5 | 0 | 0 | 0 | 20.00 |
| Z101 | ZA3-Ep10 | 1191.92 | 50 | 38.5 | 0 | 0 | 2 | 20.00 |
| Z103 | ZA3-Ep10 | 1191.92 | 50 | 38.5 | 0 | 0 | 0.5 | 20.00 |
| Z102 | ZA3-Ep10 | 1191.92 | 50 | 38.5 | 0 | 0 | 1 | 20.00 |
| Z103 | ZA3-Ep10 | 1191.92 | 50 | 38.5 | 0 | 0 | 0.5 | 20.00 |
| Z104 | ZA3-Ep10 | 1191.92 | 40 | 38.5 | 10 | 0 | 2 | 15.60 |
| Z105 | ZA3-Ep10 | 1191.92 | 40 | 38.5 | 0 | 10 | 2 | 15.69 |
| Z106 | ZA3-Ep10 | 1191.92 | 30 | 38.5 | 20 | 0 | 2 | 12.35 |
| Z107 | ZA3-Ep10 | 1191.92 | 30 | 38.5 | 0 | 20 | 2 | 12.50 |
| Z108 | ZA3-Ep10 | 1191.92 | 50 | 38.5 | 10 | 0 | 2 | 20.00 |
| Z109 | ZA3-Ep10 | 1191.92 | 50 | 38.5 | 0 | 10 | 2 | 20.00 |
| Z110 | ZA3-Ep10 | 1191.92 | 50 | 38.5 | 0 | 0 | 5 | 20.00 |
| Z111 | ZA3-Ep10 | 1191.92 | 50 | 38.5 | 0 | 0 | 10 | 20.00 |
| Z112 | ZA3-Ep10 | 1191.92 | 50 | 38.5 | 0 | 0 | 2 | 10.00 |
| Z113 | ZA3-Ep10 | 1191.92 | 50 | 77 | 0 | 4 | 2 | 10.00 |
| Z114 | ZA3-Ep10 | 1191.92 | 50 | 38.5 | 0 | 0 | 2 | 7.50 |
| Z115 | ZA3-Ep10 | 1191.92 | 50 | 38.5 | 0 | 0 | 2 | 5.00 |
| Z116 | ZA3-Ep10 | 1191.92 | 50 | 38.5 | 0 | 0 | 1 | 10.00 |
| Z117 | ZA3-Ep10 | 1191.92 | 50 | 38.5 | 0 | 0 | 0.5 | 10.00 |

TABLE 1A-continued

Zwitterionic Amino Lipid Nanoparticle Molar Compositions

| Formulation code | ZAL in formulation | Mol. Wt. | ZAL | Cholesterol | DSPC | DOPE | PEG Lipid | ZAL:nucleic acid wt ratio |
|---|---|---|---|---|---|---|---|---|
| Z118 | ZA3-Ep10 | 1191.92 | 50 | 38.5 | 0 | 0 | 1 | 7.50 |
| Z119 | ZA3-Ep10 | 1191.92 | 50 | 38.5 | 0 | 0 | 1 | 5.00 |
| Z120 | ZA3-Ep10 | 1191.92 | 50 | 38.5 | 0 | 0 | 0.5 | 7.50 |
| Z121 | ZA3-Ep10 | 1191.92 | 50 | 38.5 | 0 | 0 | 0.5 | 5.00 |
| Z122 | ZA3-Ep10 | 1191.92 | 50 | 38.5 | 0 | 0 | 5 | 10.00 |
| Z123 | ZA3-Ep10 | 1191.92 | 50 | 38.5 | 0 | 0 | 5 | 7.50 |
| Z124 | ZA3-Ep10 | 1191.92 | 50 | 38.5 | 0 | 0 | 5 | 5.00 |
| Z125 | ZA3-Ep10 | 1191.92 | 50 | 38.5 | 0 | 0 | 0 | 10.00 |
| Z202 | ZA6-Ep10 | 933.48 | 50 | 38.5 | 0 | 0 | 1 | 20.00 |
| Z302 | ZA3-Ep8 | 1051.68 | 50 | 38.5 | 0 | 0 | 1 | 20.00 |
| Z402 | ZA3-Ep12 | 1332.18 | 50 | 38.5 | 0 | 0 | 1 | 20.00 |
| Z502 | ZA3-Ep14 | 1472.48 | 50 | 38.5 | 0 | 0 | 1 | 20.00 |
| Z602 | ZA3-Ep16 | 1612.73 | 50 | 38.5 | 0 | 0 | 1 | 20.00 |
| Z702 | ZA3-Ep18 | 1753.03 | 50 | 38.5 | 0 | 0 | 1 | 20.00 |
| Z802 | ZA1-Ep10 | 765.2 | 50 | 38.5 | 0 | 0 | 1 | 20.00 |
| Z902 | ZA4-Ep10 | 850.35 | 50 | 38.5 | 0 | 0 | 1 | 20.00 |
| Z1002 | ZA6-Ac10 | 1101.66 | 50 | 38.5 | 0 | 0 | 1 | 20.00 |
| Z1102 | ZA6-Ac12 | 1185.84 | 50 | 38.5 | 0 | 0 | 1 | 20.00 |

TABLE 1B

Cationic Sulfonamide Amino Lipid Nanoparticle Molar Compositions

| Formulation code | CSAL in formulation | Mol. Wt. | ZAL | Cholesterol | DSPC | DOPE | PEG Lipid | CSAL:nucleic acid wt ratio |
|---|---|---|---|---|---|---|---|---|
| CS100 | A3OAcC2Me | 1356.19 | 50 | 38.5 | 10 | 0 | 1.5 | 32.1 |
| CS101 | A3OAcC2Me | 1356.19 | 50 | 38.5 | 10 | 0 | 1.5 | 14.3 |
| CS102 | A3OAcC2Me | 1356.19 | 50 | 38.5 | 10 | 0 | 1.5 | 21.4 |
| CS103 | A3OAcC2M | 1356.19 | 50 | 38.5 | 0 | 0 | 1.5 | 20.0 |
| CS104 | A3OAcC2M | 1356.19 | 50 | 38.5 | 0 | 0 | 1.5 | 15.0 |
| CS111 | A3OAcC2M | 1356.19 | 50 | 38.5 | 0 | 0 | 10 | 15.0 |
| CS200 | A1OAcC2Me | 804.29 | 50 | 38.5 | 10 | 0 | 1.5 | 17.9 |

Figure 25:
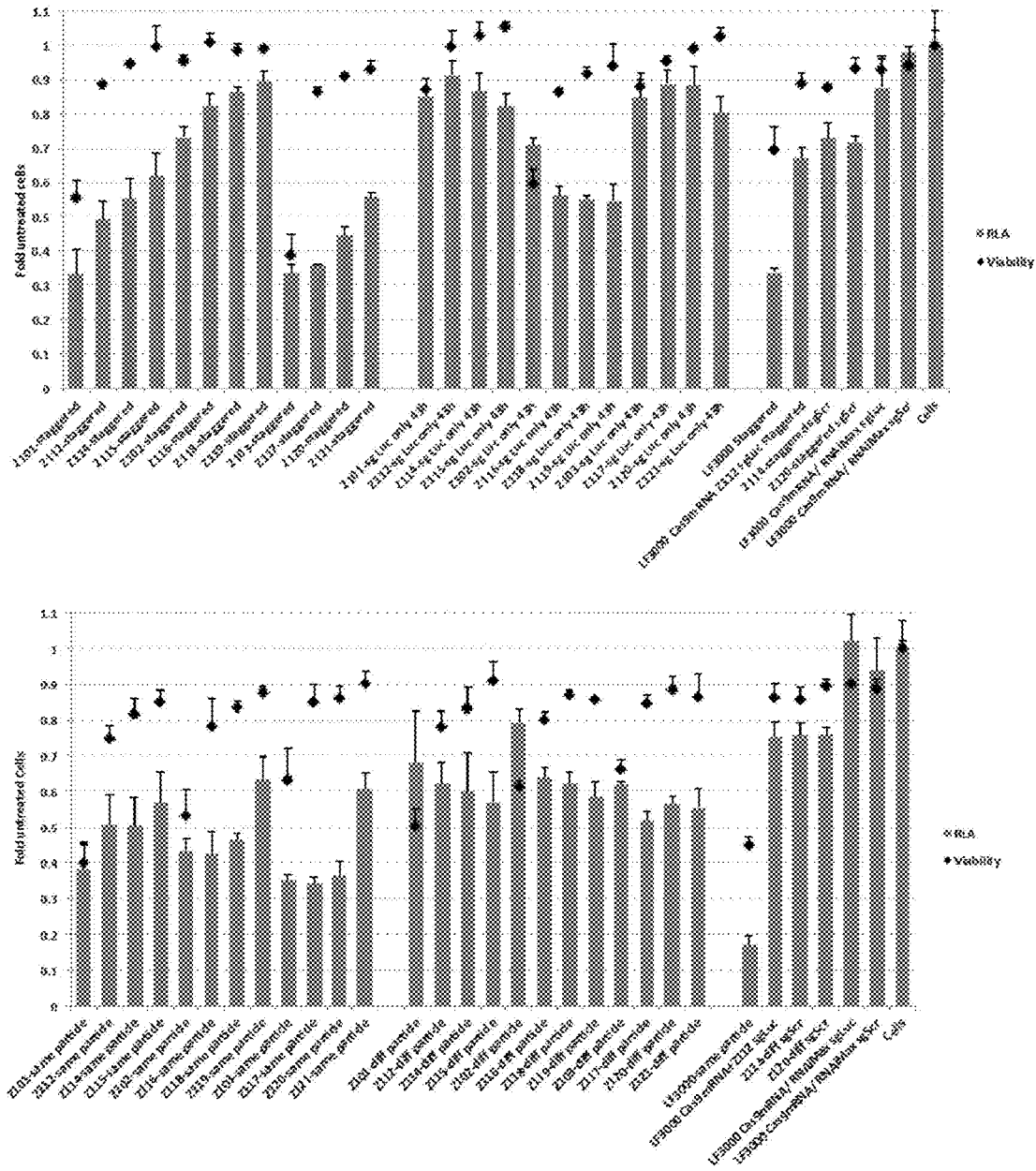
FIG. 25 shows the effects of combining multiple different nucleic acid molecules in a single nanoparticle. Co-delivery of Cas9 mRNA and sgRNA against luciferase to HeLa-Luc cells was tested with an RNA dose of 100 ng mRNA per well and 50 ng sgRNA per well in 200 μL DMEM 5% FBS. "Same particle" samples are nanoparticles packaged with both mRNA and sgRNA in the same nanoparticle formulation by co-diluting the mRNA and sgRNA together in acidic buffer prior to the addition of the lipids during formulation. "Diff particle" samples are are the mRNA-LNP and sgRNA-LNP prepared as separate nanoparticles, but added at the same time to the same wells. "Staggered" samples are mRNA-ZAL nanoparticles are formulated and added 16 h prior to sgRNA-ZAL nanoparticles. As a negative control "sgLuc only 43 h," nanoparticles with sgRNA against luciferase were added in the absence of Cas9 mRNA. Samples were read out 43 h after the initial transfection of mRNA alone or mRNA+sgRNA.
Figure 26:
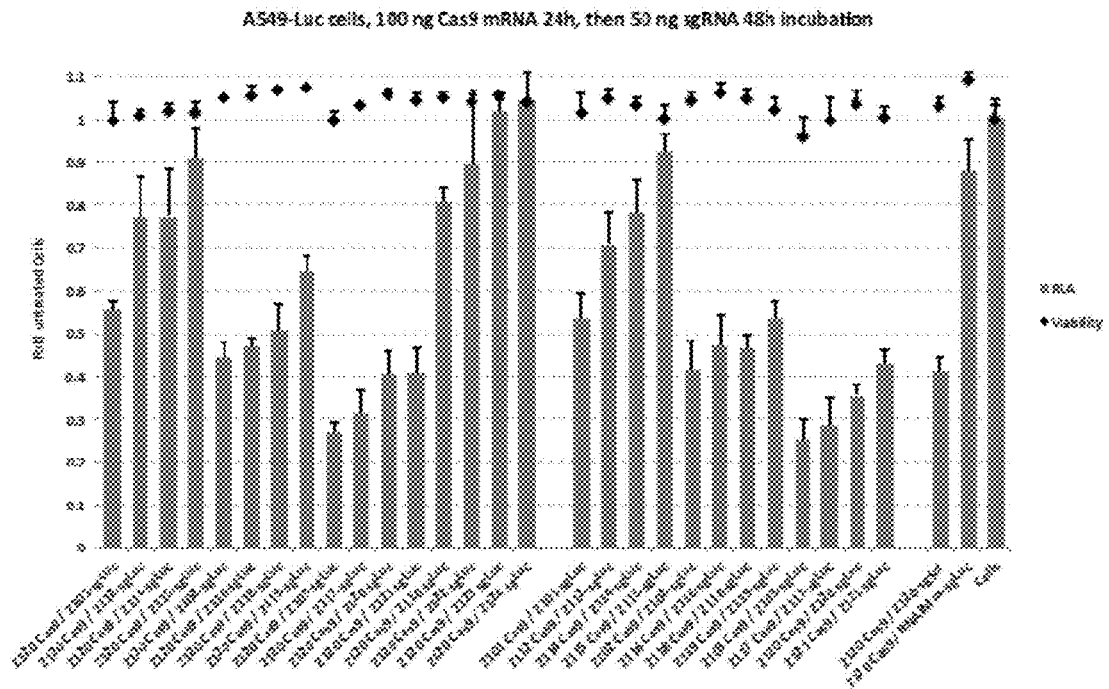
FIG. 26 shows co-delivery of Cas9 mRNA and single-guide RNA by ZA3-Ep10 nanoparticles against luciferase to A549-luc cells.
Figure 27:
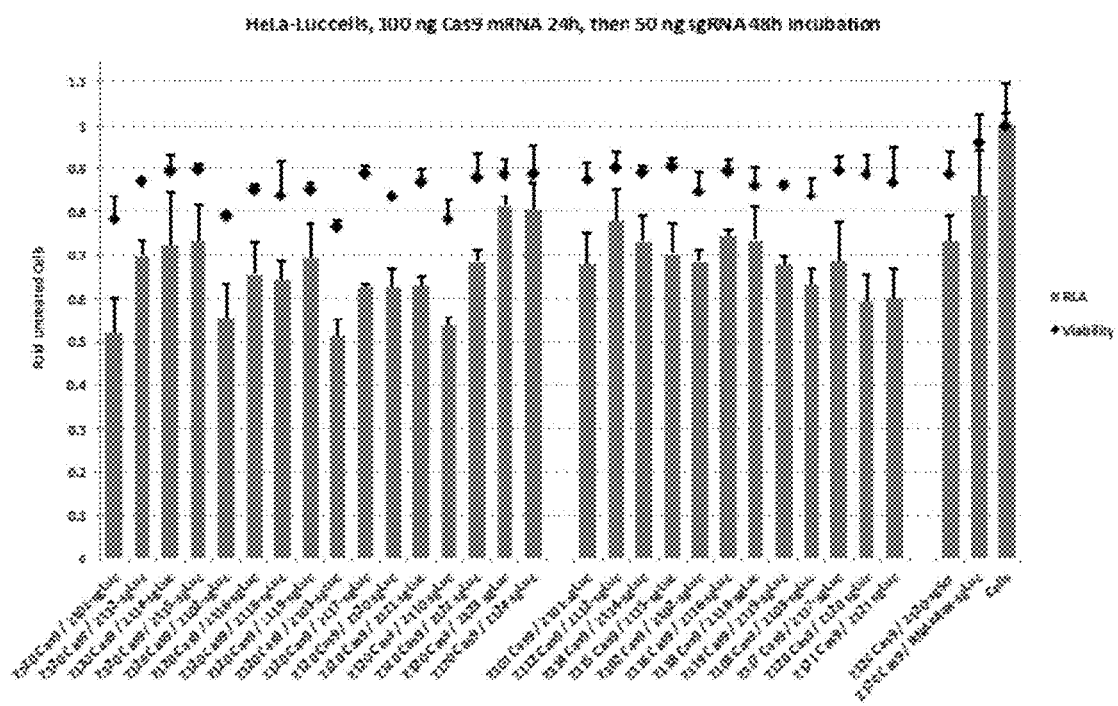
FIG. 27 shows co-delivery of Cas9 mRNA and single-guide RNA by ZA3-Ep10 nanoparticles against luciferase to HeLa-luc cells.
Figure 28:
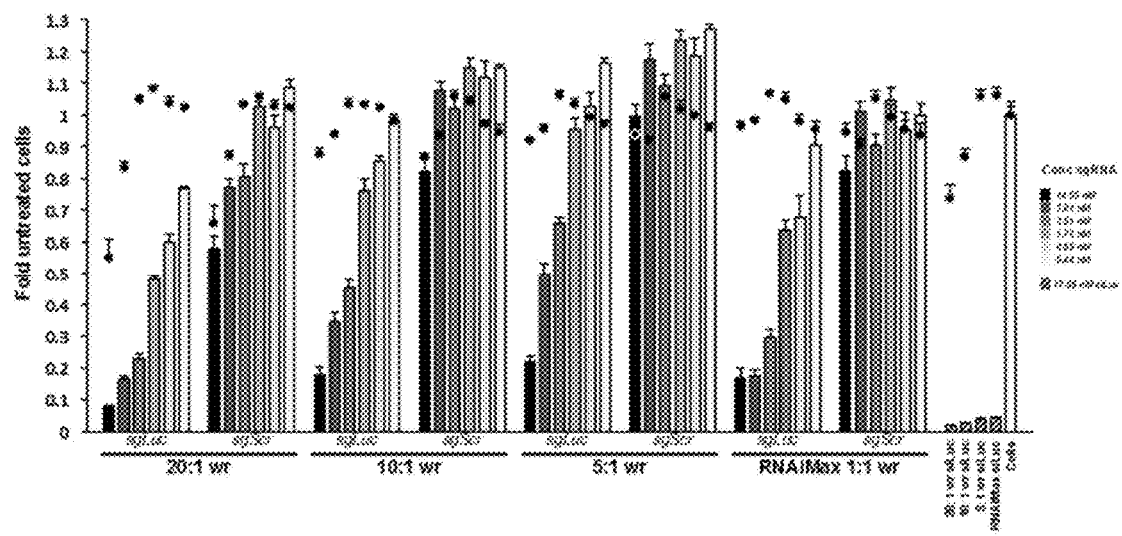
FIG. 28 shows a dose response distribution for ZAL compositions at particular weigh ratio of sgRNA. These dose response distribution was carried out with ZA3-Ep10 NPs in HeLa-Luc-Cas9 cells. The composition comprised 50:38.5:2 ZAL:Cholesterol:PEG-lipid, at 20:1, 10:1, 5:1 ZAL:sgRNA weight ratio in nanoparticle formulations. The composition was incubated for 48 hours. 50 ng siLuc was used as the siRNA positive control.

Using the ZA1Ep10 ZAL, various concentrations of PEG lipid were tested for their ability to delivery luciferase mRNA delivery to IGROV1 cells. Monitoring the amount of luminescence produced for each population, the luminescence was measured at 18 hours, 26 hours, and 45 hours post transfection. The effect of the addition of both the mRNA and the sgRNA in the same particle or sequential administration of these compounds were tested (FIG. 25). Compositions were the mRNA and the sgRNA generally showed reduced amounts of untreated cells relative to the use of different particles. Similar tests were carried out with A549-Luc cells (FIG. 26). The effect of the nanoparticle composition with a single ZAL was tested with HeLa-Luc cells against luciferase and is shown in FIG. 27. As shown, the ZAL result in a dose dependent reduction of luciferase activity (FIG. 28).

Figure 29:
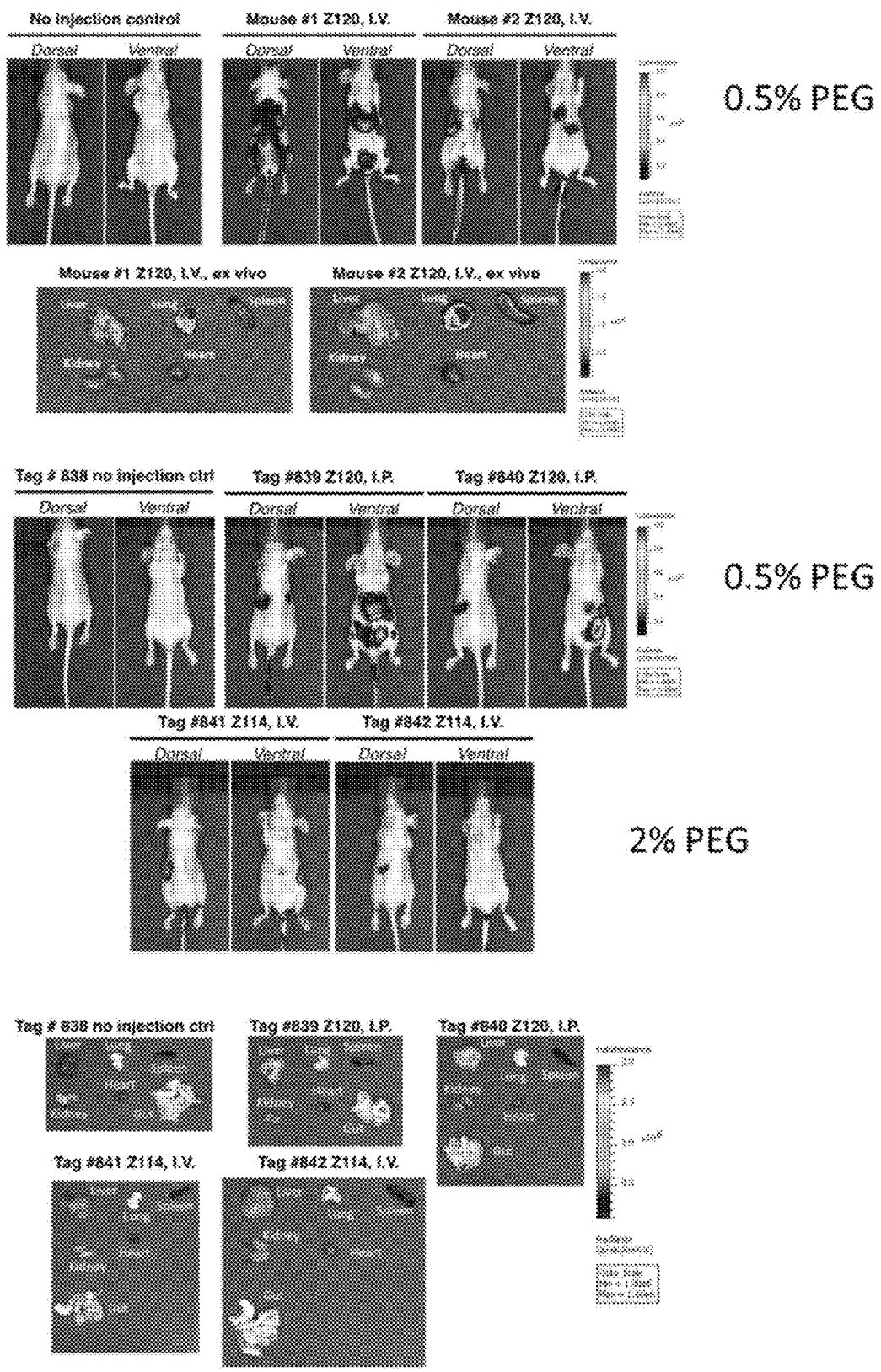
FIG. 29 shows ex vivo imaging of BALB-c-Nu mice which have been injected either intravenously or intraperitoneally with 1 mg/kg Luc mRNA. The mice were imaged 24 hours post injection. These images show the organ localization of nanoparticles.

Ex vivo imaging of the distribution of the Z120 nanoparticles with different amounts of PEG lipid was analyzed when administered by intravenously and intraperitoneally. BALB-c-Nu mice were injected by tail vein injection with 1 mg/kg Luc mRNA. The mice were then imaged 24 hours post injection. These images are shown in FIG. 29. Similar to the delivery of luciferase, in vivo delivery of Factor VII was analyzed using Z112 with 3 mg/kg of Factor VII.

Figure 30:
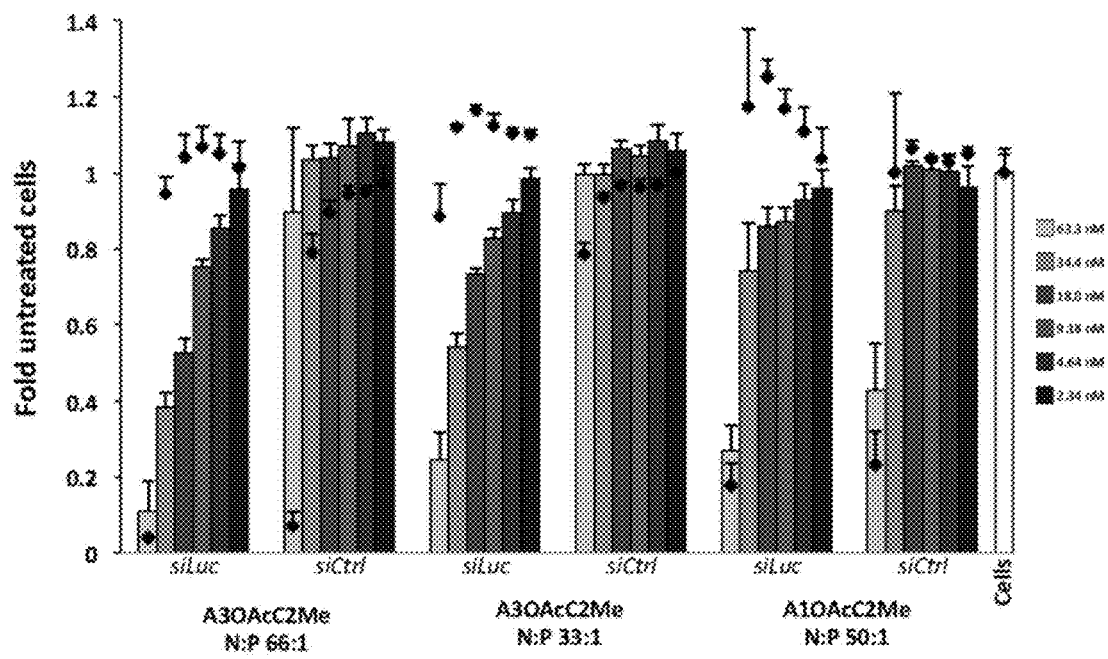
FIG. 30 shows the dose dependent activity of luciferase siRNA when delivered using CSALs at two different ratios of nucleic acid to nanoparticle ratios and two different CSALs.
Figure 31:
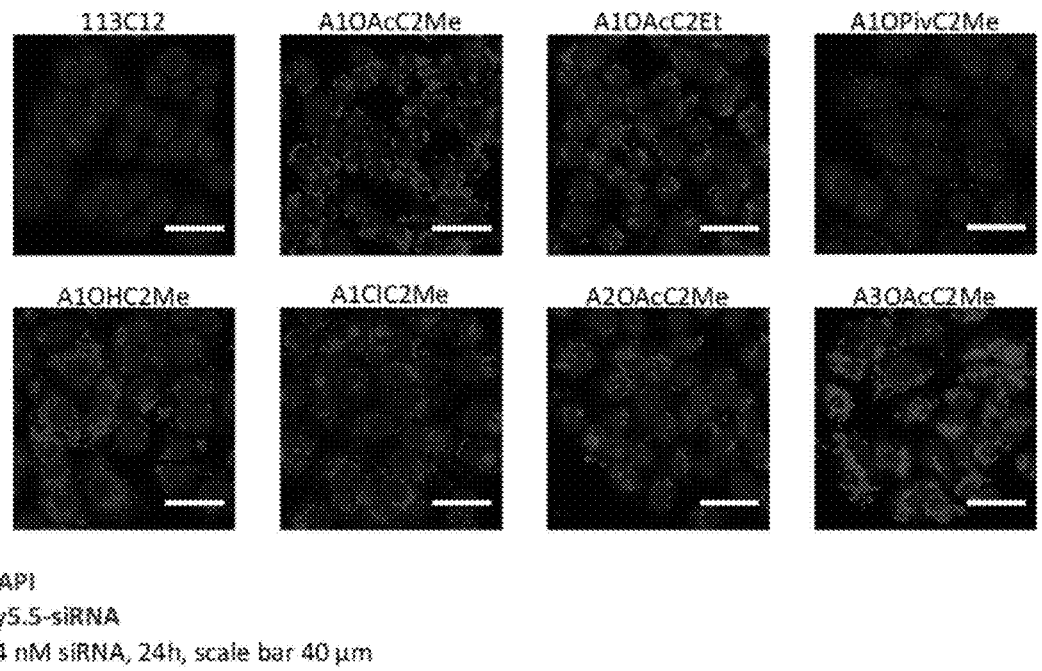
FIG. 31 shows the localization of the CSALs in A549-luc cells with 34 nM siRNA. The image is taken after 24 hours of incubation. The scale bar at the bottom right corner of the images is 40 μm.
Figure 32:
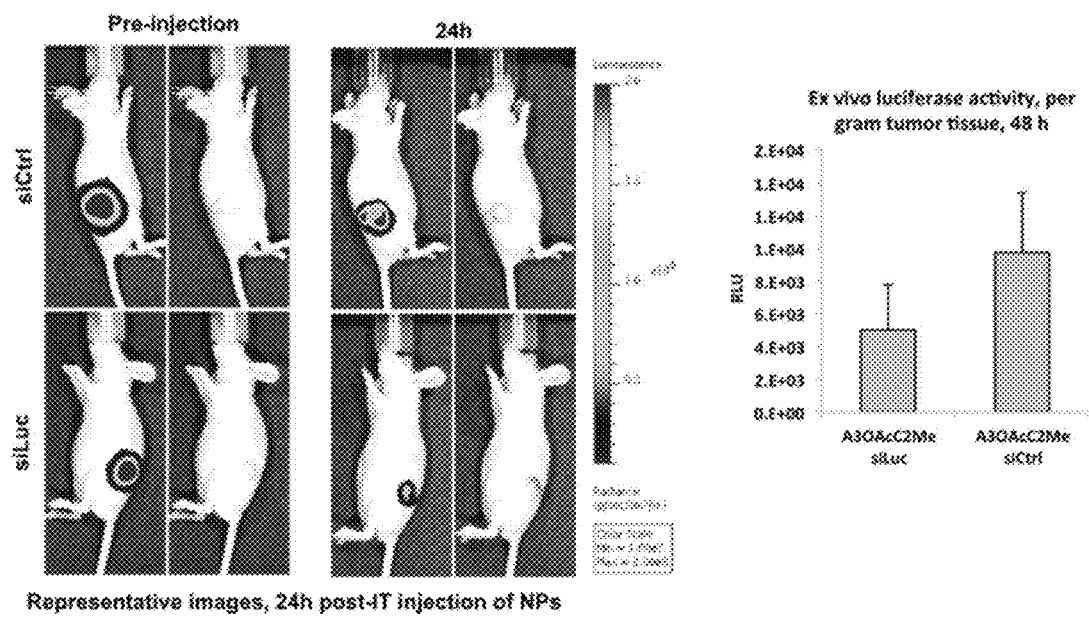
FIG. 32 shows the localization of A3OAcC2Me nanoparticles (50 CSAL:38.5 Cholesterol: 10 DSPC: 1.5 PEG mol ratios in lipid mix, 30:1 total lipid:siRNA weight ratio) in A549-luc xenografts in Balb-c nude mice. The nanoparticles were injected intratumoral injection with 1 mg/kg siRNA using bioluminescence imaging after 24 h using IVIS with IP luciferin injection. Ex vivo analysis (48 h) included sacrificing the animals and tissue collected and frozen on dry ice. Then, the tissue was homogenized by a tissue homogenizer followed by tip sonication in 1× lysis buffer (Promega) and supplemented with protease inhibitor (Pierce). The samples were normalized by total mass tumor tissue (N=4+/−S.E.M.).
Figure 33:
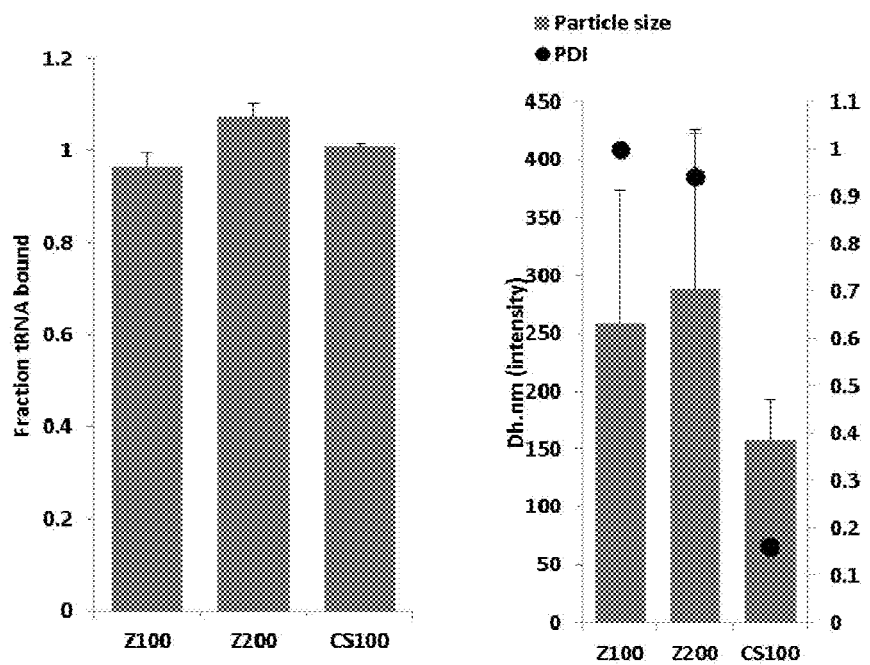
FIG. 33 shows the binding and particle size from the compositions used in tRNA delivery in Calu6 cells.
Figure 34:
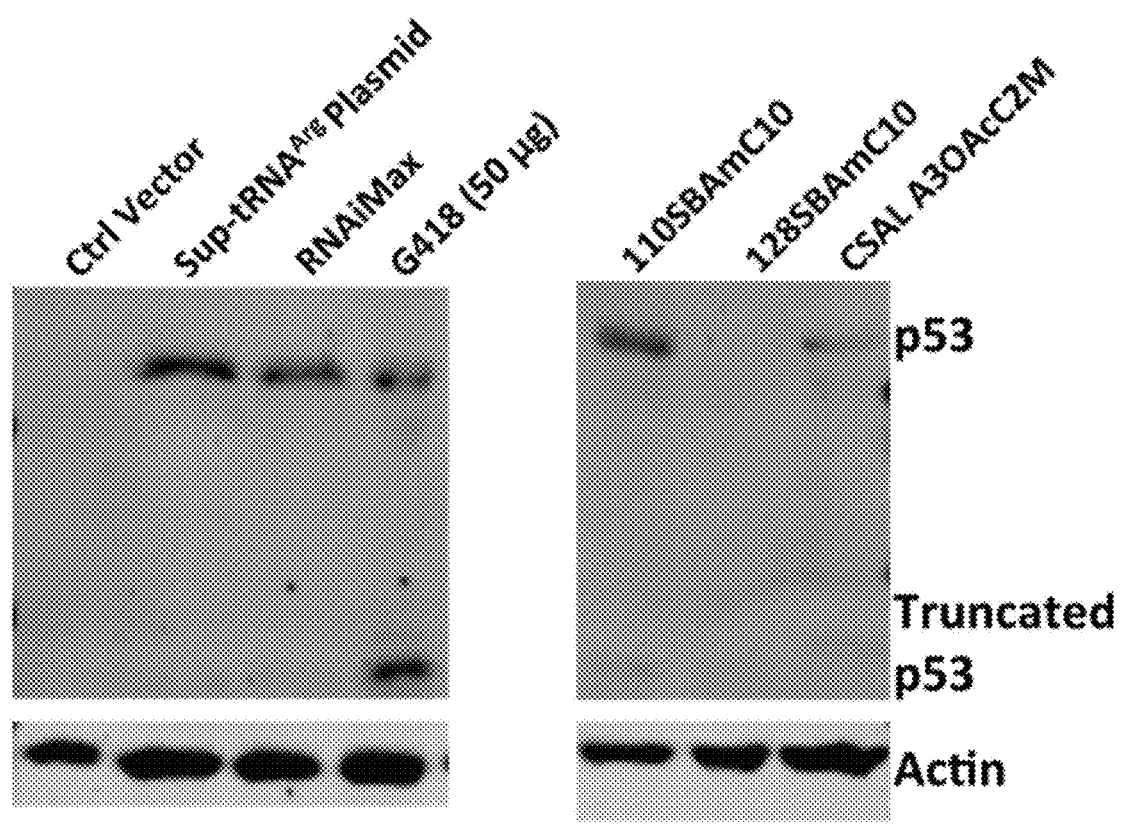
FIG. 34 shows a gel showing that both ZAL and CSAL nanoparticles enable the delivery of suppressor tRNA which result in the restoration of p53 expression.
Figure 35:
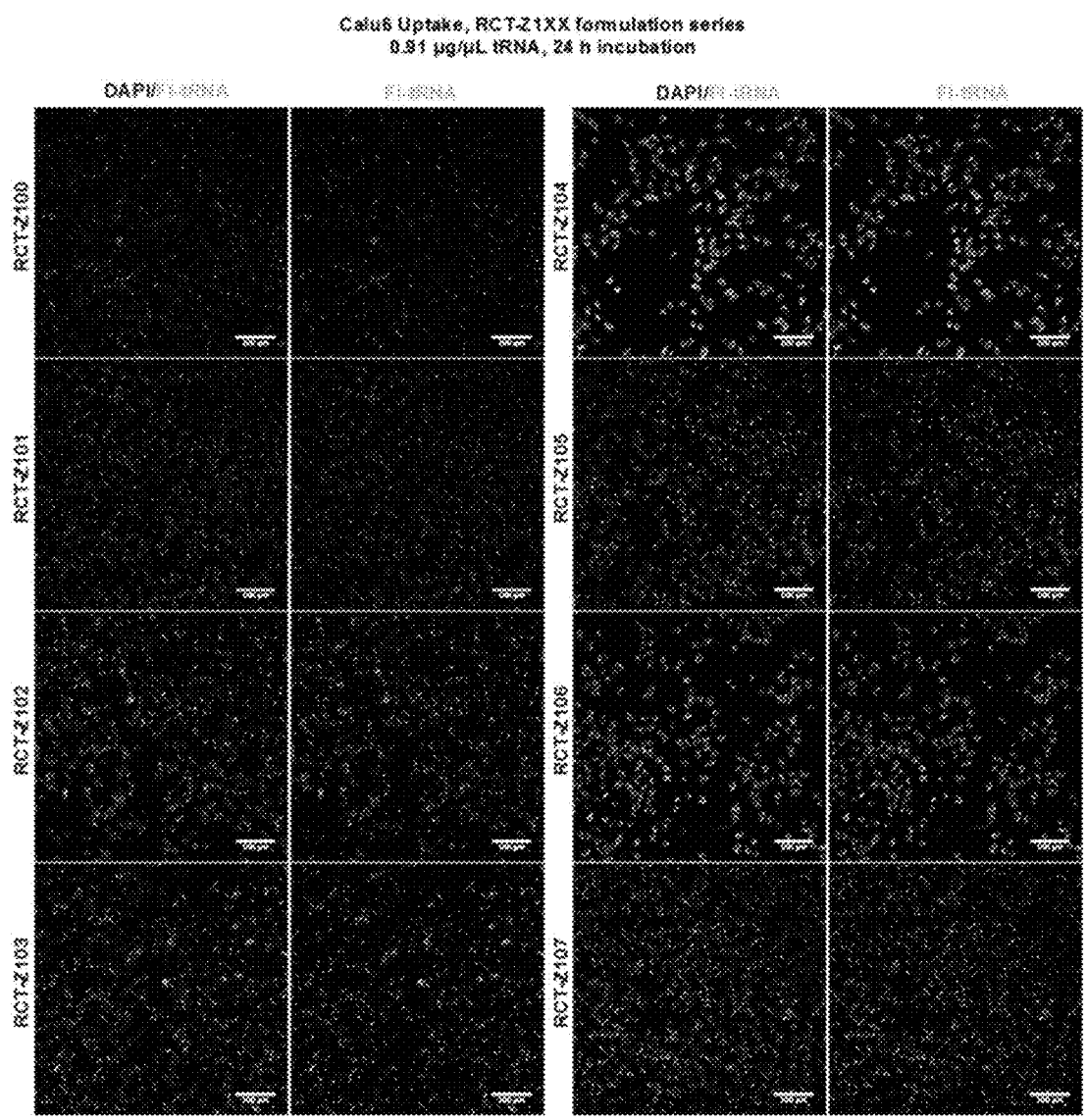
FIG. 35 shows the uptake of a variety of different ZALs with fluorescently labeled tRNA nanoparticle formations in Calu6 cells.

Using the CSALs, a dose dependent activity was observed at two different weight ratio and with two different CSALs (FIG. 30). Using fluorescence labeled nucleic acids, the internalization of the CSAL nanoparticles was observed in A549-luc cells after 24 hour incubation time with 34 nM siRNA. These images are shown in FIG. 31. Similar imaging was carried out in BALB-c nude mice showing the internalization of the nanoparticles within the body and localization of the nanoparticles into specific organs as shown in FIG. 32. Binding of suppressor tRNA within the CSAL compositions described herein is shown in FIG. 33 along with particle size. The gel electrophoresis shows that both CSALs and ZALs when loaded with suppressor tRNA polymers can restore p53 expression (FIG. 34). A variety of different ZALs have been shown to be taken up by Calu6 cells (FIG. 35) when loaded with one or more suppressor tRNA molecules.

Example 4: Delivery of CRISPR Nucleotides Using ZALs and CSALs

A. Methods and Materials
  i. Chemicals and Reagents for Synthesis.
  All chemicals were purchased from Sigma-Aldrich unless otherwise indicated. 1,2-epoxydecane was purchased from TCI America. 1,2-epoxyoctadecane was purchased from Alfa Aesar. Hydrophobic acrylates octyl acrylate (Ac8), decyl acrylate (Ac10), tetradecyl acrylate (Ac14), and hexadecyl acrylate (Ac16) were synthesized as described below. Organic solvents were purchased from Fisher Scientific and purified with a solvent purification system (Innovative Technology). Lipid PEG2000 was chemically synthesized, as previously described (Zhou et al., 2016) CDCl$_3$, methanol-d4, and DMSO-d6 were purchased from Cambridge Isotope Laboratories.

ii. Nucleic Acids and Other Reagents for Biological Assays.

All siRNAs were purchased from Sigma-Aldrich. DNA oligonucleotides were purchased from Integrated DNA Technologies. Luciferase, mCherry, and Cas9 messenger RNA (mRNA) were purchased from Tri-Link Biotechnologies. Lipofectamine 3000 and OptiMEM were purchased from Invitrogen. Single guide RNA was prepared by in vitro transcription (IVT) using the MEGAshortscript T7 transcription kit (Life Technologies) followed by purification using the MEGAclear Transcription Clean-Up Kit (Life Technologies) according to the manufacturer's protocols. The Ribogreen reagent was purchased from Life Technologies. ONE-Glo+Tox and Cell Titer Glow were purchased from Promega. RIPA buffer and TRIzol reagent were purchased from Thermo Scientific. QuickExtract DNA Extraction Solution was purchased from Epicentre. Real-time qPCR was performed using iTaq Universal SYBR Green 2× Supermix (Bio-Rad). All antibodies were purchased from Cell Signaling.

iii. Cell Culture.

Dulbecco's Modified Eagle Medium (DMEM) was purchased from Hyclone containing high glucose, L-glutamine, and without pyruvate or phenol red. RPMI-1640 was purchased from Sigma Aldrich. Dulbecco's modified phosphate buffered saline (PBS), Trypsin-EDTA (0.25%) and fetal bovine serum (FBS) were purchased from Sigma-Aldrich. HeLa-Luc and A549-Luc cells were cultured in DMEM supplemented with 5% FBS. IGROV1 cells were cultured in RPMI-1640 supplemented with 5% FBS.

iv. Animal Studies.

All experiments were approved by the Institutional Animal Care & Use Committee (IACUC) of The University of Texas Southwestern Medical Center and were consistent with local, state and federal regulations as applicable. C57BL/6 and athymic nude Foxn1$^{nu}$ mice were purchased from Envigo. NOD scid gamma (NSG) mice were purchased from the UT Southwestern animal breeding core. Rosa-CAG-LSL-tdTomato mice were purchased from The Jackson Laboratory (Stock number: 007909).

v. Methods $^1$H and $^{13}$C NMR were performed on a Varian 400 MHz spectrometer or a Varian 500 MHz spectrometer. MS was performed on a Voyager DE-Pro MALDI-TOF. LCMS was performed on an Agilent LCMS system equipped with UV-vis and evaporative light scattering detectors (ELSD). Flash chromatography was performed on a Teledyne Isco CombiFlash Rf-200i chromatography system equipped with UV-vis and evaporative light scattering detectors (ELSD). Particle sizes and zeta potentials were measured by Dynamic Light Scattering (DLS) using a Malvern Zetasizer Nano ZS (He—Ne laser, $\lambda$=632 nm). RT qPCR was run on a Bio-Rad C1000 Touch Thermal Cycler (CFX384 Real-time System). Each reaction was made with iTaq Universal SYBR Green 2× Supermix (Bio-Rad). Tissue sections were imaged using confocal laser scanning microscopy with a Zeiss LSM-700 and images were processed using ImageJ (NIH). Flow cytometry was performed with BI Fusion machine (BD Biosciences).

vi. Nanoparticle Formulation for in Vivo Studies.

Zwitterionic amino lipid (ZAL) nanoparticles (ZNPs) for in vivo studies were prepared using a two-channel microfluidic mixer with herringbone rapid mixing features (Precision Nanosystems NanoAssemblr). Ethanol solutions of lipid mixes (ZALs, cholesterol, and PEG-lipid) were rapidly combined with acidic aqueous solutions of nucleic acid at an aqueous: EtOH volumetric ratio of 3:1 and a flow rate of 12 mL/minute.

vii. Nucleic Acid Sequences
a. Small Interfering RNAs (siRNAs)
dT are DNA bases. All others are RNA bases.
siLuc (siRNA Against Luciferase).

```
                                           (SEQ ID NO: 1)
sense:      5'-GAUUAUGUCCGGUUAUGUA[dT][dT]-3'

(SEQ ID NO: 2)
antisense:  5'-UACAUAACCGGACAUAAUC[dT][dT]-3'
``` siCtrl (Non-Targeting siRNA)

```
                                           (SEQ ID NO: 3)
sense:      5'-GCGCGAUAGCGCGAAUAUA[dT][dT]-3'

(SEQ ID NO: 4)
antisense:  5'-UAUAUUCGCGCUAUCGCGC[dT][dT]-3'
```

Single guide RNAs (sgRNAs). Guide RNAs were designed using the CRISPR.mit.edu platform and cloned into pSpCas9(BB)-2A-GFP (PX458) as previously reported (Ran et al., 2013).

TABLE 2

| Guide name | Target | Guide sequence (5' to 3') | | PAM | Strand |
|---|---|---|---|---|---|
| sgLuc1 | Luciferase | CTTCGAAATGTCCGTTCGGT | (SEQ ID NO: 5) | TGG | Positive |
| sgLuc2 | Luciferase | CCCGGCGCCATTCTATCCGC | (SEQ ID NO: 6) | TGG | Positive |
| sgLuc3 | Luciferase | TCCAGCGGATAGAATGGCGC | (SEQ ID NO: 7) | CGG | Negative |
| sgLuc4 | Luciferase | GGATTCTAAAACGGATTACC | (SEQ ID NO: 8) | AGG | Positive |
| sgLuc5 | Luciferase | ATAAATAACGCGCCCAACAC | (SEQ ID NO: 9) | CGG | Negative |
| sgLoxP | LoxP | CGTATAGCATACATTATACG | (SEQ ID NO: 10) | AAG | Negative |
| sgCtrl | Mouse F7 | GCTTCGATAATATCCGCTAC | (SEQ ID NO: 11) | TGG | Positive |

TABLE 3

BbsI sgRNA cloning oligos

| Probe | Sequence (5' to 3')* | SEQ ID NO: |
|---|---|---|
| sgLuc1_Top | CACCGCTTCGAAATGTCCGTTCGGT | 12 |
| sgLuc1_Bottom | AAACACCGAACGGACATTTCGAAGC | 13 |
| sgLuc2_Top | CACCGCCCGGCGCCATTCTATCCGC | 14 |
| sgLuc2_Bottom | AAACGCGGATAGAATGGCGCCGGGC | 15 |
| sgLuc3_Top | CACCGTCCAGCGGATAGAATGGCGC | 16 |
| sgLuc3_Bottom | AAACGCGCCATTCTATCCGCTGGAC | 17 |
| sgLuc4_Top | CACCGGGATTCTAAAACGGATTACC | 18 |
| sgLuc4_Bottom | AAACGGTAATCCGTTTTAGAATCCC | 19 |
| sgLuc5_Top | CACCGATAAATAACGCGCCCAACAC | 20 |
| sgLuc5_Bottom | AAACGTGTTGGGCGCGTTATTTATC | 21 |
| sgLoxP_Top | CACCGCGTATAGCATACATTATACG | 22 |
| sgLoxP_Bottom | AAACCGTATAATGTATGCTATACGC | 23 |
| sgCtrl_Top | CACCGGCTTCGATAATATCCGCTAC | 24 |
| sgCtrl_Bottom | AAACGTAGCGGATATTATCGAAGCC | 25 |

*Guide sequence shown in bold.

TABLE 4

T7 template PCR primers

| Primer | Sequence (5' to 3') | SEQ ID NO: |
|---|---|---|
| IVT sgLuc-fwd | TAATACGACTCACTATAGGGATAAATAACGCGCCCAACAC | 26 |
| IVT sgLoxP-fwd | TAATACGACTCACTATAGGGCGTATAGCATACATTATACG | 27 |
| IVT sgCtrl-fwd | TAATACGACTCACTATAGGGGCTTCGATAATATCCGCTAC | 28 |
| IVT-rev (common) | AAAAGCACCGACTCGGTGCC | 29 |

TABLE 5

Surveyor assay PCR primers

| Primer | Sequence (5' to 3') | | Expected Amplicon | cut bands |
|---|---|---|---|---|
| Luc 1_Forward | GGAACCGCTGGAGAGCAACT | (SEQ ID NO: 30) | 510 bp | 233 bp, 277 bp |
| Luc 1_Reverse | GTCCCTATCGAAGGACTCTGGCA | (SEQ ID NO: 31) | | |
| Luc 2_Forward | GCTGGAGAGCAACTGCATAA | (SEQ ID NO: 32) | 429 bp | 202 bp, 227 bp |
| Luc 2_Reverse | CATCGACTGAAATCCCTGG-TAATC | (SEQ ID NO: 33) | | |

TABLE 6

Real time qPCR primers

| Primer | Sequence (5' to 3') | SEQ ID NO: |
|---|---|---|
| Cas9 forward | GGAACCGCTGGAGAGCAACT | 34 |
| Cas9 reverse | GTCCCTATCGAAGGACTCTGGCA | 35 |
| hActinB forward | AGAAGGATTCCTATGTGGGCG | 36 |
| hActinB reverse | CATGTCGTCCCAGTTGGTGAC | 37 | viii. sgRNA Preparation.

Single guide RNAs were designed using the CRISPR-.mit.edu platform and cloned into PX458 plasmid with standard BbsI cloning. T7 transcription templates were amplified by PCR and gel purified. sgRNAs were synthesized by in vitro transcription using the MEGAshortscript T7 transcription kit (Life Technologies) followed by purification using the MEGAclear Transcription Clean-Up Kit (Life Technologies) according to the manufacturer's protocols.

ix. Screening of sgRNA Using pDNA.

sgRNA-cloned PX458 plasmids were used to evaluated efficacy of the sgRNAs against luciferase by transfection of the plasmid encoding both sgRNA and Cas9. Lipofectamine 3000 (LF3000, Invitrogen) was used to transfect the sgRNA-Cas9 plasmids according to manufacturer's protocols. HeLa-Luc cells were seed in a 96-well white-opaque tissue culture plate at a density of 10,000 cells per well. LF3000 pDNA particles were added to the cells at a dose of 100 ng pDNA per well. After 6 hours, the medium was removed and exchanged for 200 μL fresh growth medium. After 24, 48 and 72 h, the relative expression of luciferase was determined using the One-Glo+Tox assay (Promega) and normalized to control. Non-targeting sgRNA (sgScr) and unguided Cas9 plasmids were used as a control. (N=4+/− standard deviation).

x. HeLa-Luc-Cas9 Cell Line Preparation.

HeLa-Luc-Cas9 stable cells were prepared by lentiviral transduction. Parental HeLa-Luc cells (Zhou et al., 2016; Hao et al., 2015) were seeded at a density of 70,000 cells per well in a 24-well plate in complete growth medium and allowed to attach in the incubator overnight. The medium was replaced with 1 mL pre-warmed pseudoparticle medium (DMEM, 3% FBS, 20 mM HEPES, 4 μg/mL polybrene). Cas9-Blast lentivirus supernatant was thawed on ice and 50-100 µL was added to the desired well. The cells were spinoculated at room temperature for 1 hour at 1,000×g, and returned to the incubator overnight, after which the pseudoparticle medium was exchanged for complete growth medium. After 48 h total time post spinoculation, selective pressure was applied (5 and 10 µg/mL Blasticidin S) and cells were maintained and expanded. Single cell clones were isolated by single cell sorting by flow cytometry. Cas9 protein expression was confirmed by western blot compared to parental HeLa-Luc cells by blotting for FLAG tag before single cell sorting and for Cas9 after single cell sorting.

xi. In Vitro ZAL Nanoparticle (ZNP) Formulations.

ZNPs were prepared by the ethanol dilution method. The RNA (whether an siRNA, sgRNA, or mRNA) was diluted in acidic aqueous buffer (unless otherwise indicated, 10 mM citric acid/sodium citrate buffer pH 3). The lipid mix was prepared in ethanol, with the appropriate molar ratios of ZAL, cholesterol and PEG-lipid from ethanol stock solutions of each component. Via pipette, the lipid dilution was added to the RNA dilution at a final volumetric ratio of 1:3, rapidly mixed by pipette, and incubated for 15-20 minutes. After this incubation period, the particles were either diluted 3-fold in, or dialyzed against 1× Dulbecco's Modified PBS without calcium and magnesium (Sigma-Aldrich). Dialyses were performed in Pur-A-Lyzer Midi dialysis chambers (Sigma-Aldrich) for 1 hour per 200 µL sample per chamber.

xii. ZAL siRNA Delivery Library Screen.

The library of ZALs functionalized with epoxide and acrylate hydrophobic tails was screened for siRNA delivery efficacy in HeLa-Luc cells. In a white opaque 96-well plate tissue culture plate, HeLa cells were seeded at a density of $10 \times 10^3$ cells per well in 100 µL growth medium (DMEM without phenol red, 5% FBS), and allowed to attach overnight. The medium was exchanged for 200 µL fresh growth medium the day of the assay. Crude ZALs products were prepared using a formulation lipid mixture of 50:38.5 (ZAL: cholesterol), and a ZAL:siRNA ratio such that the number of hydrophobic tails in the ZAL times the ZAL:siRNA mole ratio in the formulation was ~1000, which resulted in a weight ratio range across the library of 16:1 to 45:1 ZAL: siRNA, with an average of 29.5+/−6.3 weight ratio across the library. ZAL NP formulations were performed in a 96-well plate by rapid mixing of ZAL lipid mix (20 µL) and siLuc dilution (60 µL, 13.33 ng/µL in 10 mM citric acid-sodium citrate buffer, pH 5) at 3:1 aqueous:EtOH v:v ratio with a multichannel pipette. After a 15-20 minute incubation period, the formulations were diluted in 12 volumes (240 µL) PBS. The nanoparticles (40 µL) were added to the HeLa-Luc cells at a dose of 100 ng siRNA per well. The nanoparticles were incubated with the cells for 24 h after which time the cell viability and luciferase expression were evaluated with the ONE-Glo+Tox Assay cell viability and luciferase assay (Promega).

xiii. sgRNA Delivery to HeLa-Luc-Cas9 Cells.

Select ZALs were evaluated in the delivery of single guide RNA (sgRNA) to HeLa-Luc-Cas9 cells. In a white opaque 96-well plate tissue culture plate, HeLa-Luc-Cas9 cells were seeded at a density of $5 \times 10^3$ cells per well in 100 µL growth medium (DMEM without phenol red, 5% FBS), and allowed to attach overnight and then supplemented with an additional 100 µL DMEM. ZNPs encapsulating sgRNA were formulated using the in vitro nanoparticle formulation protocol at the indicated lipid composition and weight ratio (maintaining 50:38.5 (ZAL:cholesterol mole ratio), tuning PEG-lipid additive from 5% to 0.5%, and tuning weight ratio from 20:1 ZAL:sgRNA to 5:1 ZAL:sgRNA). Non-targeting control sgRNA (sgCtrl) was used as a negative control. The nanoparticles were added to the cells at the appropriate dose of sgRNA and incubated with the cells for 48 h. The cell viability and luciferase expression were evaluated with the ONE-Glo+Tox Assay (Promega), normalized to untreated cells (N=4+/− standard deviation).

xiv. Kinetic Assay of sgRNA and siRNA Delivery.

The kinetics of luciferase expression after silencing/editing by siRNA and sgRNA were determined in HeLa-Luc-Cas9 cells. For time points <48 h, ZNPs encapsulating sgRNA or siRNA were delivered to HeLa-Luc-Cas9 cells in 96-well plates at a density of 5K cells per well. After 0.5, 1, 2, 4, 11, 20, 30 and 44 h time point, the cell viability and luciferase expression were determined by the One-Glow+ Tox assay. For longer time points, cells were treated in 6-well plates. Beginning at the 2 day time point, cells were aspirated, washed with 1×PBS, trypsinized in 200 µL trypsin and re-suspended in 1800 µL medium. 1 mL of each cell suspension was added to a fresh 6-well plate containing 1 mL DMEM (2 mL total) and returned to the incubator. Of the remaining cell suspension, 50 µL was transferred to a 96-well white-opaque plate (10 wells per sample). Cell viability was determined using the Cell-Titer Glo assay normalized to untreated cells, while relative luciferase expression was determined using the One-Glo assay and normalized against control (siCtrl or sgCtrl). Data was plotted as an average of 5 measurements+/− standard deviation.

xv. Luciferase mRNA Delivery in Vitro Assay.

ZNPs with mRNA (Tri-Link Biotechnologies) were prepared using the in vitro nanoparticle formulation method outlined above. IGROV1 cells were seeded in white opaque 96-well tissue culture plates at a seeding density of $5 \times 10^3$ cells per well in 100 µL RPMI 1640 medium supplemented with 5% FBS, and allowed to attach overnight. After overnight incubation, an additional 100 µL medium was added to the wells. The ZAL:mRNA nanoparticles were prepared at ZAL:mRNA weight ratios of 20:1, 10:1, 7.5:1 and 5:1, and lipid mixture molar compositions of 50:38.5:n ZAL:cholesterol:PEG-lipid, where n=5, 2, 1, and 0.5 at each weight ratio. The ZAL-mRNA nanoparticles were added to the cells at the appropriate mRNA dose and incubated for the indicated time (ranging from 6 h to 48 h), after which time cell viability and luciferase expression were evaluated with the ONE-Glo+Tox Assay (Promega) and normalized to untreated cells (N=4+/− standard deviation).

xvi. In Vitro Co-Delivery of Cas9 mRNA and sgRNA.

ZNPs were evaluated in the co-delivery of Cas9 mRNA (Tri-Link biotechnologies) and single guide RNA (sgRNA) to luciferase expressing cancer cells. Cells were seeded at a density of 250,000 per well in 6-well plates and 2-mL DMEM. ZNPs were formulated using the in vitro formulation protocol. For co-delivery in a single particle, Cas9 mRNA and sgRNA were combined in acidic buffer together at pH 3 prior to the addition of ZAL lipid mix at the appropriate ZAL:total RNA weight ratio. Cells were incubated with ZNPs for 72 h prior to evaluation of editing by the surveyor assay. As a negative control, ZNPs with Cas9 only (unguided Cas9), sgLuc only, and Cas9 plus sgCtrl were added. sgRNA dose was fixed at 0.5 µg per well, while Cas9 mRNA dose was tuned from 0.5 µg (1:1) to 3 µg (6:1) per well. ZAL:total RNA ratio was fixed at 7.5:1. Staged co-delivery was carried out by the addition of Cas9 mRNA ZNPs followed by the addition of sgRNA ZNPs 24 h later at a total ratio of 2:1 Cas9 mRNA to sgRNA. Following an additional 48 h incubation time, cells were evaluated by gene editing by the surveyor assay.

xvii. Nucleic Acid Binding Experiments.

Nucleic acid binding was evaluated using the Ribogreen assay (Molecular Probes). In short, nanoparticles were prepared using the in vitro or in vivo formulation protocols. The nanoparticle formulations (5 µL) were added to a black 96-well opaque microplate (Corning). A standard curve of the appropriate nucleic acid was prepared in the same medium as the nanoparticles. Ribogreen reagent was diluted 1:1000 in 1×PBS and 50 µL was added to each well via multichannel pipette. The mixture was stirred on an orbital mixer for 5 minutes, and the fluorescence of each well was read using a plate reader ($\lambda_{Ex}$ 485 nm, $\lambda_{Em}$ 535 nm). The amount of free nucleic acid was determined by fitting the signal from each nanoparticle sample to the nucleic acid standard curve, and the fraction bound determined by the following formula: Fraction nucleic acid bound=(total nucleic acid input-free nucleic acid)/total nucleic acid input) (N=3 or 4+/− standard deviation).

xviii. In Vivo Nanoparticle Formulations:

In vivo nanoparticle formulations were performed using the NanoAssemblr microfluidic mixing system (Precision Nanosystems). Lipids were dissolved in ethanol and nucleic acids were diluted in 10 mM citric acid-sodium citrate buffer pH 3. The lipid mixture and nucleic acid dilution were combined at a volumetric ratio of 3:1 nucleic acid:lipid mix at a total flow rate of 12 mL per minute, and a waste collection of 0.1 mL at the start and end of each formulation. The nanoparticles were dialyzed against 1×PBS in Pur-A-Lyzer midi dialysis chambers (Sigma-Aldrich) for 1 hour per 200 µL volume in each chamber, and diluted in 1×PBS to the appropriate nucleic acid concentration.

xix. In Vivo Luciferase mRNA Delivery:

All experiments were approved by the Institutional Animal Care & Use Committee (IACUC) of The University of Texas Southwestern Medical Center and were consistent with local, state and federal regulations as applicable. ZA3-Ep10 was formulated with in vivo formulation at 50 ZAL: 38.5 cholesterol: 0.5, 1, or 2 PEG-lipid mole ratio in the lipid mix, and 7.5:1 ZAL:mRNA weight ratio. Mice were injected with ZAL-mRNA NPs at a dose of 1 mg/kg via tail vein injection or intraperitoneal injection. After 24 h and 48 h the luciferase expression was evaluated by live animal bioluminescence imaging Animals were anesthetized under isofluorane, and D-luciferin monosodium hydrate (GoldBio) substrate, was injected subcutaneously in the neck scruff. After 10-12 minute incubation under anesthesia, the luciferase activity was imaged on an IVIS Lumina system (Perkin Elmer), and the images processed using Living Image analysis software (Perkin Elmer). Ex vivo imaging was performed on systemic organs after resection, and the tissue frozen on dry ice for ex vivo luciferase expression analysis.

xx. Nanoparticle Property Characterization

Physical properties were measured using a Zetasizer Nano ZS (Malvern) with an He—Ne laser ($\lambda$=632 nm). Particle sizes were measured by dynamic light scattering (DLS) (5 measurements, 3 runs×10 seconds, automatic attenuator setting) by 173° back scattering. Zeta potential was measured in a folded capillary cell (Malvern) with samples diluted in PBS for ZAL NPs or citrate phosphate buffer pH 7.4 for CSAL NPs.

xxi. Surveyor Assay

Genomic DNA from transfected cells was isolated using QuickEx DNA Extraction Solution (Thermo Fisher Scientific) according to the manufacturer's protocol. Then the target region was amplified by PCR, and the PCR products were gel purified on an agarose gel (QIAquick Gel Extraction Kit, QIAgen). Surveyor assay was perforated using Surveyor Mutation Detection Kit (IDT): the PCR products were first hybridized, then half of the products were cut with Nuclease S; both the uncut and cut DNA were then run on the 4-20% polyacrylamide gel (Biorad). The gels were stained with SYBR Gold Nucleic Acid Gel Stain buffer (diluted 1:10000 in TBE buffer, Thermo Fisher Scientific) and imaged by UV light.

xxii. Western Blot

The cells were lysed in cold RIPA buffer (Thermo Scientific), the lysate cleared by centrifugation and total protein in the supernatant quantified by the BCA assay (Pierce). 50 µg total protein was loaded on 4-20% precast polyacrylamide gel and transferred to a nitrocellulose membrane (Bio-Rad). The membrane was blocked in 5% nonfat milk for 1 hour at RT, and then incubated with primary antibody at 4° C. overnight (Cas9 antibody, 1:1000, Cell Signaling, 146975; beta-actin antibody, 1:2000, Cell Signaling, 4970). Secondary antibodies were applied at RT for 1 hour (anti-rabbit IgG, HRP-linked antibody, Cell Signaling, 7074, anti-mouse IgG, HRP-linked antibody, Cell Signaling, 7076), and then the membrane was developed and detected on X-ray film.

xxiii. Real-Time RT-qPCR.

Cells were transfected with Cas9 mRNA for the indicated time point in a 6-well plate and 0.5 µg/mL mRNA for the indicated time point. Total RNA was extracted using the TRIzol reagent according to the manufacturer's protocol. The RNA was reverse transcribed using the iScript Reverse Transcription kit (BioRad) and the real-time qPCR was run on a Bio-Rad C1000 Touch Thermal Cycler (CFX384 Real-time System). Each reaction was made with iTaq Universal SYBR Green 2× Supermix (Bio-Rad). The qPCR program is as follows:

1) 95° C. for 3 min
2) 95° C. 10 s and 55° C. 30 s for 40 cycles
3) 95° C. 10 s
4) 65° C. 5 s
5) 95° C. 5 s Human β-actin was used as a control and mRNA levels were normalized to fold actin and plotted as an average of two independent experiments.

xxiv. In Vivo Delivery of Cas9 mRNA and sgLoxP.

ZA3-Ep10 ZNPs encapsulating Cas9 mRNA and sgLoxp were prepared according to the in vivo nanoparticle formulation protocol using the Nanoassemblr microfluidic mixing device. The lipid mix contained 50 ZA3-Ep10: 38.5 cholesterol: 0.5 PEG-lipid molar ratios, and the particles were formulated at a 7.5:1 ZAL:total RNA weight ratio. The Cas9 mRNA: sgLoxP weight ratio was maintained at 4:1. Rosa 26-LSL-tdTomato mice were injected at 5 mg/kg total RNA (4 mg/kg mRNA, 1 mg/kg sgRNA) via tail vein injection and monitored for 1 week. After which they were sacrificed and the major organs imaged using the IVIS Lumina system for fluorescence expression (dsRed filter set) compared to an uninjected Rosa 26-LSL-tdTomato mouse. A liver specific Cre recombinase adeno-associated virus (Cre-AAV8) injected intravenously via tail vein injection (4 days) was used as a positive control.

xxv. Tissue Sectioning

Tissue were fixed in 4% paraformaldehyde (PFA) at RT for 2 hours, then changed in 30% sucrose (in PBS) at 4° C. overnight. Then the tissues were embedded in Cryo-gel (Leica Biosystems), and frozen in dry ice. The blocks were sectioned using Cryostat machine (Leica Biosystems) at 8 µm thickness. The sections were air-dried and incubated in 0.25% Triton X-100 (Biorad) 5% FBS in PBS for 1 h at RT, Then the slides were mounted with DAPI (Vector Laboratories) and covered, xxvi. Primary Hepatocytes Isolation Primary hepatocytes were isolated by two-step collagenase perfusion. Liver perfusion medium (Thermo Fisher Scientific, 17701038), liver digest medium (Thermo Fisher Scientific, 17703034) and Hepatocytes wash medium (Thermo Fisher Scientific, 17704024) were used.

xxvii. Flow Cytometry

For detection of Tomato positive populations, primary hepatocytes ($2 \times 1.0^6$/mL) were isolated and stained with DAPI (Roche, 2 μg/mL) for dead cell exclusion. Cells were analyzed with BD FACSAria Fusion machine (BD Biosciences). Tomato positive cells were counted in DAPI negative (live cell) populations.

xxviii. Statistical Analysis

Statistical analysis was performed using a Student's t-test in GraphPad Prism.

B. Delivery of CRISPR Nucleic Acid Sequences

Figure 18:
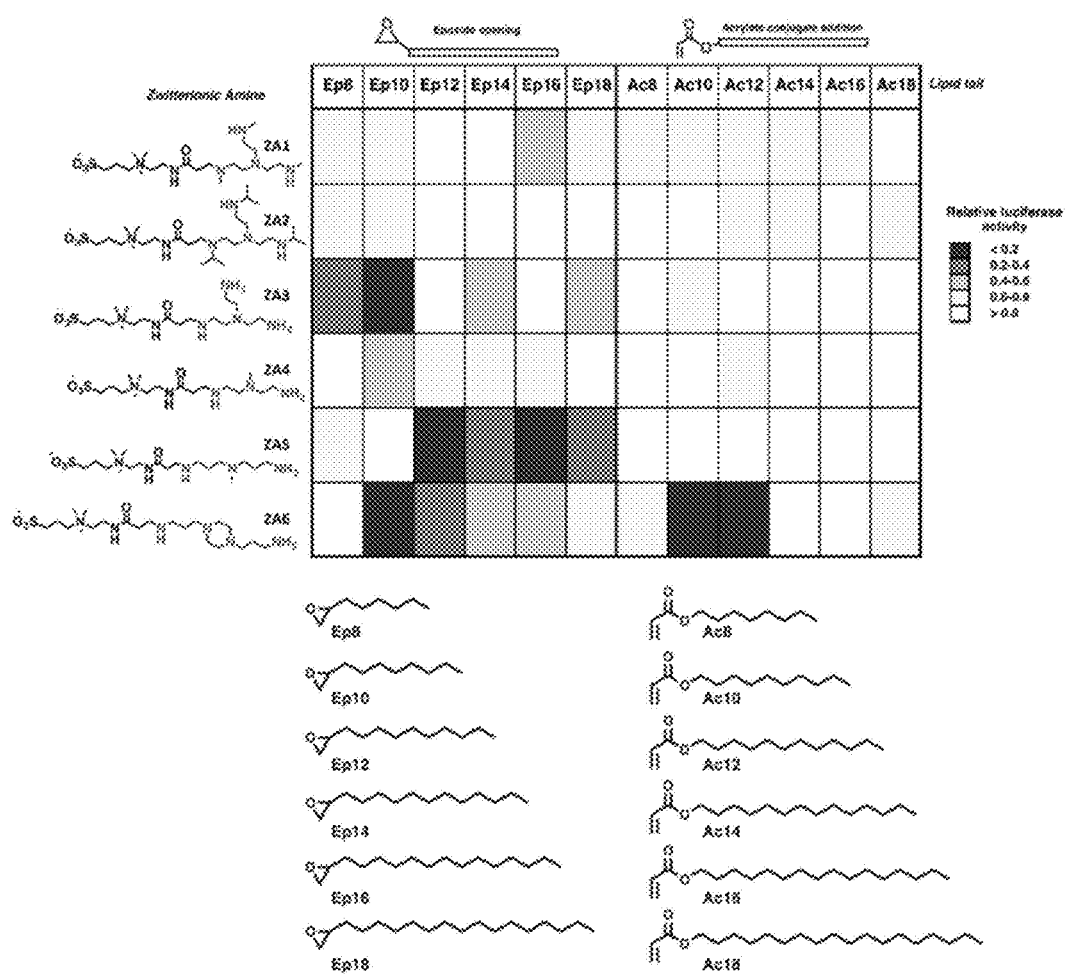
FIG. 18 shows the luciferase activity as a function of in vitro siRNA delivery in HeLa cells. Darker colors represent lower activity of luciferase and higher siRNA delivery.
Figure 19:
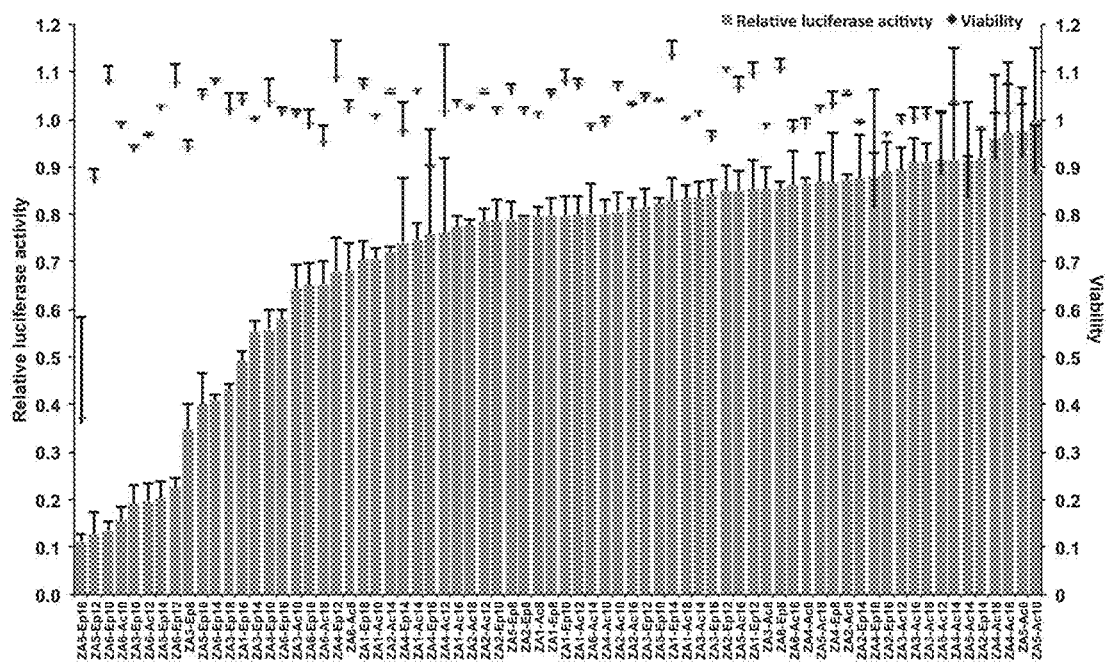
FIG. 19 shows the activity as a percentage of untreated cells (bars) and cell viability (dots) with the different lipid types noted by the color of the bars.
Figure 20A:
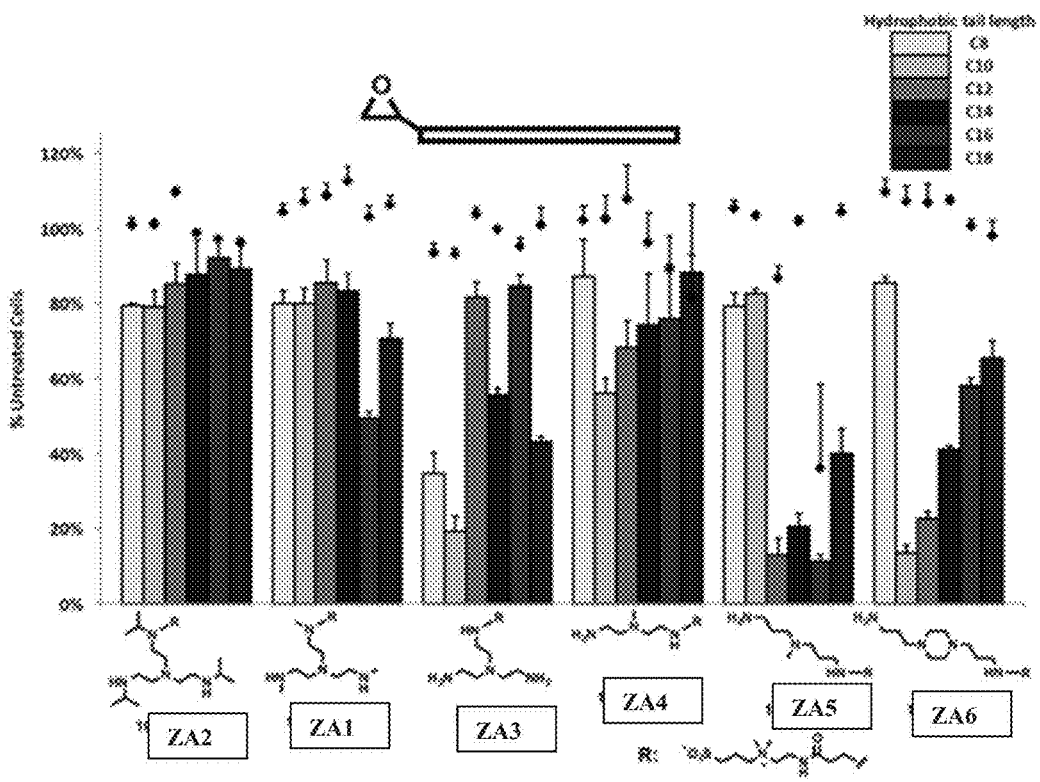
FIGS. 20A & 20B show the activity as a percentage of untreated cells (bar) and cell viability (dots) with different length and core amine for epoxide based lipids (FIG. 20A) and acrylate based lipids (FIG. 20B).
Figure 20B:
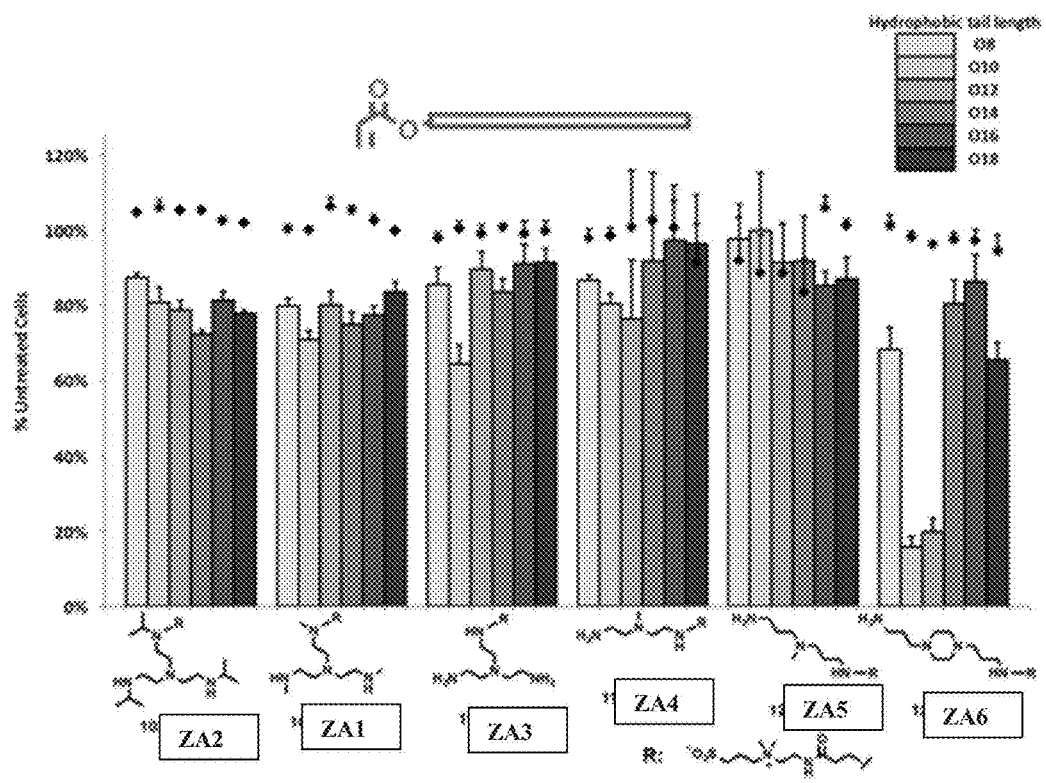

Zwitterionic amino lipids (ZALs) were rationally synthesized to contain a zwitterionic sulfobetaine head group, an amine rich linker region, and assorted hydrophobic tails (FIG. 67). A zwitterionic electrophilic precursor (SBAm) was prepared by the ring-opening reaction of 2-(dimethylamino)ethyl acrylamide with 1,3-propanesultone, which was easily isolated by in situ precipitation in acetone. Conjugate addition of different polyamines to SBAm afforded a series of zwitterionic amines that could be reacted with hydrophobic epoxides and acrylates to append 6 to 18 carbon alkyl tails and alcohol/ester groups to enhance ZAL-RNA interactions (See Example 2). To verify that ZNPs could generally bind and deliver RNA, the 72-member library was first screened for siRNA delivery to HeLa cells that stably expressed firefly luciferase (HeLa-Luc) (FIG. 19). This allowed structural identification of key amine cores, including ZA1, ZA3, and ZA6. Interestingly, epoxide-based ZALs ($ZA_x$-$Ep_n$), were also generally more active than acrylate-based ZALs ($ZA_x$-$Ac_n$) (FIG. 18). With lead compounds in hand focus turned to the delivery of sgRNAs and Cas9 mRNA. Both temporally staged and simultaneous co-delivery enabled fully exogenous gene editing.

Figures 43A, 43B, 43C:
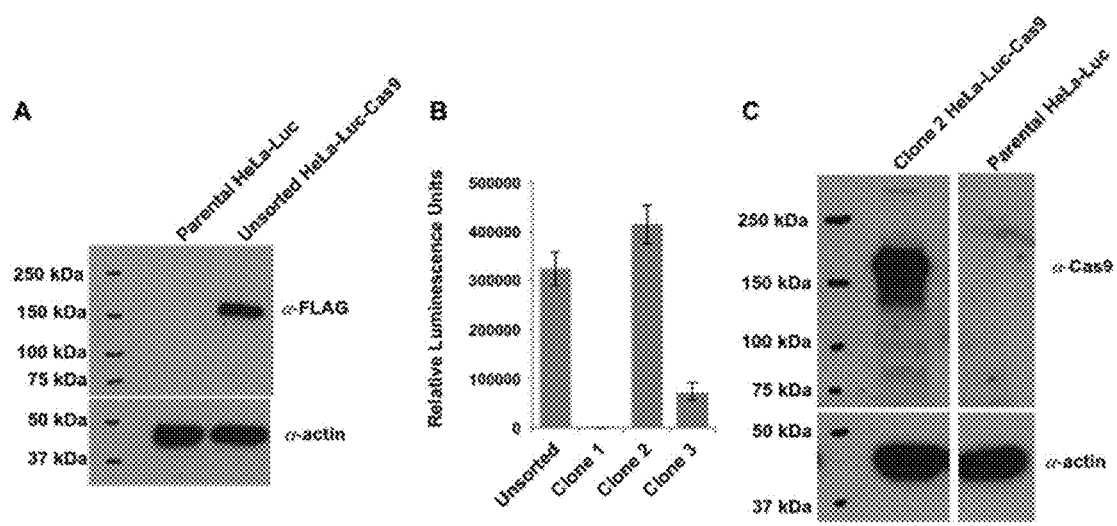
FIGS. 43A-43C show Cas9 expression was validated in HeLa-Luc-Cas9 cells by western blot.
Figure 44:
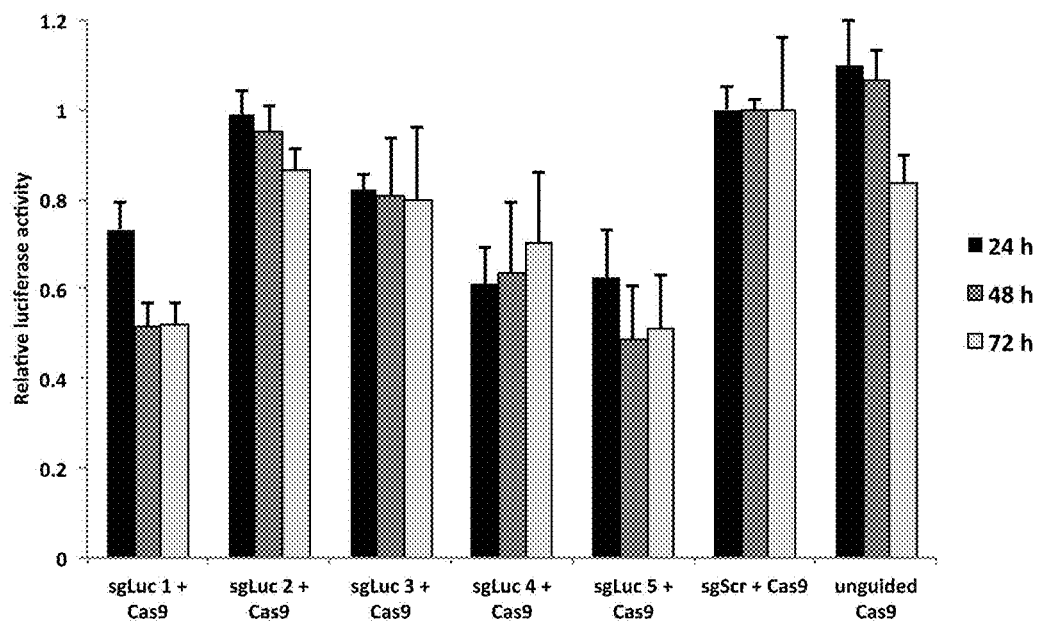
FIG. 44 shows the evaluation of panel of single guide RNAs against luciferase using commercial reagent (LF3000) transfection of plasmid DNA encoding sgRNA and Cas9 protein reveals sgLuc5 as the most potent sgRNA sequence for silencing luciferase in unsorted. HeLa-Linc cells. Values are normalized to non-targeting sgRNA control and plotted as mean+/−standard deviation (N=4).
Figures 65A, 65B, 65C, 65D, 65E, 65F:
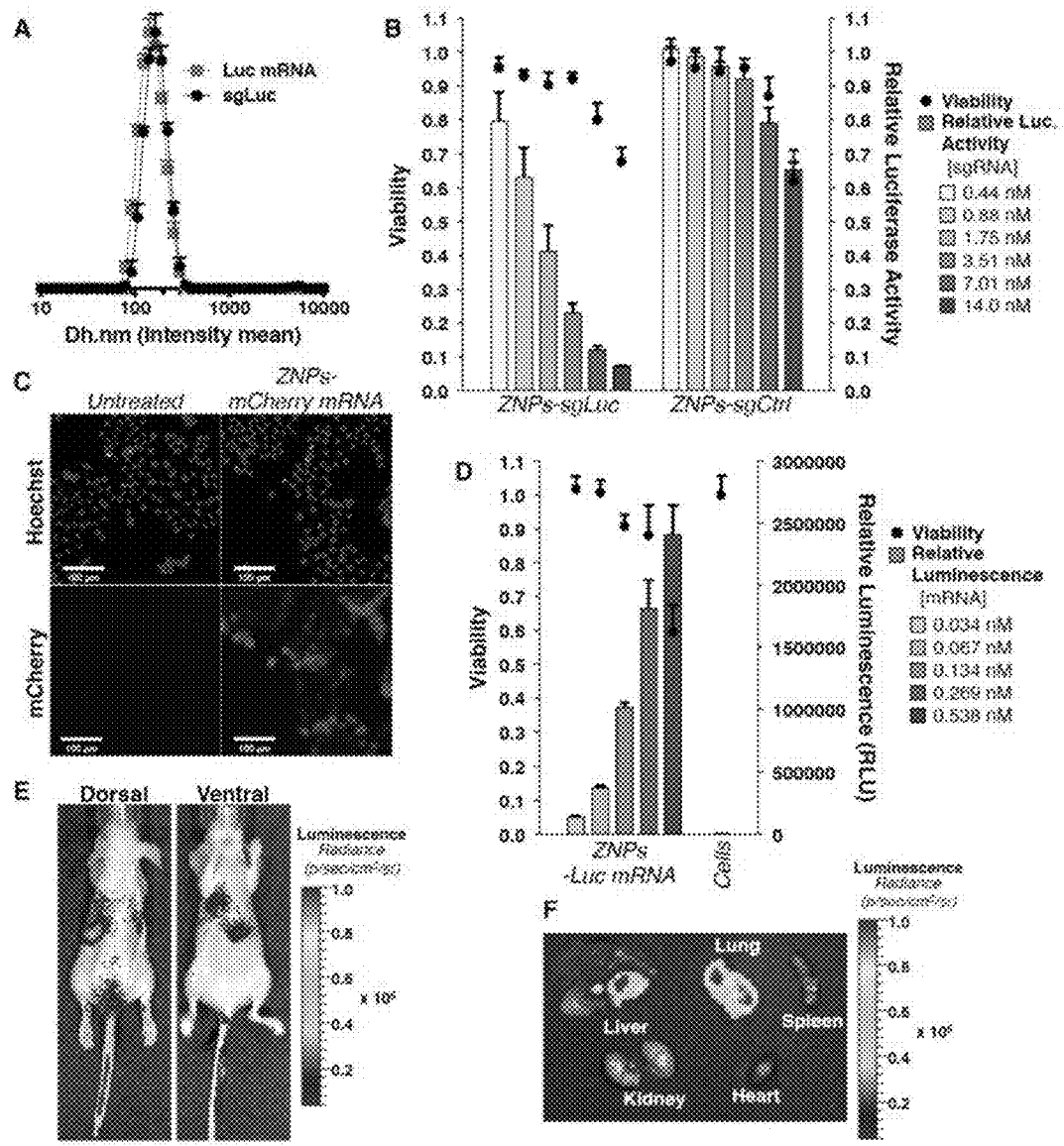

ZALs were evaluated for their ability to deliver CRISPR/Cas9 components using a stable cell line expressing both Cas9 and luciferase (HeLa-Luc-Cas9). A single HeLa-Luc-Cas9 cell clone was isolated following Cas9 lentiviral transduction of HeLa-Luc cells (FIGS. 43A-43C). sgRNAs against luciferase were designed and generated according to previously reported methods targeting the first third of the gene (Table 2) (Ran et al., 2013) and evaluated by pDNA transfection (FIG. 44). The most active sgRNA against luciferase (sgLuc5, henceforth sgLuc) as well as control sgRNAs were synthesized by in vitro transcription. Next, lead ZNPs were loaded with sgLuc and evaluated for delivery to HeLa-Luc-Cas9 cells. Luciferase and viability (Hao et al., 2015; Zhou et al., 2016; Yan et al., 2016) were measured after 48 hours (h) relative to untreated cells. As anticipated from the chemical design combining cationic and zwitterionic functionalities, ZNPs do not require inclusion of helper phospholipids (FIG. 65A).

Figure 45:
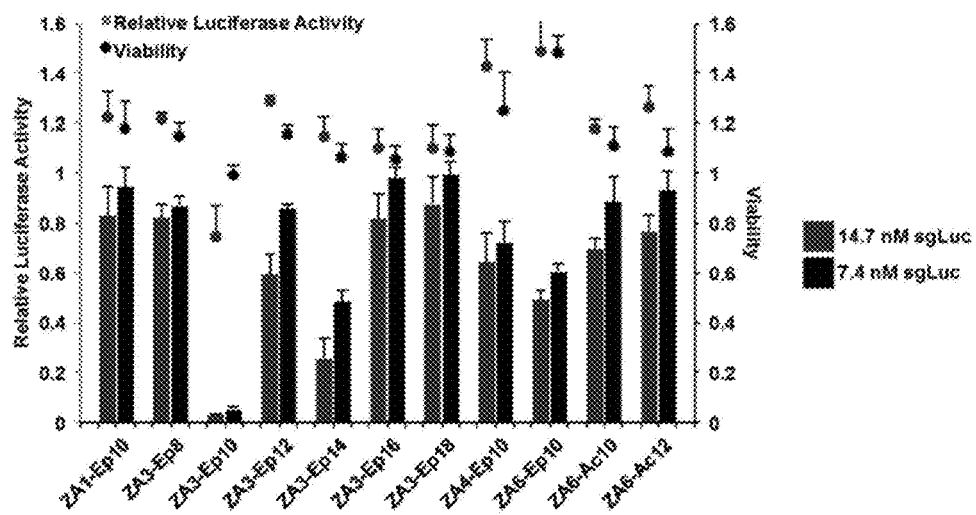
FIG. 45 shows lead ZALs identified from the snRNA screen were evaluated for sgRNA delivery to HeLa-Luc-Cas9 cells. ZNPs were formulated at 50:38.5:1 (ZAL:cholesterol:PEG-lipid molar ratios) n the lipid mix and 20:1 ZAL:sgRNA weight ratio. sgRNA was administered at both 14.7 nM and 7.4 nM for 48 h. ZA3-Ep10 emerged as the most highly potent (>95% luciferase silencing). Viability (dots) and relative luciferase activity (bars) were determined relative to untreated cells (N=4+/−standard deviation).
Figure 46:
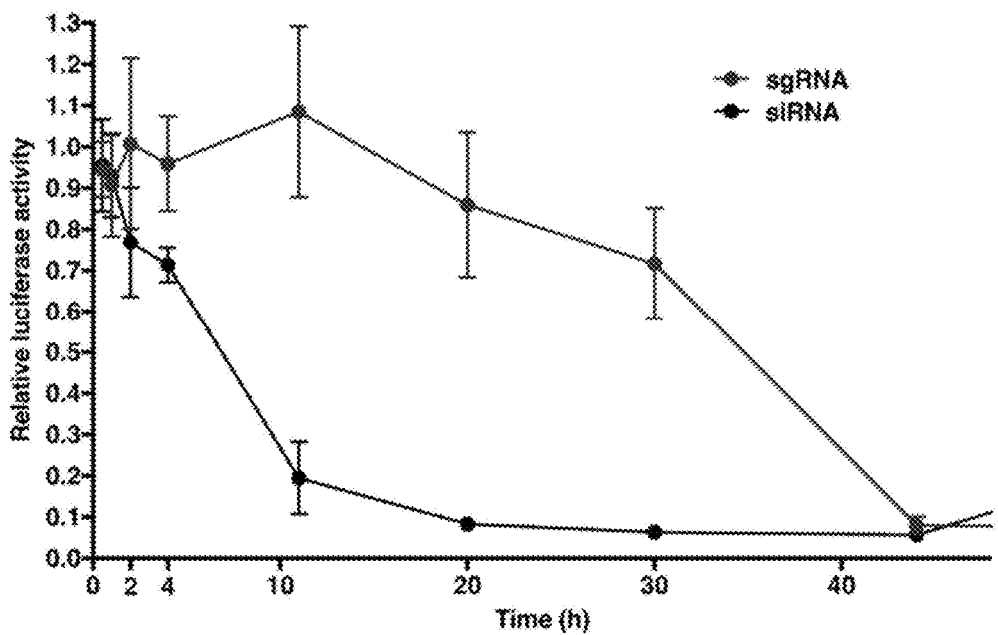
FIG. 46 shows magnification of the early time points of the kinetic curve of luciferase silencing comparing sgRNA versus siRNA by ZA3-Ep10 ZNPs shows that siRNA silencing is much faster than sgRNA editing.
Figure 47:
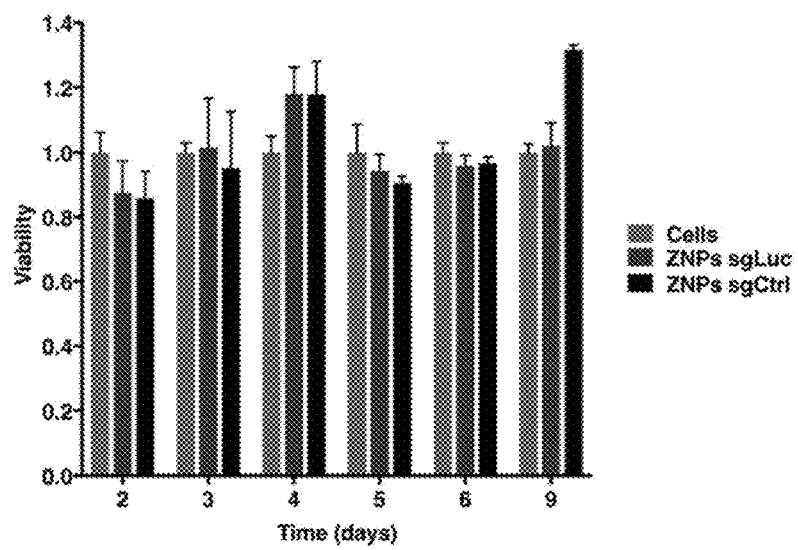
FIG. 47 shows the relative viability of ZNP edited HeLa-Luc-Cas9 cells (sgLuc) versus unedited cells (sgCtrl) shows similar growth rates by the Cell-Titer Glo assay when normalized to untreated cells (N=5+/−S.E.M.)
Figures 63A, 63B, 63C, 63D:
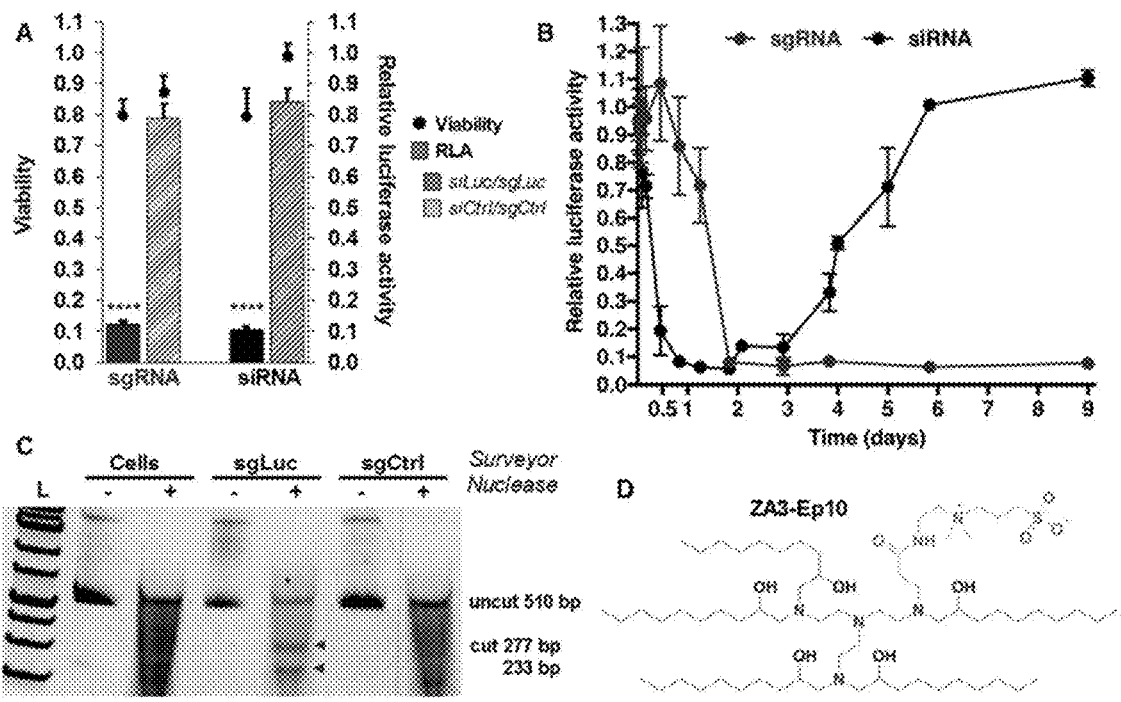

Among the lead ZALs, ZA3-Ep10 was found to be an efficacious for delivery of sgLuc (FIG. 45). Editing of luciferase DNA resulted in a dose-dependent decrease in luciferase expression (FIG. 65B). CRISPR/Cas editing were verified using the Surveyor nuclease assay, (Guschin et al., 2010) which can detect indels (FIG. 63C). Given that sgRNAs require loading into Cas9 nucleases in cells and trafficking to the nucleus to perform sequence-guided editing, understanding of the kinetics of this process was sought, particularly in comparison to RNAi-mediated gene silencing. siLuc-mediated mRNA degradation is a fast process, where expression decreased by 40% within the first 4 h. Luciferase was silenced by 92% by 20 h and remained low for about 3 days. Thereafter, the protein expression steadily increased and reached baseline level 6 days after transfection (FIG. 63B and FIG. 46 (early time points)). In contrast, sgLuc-mediated DNA editing was kinetically slower, possibly due to the requirements to load into Cas9 and survey the DNA for PAMs. It took 20 h for luciferase expression to decrease by 40%, ultimately going down by 95% after 2 days and remaining there indefinitely. The low luciferase expression (5%) persisted throughout the duration of the assay (9 days) due the permanent genomic change, even after multiple rounds of cellular division, suggesting that edited cells grew at the same rate of non-edited cells (FIGS. 63B and 47).

Figure 48:
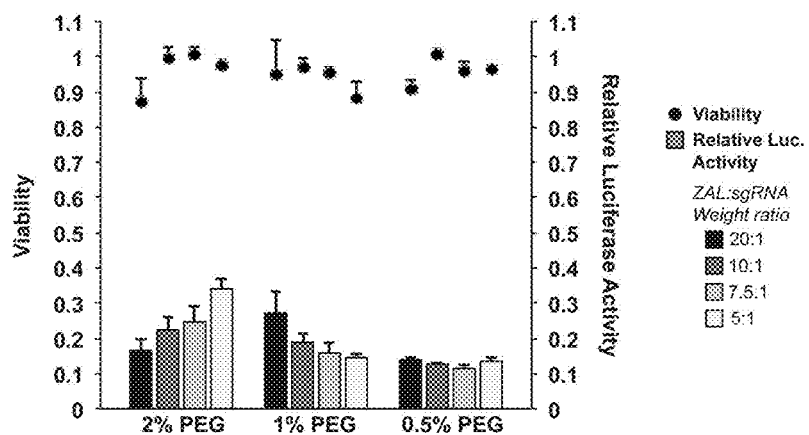
FIG. 48 shows the optimization of ZA3-Ep10 ZNPs for sgRNA delivery was explored by tuning the PEG content of the formulation (2%, 1%, and 0.5%) and the ZAL:sgRNA weight ratio (20:1, 10:1, 7.5:1 5:1). All formulations were potent for sgLuc delivery at 7.4 nM, 48 h incubation, while 7.5:1 weight ratio and 0.5% PEG showed the best luciferase editing.
Figure 49:
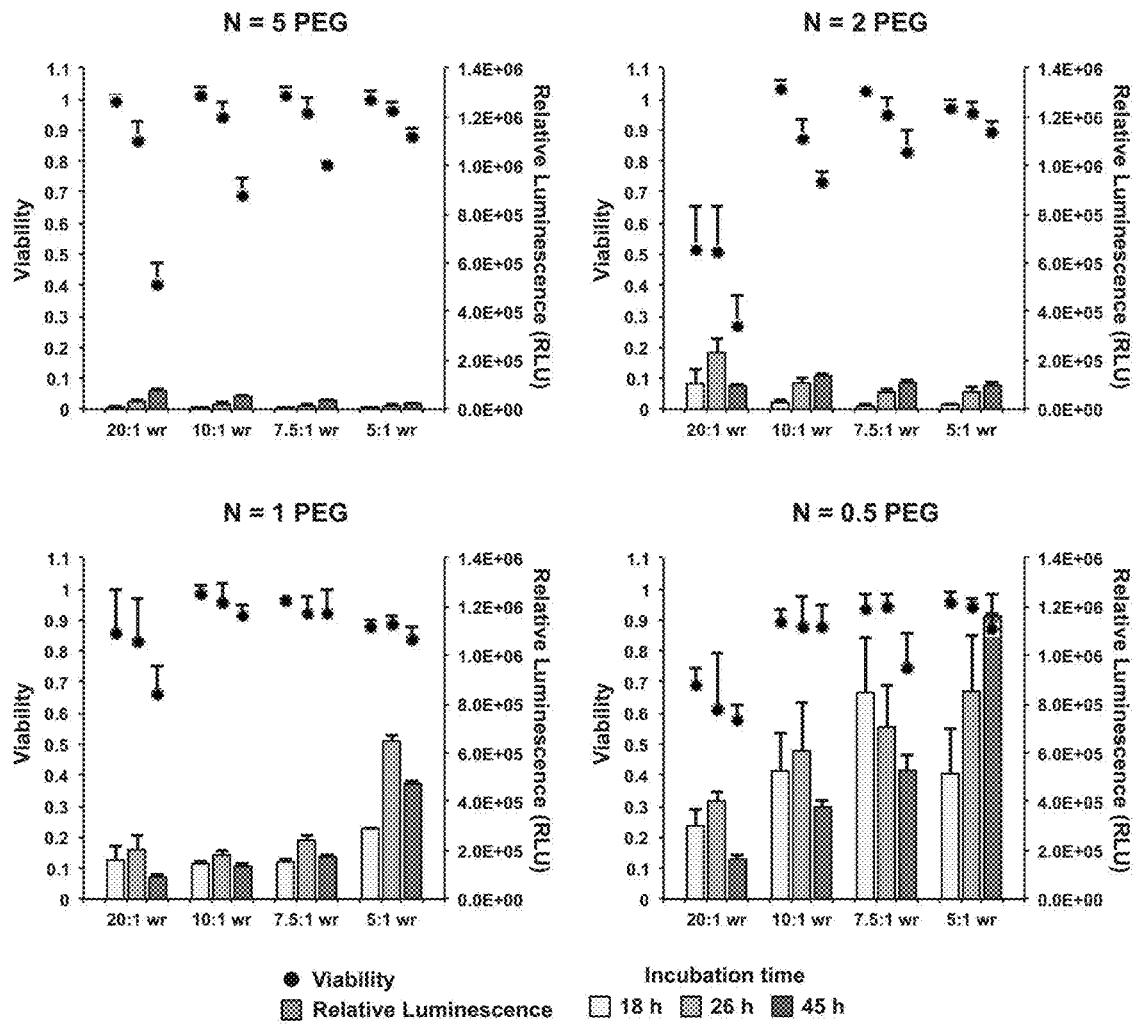

Having demonstrated that ZA3-Ep10 ZNPs could effectively deliver sgRNAs (~100 nt), their ability to deliver even longer mRNA (1,000 to 4,500 nt) was examined next. mRNA encoding mCherry mRNA (~1,000 nt) or luciferase mRNA (~2,000 nt) was delivered to IGROV1 human ovarian cancer cells. Bright mCherry expression was visible (FIG. 63C), and luciferase expression was observed to be dose-dependent (FIG. 63D). Notably, high expression required low mRNA doses (<600 pM). In contrast to sgRNA, which did not show a dependence on PEG lipid mole ratio in the formulation (FIGS. 28 & 48), delivery efficacy of mRNA decreased with higher PEG lipid ratios (FIG. 49), while there was only a modest change in ZNP size (FIG. 50). Optimization of PEGylation, particularly in view of in vitro to in vivo translation, is an ongoing challenge to be explored for each target disease, organ, and cell type (Whitehead et al., 2012). This report attempts to alleviate some of those concerns by examining different formulations in multiple cell types and mouse strains. Further supporting the design hypothesis, titration of a structurally analogous cationic lipid with increasing molar proportions of DOPE into the formulations showed an improvement in delivery of sgRNA and mRNA, while siRNA did not require additional zwitterionic content (FIG. 51). Moreover, efficacy of ZA3-Ep10 ZNPs was consistent across all RNA cargoes, and outperformed the cationic analogue supplemented with phospholipid.

The optimal formulation was next evaluated in vivo through intravenous (i.v.) administration of ZA3-Ep10 mRNA ZNPs to multiple strains of mice. Bioluminescence imaging following Luc mRNA delivery in athymic nude mice (FIG. 65E, 1 mg/kg), C57BL/6 mice (FIG. 65F, 4 mg/kg), and NOD scid gamma (NSG) mice (FIG. 52, 1 mg/kg) resulted in expression of luciferase in liver, lung and spleen tissue 24 h after injection which was quantified by ROI analysis (FIGS. 53A & 53B). Based on the high lung signal, co-delivery (one pot) CRISPR/Cas editing in lung cells was explored.

Figures 66A, 66B, 66C, 66D:
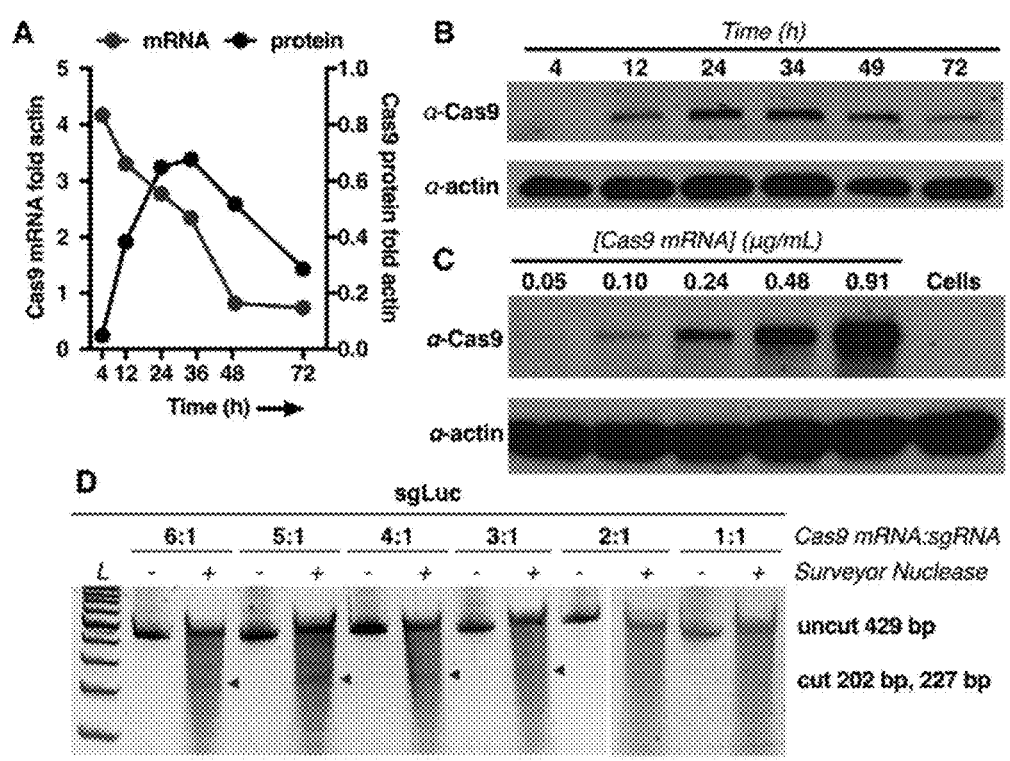

Due the very long length of Cas9 mRNA (4,500 nt), delivery using synthetic carriers is particularly challenging. Remarkably, the level of Cas9 mRNA in A549 lung cancer cells was found to be very high after only 4 h incubation with ZA3-Ep10 Cas9 mRNA ZNPs (FIG. 66A). Synthetically introduced mRNA decreased from >4 fold actin to 0.7 fold actin over the next 45 h. Because translation of mRNA takes time, protein expression was low at 4 h, increased considerably by 12 h, and was the highest by 36 h (FIGS. 66A & 66B). It was also dose dependent (FIG. 66C). For in vivo utility, the use of synthetic NP carriers alleviates concerns of viral delivery. Moreover, delivery of Cas9 mRNA allows for transient expression of Cas9, minimizing persistence that can lead to off-target genomic alteration. This can reduce the significant therapeutic danger of incorporating an exogenous nuclease into the genome.

As illustrated above, delivery of mRNA and sgRNA is kinetically different. Indeed, it was found that staged delivery in separate ZNPs was an effective treatment method. ZNP delivery of mRNA for 24 h, to enable Cas9 protein expression, followed by sgRNA delivery in separate ZNPs enabled efficacious in vitro editing in both HeLa-Luc and A549-Luc cells (FIGS. 54 & 55). However, when considering in vivo utility, Cas9 mRNA and sgRNA must be present in the same cell. It was therefore reasoned that co-delivery of mRNA and sgRNA from a single NP would provide a greater editing efficiency since this method would guarantee delivery to the same individual cells. A variety of conditions were explored and found that effective editing of the target gene by ZNPs encapsulating both Cas9 mRNA and sgRNA required a ratio of mRNA:sgRNA greater than or equal to 3:1 (wt) as confirmed by the Surveyor assay (FIG. 66D), while control ZNPs did not show any editing (FIG. 55).

To examine co-delivery in vivo, genetically engineered mice containing a homozygous Rosa26 promoter Lox-Stop-Lox tdTomato (tdTO) cassette present in all cells were utilized (Tabebordbar et al., 2016). Co-delivery of Cas9-mRNA and sgRNA against LoxP (Li et al., 2015) enabled deletion of the Stop cassette and induction of tdTO expression (FIG. 67A, Table 2). This is a challenging model for a synthetic carrier due to the need to make two cuts on the same allele for the tdTO to be expressed. ZNPs encapsulating Cas9 mRNA and sgLoxp at a 4:1 mRNA:sgRNA weight ratio were administered intravenously at a 5 mg/kg RNA dose (FIGS. 56-58). One week after administration, fluorescence signal from tdTO was detected in the liver and kidneys upon whole organ ex vivo imaging (FIG. 67B). Detailed examination of sectioned organs using confocal fluorescence microscopy showed tdTO-positive cells in liver, lung, and kidney tissues (FIG. 67C). Importantly tdTO positive cells were not detected when animals were treated with sgCtrl ZNPs (FIG. 59) and no significant change in body weight of treated animals was observed (FIG. 60). Primary hepatocytes were isolated from perfused livers and tdTO cells were counted by flow cytometry to quantify editing (FIG. 61). To further confirm editing, tissues were harvested 2 months after ZNP sgLoxP treatment, which still exhibited strong fluorescent signal in the liver and kidneys (FIG. 62). This proof-of-principle data indicates that intravenous co-delivery of Cas9 mRNA and targeted sgRNA from a single ZNP can enable CRISPR/Cas editing in vivo.

Example 5: Further Modification of ZALs and CSALs

Given the modular nature of the synthesis of the ZALs and CSALs, changes within a single portion of the molecule can be effected without hampering the ability to obtain a large variety of structural analogs. For example, the central cationic amine of the ZALs and CSALs can be modified as shown below to obtain different length chains.

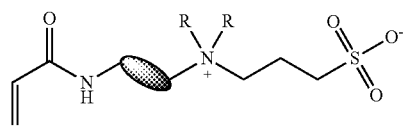

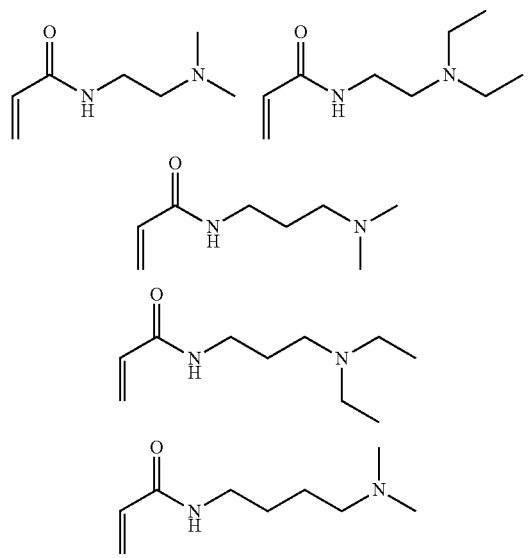

Additionally, the anionic headgroup of the ZALs may be replaced with a different anionic group or the converted to a cationic head group when the central amine has been replaced with an anionic phosphate group as shown below.

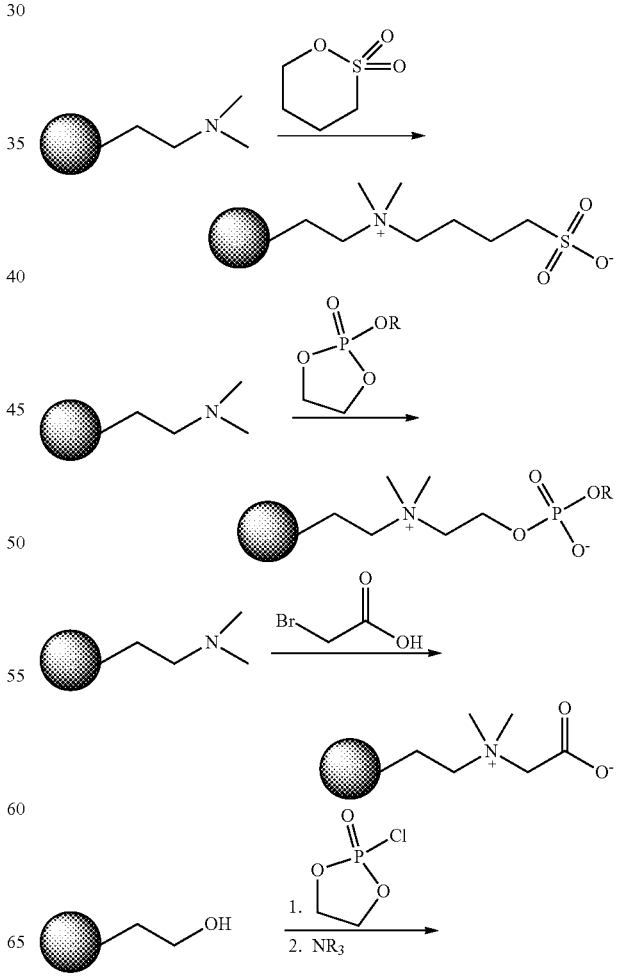

113

-continued

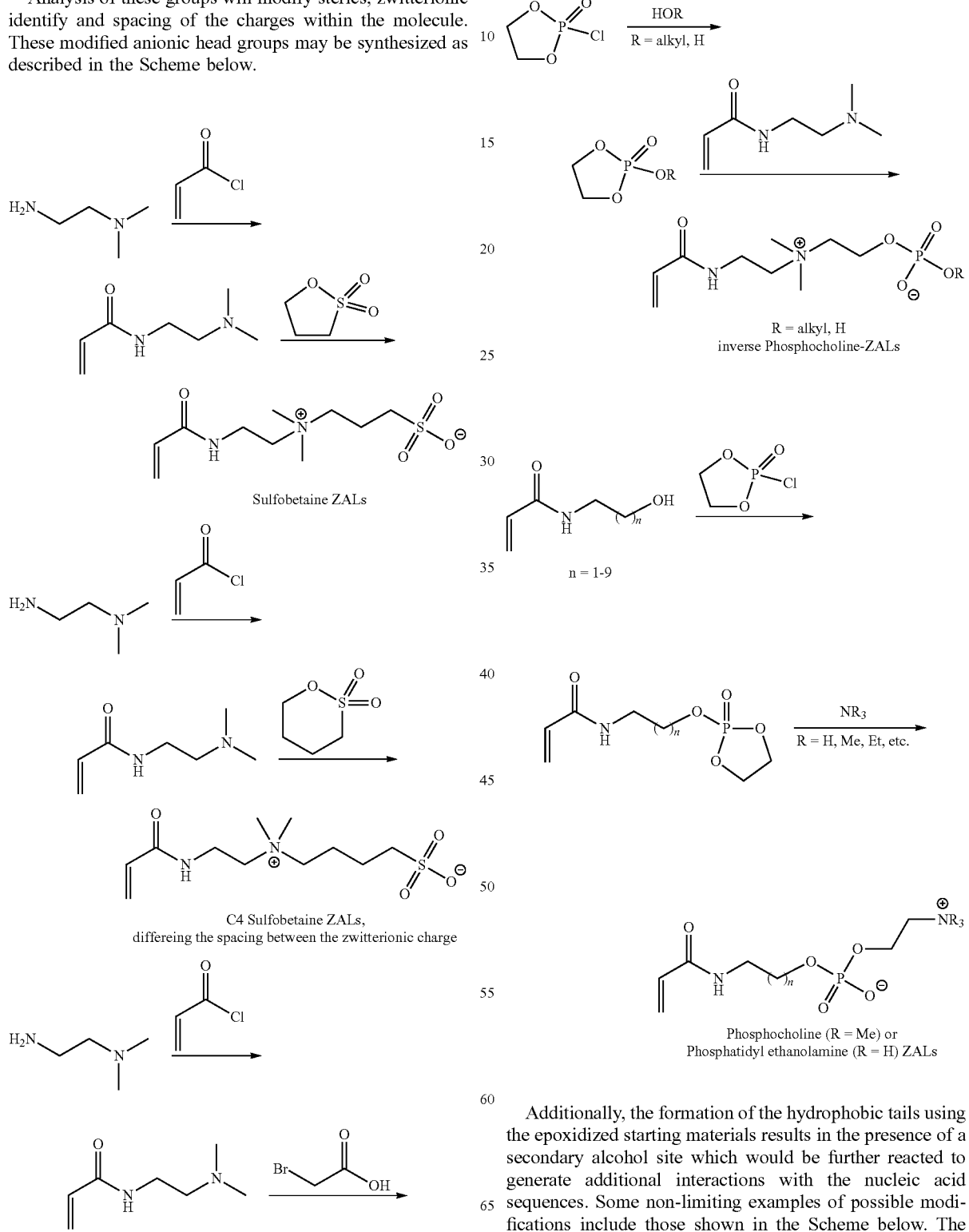

Analysis of these groups will modify sterics, zwitterionic identify and spacing of the charges within the molecule. These modified anionic head groups may be synthesized as described in the Scheme below.

Additionally, the formation of the hydrophobic tails using the epoxidized starting materials results in the presence of a secondary alcohol site which would be further reacted to generate additional interactions with the nucleic acid sequences. Some non-limiting examples of possible modifications include those shown in the Scheme below. The NMR of the acetylated ZAL is shown in FIG. 68.

115
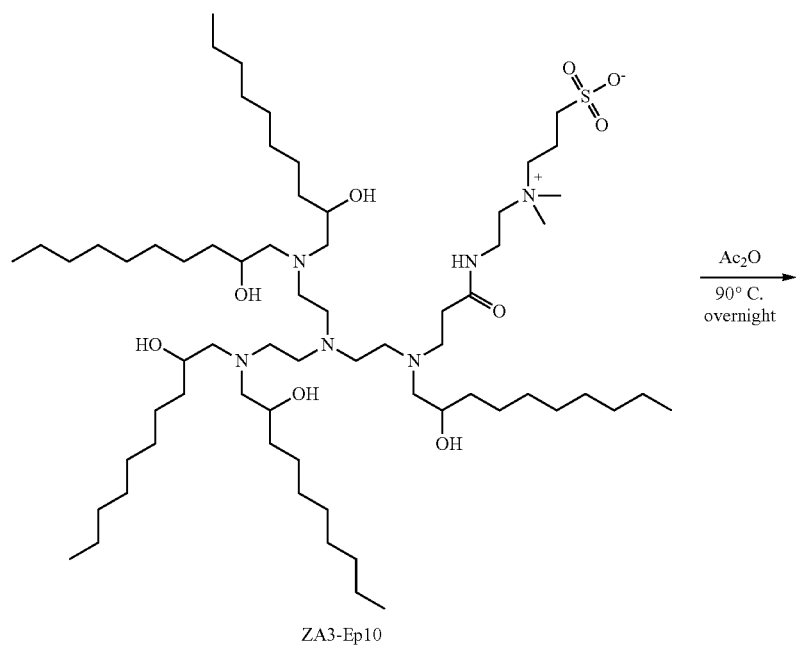
ZA3-Ep10
$\xrightarrow{\underset{\text{overnight}}{\underset{90° \text{ C.}}{Ac_2O}}}$
116
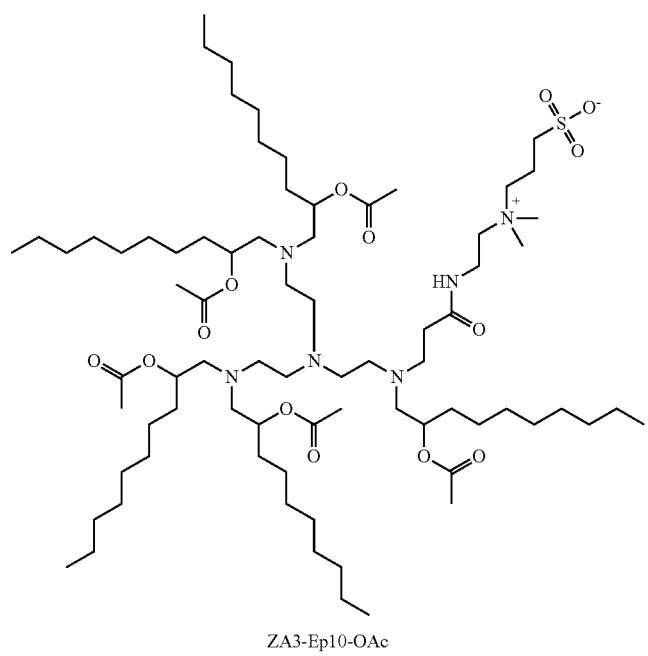
ZA3-Ep10-OAc

117
-continued
118
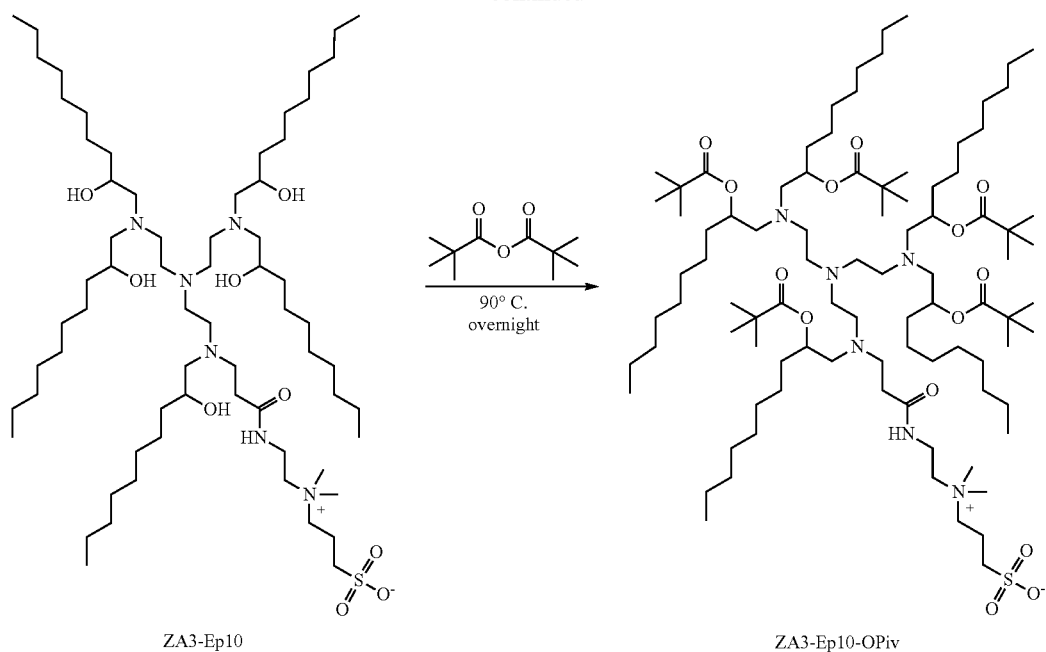
ZA3-Ep10
ZA3-Ep10-OPiv
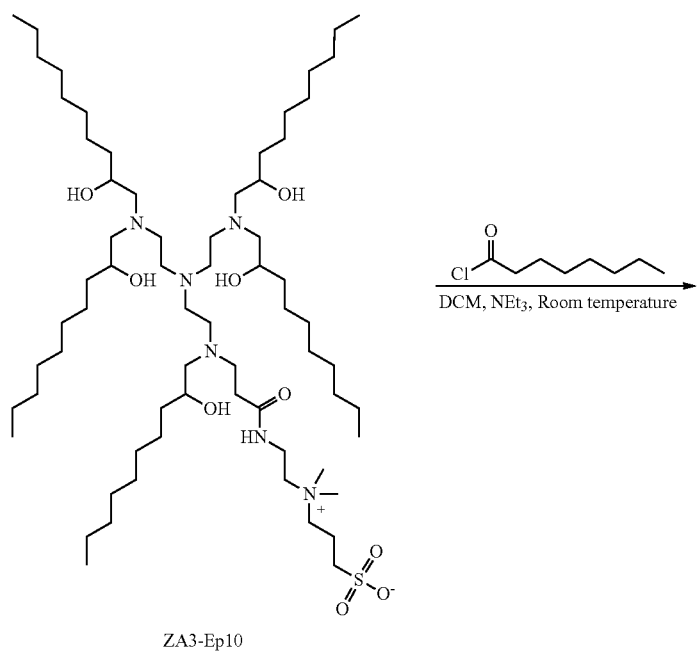
ZA3-Ep10

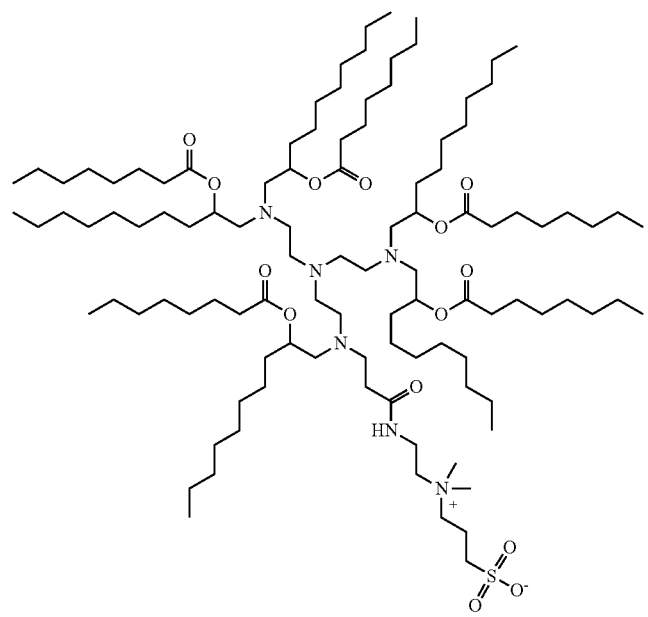
ZA3-Ep10-Octanoate
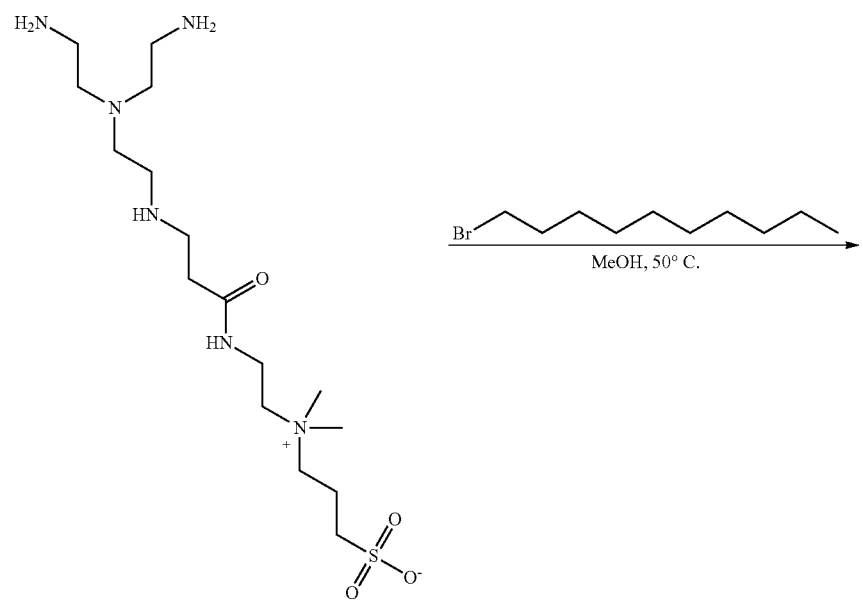
ZA3

-continued
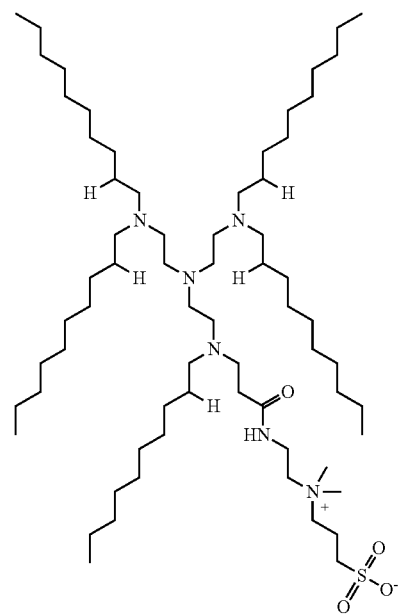
ZA3-Ep10-H
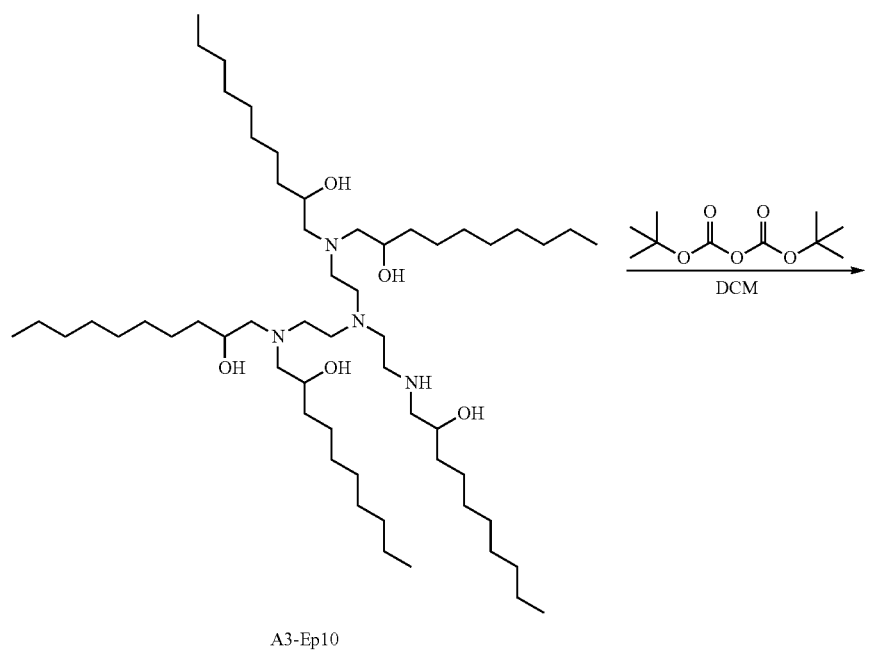
A3-Ep10

-continued
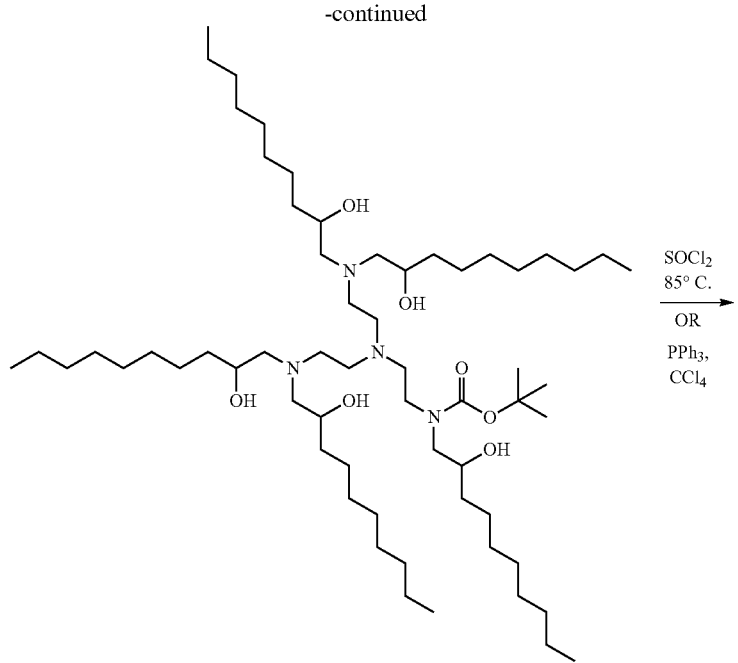
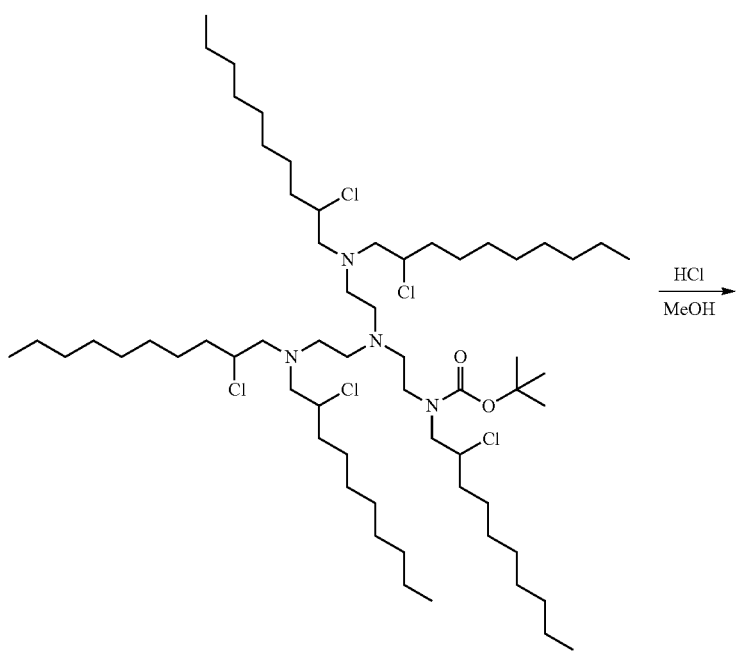

-continued

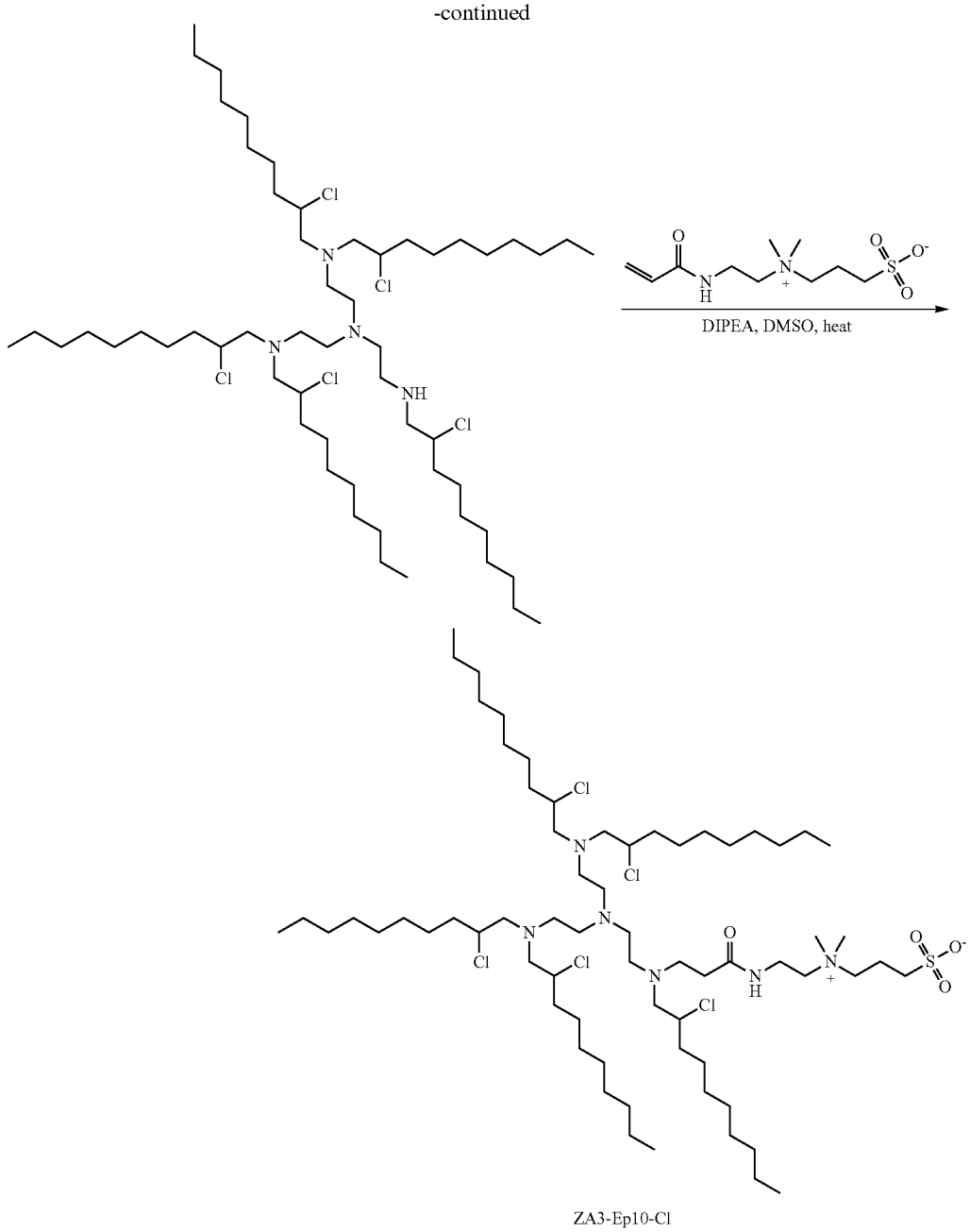

ZA3-Ep10-Cl

Additionally, the amines can be functionalized with a degradable diester such as the one shown below. This diester can be further modified with one or more mercapto alkyl groups to provide the necessarily hydrophobic groups.

Furthermore, to allow for the introduction of both degradable ester groups as well as a secondary alcohol, glycidic esters were prepared.

Formation of these compounds with different acrylates was carried out and shown via NMR in FIGS. 69A & 69B. These modified structural ZALs and CSALs were tested for their ability to bind RNA as well as the physical properties of nanoparticles formed with different RNA molecules. These particles were then tested for their ability to delivery a sgRNA to a HeLa-Luc-Cas9 cell and an mRNA to an IGROV1 cell. The mass spectral and NMR data for additional analogs is shown in FIGS. 70 and 71, respectively.

All of the compositions and methods disclosed and claimed herein can be made and executed without undue experimentation in light of the present disclosure. While the compositions and methods of this disclosure have been described in terms of certain embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the

REFERENCES

The following references, to the extent that they provide exemplary procedural or other details supplementary to those set forth herein, are specifically incorporated herein by reference.

Söll, et al., tRNA: Structure, Biosynthesis, and Function (ASM Press), 1995.
El Yacoubi, et al., Annu. Rev. Genet., 46:69-95, 2012.
Grosjean and Benne, Modification and Editing of RNA (ASM Press), 1998.
Hendrickson, et al., Annu. Rev. Biochem., 73:147-176, 2004.
Ibba and Sö, Annu. Rev. Biochem., 69:617-650, 2000.
Johnson et al., Cold Spring Harbor Symp. Quant. Biol., 60:71-82, 1995.
Johnson et al., J. Mol. Biol., 156:113-140, 1982.
Crowley et al., Cell, 78:61-71, 1994.
Beier and Grimm, Nucleic Acids Res., 29:4767-4782, 2001.
Torres, et al., Trends Mol. Med., 20:306-314, 2014.
Björk et al., Annu. Rev. Biochem., 56:263-287, 1987.
Green and Sambrook, Molecular Cloning: A Laboratory Manual (CHSL Press), 2012.
$R_{10}$ et al., RNA: A Laboratory Manual (CHSL Press), 2011.
Flanagan et al., J. Biol. Chem., 278:18628-18637, 2003.
Janiak, et al., Biochemistry, 31:5830-5840, 1992.
Zhou et al., Proc. Natl. Acad. Sci. USA, 113:520-525, 2016.
Hao et al., J. Am. Chem. Soc., 137:9206-9209, 2015.
Ran et al., Nat. Protoc., 8:2281-2308, 2013.
Love et al., Proc. Natl. Acad. Soc., 107:1864-1869, 2010.
Yan et al., Proc. Natl. Acad. Soc., 113:E5702-E5710, 2016.
Tabebordbar et al., Science, 351:407-411, 2016.
Guschin et al., Methods Mol. Biol., 649:247-256, 2010.
Whitehead et al., ACS Nano, 6:6922-6929, 2012.
Li et al., Genome Biol., 16:111, 2015.

What is claimed is:

1. A compound of the formula:

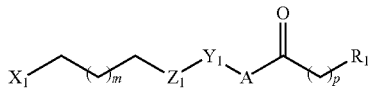

wherein:
X$_1$ is —S(O)$_2$O$^-$ or —OP(O)OR$_e$O$^-$, wherein:
  R$_e$ is hydrogen, alkyl$_{(C\leq6)}$, or substituted alkyl$_{(C\leq6)}$;
Y$_1$ is alkanediyl$_{(C\leq12)}$, alkenediyl$_{(C\leq12)}$, or a substituted version of either of these groups;
Z$_1$ is —N$^+$R$_3$R$_4$—;
A is —NR$_a$—, —S—, or —O—; wherein:
  R$_a$ is hydrogen, alkyl$_{(C\leq6)}$, or substituted alkyl$_{(C\leq6)}$, or R$_a$ is taken together with either R$_3$ or R$_4$ and is alkanediyl$_{(C\leq8)}$, or a substituted version thereof;
R$_1$ is a group of the formula:

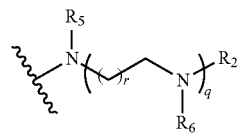

wherein:
  R$_5$, R$_6$, and R$_2$ are each independently hydrogen or alkyl$_{(C\leq8)}$, -alkanediyl$_{(C\leq6)}$-NH$_2$, -alkanediyl$_{(C\leq6)}$-alkylamino$_{(C\leq8)}$, -alkanediyl$_{(C\leq6)}$-dialkylamino$_{(C\leq12)}$, -alkanediyl$_{(C\leq6)}$—NR'R'', or a substituted version of any of these groups wherein:
    R' and R'' are each independently hydrogen, alkyl$_{(C\leq8)}$, substituted alkyl$_{(C\leq8)}$, or -Z$_2$A'R$_7$; wherein:
      Z$_2$ is alkanediyl$_{(C\leq6)}$ or substituted alkanediyl$_{(C\leq6)}$;
      A' is —CHR$_j$—, —C(O)O—, or —C(O)NR$_b$—;
        R$_b$ is hydrogen, alkyl$_{(C\leq6)}$, or substituted alkyl$_{(C\leq6)}$; and
        R$_j$ is hydrogen, halo, hydroxy, acyloxy$_{(C\leq24)}$, or substituted acyloxy$_{(C\leq24)}$;
      R$_7$ is alkyl$_{(C6-24)}$, substituted alkyl$_{(C6-24)}$, alkenyl$_{(C6-24)}$, substituted alkenyl$_{(C6-24)}$; or
  R$_5$, R$_6$, and R$_2$ are each independently -Z$_3$A''R$_8$; wherein:
    Z$_3$ is alkanediyl$_{(C\leq6)}$ or substituted alkanediyl$_{(C\leq6)}$;
    A'' is —CHR$_k$—, —C(O)O—, or —C(O)NR$_l$—;
      R$_l$ is hydrogen, alkyl$_{(C\leq6)}$, or substituted alkyl$_{(C\leq6)}$; and
      R$_k$ is hydrogen, halo, hydroxy, acyloxy$_{(C\leq24)}$, or substituted acyloxy$_{(C\leq24)}$; and
    R$_8$ is alkyl$_{(C6-24)}$, substituted alkyl$_{(C6-24)}$, alkenyl$_{(C6-24)}$, substituted alkenyl$_{(C6-24)}$;
  q is 1 or 2; and
  r is 1, 2, or 3;
R$_1$ is a group of the formula:

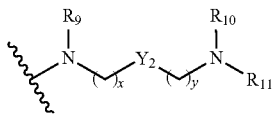

wherein:
  Y$_2$ is heterocycloalkanediyl$_{(C\leq12)}$, or a substituted version thereof;
  R$_9$, R$_{10}$, and R$_{11}$ are each independently hydrogen, alkyl$_{(C\leq8)}$, substituted alkyl$_{(C\leq8)}$, or -Z$_4$A'''R$_{12}$; wherein:
    Z$_4$ is alkanediyl$_{(C\leq6)}$, or substituted alkanediyl$_{(C\leq6)}$;
    A''' is —CHR$_k$—, —C(O)O—, or —C(O)NR$_l$—;
      R$_l$ is hydrogen, alkyl$_{(C\leq6)}$, or substituted alkyl$_{(C\leq6)}$; and
      R$_k$ is hydrogen, halo, hydroxy, acyloxy$_{(C\leq24)}$, or substituted acyloxy$_{(C\leq24)}$; and
    R$_{12}$ is alkyl$_{(C6-24)}$, substituted alkyl$_{(C6-24)}$, alkenyl$_{(C6-24)}$, substituted alkenyl$_{(C6-24)}$; and
  x and y are 1, 2, or 3;
R$_3$ and R$_4$ are each independently hydrogen, alkyl$_{(C\leq6)}$, or substituted alkyl$_{(C\leq6)}$, or R$_3$ or R$_4$ are taken together with R$_a$ and is alkanediyl$_{(C\leq8)}$, or a substituted version thereof; and
m, n, and p are each independently an integer selected from 0, 1, 2, or 3;
or a pharmaceutically acceptable salt thereof.

2. The compound of claim 1 further defined as:

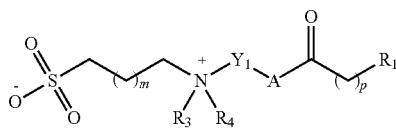

wherein:
Y$_1$ is alkanediyl$_{(C\leq12)}$, or a substituted version thereof;
A is —NR$_a$—, —S—, or —O—; wherein:
  R$_a$ is hydrogen, alkyl$_{(C\leq6)}$, or substituted alkyl$_{(C\leq6)}$, or R$_a$ is taken together with either R$_3$ or R$_4$ and is alkanediyl$_{(C\leq8)}$, or a substituted version thereof;
R$_1$ is a group of the formula:

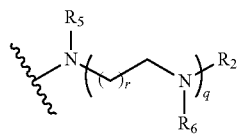

wherein:
  R$_5$, R$_6$, and R$_2$ are each independently hydrogen or alkyl$_{(C\leq8)}$, -alkanediyl$_{(C\leq6)}$-NH$_2$, -alkanediyl$_{(C\leq6)}$-alkylamino$_{(C\leq8)}$, -alkanediyl$_{(C\leq6)}$-dialkylamino$_{(C\leq12)}$, -alkanediyl$_{(C\leq6)}$—NR'R'', or a substituted version of any of these groups wherein:
    R' and R'' are each independently hydrogen, alkyl$_{(C\leq8)}$, substituted alkyl$_{(C\leq8)}$, or -Z$_2$A'R$_7$; wherein:
      Z$_2$ is alkanediyl$_{(C\leq4)}$ or substituted alkanediyl$_{(C\leq4)}$;
      A' is —CHR$_j$—, —C(O)O—, or —C(O)NR$_b$—;
        R$_b$ is hydrogen, alkyl$_{(C\leq6)}$, or substituted alkyl$_{(C\leq6)}$; and
        R$_j$ is hydrogen, halo, hydroxy, acyloxy$_{(C\leq24)}$, or substituted acyloxy$_{(C\leq24)}$;
      R$_7$ is alkyl$_{(C6-24)}$, substituted alkyl$_{(C6-24)}$, alkenyl$_{(C6-24)}$, substituted alkenyl$_{(C6-24)}$; or
  R$_5$, R$_6$, and R$_2$ are each independently —Z$_3$A''R$_8$; wherein:
    Z$_3$ is alkanediyl$_{(C\leq4)}$ or substituted alkanediyl$_{(C\leq4)}$;
    A'' is —CHR$_k$—, —C(O)O—, or —C(O)NR$_l$—;

R$_l$ is hydrogen, alkyl$_{(C\leq 6)}$, or substituted alkyl$_{(C\leq 6)}$; and

R$_k$ is hydrogen, halo, hydroxy, acyloxy$_{(C\leq 24)}$, or substituted acyloxy$_{(C\leq 24)}$; and R$_8$ is alkyl$_{(C6-24)}$, substituted alkyl$_{(C6-24)}$, alkenyl$_{(C6-24)}$, substituted alkenyl$_{(C6-24)}$;

q is 1 or 2; and r is 1, 2, or 3;

R$_1$ is a group of the formula:

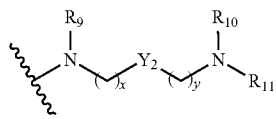

wherein:
Y$_2$ is arenediyl$_{(C\leq 12)}$, heterocycloalkanediyl$_{(C\leq 12)}$, heteroarenediyl$_{(C\leq 12)}$, alkoxydiyl$_{(C\leq 12)}$, or a substituted version of any of these groups;

R$_9$, R$_{10}$, and R$_{11}$ are each independently selected from hydrogen, alkyl$_{(C\leq 8)}$, substituted alkyl$_{(C\leq 8)}$, or -Z$_4$A'''R$_{12}$; wherein:

Z$_4$ is alkanediyl$_{(C\leq 4)}$ or substituted alkanediyl$_{(C\leq 4)}$;

A''' is —CHR$_k$—, —C(O)O—, or —C(O)NR$_l$—;

R$_l$ is hydrogen, alkyl$_{(C\leq 6)}$, or substituted alkyl$_{(C\leq 6)}$; and

R$_k$ is hydrogen, halo, hydroxy, acyloxy$_{(C\leq 24)}$, or substituted acyloxy$_{(C\leq 24)}$; and R$_{12}$ is alkyl$_{(C6-24)}$, substituted alkyl$_{(C6-24)}$, alkenyl$_{(C6-24)}$, substituted alkenyl$_{(C6-24)}$; and x and y are 1, 2, 3, or 4;

R$_3$ and R$_4$ are each independently hydrogen, alkyl$_{(C\leq 6)}$, or substituted alkyl$_{(C\leq 6)}$, or R$_3$ or R$_4$ are taken together with R$_a$ and is alkanediyl$_{(C\leq 8)}$, or a substituted version thereof; and m, n, and p are each independently an integer selected from 0, 1, 2, or 3;

or a pharmaceutically acceptable salt thereof.

3. The compound of claim 1 further defined as:

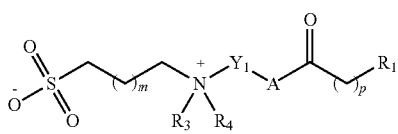

wherein:
Y$_1$ is alkanediyl$_{(C\leq 12)}$, or a substituted version thereof;

A is —NR$_a$- or —O—; wherein:

R$_a$ is hydrogen, alkyl$_{(C\leq 6)}$, or substituted alkyl$_{(C\leq 6)}$, or R$_a$ is taken together with either R$_3$ or R$_4$ and is alkanediyl$_{(C\leq 8)}$, or a substituted version thereof;

R$_1$ is a group of the formula:

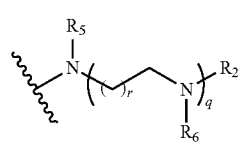

wherein:
R$_5$, R$_6$, and R$_2$ are each independently hydrogen or alkyl$_{(C\leq 8)}$, -alkanediyl$_{(C\leq 6)}$-NH$_2$, -alkanediyl$_{(C\leq 6)}$-alkylamino$_{(C\leq 8)}$, -alkanediyl$_{(C\leq 6)}$-dialkylamino$_{(C\leq 12)}$, -alkanediyl$_{(C\leq 6)}$—NR'R'', or a substituted version of any of these groups wherein:

R' and R'' are each independently hydrogen, alkyl$_{(C\leq 8)}$, substituted alkyl$_{(C\leq 8)}$, or -Z$_2$A'R$_7$; wherein:

Z$_2$ is alkanediyl$_{(C\leq 4)}$ or substituted alkanediyl$_{(C\leq 4)}$;

A' is —CHR$_j$—, —C(O)O—, or —C(O)NR$_b$—;

R$_b$ is hydrogen, alkyl$_{(C\leq 6)}$, or substituted alkyl$_{(C\leq 6)}$; and

R$_j$ is hydrogen, halo, hydroxy, acyloxy$_{(C\leq 24)}$, or substituted acyloxy$_{(C\leq 24)}$;

R$_7$ is alkyl$_{(C6-24)}$, substituted alkyl$_{(C6-24)}$, alkenyl$_{(C6-24)}$, substituted alkenyl$_{(C6-24)}$; or R$_5$, R$_6$, and R$_2$ are each independently —Z$_3$A''R$_8$; wherein:

Z$_3$ is alkanediyl$_{(C\leq 4)}$ or substituted alkanediyl$_{(C\leq 4)}$;

A'' is —CHR$_k$—, —C(O)O—, or —C(O)NR$_l$—;

R$_l$ is hydrogen, alkyl$_{(C\leq 6)}$, or substituted alkyl$_{(C\leq 6)}$; and

R$_k$ is hydrogen, halo, hydroxy, acyloxy$_{(C\leq 24)}$, or substituted acyloxy$_{(C\leq 24)}$; and R$_8$ is alkyl$_{(C6-24)}$, substituted alkyl$_{(C6-24)}$, alkenyl$_{(C6-24)}$, substituted alkenyl$_{(C6-24)}$;

q is 1 or 2; and r is 1, 2, or 3;

R$_1$ is a group of the formula:

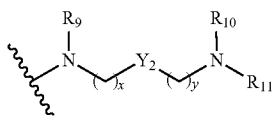

wherein:
Y$_2$ is heterocycloalkanediyl$_{(C\leq 12)}$, or a substituted version of any of these groups;

R$_9$, R$_{10}$, and R$_{11}$ are each independently selected from hydrogen, alkyl$_{(C\leq 8)}$, substituted alkyl$_{(C\leq 8)}$, or -Z$_4$A'''R$_{12}$; wherein:

Z$_4$ is alkanediyl$_{(C\leq 4)}$ or substituted alkanediyl$_{(C\leq 4)}$;

A''' is —CHR$_k$—, —C(O)O—, or —C(O)NR$_l$—;

R$_l$ is hydrogen, alkyl$_{(C\leq 6)}$, or substituted alkyl$_{(C\leq 6)}$; and

R$_k$ is hydrogen, halo, hydroxy, acyloxy$_{(C\leq 24)}$, or substituted acyloxy$_{(C\leq 24)}$; and R$_{12}$ is alkyl$_{(C6-24)}$, substituted alkyl$_{(C6-24)}$, alkenyl$_{(C6-24)}$, substituted alkenyl$_{(C6-24)}$; and x and y are 1, 2, or 3;

R$_3$ and R$_4$ are each independently hydrogen, alkyl$_{(C\leq 6)}$, or substituted alkyl$_{(C\leq 6)}$, or R$_3$ or R$_4$ are taken together with R$_a$ and is alkanediyl$_{(C\leq 8)}$, or a substituted version thereof; and m, n, and p are each independently an integer selected from 0, 1, 2, or 3;

or a pharmaceutically acceptable salt thereof.

4. The compound of claim 1 further defined as:

(IIa)

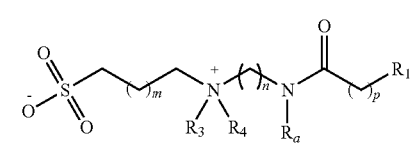

wherein:

$R_1$ is a group of the formula:

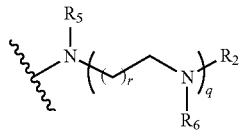

wherein:
$R_5$, $R_6$, and $R_2$ are each independently hydrogen or alkyl$_{(C\leq8)}$, -alkanediyl$_{(C\leq6)}$-NH$_2$, -alkanediyl$_{(C\leq6)}$-alkylamino$_{(C\leq8)}$, -alkanediyl$_{(C\leq6)}$-dialkylamino$_{(C\leq12)}$, -alkanediyl$_{(C\leq6)}$—NR'R", or a substituted version of any of these groups wherein:
R' and R" are each independently hydrogen, alkyl$_{(C\leq8)}$, substituted alkyl$_{(C\leq8)}$, or -Z$_2$A'R$_7$; wherein:
$Z_2$ is alkanediyl$_{(C\leq4)}$ or substituted alkanediyl$_{(C\leq4)}$;
A' is —CHR$_j$—, —C(O)O—, or —C(O)NR$_b$—;
$R_b$ is hydrogen, alkyl$_{(C\leq6)}$, or substituted alkyl$_{(C\leq6)}$; and
$R_j$ is hydrogen, halo, hydroxy, acyloxy$_{(C\leq24)}$, or substituted acyloxy$_{(C\leq24)}$;
$R_7$ is alkyl$_{(C6-24)}$, substituted alkyl$_{(C6-24)}$, alkenyl$_{(C6-24)}$, substituted alkenyl$_{(C6-24)}$; or
$R_5$, $R_6$, and $R_2$ are each independently —Z$_3$A"R$_8$; wherein:
$Z_3$ is alkanediyl$_{(C\leq4)}$ or substituted alkanediyl$_{(C\leq4)}$;
A" is —CHR$_k$—, —C(O)O—, or —C(O)NR$_l$—;
$R_l$ is hydrogen, alkyl$_{(C\leq6)}$, or substituted alkyl$_{(C\leq6)}$; and
$R_k$ is hydrogen, halo, hydroxy, acyloxy$_{(C\leq24)}$, or substituted acyloxy$_{(C\leq24)}$; and
$R_8$ is alkyl$_{(C6-24)}$, substituted alkyl$_{(C6-24)}$, alkenyl$_{(C6-24)}$, substituted alkenyl$_{(C6-24)}$;
q is 1 or 2; and
r is 1, 2, or 3;
$R_a$, $R_3$, and $R_4$ are each independently hydrogen, alkyl$_{(C\leq6)}$, or substituted alkyl$_{(C\leq6)}$; and
m, n, and p are each independently an integer selected from 0, 1, 2, or 3;

or a pharmaceutically acceptable salt thereof.

5. The compound of claim 1, wherein $R_a$ is hydrogen, $R_3$ is alkyl$_{(C\leq6)}$ or substituted alkyl$_{(C\leq6)}$, or $R_4$ is alkyl$_{(C\leq6)}$ or substituted alkyl$_{(C\leq6)}$.

6. The compound of claim 1, wherein m is 1 or 2, n is 2 or 3, or p is 1, 2, or 3.

7. The compound of claim 1, wherein $R_1$ is a group of the formula:

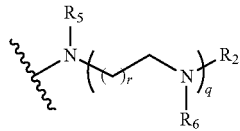

wherein:
$R_5$, $R_6$, and $R_2$ are each independently hydrogen or alkyl$_{(C\leq8)}$, -alkanediyl$_{(C\leq6)}$-NH$_2$, -alkanediyl$_{(C\leq6)}$-alkylamino$_{(C\leq8)}$, -alkanediyl$_{(C\leq6)}$-dialkylamino$_{(C\leq12)}$, -alkanediyl$_{(C\leq6)}$—NR'R", or a substituted version of any of these groups wherein:
R' and R" are each independently hydrogen, alkyl$_{(C\leq8)}$, substituted alkyl$_{(C\leq8)}$, —Z$_2$A'R$_7$; wherein:

$Z_2$ is alkanediyl$_{(C\leq4)}$ or substituted alkanediyl$_{(C\leq4)}$;
A' is —CHR$_j$—, —C(O)O—, or —C(O)NR$_b$—;
$R_b$ is hydrogen, alkyl$_{(C\leq6)}$, or substituted alkyl$_{(C\leq6)}$; and
$R_j$ is hydrogen, halo, hydroxy, acyloxy$_{(C\leq24)}$, or substituted acyloxy$_{(C\leq24)}$;
$R_7$ is alkyl$_{(C6-24)}$, substituted alkyl$_{(C6-24)}$, alkenyl$_{(C6-24)}$, substituted alkenyl$_{(C6-24)}$; or
$R_5$, $R_6$, and $X_1$ are each independently —Z$_3$A"R$_8$; wherein:
$Z_3$ is alkanediyl$_{(C\leq4)}$ or substituted alkanediyl$_{(C\leq4)}$;
A" is —CHR$_k$—, —C(O)O—, or —C(O)NR$_l$—;
$R_l$ is hydrogen, alkyl$_{(C\leq6)}$, or substituted alkyl$_{(C\leq6)}$; and
$R_k$ is hydrogen, halo, hydroxy, acyloxy$_{(C\leq24)}$, or substituted acyloxy$_{(C\leq24)}$; and
$R_8$ is alkyl$_{(C6-24)}$, substituted alkyl$_{(C6-24)}$, alkenyl$_{(C6-24)}$, substituted alkenyl$_{(C6-24)}$;
q is 1 or 2; and
r is 1, 2, or 3.

8. The compound of claim 7, wherein r is 1 or 2.

9. The compound of claim 1, wherein $R_5$ is —Z$_3$A"R$_8$; wherein:
$Z_3$ is alkanediyl$_{(C\leq4)}$ or substituted alkanediyl$_{(C\leq4)}$;
A" is —CHR$_k$—, —C(O)O—, or —C(O)NR$_l$—;
$R_l$ is hydrogen, alkyl$_{(C\leq6)}$, or substituted alkyl$_{(C\leq6)}$; and
$R_k$ is hydrogen, halo, hydroxy, acyloxy$_{(C\leq24)}$, or substituted acyloxy$_{(C\leq24)}$; and
$R_8$ is alkyl$_{(C6-24)}$, substituted alkyl$_{(C6-24)}$, alkenyl$_{(C6-24)}$, substituted alkenyl$_{(C6-24)}$.

10. The compound of claim 1, wherein $R_6$ is —Z$_3$A"R$_8$; wherein:
$Z_3$ is alkanediyl$_{(C\leq4)}$ or substituted alkanediyl$_{(C\leq4)}$;
A" is —CHR$_k$—, —C(O)O—, or —C(O)NR$_l$—;
$R_l$ is hydrogen, alkyl$_{(C\leq6)}$, or substituted alkyl$_{(C\leq6)}$; and
$R_k$ is hydrogen, halo, hydroxy, acyloxy$_{(C\leq24)}$, or substituted acyloxy$_{(C\leq24)}$; and
$R_8$ is alkyl$_{(C6-24)}$, substituted alkyl$_{(C6-24)}$, alkenyl$_{(C6-24)}$, substituted alkenyl$_{(C6-24)}$.

11. The compound of claim 1, wherein $R_2$ is —Z$_3$A"R$_8$; wherein:
$Z_3$ is alkanediyl$_{(C\leq4)}$ or substituted alkanediyl$_{(C\leq4)}$;
A" is —CHR$_k$—, —C(O)O—, or —C(O)NR$_l$—;
$R_l$ is hydrogen, alkyl$_{(C\leq6)}$, or substituted alkyl$_{(C\leq6)}$; and
$R_k$ is hydrogen, halo, hydroxy, acyloxy$_{(C\leq24)}$, or substituted acyloxy$_{(C\leq24)}$; and
$R_8$ is alkyl$_{(C6-24)}$, substituted alkyl$_{(C6-24)}$, alkenyl$_{(C6-24)}$, substituted alkenyl$_{(C6-24)}$.

12. The compound of claim 1, wherein $Z_3$ is alkanediyl$_{(C1-2)}$.

13. The compound of claim 1, wherein A" is —CHR$_k$— and $R_k$ is hydroxy.

14. The compound of claim 1, wherein $R_8$ is alkyl$_{(C6-24)}$ or substituted alkyl$_{(C6-24)}$.

15. A composition comprising:
(A) a compound of claim 1; and
(B) a nucleic acid.

16. The composition of claim 15, wherein the nucleic acid is a therapeutic nucleic acid.

17. The composition of claim 15, wherein the composition further comprises a steroid or steroid derivative, a phospholipid, or a PEG lipid.

18. The composition of claim 15 further comprising a pharmaceutically acceptable carrier.

* * * * *

UNITED STATES PATENT AND TRADEMARK OFFICE
CERTIFICATE OF CORRECTION

PATENT NO. : 10,562,849 B2
APPLICATION NO. : 15/597049
DATED : February 18, 2020
INVENTOR(S) : Daniel J. Siegwart and Jason B. Miller It is certified that error appears in the above-identified patent and that said Letters Patent is hereby corrected as shown below:

In Claim 1, Column 139, Line 16, delete "$-N^+R_3R_4^-;$" and insert -- $-N^+R_3R_4-;$-- therefor.

In Claim 3, Column 142, Line 41, delete "$R_2$" and insert --$R_{12}$-- therefor.

Signed and Sealed this
Second Day of June, 2020

Andrei Iancu
*Director of the United States Patent and Trademark Office*